US012576132B2

(12) United States Patent
Ge et al.

(10) Patent No.: US 12,576,132 B2
(45) Date of Patent: Mar. 17, 2026

(54) ISTHMIN 1 FOR TREATMENT OF LUNG INFLAMMATION

(71) Applicant: National University of Singapore, Singapore (SG)

(72) Inventors: Ruowen Ge, Singapore (SG); Yin Weng Terence Lam, Singapore (SG); Wai-Shiu Fred Wong, Singapore (SG)

(73) Assignee: National University of Singapore, Republic of (SG)

( * ) Notice: Subject to any disclaimer, the term of this patent is extended or adjusted under 35 U.S.C. 154(b) by 625 days.

(21) Appl. No.: 17/436,785

(22) PCT Filed: Mar. 6, 2020

(86) PCT No.: PCT/SG2020/050111
§ 371 (c)(1),
(2) Date: Sep. 7, 2021

(87) PCT Pub. No.: WO2020/180256
PCT Pub. Date: Sep. 10, 2020

(65) Prior Publication Data
US 2023/0190868 A1     Jun. 22, 2023

(30) Foreign Application Priority Data
Mar. 6, 2019     (SG) ........................... 10201902000Y

(51) Int. Cl.
| | |
|---|---|
| A61K 38/17 | (2006.01) |
| A61K 9/00 | (2006.01) |
| A61P 11/00 | (2006.01) |
| A61P 11/06 | (2006.01) |
| A61P 29/00 | (2006.01) |

(52) U.S. Cl.
CPC .......... *A61K 38/1709* (2013.01); *A61K 9/007* (2013.01); *A61P 11/00* (2018.01); *A61P 11/06* (2018.01); *A61P 29/00* (2018.01)

(58) Field of Classification Search
None
See application file for complete search history.

(56) References Cited

U.S. PATENT DOCUMENTS

| | | | | |
|---|---|---|---|---|
| 2006/0058228 A1* | 3/2006 | Kelly | ....................... | C07K 7/06 |
| | | | | 514/19.3 |
| 2012/0288474 A1 | 11/2012 | Kungl et al. | | |
| 2017/0000752 A1 | 1/2017 | Ogawa et al. | | |

FOREIGN PATENT DOCUMENTS

| | | |
|---|---|---|
| CN | 102596227 A | 7/2012 |
| WO | WO-2008/023947 A1 | 2/2008 |
| WO | WO-2009/043836 A1 | 4/2009 |
| WO | WO-2009/113965 A1 | 9/2009 |
| WO | WO-2015/111701 A1 | 7/2015 |

OTHER PUBLICATIONS

Guo, Haiwei H. et al., "Protein tolerance to random amino acid change." (PNAS (2004) 101(25) p. 9205-9210.*
Yampolsky, Lev Y. and Stoltzfus, Arlin; "The exchangeability of amino acids in proteins." Genetics (2005) 170 p. 1459-1472.*
The uniport map of known variants of human ISM1, https://www.uniprot.org/uniprotkb/B1AKI9/variant-viewer downloaded Apr. 18, 2024.*
Walsh, David A. and Pearson, Claire I.' "Angiogenesis in the pathogenesis of inflammatory joint and lung diseases." Arthritis Res. (2001) 3 p. 147-153.*
Ar, Arzu; "Jet, ultrasonic, and mesh nebulizers: an evaluation of nebulizers for better clinical outcomes." Eurasian J. Pulmonol. (2014) 16 p. 1-7.*
Pfaffenbach, Kyle T. and Lee, Amy S.; "The critical role of grp78 in physiologic and pathologic stress." Curr. Opin. Cell Biol. (2011) 23(2) p. 150-156.*
Reynolds, Fred et al, "Method of determining nanoparticle core weight." Anal. Chem. (2005) 77 p. 814-817.*
Mahadevan, Navin R. et al, "Transmission of endoplasmic reticular stress and pro-inflammation from tumor cells to myeloid cells." PNAS (2011) 108(16) p. 6561-6566.*
Ayaub E.A., et al. "GRP78 and CHOP modulate macrophage apoptosis and the development of bleomycin-induced pulmonary fibrosis," J Pathol. 239(4):411-25 (2016).
Chen M., et al. "Isthmin targets cell-surface GRP78 and triggers apoptosis via induction of mitochondrial dysfunction," Cell Death Differ. 21(5):797-810 (2014).
Extended European Search Report for European Patent Application No. 20766781.7, dated Dec. 12, 2022 (12 pages).
International Search Report and Written Opinion for International Patent Application No. PCT/SG2020/050111, mailed Jun. 11, 2020 (9 pages).
Lam et al., "ISM1 protects lung homeostasis via cell-surface GRP78-mediated alveolar macrophage apoptosis," Proc Natl Acad Sci U S A. 119(4):e2019161119 (Jan. 2022) (11 pages).
Nguyen et al., "ISM1 suppresses LPS-induced acute lung injury and post-injury lung fibrosis in mice," Mol Med. 28(1):72 (Jun. 2022) (17 pages).
Osório et al., "Distinct spatiotemporal expression of ISM1 during mouse and chick development," Cell Cycle. 13(10):1571-82 (Mar. 2014).
Rao et al., "Novel endogenous angiogenesis inhibitors and their therapeutic potential," Acta Pharmacol Sin. 36(10):1177-90 (Oct. 2015).
Rivera-Torruco et al., "Isthmin 1 identifies a subset of lung hematopoietic stem cells and it is associated with systemic inflammation," J Immunol. 202(1_Supplement):118.18 (May 2019) (1 page).

(Continued)

*Primary Examiner* — Fred H Reynolds
(74) *Attorney, Agent, or Firm* — Clark & Elbing LLP

(57) ABSTRACT

Provided herein are polypeptides including an amino acid sequence having at least 70% sequence identity with an Isthmin 1 (ISM1) protein or a GRP78-activating fragment thereof, as well as expressible nucleic acids encoding said polypeptides. Uses of such agents, as well as methods for inducing apoptosis in alveolar macrophages and/or for treating, ameliorating, or preventing inflammation or lung disease such as chronic obstructive pulmonary disease (COPD), emphysema, asthma, acute lung injury (ALI), lung fibrosis, and/or acute respiratory distress syndrome.

5 Claims, 35 Drawing Sheets

Specification includes a Sequence Listing.

(56)                    References Cited

OTHER PUBLICATIONS

Xiang W., et al. "Isthmin is a novel secreted angiogenesis inhibitor that inhibits tumour growth in mice," J Cell Mol Med. 15(2):359-74 (2011).

Zhang et al., "Isthmin exerts pro-survival and death-promoting effect on endothelial cells through alphavbeta5 integrin depending on its physical state," Cell Death Dis. 2(5):e153 (May 2011) (10 pages).

Kao et al. "Proapoptotic Cyclic Peptide BC71 Targets Cell-Surface GRP78 and Functions as an Anticancer Therapeutic in Mice" EBioMedicine 33:22-32 (Jun. 12, 2018) (11 pages).

Zheng et al. "Effect of isthmin 1 on convergent extension movements in zebrafish embryos," Chinese Journal of Comparative Medicine. 28(2):40-45 (Feb. 2018).

Baran et al., "Delivery systems for biologics" European Pharmaceutical Review, Issue 1 2024, https://www.europeanpharmaceuticalreview.com/article/215232/delivery-systems-for-biologics/, dated Mar. 4, 2024, retrieved on Jul. 23, 2024 (10 pages).

Dantas et al., "Exploring the Potential of Nebulised Biologics" Ondrugdelivery 148: pp. 12-14. (Apr. 2024) (3 pages).

Fellner et al., "Inhaled protein/peptide-based therapies for respiratory disease." Mol Cell Pediatr. 3(16): 1-5 (Dec. 2016) (5 pages).

Gopal et al., "Chapter 2—The Endoplasmic Reticulum Chaperone GRP78 Also Functions as a Cell Surface Signaling Receptor" Salvatore V. Pizzo, Academic Press. pp. 16-31, (Mar. 2018) (16 pages).

Labiris et al., "Pulmonary drug delivery. Part I: physiological factors affecting therapeutic effectiveness of aerosolized medications." Br J Clin Pharmacol. 56(6):588-599 (Dec. 2003) (12 pages).

Liang et al. "Pulmonary Delivery of Biological Drugs" Pharmaceutics. 12(11):1025 (Oct. 26, 2020) (30 pages).

Matthews et al. "Developing inhaled protein therapeutics for lung diseases." Molecular biomedicine. 1(11): 1-14 (Oct. 2020) (14 pages).

Ni et al., "Beyond the endoplasmic reticulum: atypical GRP78 in cell viability, signaling and therapeutic targeting" Biochem J. 434(2): 181-188 (Mar. 1, 2011) (15 pages).

Patton et al. "The lungs as a portal of entry for systemic drug delivery." Proceedings of the American Thoracic Society, 1(4): 338-344 (Sep. 2004) (7 pages).

Peacock et al. "A novel angiogenesis inhibitor suppresses rat adjuvant arthritis." Cellular immunology, 160(2):178-184 (Feb. 1995) (7 pages).

Peacock et al., "Angiogenesis inhibition suppresses collagen arthritis." J Exp Med. 175(4): 1135-1138 (Apr. 1992) (4 pages).

Pfister et al., "Bioavailability of Therapeutic Proteins by Inhalation—Worker Safety Aspects" The Annals of Occupational Hygiene, 58(7): 899-911 (Jun. 2014) (13 pages).

Pizzo, Salvatore V, "Chapter 1—An Historical Perspective: Cell Surface GRP78, a New Paradigm in Signal Transduction Biology" Salvatore V. Pizzo, Academic Press. pp. 12-15, (Mar. 2018) (4 pages).

Qin et al., "Challenges and Strategies to Enhance the Systemic Absorption of Inhaled Peptides and Proteins" Pharmaceutical Research. 40: 1037-1055 (Nov. 16, 2022) (19 pages).

Saalbach, Klaus P. "Chapter 23—Nasal and pulmonary routes of drug delivery" Novel Platforms for Drug Delivery Applications, Woodhead Publishing, pp. 569-606, (2023) (38 pages).

Storgard et al., "Decreased angiogenesis and arthritic disease in rabbits treated with an alphavbeta3 antagonist." J Clin Invest. 103(1):47-54 (Jan. 1999) (8 pages).

Tsai et al., "Chapter 3—Cell Surface GRP78: Anchoring and Translocation Mechanisms and Therapeutic Potential in Cancer" Salvatore V. Pizzo, Academic Press. pp. 32-41, Mar. 2018, (10 pages).

Tsai et al., "Characterization and mechanism of stress-induced translocation of 78-kilodalton glucose-regulated protein (GRP78) to the cell surface." The Journal of biological chemistry. 290(13):8049-8064 (Mar. 2015) (16 pages).

Yang et al., "Influence of Isthmin on collagen deposition and angiogenesis in mouse with bleomycin-induced pulmonary fibrosis" Chin J Lung Dis (Electronic Edition). 7(1): 12-18 (Feb. 2014) (7 pages).

Zhang, Yi et al. "Cell surface relocalization of the endoplasmic reticulum chaperone and unfolded protein response regulator GRP78/BiP." The Journal of biological chemistry. 285(20):15065-15075 (May 2010) (11 pages).

* cited by examiner

Cells under stress: tumor cells, ECs, activated inflammatory cells

Normal cells

ISM1/fragment

Cell
Death

Diagnostic/Predictive

Therapeutic

FIGURE 24
A
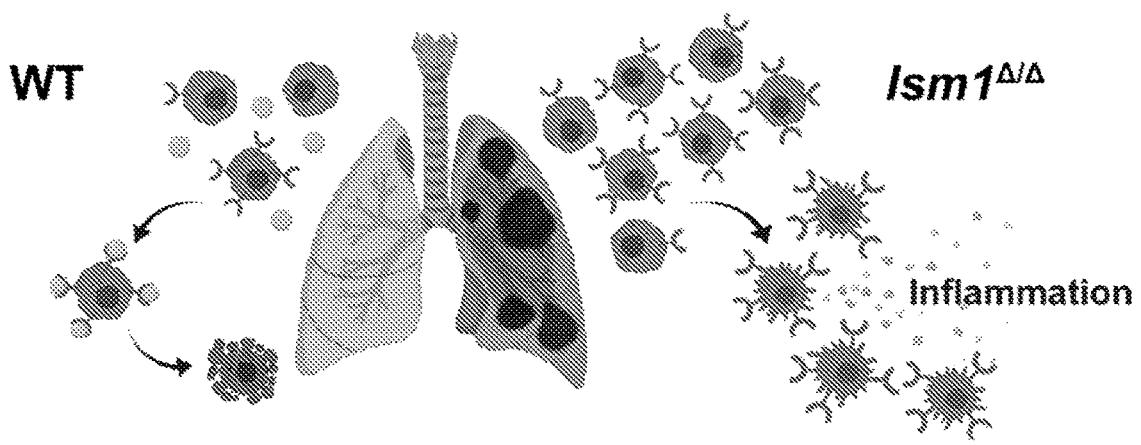
WT
*Ism1*<sup>Δ/Δ</sup>
Inflammation
Lung homeostasis
Chronic inflammation
(COPD)
 Isthmin 1
 Alveolar Macrophage
Proinflammatory
Alveolar Macrophages
 Cell-surface
GRP78
Apoptosis
B
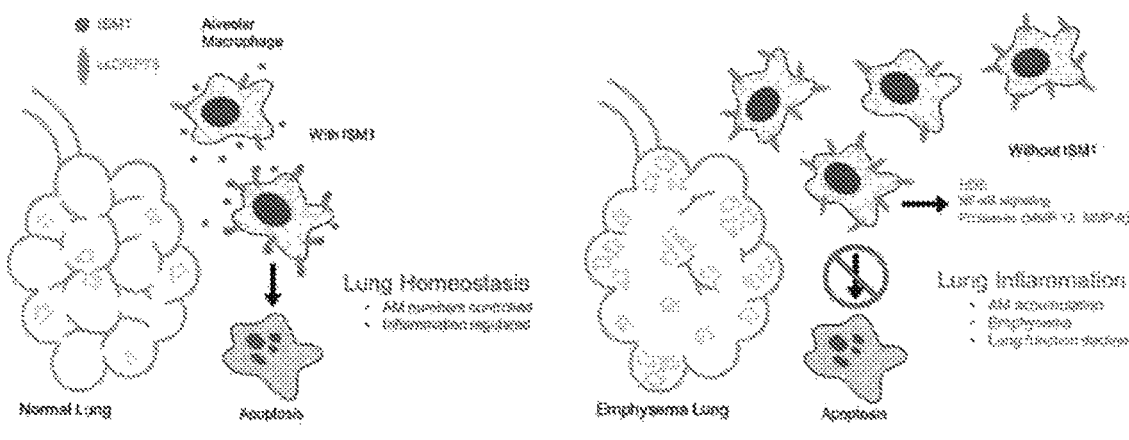

FIGURE 27
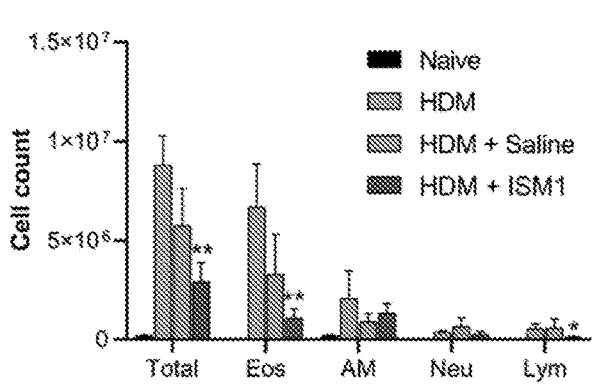
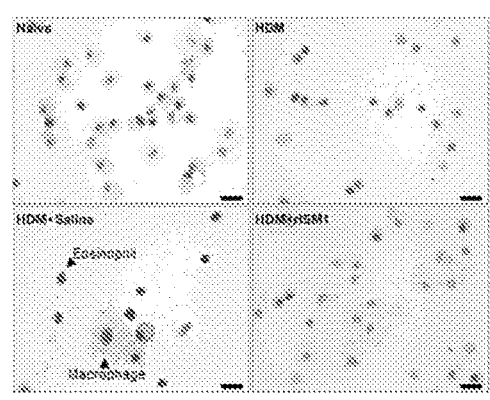
FIGURE 28
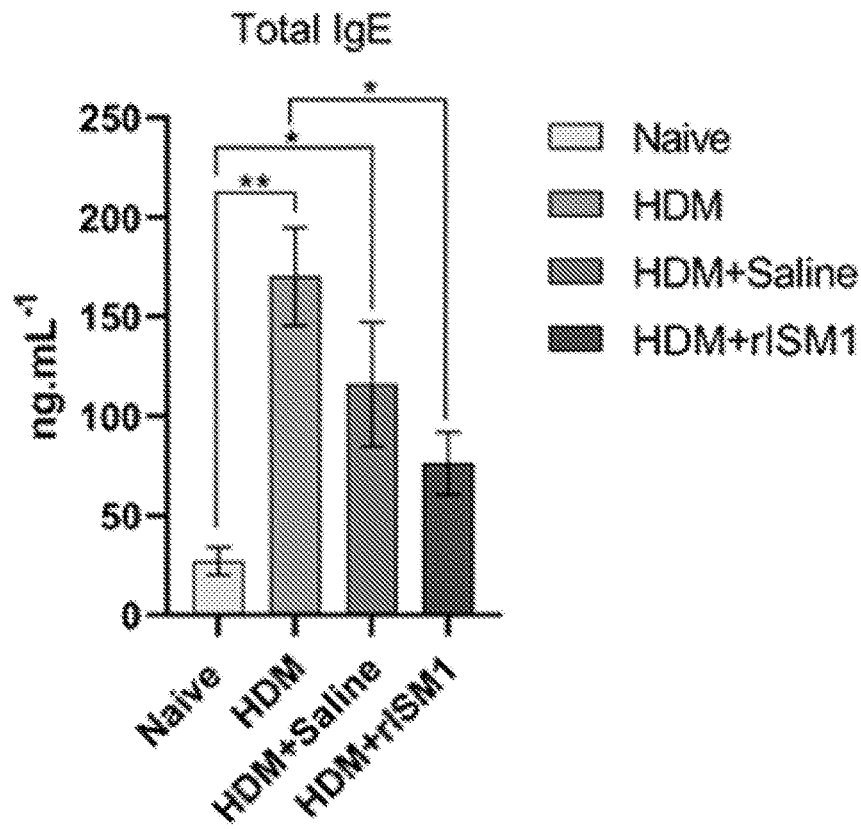

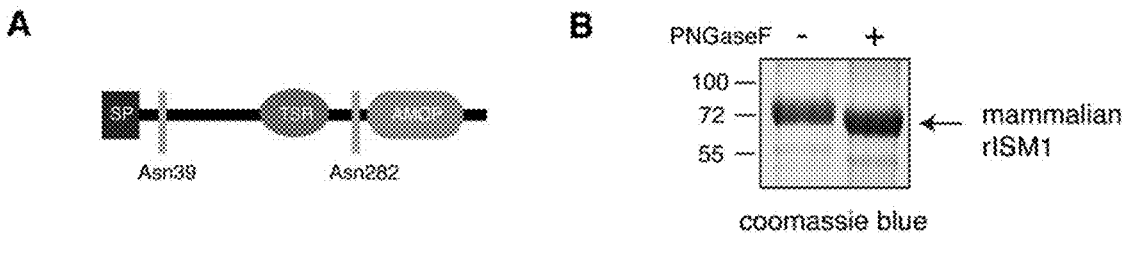

B

PNGaseF   −   +

100 —
72 —          ← mammalian rISM1
55 — coomassie blue

C

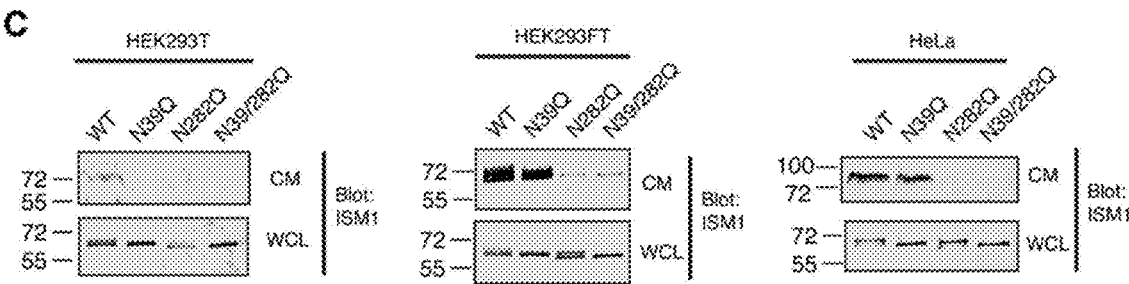

D

```
 27  30                        55 56 57 59 60   64
GSGASDRQDAAAGNVSGSQLQNNLNLESDSTSETSFPLSKEAPEEHQVVHQPFPRQRFPPETGHPSL
                          125          134              147 149
QRDGPRSFLLDLPNFPDLSKADINGQNPNIQVTIEVVDGPDSEAEKDQHPENKPSWSLPAPDWRAWW
 162 164   168 170      179180181184   188                              220
QRSLSLARTNSGDQDDKYDSTSDDSNFLSVPRGWDRPAPGHRTFETKEQPEYDSTDGEGDWSLWSVC
 229
SVTCGNGNQKRTRSCGYACIATESRTCDRPNCPGIEDTFRTAATEVSLLAGSEEFNATKLFEVDMDS
                            325   330 331
CERWMSCKSEFLKKYMHKVINDLPSCPCSYPTEVAYSTADIFDRIKRKDFRWKDASGPKEKLEIYKP
                            392
TARYCIRSMLSLESTTLAAQHCCYGDNMQLITRGKGAGTPNLISTEFSAELHYKVDVLPWIICKGDW
      443 445 447
SRYNEARPPNNGQKCTESPSDEDYIKQFQEAREY   (SEQ ID NO: 4)
```

E

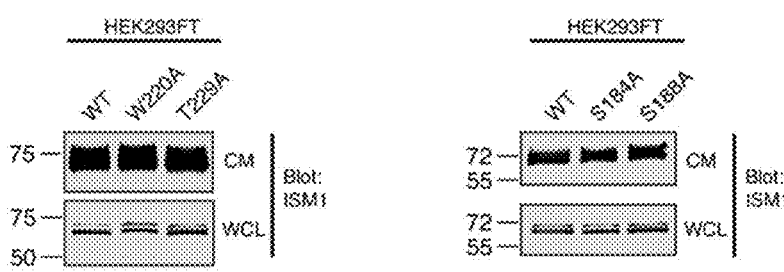

FIGURE 33
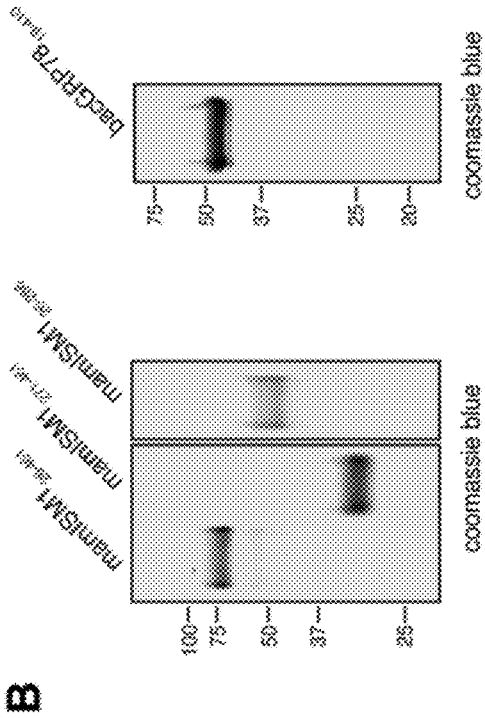
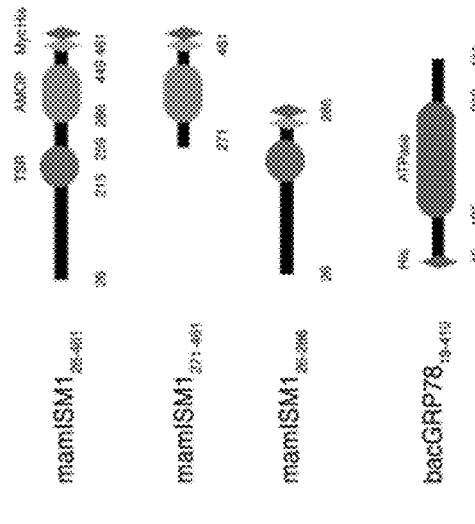

C

FIGURE 33 (Continued)
D
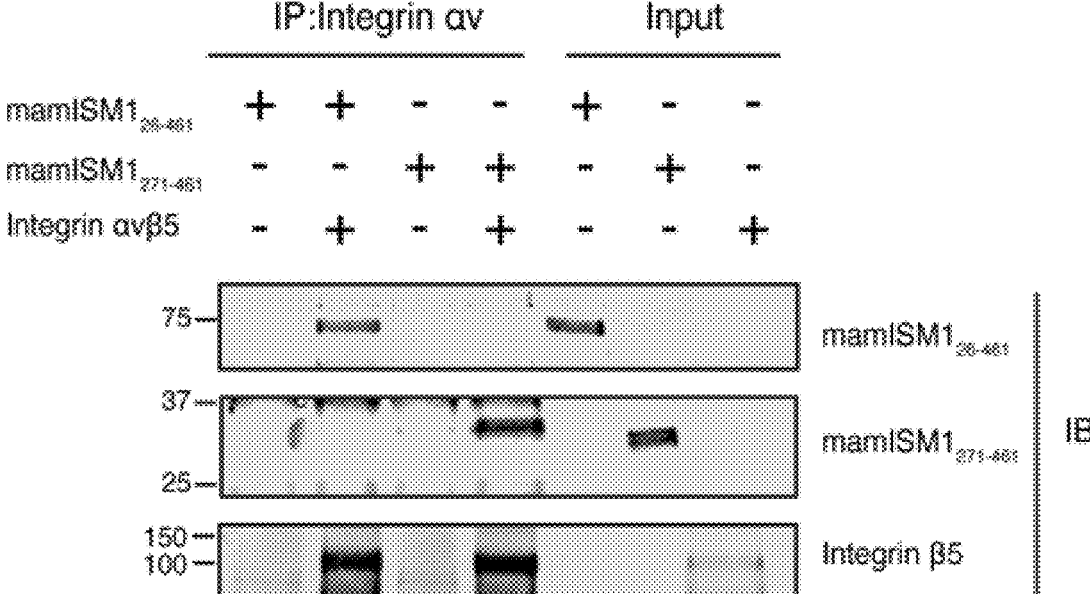
E
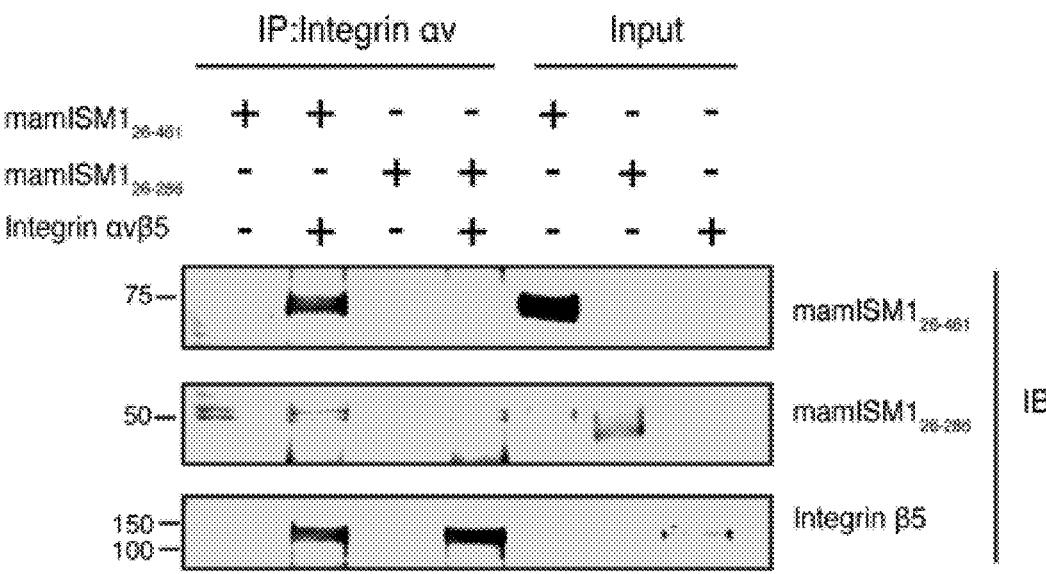

FIGURE 34
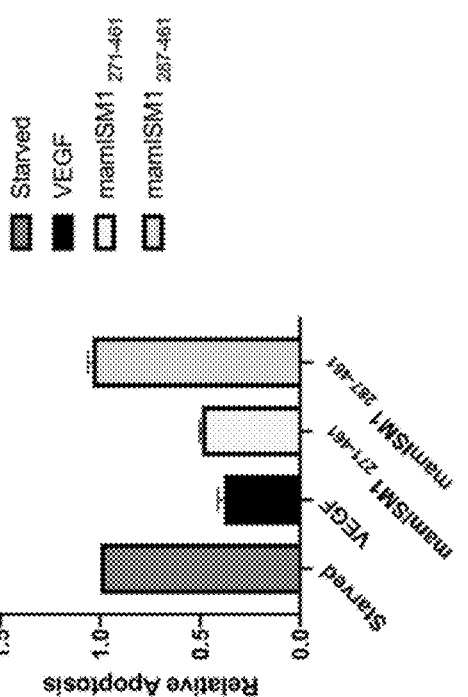
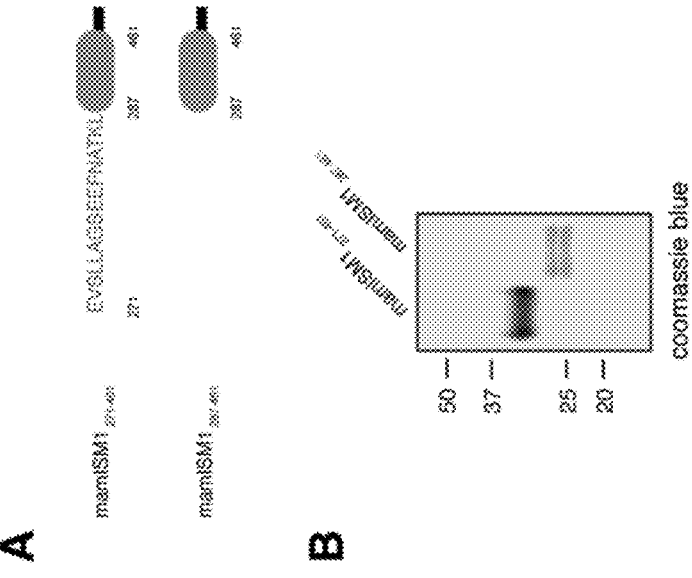

SEQUENCE LISTING

```
<160> NUMBER OF SEQ ID NOS: 39

<210> SEQ ID NO 1
<211> LENGTH: 464
<212> TYPE: PRT
<213> ORGANISM: Homo sapiens

<400> SEQUENCE: 1

Met Val Arg Leu Ala Ala Glu Leu Leu Leu Leu Leu Gly Leu Leu Leu
1               5                   10                  15

Leu Thr Leu His Ile Thr Val Leu Arg Gly Ser Gly Ala Ala Asp Gly
            20                  25                  30

Pro Asp Ala Ala Ala Gly Asn Ala Ser Gln Ala Gln Leu Gln Asn Asn
        35                  40                  45

Leu Asn Val Gly Ser Asp Thr Thr Ser Glu Thr Ser Phe Ser Leu Ser
    50                  55                  60

Lys Glu Ala Pro Arg Glu His Leu Asp His Gln Ala Ala His Gln Pro
65                  70                  75                  80

Phe Pro Arg Pro Arg Phe Arg Gln Glu Thr Gly His Pro Ser Leu Gln
                85                  90                  95

Arg Asp Phe Pro Arg Ser Phe Leu Leu Asp Leu Pro Asn Phe Pro Asp
            100                 105                 110

Leu Ser Lys Ala Asp Ile Asn Gly Gln Asn Pro Asn Ile Gln Val Thr
        115                 120                 125

Ile Glu Val Val Asp Gly Pro Asp Ser Glu Ala Asp Lys Asp Gln His
    130                 135                 140

Pro Glu Asn Lys Pro Ser Trp Ser Val Pro Ser Pro Asp Trp Arg Ala
145                 150                 155                 160

Trp Trp Gln Arg Ser Leu Ser Leu Ala Arg Ala Asn Ser Gly Asp Gln
                165                 170                 175

Asp Tyr Lys Tyr Asp Ser Thr Ser Asp Asp Ser Asn Phe Leu Asn Pro
            180                 185                 190

Pro Arg Gly Trp Asp His Thr Ala Pro Gly His Arg Thr Phe Glu Thr
        195                 200                 205

Lys Asp Gln Pro Glu Tyr Asp Ser Thr Asp Gly Glu Gly Asp Trp Ser
    210                 215                 220

Leu Trp Ser Val Cys Ser Val Thr Cys Gly Asn Gly Asn Gln Lys Arg
225                 230                 235                 240

Thr Arg Ser Cys Gly Tyr Ala Cys Thr Ala Thr Glu Ser Arg Thr Cys
                245                 250                 255

Asp Arg Pro Asn Cys Pro Gly Ile Glu Asp Thr Phe Arg Thr Ala Ala
            260                 265                 270

Thr Glu Val Ser Leu Leu Ala Gly Ser Glu Glu Phe Asn Ala Thr Lys
        275                 280                 285

Leu Phe Glu Val Asp Thr Asp Ser Cys Glu Arg Trp Met Ser Cys Lys
```

-continued

```
        290             295             300

Ser Glu Phe Leu Lys Lys Tyr Met His Lys Val Met Asn Asp Leu Pro
305             310             315             320

Ser Cys Pro Cys Ser Tyr Pro Thr Glu Val Ala Tyr Ser Thr Ala Asp
                325             330             335

Ile Phe Asp Arg Ile Lys Arg Lys Asp Phe Arg Trp Lys Asp Ala Ser
            340             345             350

Gly Pro Lys Glu Lys Leu Glu Ile Tyr Lys Pro Thr Ala Arg Tyr Cys
        355             360             365

Ile Arg Ser Met Leu Ser Leu Glu Ser Thr Thr Leu Ala Ala Gln His
        370             375             380

Cys Cys Tyr Gly Asp Asn Met Gln Leu Ile Thr Arg Gly Lys Gly Ala
385             390             395             400

Gly Thr Pro Asn Leu Ile Ser Thr Glu Phe Ser Ala Glu Leu His Tyr
                405             410             415

Lys Val Asp Val Leu Pro Trp Ile Ile Cys Lys Gly Asp Trp Ser Arg
            420             425             430

Tyr Asn Glu Ala Arg Pro Pro Asn Asn Gly Gln Lys Cys Thr Glu Ser
        435             440             445

Pro Ser Asp Glu Asp Tyr Ile Lys Gln Phe Gln Glu Ala Arg Glu Tyr
        450             455             460
```

<210> SEQ ID NO 2
<211> LENGTH: 461
<212> TYPE: PRT
<213> ORGANISM: Mus musculus

<400> SEQUENCE: 2

```
Met Val Arg Leu Ala Ala Glu Leu Leu Leu Leu Leu Gly Leu Leu Leu
1               5               10              15

Leu Thr Leu His Ile Thr Val Leu Arg Gly Ser Gly Ala Ser Asp Arg
                20              25              30

Gln Asp Ala Ala Ala Gly Asn Val Ser Gly Ser Gln Leu Gln Asn Asn
            35              40              45

Leu Asn Leu Glu Ser Asp Ser Thr Ser Glu Thr Ser Phe Pro Leu Ser
        50              55              60

Lys Glu Ala Pro Glu Glu His Gln Val Val His Gln Pro Phe Pro Arg
65              70              75              80

Gln Arg Phe Pro Pro Glu Thr Gly His Pro Ser Leu Gln Arg Asp Gly
                85              90              95

Pro Arg Ser Phe Leu Leu Asp Leu Pro Asn Phe Pro Asp Leu Ser Lys
            100             105             110

Ala Asp Ile Asn Gly Gln Asn Pro Asn Ile Gln Val Thr Ile Glu Val
            115             120             125

Val Asp Gly Pro Asp Ser Glu Ala Glu Lys Asp Gln His Pro Glu Asn
        130             135             140

Lys Pro Ser Trp Ser Leu Pro Ala Pro Asp Trp Arg Ala Trp Trp Gln
145             150             155             160

Arg Ser Leu Ser Leu Ala Arg Thr Asn Ser Gly Asp Gln Asp Lys
            165             170             175

Tyr Asp Ser Thr Ser Asp Asp Ser Asn Phe Leu Ser Val Pro Arg Gly
            180             185             190

Trp Asp Arg Pro Ala Pro Gly His Arg Thr Phe Glu Thr Lys Glu Gln
        195             200             205
```

-continued

```
Pro Glu Tyr Asp Ser Thr Asp Gly Glu Gly Asp Trp Ser Leu Trp Ser
    210             215             220

Val Cys Ser Val Thr Cys Gly Asn Gly Asn Gln Lys Arg Thr Arg Ser
225             230             235             240

Cys Gly Tyr Ala Cys Ile Ala Thr Glu Ser Arg Thr Cys Asp Arg Pro
            245             250             255

Asn Cys Pro Gly Ile Glu Asp Thr Phe Arg Thr Ala Ala Thr Glu Val
            260             265             270

Ser Leu Leu Ala Gly Ser Glu Glu Phe Asn Ala Thr Lys Leu Phe Glu
        275             280             285

Val Asp Met Asp Ser Cys Glu Arg Trp Met Ser Cys Lys Ser Glu Phe
    290             295             300

Leu Lys Lys Tyr Met His Lys Val Ile Asn Asp Leu Pro Ser Cys Pro
305             310             315             320

Cys Ser Tyr Pro Thr Glu Val Ala Tyr Ser Thr Ala Asp Ile Phe Asp
            325             330             335

Arg Ile Lys Arg Lys Asp Phe Arg Trp Lys Asp Ala Ser Gly Pro Lys
            340             345             350

Glu Lys Leu Glu Ile Tyr Lys Pro Thr Ala Arg Tyr Cys Ile Arg Ser
        355             360             365

Met Leu Ser Leu Glu Ser Thr Thr Leu Ala Ala Gln His Cys Cys Tyr
    370             375             380

Gly Asp Asn Met Gln Leu Ile Thr Arg Gly Lys Gly Ala Gly Thr Pro
385             390             395             400

Asn Leu Ile Ser Thr Glu Phe Ser Ala Glu Leu His Tyr Lys Val Asp
            405             410             415

Val Leu Pro Trp Ile Ile Cys Lys Gly Asp Trp Ser Arg Tyr Asn Glu
            420             425             430

Ala Arg Pro Pro Asn Asn Gly Gln Lys Cys Thr Glu Ser Pro Ser Asp
        435             440             445

Glu Asp Tyr Ile Lys Gln Phe Gln Glu Ala Arg Glu Tyr
    450             455             460
```

<210> SEQ ID NO 3
<211> LENGTH: 439
<212> TYPE: PRT
<213> ORGANISM: Homo sapiens

<400> SEQUENCE: 3

```
Gly Ser Gly Ala Ala Asp Gly Pro Asp Ala Ala Ala Gly Asn Ala Ser
1               5               10              15

Gln Ala Gln Leu Gln Asn Asn Leu Asn Val Gly Ser Asp Thr Thr Ser
            20              25              30

Glu Thr Ser Phe Ser Leu Ser Lys Glu Ala Pro Arg Glu His Leu Asp
        35              40              45

His Gln Ala Ala His Gln Pro Phe Pro Arg Pro Arg Phe Arg Gln Glu
    50              55              60

Thr Gly His Pro Ser Leu Gln Arg Asp Phe Pro Arg Ser Phe Leu Leu
65              70              75              80

Asp Leu Pro Asn Phe Pro Asp Leu Ser Lys Ala Asp Ile Asn Gly Gln
            85              90              95

Asn Pro Asn Ile Gln Val Thr Ile Glu Val Val Asp Gly Pro Asp Ser
            100             105             110

Glu Ala Asp Lys Asp Gln His Pro Glu Asn Lys Pro Ser Trp Ser Val
        115             120             125
```

-continued

```
Pro Ser Pro Asp Trp Arg Ala Trp Trp Gln Arg Ser Leu Ser Leu Ala
    130                 135                 140

Arg Ala Asn Ser Gly Asp Gln Asp Tyr Lys Tyr Asp Ser Thr Ser Asp
145                 150                 155                 160

Asp Ser Asn Phe Leu Asn Pro Pro Arg Gly Trp Asp His Thr Ala Pro
                165                 170                 175

Gly His Arg Thr Phe Glu Thr Lys Asp Gln Pro Glu Tyr Asp Ser Thr
                180                 185                 190

Asp Gly Glu Gly Asp Trp Ser Leu Trp Ser Val Cys Ser Val Thr Cys
            195                 200                 205

Gly Asn Gly Asn Gln Lys Arg Thr Arg Ser Cys Gly Tyr Ala Cys Thr
    210                 215                 220

Ala Thr Glu Ser Arg Thr Cys Asp Arg Pro Asn Cys Pro Gly Ile Glu
225                 230                 235                 240

Asp Thr Phe Arg Thr Ala Ala Thr Glu Val Ser Leu Leu Ala Gly Ser
                245                 250                 255

Glu Glu Phe Asn Ala Thr Lys Leu Phe Glu Val Asp Thr Asp Ser Cys
                260                 265                 270

Glu Arg Trp Met Ser Cys Lys Ser Glu Phe Leu Lys Lys Tyr Met His
            275                 280                 285

Lys Val Met Asn Asp Leu Pro Ser Cys Pro Cys Ser Tyr Pro Thr Glu
    290                 295                 300

Val Ala Tyr Ser Thr Ala Asp Ile Phe Asp Arg Ile Lys Arg Lys Asp
305                 310                 315                 320

Phe Arg Trp Lys Asp Ala Ser Gly Pro Lys Glu Lys Leu Glu Ile Tyr
                325                 330                 335

Lys Pro Thr Ala Arg Tyr Cys Ile Arg Ser Met Leu Ser Leu Glu Ser
                340                 345                 350

Thr Thr Leu Ala Ala Gln His Cys Cys Tyr Gly Asp Asn Met Gln Leu
            355                 360                 365

Ile Thr Arg Gly Lys Gly Ala Gly Thr Pro Asn Leu Ile Ser Thr Glu
    370                 375                 380

Phe Ser Ala Glu Leu His Tyr Lys Val Asp Val Leu Pro Trp Ile Ile
385                 390                 395                 400

Cys Lys Gly Asp Trp Ser Arg Tyr Asn Glu Ala Arg Pro Pro Asn Asn
                405                 410                 415

Gly Gln Lys Cys Thr Glu Ser Pro Ser Asp Glu Asp Tyr Ile Lys Gln
                420                 425                 430

Phe Gln Glu Ala Arg Glu Tyr
        435
```

```
<210> SEQ ID NO 4
<211> LENGTH: 436
<212> TYPE: PRT
<213> ORGANISM: Mus musculus

<400> SEQUENCE: 4
```

```
Gly Ser Gly Ala Ser Asp Arg Gln Asp Ala Ala Ala Gly Asn Val Ser
1                   5                   10                  15

Gly Ser Gln Leu Gln Asn Asn Leu Asn Leu Glu Ser Asp Ser Thr Ser
                20                  25                  30

Glu Thr Ser Phe Pro Leu Ser Lys Glu Ala Pro Glu Glu His Gln Val
            35                  40                  45

Val His Gln Pro Phe Pro Arg Gln Arg Phe Pro Pro Glu Thr Gly His
```

```
        50              55              60

Pro Ser Leu Gln Arg Asp Gly Pro Arg Ser Phe Leu Leu Asp Leu Pro
65              70              75              80

Asn Phe Pro Asp Leu Ser Lys Ala Asp Ile Asn Gly Gln Asn Pro Asn
            85              90              95

Ile Gln Val Thr Ile Glu Val Val Asp Gly Pro Asp Ser Glu Ala Glu
            100             105             110

Lys Asp Gln His Pro Glu Asn Lys Pro Ser Trp Ser Leu Pro Ala Pro
            115             120             125

Asp Trp Arg Ala Trp Trp Gln Arg Ser Leu Ser Leu Ala Arg Thr Asn
            130             135             140

Ser Gly Asp Gln Asp Asp Lys Tyr Asp Ser Thr Ser Asp Asp Ser Asn
145             150             155             160

Phe Leu Ser Val Pro Arg Gly Trp Asp Arg Pro Ala Pro Gly His Arg
            165             170             175

Thr Phe Glu Thr Lys Glu Gln Pro Glu Tyr Asp Ser Thr Asp Gly Glu
            180             185             190

Gly Asp Trp Ser Leu Trp Ser Val Cys Ser Val Thr Cys Gly Asn Gly
            195             200             205

Asn Gln Lys Arg Thr Arg Ser Cys Gly Tyr Ala Cys Ile Ala Thr Glu
            210             215             220

Ser Arg Thr Cys Asp Arg Pro Asn Cys Pro Gly Ile Glu Asp Thr Phe
225             230             235             240

Arg Thr Ala Ala Thr Glu Val Ser Leu Leu Ala Gly Ser Glu Glu Phe
            245             250             255

Asn Ala Thr Lys Leu Phe Glu Val Asp Met Asp Ser Cys Glu Arg Trp
            260             265             270

Met Ser Cys Lys Ser Glu Phe Leu Lys Lys Tyr Met His Lys Val Ile
            275             280             285

Asn Asp Leu Pro Ser Cys Pro Cys Ser Tyr Pro Thr Glu Val Ala Tyr
            290             295             300

Ser Thr Ala Asp Ile Phe Asp Arg Ile Lys Arg Lys Asp Phe Arg Trp
305             310             315             320

Lys Asp Ala Ser Gly Pro Lys Glu Lys Leu Glu Ile Tyr Lys Pro Thr
            325             330             335

Ala Arg Tyr Cys Ile Arg Ser Met Leu Ser Leu Glu Ser Thr Thr Leu
            340             345             350

Ala Ala Gln His Cys Cys Tyr Gly Asp Asn Met Gln Leu Ile Thr Arg
            355             360             365

Gly Lys Gly Ala Gly Thr Pro Asn Leu Ile Ser Thr Glu Phe Ser Ala
            370             375             380

Glu Leu His Tyr Lys Val Asp Val Leu Pro Trp Ile Ile Cys Lys Gly
385             390             395             400

Asp Trp Ser Arg Tyr Asn Glu Ala Arg Pro Pro Asn Asn Gly Gln Lys
            405             410             415

Cys Thr Glu Ser Pro Ser Asp Glu Asp Tyr Ile Lys Gln Phe Gln Glu
            420             425             430

Ala Arg Glu Tyr
            435
```

```
<210> SEQ ID NO 5
<211> LENGTH: 23
<212> TYPE: RNA
<213> ORGANISM: Artificial Sequence
```

<220> FEATURE:
<223> OTHER INFORMATION: gRNA1

<400> SEQUENCE: 5
cugcacauca cgguucugcg cgg                                                        23

<210> SEQ ID NO 6
<211> LENGTH: 23
<212> TYPE: RNA
<213> ORGANISM: Artificial Sequence
<220> FEATURE:
<223> OTHER INFORMATION: gRNA2

<400> SEQUENCE: 6
gcggauccgg agccuccgac cgg                                                        23

<210> SEQ ID NO 7
<211> LENGTH: 20
<212> TYPE: DNA
<213> ORGANISM: Artificial Sequence
<220> FEATURE:
<223> OTHER INFORMATION: primer P1

<400> SEQUENCE: 7
cagctcctgg gattgctccg                                                            20

<210> SEQ ID NO 8
<211> LENGTH: 23
<212> TYPE: DNA
<213> ORGANISM: Artificial Sequence
<220> FEATURE:
<223> OTHER INFORMATION: primer P2

<400> SEQUENCE: 8
ccttctgcaa tgtaccaagc tct                                                        23

<210> SEQ ID NO 9
<211> LENGTH: 458
<212> TYPE: PRT
<213> ORGANISM: Artificial Sequence
<220> FEATURE:
<223> OTHER INFORMATION: mouse rISM1 with His Tag

<400> SEQUENCE: 9

Met His His His His His His Ser Ser Gly Leu Val Pro Arg Gly Ser
1               5                   10                  15

Gly Ala Ser Asp Arg Gln Asp Ala Ala Ala Gly Asn Val Ser Gly Ser
            20                  25                  30

Gln Leu Gln Asn Asn Leu Asn Leu Glu Ser Asp Ser Thr Ser Glu Thr
        35                  40                  45

Ser Phe Pro Leu Ser Lys Glu Ala Pro Glu Glu His Gln Val Val His
    50                  55                  60

Gln Pro Phe Pro Arg Gln Arg Phe Pro Pro Glu Thr Gly His Pro Ser
65                  70                  75                  80

Leu Gln Arg Asp Gly Pro Arg Ser Phe Leu Leu Asp Leu Pro Asn Phe
                85                  90                  95

Pro Asp Leu Ser Lys Ala Asp Ile Asn Gly Gln Asn Pro Asn Ile Gln
            100                 105                 110

Val Thr Ile Glu Val Val Asp Gly Pro Asp Ser Glu Ala Glu Lys Asp
        115                 120                 125

Gln His Pro Glu Asn Lys Pro Ser Trp Ser Leu Pro Ala Pro Asp Trp
    130                 135                 140

-continued

```
Arg Ala Trp Trp Gln Arg Ser Leu Ser Leu Ala Arg Thr Asn Ser Gly
145                 150                 155                 160

Asp Gln Asp Asp Lys Tyr Asp Ser Thr Ser Asp Asp Ser Asn Phe Leu
                165                 170                 175

Ser Val Pro Arg Gly Trp Asp Arg Pro Ala Pro Gly His Arg Thr Phe
            180                 185                 190

Glu Thr Lys Glu Gln Pro Glu Tyr Asp Ser Thr Asp Gly Glu Gly Asp
        195                 200                 205

Trp Ser Leu Trp Ser Val Cys Ser Val Thr Cys Gly Asn Gly Asn Gln
    210                 215                 220

Lys Arg Thr Arg Ser Cys Gly Tyr Ala Cys Ile Ala Thr Glu Ser Arg
225                 230                 235                 240

Thr Cys Asp Arg Pro Asn Cys Pro Gly Ile Glu Asp Thr Phe Arg Thr
                245                 250                 255

Ala Ala Thr Glu Val Ser Leu Leu Ala Gly Ser Glu Glu Phe Asn Ala
            260                 265                 270

Thr Lys Leu Phe Glu Val Asp Met Asp Ser Cys Glu Arg Trp Met Ser
        275                 280                 285

Cys Lys Ser Glu Phe Leu Lys Lys Tyr Met His Lys Val Ile Asn Asp
    290                 295                 300

Leu Pro Ser Cys Pro Cys Ser Tyr Pro Thr Glu Val Ala Tyr Ser Thr
305                 310                 315                 320

Ala Asp Ile Phe Asp Arg Ile Lys Arg Lys Asp Phe Arg Trp Lys Asp
                325                 330                 335

Ala Ser Gly Pro Lys Glu Lys Leu Glu Ile Tyr Lys Pro Thr Ala Arg
            340                 345                 350

Tyr Cys Ile Arg Ser Met Leu Ser Leu Glu Ser Thr Thr Leu Ala Ala
            355                 360                 365

Gln His Cys Cys Tyr Gly Asp Asn Met Gln Leu Ile Thr Arg Gly Lys
        370                 375                 380

Gly Ala Gly Thr Pro Asn Leu Ile Ser Thr Glu Phe Ser Ala Glu Leu
385                 390                 395                 400

His Tyr Lys Val Asp Val Leu Pro Trp Ile Ile Cys Lys Gly Asp Trp
                405                 410                 415

Ser Arg Tyr Asn Glu Ala Arg Pro Pro Asn Asn Gly Gln Lys Cys Thr
                420                 425                 430

Glu Ser Pro Ser Asp Glu Asp Tyr Ile Lys Gln Phe Gln Glu Ala Arg
        435                 440                 445

Glu Tyr Leu Glu His His His His His His
    450                 455
```

<210> SEQ ID NO 10
<211> LENGTH: 164
<212> TYPE: PRT
<213> ORGANISM: Artificial Sequence
<220> FEATURE:
<223> OTHER INFORMATION: Human ISM1 AMOP domain

<400> SEQUENCE: 10

```
Phe Glu Val Asp Thr Asp Ser Cys Glu Arg Trp Met Ser Cys Lys Ser
1               5                   10                  15

Glu Phe Leu Lys Lys Tyr Met His Lys Val Met Asn Asp Leu Pro Ser
                20                  25                  30

Cys Pro Cys Ser Tyr Pro Thr Glu Val Ala Tyr Ser Thr Ala Asp Ile
            35                  40                  45
```

-continued

```
Phe Asp Arg Ile Lys Arg Lys Asp Phe Arg Trp Lys Asp Ala Ser Gly
    50                  55                  60

Pro Lys Glu Lys Leu Glu Ile Tyr Lys Pro Thr Ala Arg Tyr Cys Ile
65                  70                  75                  80

Arg Ser Met Leu Ser Leu Glu Ser Thr Thr Leu Ala Ala Gln His Cys
                85                  90                  95

Cys Tyr Gly Asp Asn Met Gln Leu Ile Thr Arg Gly Lys Gly Ala Gly
                100                 105                 110

Thr Pro Asn Leu Ile Ser Thr Glu Phe Ser Ala Glu Leu His Tyr Lys
        115                 120                 125

Val Asp Val Leu Pro Trp Ile Ile Cys Lys Gly Asp Trp Ser Arg Tyr
    130                 135                 140

Asn Glu Ala Arg Pro Pro Asn Asn Gly Gln Lys Cys Thr Glu Ser Pro
145                 150                 155                 160

Ser Asp Glu Asp
```

```
<210> SEQ ID NO 11
<211> LENGTH: 164
<212> TYPE: PRT
<213> ORGANISM: Artificial Sequence
<220> FEATURE:
<223> OTHER INFORMATION: Mouse ISM1 AMOP domain

<400> SEQUENCE: 11
```

```
Phe Glu Val Asp Met Asp Ser Cys Glu Arg Trp Met Ser Cys Lys Ser
1               5                   10                  15

Glu Phe Leu Lys Lys Tyr Met His Lys Val Ile Asn Asp Leu Pro Ser
                20                  25                  30

Cys Pro Cys Ser Tyr Pro Thr Glu Val Ala Tyr Ser Thr Ala Asp Ile
        35                  40                  45

Phe Asp Arg Ile Lys Arg Lys Asp Phe Arg Trp Lys Asp Ala Ser Gly
    50                  55                  60

Pro Lys Glu Lys Leu Glu Ile Tyr Lys Pro Thr Ala Arg Tyr Cys Ile
65                  70                  75                  80

Arg Ser Met Leu Ser Leu Glu Ser Thr Thr Leu Ala Ala Gln His Cys
                85                  90                  95

Cys Tyr Gly Asp Asn Met Gln Leu Ile Thr Arg Gly Lys Gly Ala Gly
                100                 105                 110

Thr Pro Asn Leu Ile Ser Thr Glu Phe Ser Ala Glu Leu His Tyr Lys
        115                 120                 125

Val Asp Val Leu Pro Trp Ile Ile Cys Lys Gly Asp Trp Ser Arg Tyr
    130                 135                 140

Asn Glu Ala Arg Pro Pro Asn Asn Gly Gln Lys Cys Thr Glu Ser Pro
145                 150                 155                 160

Ser Asp Glu Asp
```

```
<210> SEQ ID NO 12
<211> LENGTH: 103
<212> TYPE: PRT
<213> ORGANISM: Artificial Sequence
<220> FEATURE:
<223> OTHER INFORMATION: N-terminal portion of C-terminal region of
      mouse ISM1

<400> SEQUENCE: 12
```

```
Glu Val Ser Leu Leu Ala Gly Ser Glu Glu Phe Asn Ala Thr Lys Leu
1               5                   10                  15
```

-continued

```
Phe Glu Val Asp Met Asp Ser Cys Glu Arg Trp Met Ser Cys Lys Ser
             20                  25                  30

Glu Phe Leu Lys Lys Tyr Met His Lys Val Ile Asn Asp Leu Pro Ser
             35                  40                  45

Cys Pro Cys Ser Tyr Pro Thr Glu Val Ala Tyr Ser Thr Ala Asp Ile
    50                  55                  60

Phe Asp Arg Ile Lys Arg Lys Asp Phe Arg Trp Lys Asp Ala Ser Gly
65                  70                  75                  80

Pro Lys Glu Lys Leu Glu Ile Tyr Lys Pro Thr Ala Arg Tyr Cys Ile
             85                  90                  95

Arg Ser Met Leu Ser Leu Glu
            100
```

<210> SEQ ID NO 13
<211> LENGTH: 191
<212> TYPE: PRT
<213> ORGANISM: Artificial Sequence
<220> FEATURE:
<223> OTHER INFORMATION: C-terminal region of mouse ISM1 containing AMOP
      but not TSR

<400> SEQUENCE: 13

```
Glu Val Ser Leu Leu Ala Gly Ser Glu Glu Phe Asn Ala Thr Lys Leu
1               5                   10                  15

Phe Glu Val Asp Met Asp Ser Cys Glu Arg Trp Met Ser Cys Lys Ser
             20                  25                  30

Glu Phe Leu Lys Lys Tyr Met His Lys Val Ile Asn Asp Leu Pro Ser
             35                  40                  45

Cys Pro Cys Ser Tyr Pro Thr Glu Val Ala Tyr Ser Thr Ala Asp Ile
    50                  55                  60

Phe Asp Arg Ile Lys Arg Lys Asp Phe Arg Trp Lys Asp Ala Ser Gly
65                  70                  75                  80

Pro Lys Glu Lys Leu Glu Ile Tyr Lys Pro Thr Ala Arg Tyr Cys Ile
             85                  90                  95

Arg Ser Met Leu Ser Leu Glu Ser Thr Thr Leu Ala Ala Gln His Cys
            100                 105                 110

Cys Tyr Gly Asp Asn Met Gln Leu Ile Thr Arg Gly Lys Gly Ala Gly
            115                 120                 125

Thr Pro Asn Leu Ile Ser Thr Glu Phe Ser Ala Glu Leu His Tyr Lys
    130                 135                 140

Val Asp Val Leu Pro Trp Ile Ile Cys Lys Gly Asp Trp Ser Arg Tyr
145                 150                 155                 160

Asn Glu Ala Arg Pro Pro Asn Asn Gly Gln Lys Cys Thr Glu Ser Pro
            165                 170                 175

Ser Asp Glu Asp Tyr Ile Lys Gln Phe Gln Glu Ala Arg Glu Tyr
            180                 185                 190
```

<210> SEQ ID NO 14
<211> LENGTH: 87
<212> TYPE: PRT
<213> ORGANISM: Artificial Sequence
<220> FEATURE:
<223> OTHER INFORMATION: ISM1C-N with KD341AA mutation

<400> SEQUENCE: 14

```
Phe Glu Val Asp Met Asp Ser Cys Glu Arg Trp Met Ser Cys Lys Ser
1               5                   10                  15
```

```
Glu Phe Leu Lys Lys Tyr Met His Lys Val Ile Asn Asp Leu Pro Ser
            20              25              30

Cys Pro Cys Ser Tyr Pro Thr Glu Val Ala Tyr Ser Thr Ala Asp Ile
        35              40              45

Phe Asp Arg Ile Lys Arg Ala Ala Phe Arg Trp Lys Asp Ala Ser Gly
    50              55              60

Pro Lys Glu Lys Leu Glu Ile Tyr Lys Pro Thr Ala Arg Tyr Cys Ile
65              70              75              80

Arg Ser Met Leu Ser Leu Glu
                85
```

```
<210> SEQ ID NO 15
<211> LENGTH: 87
<212> TYPE: PRT
<213> ORGANISM: Artificial Sequence
<220> FEATURE:
<223> OTHER INFORMATION: ISM1C-N with RKD340AAA mutation

<400> SEQUENCE: 15
```

```
Phe Glu Val Asp Met Asp Ser Cys Glu Arg Trp Met Ser Cys Lys Ser
1               5               10              15

Glu Phe Leu Lys Lys Tyr Met His Lys Val Ile Asn Asp Leu Pro Ser
            20              25              30

Cys Pro Cys Ser Tyr Pro Thr Glu Val Ala Tyr Ser Thr Ala Asp Ile
        35              40              45

Phe Asp Arg Ile Lys Ala Ala Ala Phe Arg Trp Lys Asp Ala Ser Gly
    50              55              60

Pro Lys Glu Lys Leu Glu Ile Tyr Lys Pro Thr Ala Arg Tyr Cys Ile
65              70              75              80

Arg Ser Met Leu Ser Leu Glu
                85
```

```
<210> SEQ ID NO 16
<211> LENGTH: 20
<212> TYPE: DNA
<213> ORGANISM: Artificial Sequence
<220> FEATURE:
<223> OTHER INFORMATION: T7E1 forward PCR primer

<400> SEQUENCE: 16
```

```
cagctcctgg gattgctccg                                              20
```

```
<210> SEQ ID NO 17
<211> LENGTH: 23
<212> TYPE: DNA
<213> ORGANISM: Artificial Sequence
<220> FEATURE:
<223> OTHER INFORMATION: T7E1 reverse PCR primer

<400> SEQUENCE: 17
```

```
taagacttct tcctggtgcc aaa                                          23
```

```
<210> SEQ ID NO 18
<211> LENGTH: 21
<212> TYPE: DNA
<213> ORGANISM: Artificial Sequence
<220> FEATURE:
<223> OTHER INFORMATION: Forward PCR primer for mouse genotyping

<400> SEQUENCE: 18
```

```
gacagctcct gggattgctc c                                            21
```

<210> SEQ ID NO 19
<211> LENGTH: 23
<212> TYPE: DNA
<213> ORGANISM: Artificial Sequence
<220> FEATURE:
<223> OTHER INFORMATION: reverse PCR primer for mouse genotyping

<400> SEQUENCE: 19
ttctgcaatg taccaagctc tct                                                          23

<210> SEQ ID NO 20
<211> LENGTH: 103
<212> TYPE: PRT
<213> ORGANISM: Artificial Sequence
<220> FEATURE:
<223> OTHER INFORMATION: HUMAN ISM1C-N

<400> SEQUENCE: 20

Glu Val Ser Leu Leu Ala Gly Ser Glu Glu Phe Asn Ala Thr Lys Leu
1               5                   10                  15

Phe Glu Val Asp Thr Asp Ser Cys Glu Arg Trp Met Ser Cys Lys Ser
            20                  25                  30

Glu Phe Leu Lys Lys Tyr Met His Lys Val Met Asn Asp Leu Pro Ser
        35                  40                  45

Cys Pro Cys Ser Tyr Pro Thr Glu Val Ala Tyr Ser Thr Ala Asp Ile
    50                  55                  60

Phe Asp Arg Ile Lys Arg Lys Asp Phe Arg Trp Lys Asp Ala Ser Gly
65                  70                  75                  80

Pro Lys Glu Lys Leu Glu Ile Tyr Lys Pro Thr Ala Arg Tyr Cys Ile
                85                  90                  95

Arg Ser Met Leu Ser Leu Glu
            100

<210> SEQ ID NO 21
<211> LENGTH: 191
<212> TYPE: PRT
<213> ORGANISM: Artificial Sequence
<220> FEATURE:
<223> OTHER INFORMATION: human ISM1C

<400> SEQUENCE: 21

Glu Val Ser Leu Leu Ala Gly Ser Glu Glu Phe Asn Ala Thr Lys Leu
1               5                   10                  15

Phe Glu Val Asp Thr Asp Ser Cys Glu Arg Trp Met Ser Cys Lys Ser
            20                  25                  30

Glu Phe Leu Lys Lys Tyr Met His Lys Val Met Asn Asp Leu Pro Ser
        35                  40                  45

Cys Pro Cys Ser Tyr Pro Thr Glu Val Ala Tyr Ser Thr Ala Asp Ile
    50                  55                  60

Phe Asp Arg Ile Lys Arg Lys Asp Phe Arg Trp Lys Asp Ala Ser Gly
65                  70                  75                  80

Pro Lys Glu Lys Leu Glu Ile Tyr Lys Pro Thr Ala Arg Tyr Cys Ile
                85                  90                  95

Arg Ser Met Leu Ser Leu Glu Ser Thr Thr Leu Ala Ala Gln His Cys
            100                 105                 110

Cys Tyr Gly Asp Asn Met Gln Leu Ile Thr Arg Gly Lys Gly Ala Gly
        115                 120                 125

Thr Pro Asn Leu Ile Ser Thr Glu Phe Ser Ala Glu Leu His Tyr Lys
        130                 135                 140

-continued

Val Asp Val Leu Pro Trp Ile Ile Cys Lys Gly Asp Trp Ser Arg Tyr
145                 150                 155                 160

Asn Glu Ala Arg Pro Pro Asn Asn Gly Gln Lys Cys Thr Glu Ser Pro
                165                 170                 175

Ser Asp Glu Asp Tyr Ile Lys Gln Phe Gln Glu Ala Arg Glu Tyr
            180                 185                 190

<210> SEQ ID NO 22
<211> LENGTH: 20
<212> TYPE: DNA
<213> ORGANISM: Artificial Sequence
<220> FEATURE:
<223> OTHER INFORMATION: genotyping primer 1

<400> SEQUENCE: 22
cgcgcgactc aagaggatgg                                                                        20

<210> SEQ ID NO 23
<211> LENGTH: 20
<212> TYPE: DNA
<213> ORGANISM: Artificial Sequence
<220> FEATURE:
<223> OTHER INFORMATION: genotyping primer 2

<400> SEQUENCE: 23
actgggaccc gctgacgttg                                                                        20

<210> SEQ ID NO 24
<211> LENGTH: 175
<212> TYPE: PRT
<213> ORGANISM: Artificial Sequence
<220> FEATURE:
<223> OTHER INFORMATION: C-terminal AMOP domain aa 287-461 mouse

<400> SEQUENCE: 24

Phe Glu Val Asp Met Asp Ser Cys Glu Arg Trp Met Ser Cys Lys Ser
1                   5                   10                  15

Glu Phe Leu Lys Lys Tyr Met His Lys Val Ile Asn Asp Leu Pro Ser
                20                  25                  30

Cys Pro Cys Ser Tyr Pro Thr Glu Val Ala Tyr Ser Thr Ala Asp Ile
            35                  40                  45

Phe Asp Arg Ile Lys Arg Lys Asp Phe Arg Trp Lys Asp Ala Ser Gly
        50                  55                  60

Pro Lys Glu Lys Leu Glu Ile Tyr Lys Pro Thr Ala Arg Tyr Cys Ile
65                  70                  75                  80

Arg Ser Met Leu Ser Leu Glu Ser Thr Thr Leu Ala Ala Gln His Cys
                85                  90                  95

Cys Tyr Gly Asp Asn Met Gln Leu Ile Thr Arg Gly Lys Gly Ala Gly
            100                 105                 110

Thr Pro Asn Leu Ile Ser Thr Glu Phe Ser Ala Glu Leu His Tyr Lys
        115                 120                 125

Val Asp Val Leu Pro Trp Ile Ile Cys Lys Gly Asp Trp Ser Arg Tyr
        130                 135                 140

Asn Glu Ala Arg Pro Pro Asn Asn Gly Gln Lys Cys Thr Glu Ser Pro
145                 150                 155                 160

Ser Asp Glu Asp Tyr Ile Lys Gln Phe Gln Glu Ala Arg Glu Tyr
                165                 170                 175

<210> SEQ ID NO 25

```
<211> LENGTH: 175
<212> TYPE: PRT
<213> ORGANISM: Artificial Sequence
<220> FEATURE:
<223> OTHER INFORMATION: C-terminal AMOP domain aa 290-464 human

<400> SEQUENCE: 25

Phe Glu Val Asp Thr Asp Ser Cys Glu Arg Trp Met Ser Cys Lys Ser
1               5                   10                  15

Glu Phe Leu Lys Lys Tyr Met His Lys Val Met Asn Asp Leu Pro Ser
            20                  25                  30

Cys Pro Cys Ser Tyr Pro Thr Glu Val Ala Tyr Ser Thr Ala Asp Ile
        35                  40                  45

Phe Asp Arg Ile Lys Arg Lys Asp Phe Arg Trp Lys Asp Ala Ser Gly
    50                  55                  60

Pro Lys Glu Lys Leu Glu Ile Tyr Lys Pro Thr Ala Arg Tyr Cys Ile
65                  70                  75                  80

Arg Ser Met Leu Ser Leu Glu Ser Thr Thr Leu Ala Ala Gln His Cys
                85                  90                  95

Cys Tyr Gly Asp Asn Met Gln Leu Ile Thr Arg Gly Lys Gly Ala Gly
            100                 105                 110

Thr Pro Asn Leu Ile Ser Thr Glu Phe Ser Ala Glu Leu His Tyr Lys
        115                 120                 125

Val Asp Val Leu Pro Trp Ile Ile Cys Lys Gly Asp Trp Ser Arg Tyr
    130                 135                 140

Asn Glu Ala Arg Pro Pro Asn Asn Gly Gln Lys Cys Thr Glu Ser Pro
145                 150                 155                 160

Ser Asp Glu Asp Tyr Ile Lys Gln Phe Gln Glu Ala Arg Glu Tyr
                165                 170                 175

<210> SEQ ID NO 26
<211> LENGTH: 87
<212> TYPE: PRT
<213> ORGANISM: Artificial Sequence
<220> FEATURE:
<223> OTHER INFORMATION: N-terminal subportion of C-terminal region of
      mouse ISM1

<400> SEQUENCE: 26

Phe Glu Val Asp Met Asp Ser Cys Glu Arg Trp Met Ser Cys Lys Ser
1               5                   10                  15

Glu Phe Leu Lys Lys Tyr Met His Lys Val Ile Asn Asp Leu Pro Ser
            20                  25                  30

Cys Pro Cys Ser Tyr Pro Thr Glu Val Ala Tyr Ser Thr Ala Asp Ile
        35                  40                  45

Phe Asp Arg Ile Lys Arg Lys Asp Phe Arg Trp Lys Asp Ala Ser Gly
    50                  55                  60

Pro Lys Glu Lys Leu Glu Ile Tyr Lys Pro Thr Ala Arg Tyr Cys Ile
65                  70                  75                  80

Arg Ser Met Leu Ser Leu Glu
                85

<210> SEQ ID NO 27
<211> LENGTH: 87
<212> TYPE: PRT
<213> ORGANISM: Artificial Sequence
<220> FEATURE:
<223> OTHER INFORMATION: human ISM1C-N subportion

<400> SEQUENCE: 27
```

-continued

```
Phe Glu Val Asp Thr Asp Ser Cys Glu Arg Trp Met Ser Cys Lys Ser
1               5                   10                  15

Glu Phe Leu Lys Lys Tyr Met His Lys Val Met Asn Asp Leu Pro Ser
                20                  25                  30

Cys Pro Cys Ser Tyr Pro Thr Glu Val Ala Tyr Ser Thr Ala Asp Ile
            35                  40                  45

Phe Asp Arg Ile Lys Arg Lys Asp Phe Arg Trp Lys Asp Ala Ser Gly
        50                  55                  60

Pro Lys Glu Lys Leu Glu Ile Tyr Lys Pro Thr Ala Arg Tyr Cys Ile
65                  70                  75                  80

Arg Ser Met Leu Ser Leu Glu
                85
```

<210> SEQ ID NO 28
<211> LENGTH: 548
<212> TYPE: PRT
<213> ORGANISM: Artificial Sequence
<220> FEATURE:
<223> OTHER INFORMATION: bacISM126-461

<400> SEQUENCE: 28

```
Met Gly Ser Ser His His His His His His Ser Gln Gly Ser Met Ser
1               5                   10                  15

Asp Ser Glu Val Asn Gln Glu Ala Lys Pro Glu Val Lys Pro Glu Val
                20                  25                  30

Lys Pro Glu Thr His Ile Asn Leu Lys Val Ser Asp Gly Ser Ser Glu
            35                  40                  45

Ile Phe Phe Lys Ile Lys Lys Thr Thr Pro Leu Arg Arg Leu Met Glu
        50                  55                  60

Ala Phe Ala Lys Arg Gln Gly Lys Glu Met Asp Ser Leu Arg Phe Leu
65                  70                  75                  80

Tyr Asp Gly Ile Arg Ile Gln Ala Asp Gln Thr Pro Glu Asp Leu Asp
                85                  90                  95

Met Glu Asp Asn Asp Ile Ile Glu Ala His Arg Glu Gln Ile Gly Gly
                100                 105                 110

Gly Ser Gly Ala Ser Asp Arg Gln Asp Ala Ala Ala Gly Asn Val Ser
            115                 120                 125

Gly Ser Gln Leu Gln Asn Asn Leu Asn Leu Glu Ser Asp Ser Thr Ser
        130                 135                 140

Glu Thr Ser Phe Pro Leu Ser Lys Glu Ala Pro Glu Glu His Gln Val
145                 150                 155                 160

Val His Gln Pro Phe Pro Arg Gln Arg Phe Pro Pro Glu Thr Gly His
                165                 170                 175

Pro Ser Leu Gln Arg Asp Gly Pro Arg Ser Phe Leu Leu Asp Leu Pro
                180                 185                 190

Asn Phe Pro Asp Leu Ser Lys Ala Asp Ile Asn Gly Gln Asn Pro Asn
                195                 200                 205

Ile Gln Val Thr Ile Glu Val Val Asp Gly Pro Asp Ser Glu Ala Glu
        210                 215                 220

Lys Asp Gln His Pro Glu Asn Lys Pro Ser Trp Ser Leu Pro Ala Pro
225                 230                 235                 240

Asp Trp Arg Ala Trp Trp Gln Arg Ser Leu Ser Leu Ala Arg Thr Asn
                245                 250                 255

Ser Gly Asp Gln Asp Asp Lys Tyr Asp Ser Thr Ser Asp Asp Ser Asn
                260                 265                 270
```

```
Phe Leu Ser Val Pro Arg Gly Trp Asp Arg Pro Ala Pro Gly His Arg
        275             280             285

Thr Phe Glu Thr Lys Glu Gln Pro Glu Tyr Asp Ser Thr Asp Gly Glu
    290             295             300

Gly Asp Trp Ser Leu Trp Ser Val Cys Ser Val Thr Cys Gly Asn Gly
305             310             315             320

Asn Gln Lys Arg Thr Arg Ser Cys Gly Tyr Ala Cys Ile Ala Thr Glu
            325             330             335

Ser Arg Thr Cys Asp Arg Pro Asn Cys Pro Gly Ile Glu Asp Thr Phe
            340             345             350

Arg Thr Ala Ala Thr Glu Val Ser Leu Leu Ala Gly Ser Glu Glu Phe
            355             360             365

Asn Ala Thr Lys Leu Phe Glu Val Asp Met Asp Ser Cys Glu Arg Trp
    370             375             380

Met Ser Cys Lys Ser Glu Phe Leu Lys Lys Tyr Met His Lys Val Ile
385             390             395             400

Asn Asp Leu Pro Ser Cys Pro Cys Ser Tyr Pro Thr Glu Val Ala Tyr
            405             410             415

Ser Thr Ala Asp Ile Phe Asp Arg Ile Lys Arg Lys Asp Phe Arg Trp
            420             425             430

Lys Asp Ala Ser Gly Pro Lys Glu Lys Leu Glu Ile Tyr Lys Pro Thr
            435             440             445

Ala Arg Tyr Cys Ile Arg Ser Met Leu Ser Leu Glu Ser Thr Thr Leu
    450             455             460

Ala Ala Gln His Cys Cys Tyr Gly Asp Asn Met Gln Leu Ile Thr Arg
465             470             475             480

Gly Lys Gly Ala Gly Thr Pro Asn Leu Ile Ser Thr Glu Phe Ser Ala
            485             490             495

Glu Leu His Tyr Lys Val Asp Val Leu Pro Trp Ile Ile Cys Lys Gly
            500             505             510

Asp Trp Ser Arg Tyr Asn Glu Ala Arg Pro Pro Asn Asn Gly Gln Lys
            515             520             525

Cys Thr Glu Ser Pro Ser Asp Glu Asp Tyr Ile Lys Gln Phe Gln Glu
    530             535             540

Ala Arg Glu Tyr
545

<210> SEQ ID NO 29
<211> LENGTH: 287
<212> TYPE: PRT
<213> ORGANISM: Artificial Sequence
<220> FEATURE:
<223> OTHER INFORMATION: bacISM1287-461

<400> SEQUENCE: 29

Met Gly Ser Ser His His His His His His Ser Gln Gly Ser Met Ser
1               5               10              15

Asp Ser Glu Val Asn Gln Glu Ala Lys Pro Glu Val Lys Pro Glu Val
            20              25              30

Lys Pro Glu Thr His Ile Asn Leu Lys Val Ser Asp Gly Ser Ser Glu
        35              40              45

Ile Phe Phe Lys Ile Lys Lys Thr Thr Pro Leu Arg Arg Leu Met Glu
    50              55              60

Ala Phe Ala Lys Arg Gln Gly Lys Glu Met Asp Ser Leu Arg Phe Leu
65              70              75              80
```

-continued

```
Tyr Asp Gly Ile Arg Ile Gln Ala Asp Gln Thr Pro Glu Asp Leu Asp
             85              90              95

Met Glu Asp Asn Asp Ile Ile Glu Ala His Arg Glu Gln Ile Gly Gly
            100             105             110

Phe Glu Val Asp Met Asp Ser Cys Glu Arg Trp Met Ser Cys Lys Ser
        115             120             125

Glu Phe Leu Lys Lys Tyr Met His Lys Val Ile Asn Asp Leu Pro Ser
        130             135             140

Cys Pro Cys Ser Tyr Pro Thr Glu Val Ala Tyr Ser Thr Ala Asp Ile
145             150             155             160

Phe Asp Arg Ile Lys Arg Lys Asp Phe Arg Trp Lys Asp Ala Ser Gly
                165             170             175

Pro Lys Glu Lys Leu Glu Ile Tyr Lys Pro Thr Ala Arg Tyr Cys Ile
            180             185             190

Arg Ser Met Leu Ser Leu Glu Ser Thr Thr Leu Ala Ala Gln His Cys
            195             200             205

Cys Tyr Gly Asp Asn Met Gln Leu Ile Thr Arg Gly Lys Gly Ala Gly
        210             215             220

Thr Pro Asn Leu Ile Ser Thr Glu Phe Ser Ala Glu Leu His Tyr Lys
225             230             235             240

Val Asp Val Leu Pro Trp Ile Ile Cys Lys Gly Asp Trp Ser Arg Tyr
            245             250             255

Asn Glu Ala Arg Pro Pro Asn Asn Gly Gln Lys Cys Thr Glu Ser Pro
            260             265             270

Ser Asp Glu Asp Tyr Ile Lys Gln Phe Gln Glu Ala Arg Glu Tyr
            275             280             285
```

```
<210> SEQ ID NO 30
<211> LENGTH: 480
<212> TYPE: PRT
<213> ORGANISM: Artificial Sequence
<220> FEATURE:
<223> OTHER INFORMATION: mamISM126-461

<400> SEQUENCE: 30
```

```
Asp Ala Ala Gln Pro Ala Arg Arg Ala Arg Arg Thr Lys Leu Gly Thr
1               5               10              15

Glu Leu Gly Ser Gly Ala Ser Asp Arg Gln Asp Ala Ala Ala Gly Asn
            20              25              30

Val Ser Gly Ser Gln Leu Gln Asn Asn Leu Asn Leu Glu Ser Asp Ser
            35              40              45

Thr Ser Glu Thr Ser Phe Pro Leu Ser Lys Glu Ala Pro Glu Glu His
        50              55              60

Gln Val Val His Gln Pro Phe Pro Arg Gln Phe Pro Pro Glu Thr
65              70              75              80

Gly His Pro Ser Leu Gln Arg Asp Gly Pro Arg Ser Phe Leu Leu Asp
            85              90              95

Leu Pro Asn Phe Pro Asp Leu Ser Lys Ala Asp Ile Asn Gly Gln Asn
            100             105             110

Pro Asn Ile Gln Val Thr Ile Glu Val Val Asp Gly Pro Asp Ser Glu
        115             120             125

Ala Glu Lys Asp Gln His Pro Glu Asn Lys Pro Ser Trp Ser Leu Pro
        130             135             140

Ala Pro Asp Trp Arg Ala Trp Trp Gln Arg Ser Leu Ser Leu Ala Arg
145             150             155             160
```

-continued

```
Thr Asn Ser Gly Asp Gln Asp Lys Tyr Asp Ser Thr Ser Asp Asp
             165             170             175

Ser Asn Phe Leu Ser Val Pro Arg Gly Trp Asp Arg Pro Ala Pro Gly
             180             185             190

His Arg Thr Phe Glu Thr Lys Glu Gln Pro Glu Tyr Asp Ser Thr Asp
             195             200             205

Gly Glu Gly Asp Trp Ser Leu Trp Ser Val Cys Ser Val Thr Cys Gly
             210             215             220

Asn Gly Asn Gln Lys Arg Thr Arg Ser Cys Gly Tyr Ala Cys Ile Ala
225             230             235             240

Thr Glu Ser Arg Thr Cys Asp Arg Pro Asn Cys Pro Gly Ile Glu Asp
             245             250             255

Thr Phe Arg Thr Ala Ala Thr Glu Val Ser Leu Leu Ala Gly Ser Glu
             260             265             270

Glu Phe Asn Ala Thr Lys Leu Phe Glu Val Asp Met Asp Ser Cys Glu
             275             280             285

Arg Trp Met Ser Cys Lys Ser Glu Phe Leu Lys Lys Tyr Met His Lys
     290             295             300

Val Ile Asn Asp Leu Pro Ser Cys Pro Cys Ser Tyr Pro Thr Glu Val
305             310             315             320

Ala Tyr Ser Thr Ala Asp Ile Phe Asp Arg Ile Lys Arg Lys Asp Phe
             325             330             335

Arg Trp Lys Asp Ala Ser Gly Pro Lys Glu Lys Leu Glu Ile Tyr Lys
             340             345             350

Pro Thr Ala Arg Tyr Cys Ile Arg Ser Met Leu Ser Leu Glu Ser Thr
             355             360             365

Thr Leu Ala Ala Gln His Cys Cys Tyr Gly Asp Asn Met Gln Leu Ile
     370             375             380

Thr Arg Gly Lys Gly Ala Gly Thr Pro Asn Leu Ile Ser Thr Glu Phe
385             390             395             400

Ser Ala Glu Leu His Tyr Lys Val Asp Val Leu Pro Trp Ile Ile Cys
             405             410             415

Lys Gly Asp Trp Ser Arg Tyr Asn Glu Ala Arg Pro Pro Asn Asn Gly
             420             425             430

Gln Lys Cys Thr Glu Ser Pro Ser Asp Glu Asp Tyr Ile Lys Gln Phe
             435             440             445

Gln Glu Ala Arg Glu Tyr Pro Arg Gly Gly Pro Glu Gln Lys Leu Ile
     450             455             460

Ser Glu Glu Asp Leu Asn Ser Ala Val Asp His His His His His His
465             470             475             480
```

```
<210> SEQ ID NO 31
<211> LENGTH: 221
<212> TYPE: PRT
<213> ORGANISM: Artificial Sequence
<220> FEATURE:
<223> OTHER INFORMATION: mamISM1287-461

<400> SEQUENCE: 31
```

```
Asp Ala Ala Gln Pro Ala Arg Arg Ala Arg Arg Thr Lys Leu Gly Thr
1               5               10              15

Glu Leu Gly Ser Phe Glu Val Asp Met Asp Ser Cys Glu Arg Trp Met
             20              25              30

Ser Cys Lys Ser Glu Phe Leu Lys Lys Tyr Met His Lys Val Ile Asn
             35              40              45
```

```
Asp Leu Pro Ser Cys Pro Cys Ser Tyr Pro Thr Glu Val Ala Tyr Ser
    50              55                  60

Thr Ala Asp Ile Phe Asp Arg Ile Lys Arg Lys Asp Phe Arg Trp Lys
65              70                  75                  80

Asp Ala Ser Gly Pro Lys Glu Lys Leu Glu Ile Tyr Lys Pro Thr Ala
                85                  90                  95

Arg Tyr Cys Ile Arg Ser Met Leu Ser Leu Glu Ser Thr Thr Leu Ala
            100                 105                 110

Ala Gln His Cys Cys Tyr Gly Asp Asn Met Gln Leu Ile Thr Arg Gly
        115                 120                 125

Lys Gly Ala Gly Thr Pro Asn Leu Ile Ser Thr Glu Phe Ser Ala Glu
    130                 135                 140

Leu His Tyr Lys Val Asp Val Leu Pro Trp Ile Ile Cys Lys Gly Asp
145                 150                 155                 160

Trp Ser Arg Tyr Asn Glu Ala Arg Pro Pro Asn Asn Gly Gln Lys Cys
                165                 170                 175

Thr Glu Ser Pro Ser Asp Glu Asp Tyr Ile Lys Gln Phe Gln Glu Ala
            180                 185                 190

Arg Glu Tyr Pro Arg Gly Gly Pro Glu Gln Lys Leu Ile Ser Glu Glu
        195                 200                 205

Asp Leu Asn Ser Ala Val Asp His His His His His His
    210                 215                 220
```

```
<210> SEQ ID NO 32
<211> LENGTH: 483
<212> TYPE: PRT
<213> ORGANISM: Artificial Sequence
<220> FEATURE:
<223> OTHER INFORMATION: mamISM126-464

<400> SEQUENCE: 32
```

```
Asp Ala Ala Gln Pro Ala Arg Arg Ala Arg Arg Thr Lys Leu Gly Thr
1               5                   10                  15

Glu Leu Gly Ser Gly Ala Ala Asp Gly Pro Asp Ala Ala Ala Gly Asn
            20                  25                  30

Ala Ser Gln Ala Gln Leu Gln Asn Asn Leu Asn Val Gly Ser Asp Thr
        35                  40                  45

Thr Ser Glu Thr Ser Phe Ser Leu Ser Lys Glu Ala Pro Arg Glu His
    50                  55                  60

Leu Asp His Gln Ala Ala His Gln Pro Phe Pro Arg Pro Arg Phe Arg
65                  70                  75                  80

Gln Glu Thr Gly His Pro Ser Leu Gln Arg Asp Phe Pro Arg Ser Phe
                85                  90                  95

Leu Leu Asp Leu Pro Asn Phe Pro Asp Leu Ser Lys Ala Asp Ile Asn
            100                 105                 110

Gly Gln Asn Pro Asn Ile Gln Val Thr Ile Glu Val Val Asp Gly Pro
        115                 120                 125

Asp Ser Glu Ala Asp Lys Asp Gln His Pro Glu Asn Lys Pro Ser Trp
    130                 135                 140

Ser Val Pro Ser Pro Asp Trp Arg Ala Trp Trp Gln Arg Ser Leu Ser
145                 150                 155                 160

Leu Ala Arg Ala Asn Ser Gly Asp Gln Asp Tyr Lys Tyr Asp Ser Thr
                165                 170                 175

Ser Asp Asp Ser Asn Phe Leu Asn Pro Pro Arg Gly Trp Asp His Thr
            180                 185                 190
```

```
Ala Pro Gly His Arg Thr Phe Glu Thr Lys Asp Gln Pro Glu Tyr Asp
        195                 200                 205

Ser Thr Asp Gly Glu Gly Asp Trp Ser Leu Trp Ser Val Cys Ser Val
        210                 215                 220

Thr Cys Gly Asn Gly Asn Gln Lys Arg Thr Arg Ser Cys Gly Tyr Ala
225                 230                 235                 240

Cys Thr Ala Thr Glu Ser Arg Thr Cys Asp Arg Pro Asn Cys Pro Gly
                245                 250                 255

Ile Glu Asp Thr Phe Arg Thr Ala Ala Thr Glu Val Ser Leu Leu Ala
                260                 265                 270

Gly Ser Glu Glu Phe Asn Ala Thr Lys Leu Phe Glu Val Asp Thr Asp
                275                 280                 285

Ser Cys Glu Arg Trp Met Ser Cys Lys Ser Glu Phe Leu Lys Lys Tyr
        290                 295                 300

Met His Lys Val Met Asn Asp Leu Pro Ser Cys Pro Cys Ser Tyr Pro
305                 310                 315                 320

Thr Glu Val Ala Tyr Ser Thr Ala Asp Ile Phe Asp Arg Ile Lys Arg
                325                 330                 335

Lys Asp Phe Arg Trp Lys Asp Ala Ser Gly Pro Lys Glu Lys Leu Glu
                340                 345                 350

Ile Tyr Lys Pro Thr Ala Arg Tyr Cys Ile Arg Ser Met Leu Ser Leu
        355                 360                 365

Glu Ser Thr Thr Leu Ala Ala Gln His Cys Cys Tyr Gly Asp Asn Met
        370                 375                 380

Gln Leu Ile Thr Arg Gly Lys Gly Ala Gly Thr Pro Asn Leu Ile Ser
385                 390                 395                 400

Thr Glu Phe Ser Ala Glu Leu His Tyr Lys Val Asp Val Leu Pro Trp
                405                 410                 415

Ile Ile Cys Lys Gly Asp Trp Ser Arg Tyr Asn Glu Ala Arg Pro Pro
                420                 425                 430

Asn Asn Gly Gln Lys Cys Thr Glu Ser Pro Ser Asp Glu Asp Tyr Ile
        435                 440                 445

Lys Gln Phe Gln Glu Ala Arg Glu Tyr Pro Arg Gly Gly Pro Glu Gln
        450                 455                 460

Lys Leu Ile Ser Glu Glu Asp Leu Asn Ser Ala Val Asp His His His
465                 470                 475                 480

His His His
```

```
<210> SEQ ID NO 33
<211> LENGTH: 559
<212> TYPE: PRT
<213> ORGANISM: Artificial Sequence
<220> FEATURE:
<223> OTHER INFORMATION: bacISM126-464

<400> SEQUENCE: 33
```

```
Met Gly Ser Ser His His His His His His Ser Gln Gly Ser Met Ser
1                   5                   10                  15

Asp Ser Glu Val Asn Gln Glu Ala Lys Pro Glu Val Lys Pro Glu Val
                20                  25                  30

Lys Pro Glu Thr His Ile Asn Leu Lys Val Ser Asp Gly Ser Ser Glu
        35                  40                  45

Ile Phe Phe Lys Ile Lys Lys Thr Thr Pro Leu Arg Arg Leu Met Glu
        50                  55                  60
```

-continued

```
Ala Phe Ala Lys Arg Gln Gly Lys Glu Met Asp Ser Leu Arg Phe Leu
65                  70                  75                  80

Tyr Asp Gly Ile Arg Ile Gln Ala Asp Gln Thr Pro Glu Asp Leu Asp
                    85                  90                  95

Met Glu Asp Asn Asp Ile Ile Glu Ala His Arg Glu Gln Ile Gly Gly
                100                 105                 110

Gly Ser Gly Ala Ala Asp Gly Pro Asp Ala Ala Ala Gly Asn Ala Ser
                115                 120                 125

Gln Ala Gln Leu Gln Asn Asn Leu Asn Val Gly Ser Asp Thr Thr Ser
        130                 135                 140

Glu Thr Ser Phe Ser Leu Ser Lys Glu Ala Pro Arg Glu His Leu Asp
145                 150                 155                 160

His Gln Ala Ala His Gln Pro Phe Pro Arg Pro Arg Phe Arg Gln Glu
                165                 170                 175

Thr Gly His Pro Ser Leu Gln Arg Asp Phe Pro Arg Ser Phe Leu Leu
                180                 185                 190

Asp Leu Pro Asn Phe Pro Asp Leu Ser Lys Ala Asp Ile Asn Gly Gln
                195                 200                 205

Asn Pro Asn Ile Gln Val Thr Ile Glu Val Val Asp Gly Pro Asp Ser
        210                 215                 220

Glu Ala Asp Lys Asp Gln His Pro Glu Asn Lys Pro Ser Trp Ser Val
225                 230                 235                 240

Pro Ser Pro Asp Trp Arg Ala Trp Trp Gln Arg Ser Leu Ser Leu Ala
                245                 250                 255

Arg Ala Asn Ser Gly Asp Gln Asp Tyr Lys Tyr Asp Ser Thr Ser Asp
                260                 265                 270

Asp Ser Asn Phe Leu Asn Pro Pro Arg Gly Trp Asp His Thr Ala Pro
                275                 280                 285

Gly His Arg Thr Phe Glu Thr Lys Asp Gln Pro Glu Tyr Asp Ser Thr
        290                 295                 300

Asp Gly Glu Gly Asp Trp Ser Leu Trp Ser Val Cys Ser Val Thr Cys
305                 310                 315                 320

Gly Asn Gly Asn Gln Lys Arg Thr Arg Ser Cys Gly Tyr Ala Cys Thr
                325                 330                 335

Ala Thr Glu Ser Arg Thr Cys Asp Arg Pro Asn Cys Pro Gly Ile Glu
                340                 345                 350

Asp Thr Phe Arg Thr Ala Ala Thr Glu Val Ser Leu Leu Ala Gly Ser
                355                 360                 365

Glu Glu Phe Asn Ala Thr Lys Leu Phe Glu Val Asp Thr Asp Ser Cys
        370                 375                 380

Glu Arg Trp Met Ser Cys Lys Ser Glu Phe Leu Lys Lys Tyr Met His
385                 390                 395                 400

Lys Val Met Asn Asp Leu Pro Ser Cys Pro Cys Ser Tyr Pro Thr Glu
                405                 410                 415

Val Ala Tyr Ser Thr Ala Asp Ile Phe Asp Arg Ile Lys Arg Lys Asp
                420                 425                 430

Phe Arg Trp Lys Asp Ala Ser Gly Pro Lys Glu Lys Leu Glu Ile Tyr
                435                 440                 445

Lys Pro Thr Ala Arg Tyr Cys Ile Arg Ser Met Leu Ser Leu Glu Ser
        450                 455                 460

Thr Thr Leu Ala Ala Gln His Cys Cys Tyr Gly Asp Asn Met Gln Leu
465                 470                 475                 480

Ile Thr Arg Gly Lys Gly Ala Gly Thr Pro Asn Leu Ile Ser Thr Glu
```

```
                    485                 490                 495

Phe Ser Ala Glu Leu His Tyr Lys Val Asp Val Leu Pro Trp Ile Ile
            500                 505                 510

Cys Lys Gly Asp Trp Ser Arg Tyr Asn Glu Ala Arg Pro Pro Asn Asn
            515                 520                 525

Gly Gln Lys Cys Thr Glu Ser Pro Ser Asp Glu Asp Tyr Ile Lys Gln
            530                 535                 540

Phe Gln Glu Ala Arg Glu Tyr Asp Tyr Lys Asp Asp Asp Asp Lys
545                 550                 555

<210> SEQ ID NO 34
<211> LENGTH: 295
<212> TYPE: PRT
<213> ORGANISM: Artificial Sequence
<220> FEATURE:
<223> OTHER INFORMATION: bacISM1290-464

<400> SEQUENCE: 34

Met Gly Ser Ser His His His His His His Ser Gln Gly Ser Met Ser
1                   5                   10                  15

Asp Ser Glu Val Asn Gln Glu Ala Lys Pro Glu Val Lys Pro Glu Val
            20                  25                  30

Lys Pro Glu Thr His Ile Asn Leu Lys Val Ser Asp Gly Ser Ser Glu
            35                  40                  45

Ile Phe Phe Lys Ile Lys Lys Thr Thr Pro Leu Arg Arg Leu Met Glu
            50                  55                  60

Ala Phe Ala Lys Arg Gln Gly Lys Glu Met Asp Ser Leu Arg Phe Leu
65                  70                  75                  80

Tyr Asp Gly Ile Arg Ile Gln Ala Asp Gln Thr Pro Glu Asp Leu Asp
                85                  90                  95

Met Glu Asp Asn Asp Ile Ile Glu Ala His Arg Glu Gln Ile Gly Gly
            100                 105                 110

Phe Glu Val Asp Thr Asp Ser Cys Glu Arg Trp Met Ser Cys Lys Ser
            115                 120                 125

Glu Phe Leu Lys Lys Tyr Met His Lys Val Met Asn Asp Leu Pro Ser
            130                 135                 140

Cys Pro Cys Ser Tyr Pro Thr Glu Val Ala Tyr Ser Thr Ala Asp Ile
145                 150                 155                 160

Phe Asp Arg Ile Lys Arg Lys Asp Phe Arg Trp Lys Asp Ala Ser Gly
                165                 170                 175

Pro Lys Glu Lys Leu Glu Ile Tyr Lys Pro Thr Ala Arg Tyr Cys Ile
            180                 185                 190

Arg Ser Met Leu Ser Leu Glu Ser Thr Thr Leu Ala Ala Gln His Cys
            195                 200                 205

Cys Tyr Gly Asp Asn Met Gln Leu Ile Thr Arg Gly Lys Gly Ala Gly
            210                 215                 220

Thr Pro Asn Leu Ile Ser Thr Glu Phe Ser Ala Glu Leu His Tyr Lys
225                 230                 235                 240

Val Asp Val Leu Pro Trp Ile Ile Cys Lys Gly Asp Trp Ser Arg Tyr
                245                 250                 255

Asn Glu Ala Arg Pro Pro Asn Asn Gly Gln Lys Cys Thr Glu Ser Pro
            260                 265                 270

Ser Asp Glu Asp Tyr Ile Lys Gln Phe Gln Glu Ala Arg Glu Tyr Asp
            275                 280                 285

Tyr Lys Asp Asp Asp Asp Lys
```

```
      290                295
```

<210> SEQ ID NO 35
<211> LENGTH: 221
<212> TYPE: PRT
<213> ORGANISM: Artificial Sequence
<220> FEATURE:
<223> OTHER INFORMATION: mamISM1 290-464

<400> SEQUENCE: 35

```
Asp Ala Ala Gln Pro Ala Arg Arg Ala Arg Arg Thr Lys Leu Gly Thr
1               5                   10                  15

Glu Leu Gly Ser Phe Glu Val Asp Thr Asp Ser Cys Glu Arg Trp Met
            20                  25                  30

Ser Cys Lys Ser Glu Phe Leu Lys Lys Tyr Met His Lys Val Met Asn
        35                  40                  45

Asp Leu Pro Ser Cys Pro Cys Ser Tyr Pro Thr Glu Val Ala Tyr Ser
    50                  55                  60

Thr Ala Asp Ile Phe Asp Arg Ile Lys Arg Lys Asp Phe Arg Trp Lys
65                  70                  75                  80

Asp Ala Ser Gly Pro Lys Glu Lys Leu Glu Ile Tyr Lys Pro Thr Ala
                85                  90                  95

Arg Tyr Cys Ile Arg Ser Met Leu Ser Leu Glu Ser Thr Thr Leu Ala
            100                 105                 110

Ala Gln His Cys Cys Tyr Gly Asp Asn Met Gln Leu Ile Thr Arg Gly
        115                 120                 125

Lys Gly Ala Gly Thr Pro Asn Leu Ile Ser Thr Glu Phe Ser Ala Glu
    130                 135                 140

Leu His Tyr Lys Val Asp Val Leu Pro Trp Ile Ile Cys Lys Gly Asp
145                 150                 155                 160

Trp Ser Arg Tyr Asn Glu Ala Arg Pro Pro Asn Asn Gly Gln Lys Cys
                165                 170                 175

Thr Glu Ser Pro Ser Asp Glu Asp Tyr Ile Lys Gln Phe Gln Glu Ala
            180                 185                 190

Arg Glu Tyr Pro Arg Gly Gly Pro Glu Gln Lys Leu Ile Ser Glu Glu
            195                 200                 205

Asp Leu Asn Ser Ala Val Asp His His His His His His
    210                 215                 220
```

<210> SEQ ID NO 36
<211> LENGTH: 60
<212> TYPE: DNA
<213> ORGANISM: Mus musculus

<400> SEQUENCE: 36

```
gctgctcacg ctgcacatca cggttctgcg cggatccgga gcctccgacc ggcaggacgc     60
```

<210> SEQ ID NO 37
<211> LENGTH: 92
<212> TYPE: DNA
<213> ORGANISM: Mus musculus

<400> SEQUENCE: 37

```
tactgctgct cacgctgcac atcacggttc tgcgcggatc cggagcctcc gaccggcagg     60
acgcggccgc cggcaacgtc agcgggtccc ag                                    92
```

<210> SEQ ID NO 38
<211> LENGTH: 69

<210> SEQ ID NO 39
<211> LENGTH: 16
<212> TYPE: PRT
<213> ORGANISM: Homo sapiens
```

<400> SEQUENCE: 39

Glu Val Ser Leu Leu Ala Gly Ser Glu Glu Phe Asn Ala Thr Lys Leu
1               5                   10                  15
```
<212> TYPE: DNA
<213> ORGANISM: Artificial Sequence
<220> FEATURE:
<223> OTHER INFORMATION: Synthetic Construct
```

<400> SEQUENCE: 38
tactgctgct cacgctgcac atcacggttc tgcgcggatc cggccgccgg caacgtcagc        60
gggtcccag                                                              69
```

ISTHMIN 1 FOR TREATMENT OF LUNG INFLAMMATION

SEQUENCE LISTING

The instant application contains a Sequence Listing which has been submitted electronically in ASCII format and is hereby incorporated by reference in its entirety. Said ASCII copy, created on Aug. 14, 2024, is named 50352-017001 Sequence Listing 8 14 24 ST25 and is 65,217 bytes in size.

FIELD OF INVENTION

The present invention relates generally to the treatment of inflammation. More specifically, the present invention relates to Isthmin 1 (ISM1)-based treatments for lung inflammation.

BACKGROUND

Inflammation of the lung, be it acute or chronic, may have serious health consequences. According to the World Health Organization (WHO), chronic obstructive pulmonary disease (COPD) was the third most common cause of death in 2016. It is considered a major socio-economical and health burden with direct healthcare costs that amounted to US$20 billion in the USA alone in 2004. In Singapore, COPD is estimated to cost patients and healthcare facilities S$165 million a year with more than 10,000 hospital admissions in 2010, representing a significant burden to the public health system. COPD may be characterized by progressive emphysema (irreversible expansion of the alveoli or destruction of alveolar walls of the lung) and chronic respiratory inflammation, leading to severe decline in lung function. Currently, no effective treatment is available to slow/reverse emphysema. Cigarette smoking may be a major risk factor for COPD and is closely linked to COPD's progression and exacerbation. Other risk factors may include air pollution.

Indeed, COPD currently stands as the third leading cause of death globally with an estimated cumulated lifetime risk of 25% and high socioeconomical burden (Gershon, Warner et al., 2011, Mortality & Causes of Death, 2016). The pathogenesis of COPD is believed to involve perturbation of lung homeostasis and a dysregulated immune response to exogenous agents from the environment, with cigarette smoke (CS), biomass fuel exposure and air pollution as the main risk factors (Singh, Agusti et al., 2019). Hallmark features of COPD include emphysema and chronic obstructive bronchitis (inflamed airways). COPD patients present persistent respiratory symptoms with progressive long-term lung function impairment. However, traditional pharmacological interventions only provide symptomatic relief for patients and do not target the underlying tissue damage and inflammation, hence they cannot effectively block COPD progression or reduce mortality. Therefore, there is an urgent unmet need for novel COPD therapeutics.

The respiratory tract is constantly exposed to the external environment containing dust and microbes. To avoid inflammatory responses to ambient environmental stimulation, the healthy airway and lung have mechanisms to inhibit immune response and inflammation. Furthermore, in response to injury or pathogen, the acute pulmonary inflammatory response protects the host from systemic infection and restores tissue homeostasis. However, when acute inflammation is unrestrained in amplitude or duration, it can lead to lung diseases that are characterized by excess or chronic inflammation including asthma and/or COPD. While asthma mainly affects the large airway, COPD affects the small airway and lung parenchyma. The molecular mechanisms of COPD are poorly understood.

Meanwhile, severe acute lung inflammation such as acute lung injury (ALI) and acute respiratory distress syndrome (ARDS) due to infection or injury are serious clinical syndromes with up to 50% mortality rate without effective pharmacological therapies. There is an unmet need to develop therapeutics for both acute and chronic lung inflammation.

Alternative, additional, and/or improved treatments and/or treatment methods for inflammation-associated diseases or disorders, and particularly those affecting the lung, are desirable.

SUMMARY OF INVENTION

Healthy adults have the ability to regulate and maintain lung homeostasis under ambient environmental conditions, preventing sterile inflammation. An immune response may be triggered by injury and/or infection, leading to acute inflammation which is eventually resolved to allow wound healing and recovery. Failure to resolve acute inflammation may lead to chronic inflammation and/or inflammatory-related diseases such as chronic obstructive pulmonary disorder (COPD), emphysema, chronic obstructive bronchitis, and/or lung fibrosis. Acute lung diseases such as acute lung injury (ALI), and acute respiratory distress syndrome (ARDS), are also related to inflammation in the lung.

As described in detail herein, the present inventors have now developed polypeptides, nucleic acids, compositions, and methods for treating inflammation, such as lung inflammation, which are derived from Isthmin 1, which is a secreted protein that is indicated by the studies described herein as playing a role in inhibiting, suppressing, and/or resolving inflammation, and particularly inflammation of the lung. In the studies described herein, supplementation of exogenous recombinant ISM1 protein (rISM1) to the lung inhibited the lung inflammation phenotype in ISM1-deficient lung, and results indicate that ISM1 may help to resolve inflammation by inducing alveolar macrophage apoptosis. Results indicate that ISM1 may play an important role in suppression and/or resolution of sterile lung inflammation and/or inflammation triggered by infection and/or injury.

In an embodiment, there is provided herein a composition comprising:

a polypeptide or peptide comprising an amino acid sequence having at least 70% sequence identity with an Isthmin 1 (ISM1) protein or a GRP78-activating fragment thereof, or an expressible nucleic acid encoding said polypeptide or peptide; and a pharmaceutically acceptable carrier, diluent, or excipient;

the composition being formulated for administration to the lung of a subject.

In another embodiment of the above composition, the composition may be formulated for intratracheal administration, intranasal administration, or inhalation administration.

In still another embodiment of any of the above composition or compositions, the composition may be formulated for administration as an aerosol, an inhaler, or a nebulizer.

In yet another embodiment of any of the above composition or compositions, the composition may be formulated as a dry powder for administration to the lung by aerosolization, or as a liquid for administration to the lung by nebulization.

In another embodiment of any of the above composition or compositions, the composition may be for use in targeting cell surface GRP78 (csGRP78) in a subject in need thereof.

In still another embodiment of any of the above composition or compositions, the composition may be for use in inducing apoptosis in pro-inflammatory cells in a subject in need thereof.

In yet another embodiment of any of the above composition or compositions, the composition may be for use in inducing apoptosis in alveolar macrophages (AM), or for reducing AM levels in a subject in need thereof.

In another embodiment of any of the above composition or compositions, the composition may be for use in treating, ameliorating, or preventing lung inflammation in a subject in need thereof.

In still another embodiment of any of the above composition or compositions, the composition may be for use in treating, ameliorating, or preventing a lung disease or disorder associated with lung inflammation in a subject in need thereof.

In yet another embodiment of any of the above composition or compositions, the composition may be for use in treating, ameliorating, or preventing chronic obstructive pulmonary disease (COPD), chronic obstructive bronchitis, asthma, or emphysema in a subject in need thereof.

In another embodiment of any of the above composition or compositions, the composition may be for use in treating, ameliorating, or preventing acute lung injury (ALI) or acute respiratory distress syndrome (ARDS) in a subject in need thereof.

In still another embodiment of any of the above composition or compositions, the composition may be for use in preventing or reducing hyper-proliferation of alveolar wall surface type II (AE2) cells in a subject in need thereof.

In yet another embodiment of any of the above composition or compositions, the composition may be for use in treating, ameliorating, or preventing lung fibrosis in subject in need thereof.

In still another embodiment, there is provided herein a use of a polypeptide or peptide comprising an amino acid sequence having at least 70% sequence identity with an Isthmin 1 (ISM1) protein or a GRP78-activating fragment thereof, or an expressible nucleic acid encoding said polypeptide or peptide, for modulating GRP78 activity in a subject in need thereof.

In still another embodiment, there is provided herein a use of a polypeptide or peptide comprising an amino acid sequence having at least 70% sequence identity with Isthmin 1 (ISM1) protein or a GRP78-activating fragment thereof, or an expressible nucleic acid encoding said polypeptide or peptide, for inducing apoptosis in pro-inflammatory cells in a subject in need thereof.

In still another embodiment, there is provided herein a use of a polypeptide or peptide comprising an amino acid sequence having at least 70% sequence identity with an Isthmin 1 (ISM1) protein or a GRP78-activating fragment thereof, or an expressible nucleic acid encoding said polypeptide or peptide, for inducing apoptosis in alveolar macrophages (AM), or for reducing AM levels, in a subject in need thereof.

In still another embodiment, there is provided herein a use of a polypeptide or peptide comprising an amino acid sequence having at least 70% sequence identity with an Isthmin 1 (ISM1) protein or a GRP78-activating fragment thereof, or an expressible nucleic acid encoding said polypeptide or peptide, for treating, ameliorating, or preventing lung inflammation in a subject in need thereof.

In still another embodiment, there is provided herein a use of a polypeptide or peptide comprising an amino acid sequence having at least 70% sequence identity with an Isthmin 1 (ISM1) protein or a GRP78-activating fragment thereof, or an expressible nucleic acid encoding said polypeptide or peptide, for treating, ameliorating, or preventing a lung disease or disorder associated with lung inflammation in a subject in need thereof.

In still another embodiment, there is provided herein a use of a polypeptide or peptide comprising an amino acid sequence having at least 70% sequence identity with an Isthmin 1 (ISM1) protein or a GRP78-activating fragment thereof, or an expressible nucleic acid encoding said polypeptide or peptide, for treating, ameliorating, or preventing chronic obstructive pulmonary disease (COPD), chronic obstructive bronchitis, asthma or emphysema in a subject in need thereof.

In still another embodiment, there is provided herein a use of a polypeptide or peptide comprising an amino acid sequence having at least 70% sequence identity with an Isthmin 1 (ISM1) protein or a GRP78-activating fragment thereof, or an expressible nucleic acid encoding said polypeptide or peptide, for treating, ameliorating, or preventing acute lung injury (ALI) or acute respiratory distress syndrome (ARDS) in a subject in need thereof.

In still another embodiment, there is provided herein a use of a polypeptide or peptide comprising an amino acid sequence having at least 70% sequence identity with an Isthmin 1 (ISM1) protein or a GRP78-activating fragment thereof, or an expressible nucleic acid encoding said polypeptide or peptide, for preventing or reducing hyper-proliferation of alveolar wall surface type II (AE2) cells in a subject in need thereof.

In still another embodiment, there is provided herein a use of a polypeptide or peptide comprising an amino acid sequence having at least 70% sequence identity with an Isthmin 1 (ISM1) protein or a GRP78-activating fragment thereof, or an expressible nucleic acid encoding said polypeptide or peptide, for treating, ameliorating, or preventing lung fibrosis in subject in need thereof.

In yet another embodiment of any of the above use or uses, the polypeptide or peptide or nucleic acid may be for administration to the lung of the subject.

In another embodiment of any of the above use or uses, the polypeptide or peptide or nucleic acid may be for intratracheal administration, intranasal administration, or inhalation administration to the subject.

In still another embodiment of any of the above use or uses, the polypeptide or peptide or nucleic acid may be for administration as an aerosol, an inhaler, or a neubulizer.

In yet another embodiment of any of the above use or uses, the polypeptide or peptide or nucleic acid may be formulated as a dry powder for administration to the lung by aerosolization, or as a liquid for administration to the lung by nebulization.

In another embodiment, there is provided herein a method for modulating GRP78 activity, for targeting and binding to GRP78, or both, in a subject in need thereof, said method comprising:

administering a polypeptide or peptide comprising an amino acid sequence having at least 70% sequence identity with an Isthmin 1 (ISM1) protein or a GRP78-activating fragment thereof, or an expressible nucleic acid encoding said polypeptide or peptide, to the subject in need thereof.

In another embodiment, there is provided herein a method for inducing apoptosis in pro-inflammatory cells in a subject in need thereof, said method comprising:

administering a polypeptide or peptide comprising an amino acid sequence having at least 70% sequence identity with an Isthmin 1 (ISM1) protein or a GRP78-activating fragment thereof, or an expressible nucleic acid encoding said polypeptide or peptide, to the subject in need thereof.

In another embodiment, there is provided herein a method for inducing apoptosis in alveolar macrophages (AM), or for reducing AM levels, in a subject in need thereof, said method comprising:

administering a polypeptide or peptide comprising an amino acid sequence having at least 70% sequence identity with an Isthmin 1 (ISM1) protein or a GRP78-activating fragment thereof, or an expressible nucleic acid encoding said polypeptide or peptide, to the subject in need thereof.

In another embodiment, there is provided herein a method for treating, ameliorating, or preventing lung inflammation in a subject in need thereof, said method comprising:

administering a polypeptide or peptide comprising an amino acid sequence having at least 70% sequence identity with an Isthmin 1 (ISM1) protein or a GRP78-activating fragment thereof, or an expressible nucleic acid encoding said polypeptide or peptide, to the subject in need thereof.

In another embodiment, there is provided herein a method for treating, ameliorating, or preventing a lung disease or disorder associated with lung inflammation in a subject in need thereof, said method comprising:

administering a polypeptide or peptide comprising an amino acid sequence having at least 70% sequence identity with an Isthmin 1 (ISM1) protein or a GRP78-activating fragment thereof, or an expressible nucleic acid encoding said polypeptide or peptide, to the subject in need thereof.

In another embodiment, there is provided herein a method for treating, ameliorating, or preventing chronic obstructive pulmonary disease (COPD), chronic obstructive bronchitis, asthma, or emphysema in a subject in need thereof, said method comprising:

administering a polypeptide or peptide comprising an amino acid sequence having at least 70% sequence identity with an Isthmin 1 (ISM1) protein or a GRP78-activating fragment thereof, or an expressible nucleic acid encoding said polypeptide or peptide, to the subject in need thereof.

In another embodiment, there is provided herein a method for treating, ameliorating, or preventing acute lung injury (ALI) or acute respiratory distress syndrome (ARDS) in a subject in need thereof, said method comprising:

administering a polypeptide or peptide comprising an amino acid sequence having at least 70% sequence identity with an Isthmin 1 (ISM1) protein or a GRP78-activating fragment thereof, or an expressible nucleic acid encoding said polypeptide or peptide, to the subject in need thereof.

In another embodiment, there is provided herein a method for preventing or reducing hyper-proliferation of alveolar wall surface type II (AE2) cells in subject in need thereof, said method comprising:

administering a polypeptide or peptide comprising an amino acid sequence having at least 70% sequence identity with an Isthmin 1 (ISM1) protein or a GRP78-activating fragment thereof, or an expressible nucleic acid encoding said polypeptide or peptide, to the subject in need thereof.

In another embodiment, there is provided herein a method for treating, ameliorating, or preventing lung fibrosis in subject in need thereof, said method comprising:

administering a polypeptide or peptide comprising an amino acid sequence having at least 70% sequence identity with an Isthmin 1 (ISM1) protein or a GRP78-activating fragment thereof, or an expressible nucleic acid encoding said polypeptide or peptide, to the subject in need thereof.

In still another embodiment of any of the method or methods above, the polypeptide or peptide or nucleic acid may be for administration to the lung of the subject in need thereof.

In yet another embodiment of any of the method or methods above, the polypeptide or peptide or nucleic acid may be for intratracheal administration, intranasal administration, or inhalation administration to the subject.

In another embodiment of any of the method or methods above, the polypeptide or peptide or nucleic acid may be for administration as an aerosol, an inhaler, or a neubulizer.

In still another embodiment of any of the method or methods above, the polypeptide or peptide or nucleic acid may be formulated as a dry powder for administration to the lung by aerosolization, or as a liquid for administration to the lung by nebulization.

In yet another embodiment of any of the method or methods above, the method may further comprise a step of:

determining an ISM1 level in the subject, determining a GRP78 protein level in the subject, or both; and performing or repeating the step of administering where a reduced ISM1 level in the subject relative to a healthy control level, or relative to a low severity disease control level, is determined; where an increased GRP78 protein level in the subject relative to a healthy control level, or relative to a low severity disease control level, is determined; or both.

In still another embodiment, there is provided herein a pulmonary drug delivery device comprising a polypeptide or peptide comprising an amino acid sequence having at least 70% sequence identity with an Isthmin 1 (ISM1) protein or a GRP78-activating fragment thereof, or an expressible nucleic acid encoding said polypeptide or peptide.

In yet another embodiment of the above pulmonary drug delivery device, the pulmonary drug delivery device may comprise a composition as defined herein.

In still another embodiment of any of the above pulmonary drug delivery device or devices, the pulmonary drug delivery device may be an intratracheal drug delivery device, an intranasal drug delivery device, or an inhalation drug delivery device.

In yet another embodiment of any of the above pulmonary drug delivery device or devices, the pulmonary drug delivery device may be an aerosol, an inhaler, or a nebulizer.

In another embodiment of any of the above pulmonary drug delivery device or devices, the pulmonary drug delivery device may be an aerosol and the polypeptide or peptide or nucleic acid may be formulated as a dry powder, or wherein the pulmonary drug delivery device may be a nebulizer and the polypeptide or peptide or nucleic acid may be formulated as a liquid.

In still another embodiment of any of the above pulmonary drug delivery device or devices, the pulmonary drug delivery device may be for use in modulating GRP78 activity in a subject in need thereof.

In yet another embodiment of any of the above pulmonary drug delivery device or devices, the pulmonary drug delivery device may be for use in inducing apoptosis in pro-inflammatory cells in a subject in need thereof.

In another embodiment of any of the above pulmonary drug delivery device or devices, the pulmonary drug delivery device may be for use in inducing apoptosis in alveolar macrophages (AM), or for reducing AM levels in a subject in need thereof.

In still another embodiment of any of the above pulmonary drug delivery device or devices, the pulmonary drug device may be for use in treating, ameliorating, or preventing lung inflammation in a subject in need thereof.

In yet another embodiment of any of the above pulmonary drug delivery device or devices, the pulmonary drug device may be for use in treating, ameliorating, or preventing a lung disease or disorder associated with lung inflammation in a subject in need thereof.

In another embodiment of any of the above pulmonary drug delivery device or devices, the pulmonary drug device may be for use in treating, ameliorating, or preventing chronic obstructive pulmonary disease (COPD), chronic obstructive bronchitis, asthma, or emphysema in a subject in need thereof.

In still another embodiment of any of the above pulmonary drug delivery device or devices, the pulmonary drug device may be for use in treating, ameliorating, or preventing acute lung injury (ALI) or acute respiratory distress syndrome (ARDS) in a subject in need thereof.

In yet another embodiment of any of the above pulmonary drug delivery device or devices, the pulmonary drug device may be for use in preventing or reducing hyper-proliferation of alveolar wall surface type II (AE2) cells in a subject in need thereof.

In another embodiment of any of the above pulmonary drug delivery device or devices, the pulmonary drug device may be for use in treating, ameliorating, or preventing lung fibrosis in subject in need thereof.

In still another embodiment of any of the above pulmonary drug delivery device or devices, the pulmonary drug delivery device may be a nebulizer, a metered-dose inhaler (MDI), or a dry powder inhaler (DPI).

In still another embodiment of any of the composition or compositions above, the composition may further comprise an agent for preventing or reducing lung inflammation.

In yet another embodiment of any of the use or uses above, the polypeptide or peptide or nucleic acid may be for use in combination with an agent for preventing or reducing lung inflammation.

In another embodiment of any of the method or methods above, the method may further comprise a step of administering an agent for preventing or reducing lung inflammation to the subject in combination with, simultaneously with, or sequentially with the polypeptide or peptide or nucleic acid.

In still another embodiment of any of the above pulmonary drug delivery device or devices, the pulmonary drug delivery device may further comprise an agent for preventing or reducing lung inflammation.

In another embodiment, there is provided herein a polypeptide or peptide comprising an amino acid sequence having at least 70% sequence identity with an Isthmin 1 (ISM1) protein or a GRP78-activating fragment thereof, or an expressible nucleic acid encoding said polypeptide or peptide, for use in treating, ameliorating, or preventing a disease or disorder associated with macrophage-mediated inflammation in a subject in need thereof.

In another embodiment, there is provided herein a use of a polypeptide or peptide comprising an amino acid sequence having at least 70% sequence identity with an Isthmin 1 (ISM1) protein or a GRP78-activating fragment thereof, or an expressible nucleic acid encoding said polypeptide or peptide, for treating, ameliorating, or preventing a disease or disorder associated with macrophage-mediated inflammation in a subject in need thereof.

In another embodiment, there is provided herein a method for treating, ameliorating, or preventing a disease or disorder associated with macrophage-mediated inflammation in a subject in need thereof, said method comprising:

administering a polypeptide or peptide comprising an amino acid sequence having at least 70% sequence identity with an Isthmin 1 (ISM1) protein or a GRP78-activating fragment thereof, or an expressible nucleic acid encoding said polypeptide peptide, to the subject.

In another embodiment, there is provided herein a use of a polypeptide or peptide comprising an amino acid sequence having at least 70% sequence identity with an Isthmin 1 (ISM1) protein or a GRP78-activating fragment thereof, or an expressible nucleic acid encoding said polypeptide or peptide, in the manufacture of a medicament.

In another embodiment, there is provided herein a method for treating, ameliorating, or preventing a lung disease or disorder associated with lung inflammation in a subject in need thereof, said method comprising:

administering a GRP78-activating agent to the lung of the subject.

In another embodiment, there is provided herein a method for identifying a subject having or being at risk of developing a lung disease or disorder associated with lung inflammation, said method comprising:

determining an ISM1 level in the subject, determining a GRP78 protein level in the subject, or both; and identifying the subject as having or being at risk of developing the lung disease or disorder associated with lung inflammation where a reduced ISM1 level in the subject relative to a healthy control level, or relative to a low severity disease control level, is determined; where an increased GRP78 protein level in the subject relative to a healthy control level, or relative to a low severity disease control level, is determined; or both.

In another embodiment, there is provided herein a method for identifying candidate subjects for treatment with a method as defined herein, said method comprising:

determining an ISM1 level in a subject, determining a GRP78 protein level in the subject, or both; and identifying the subject as being a candidate subject for treatment where a reduced ISM1 level in the subject relative to a healthy control level, or relative to a low severity disease control level, is determined; where an increased GRP78 protein level relative to a healthy control level, or relative to a low severity disease control level, is determined; or both.

In another embodiment, there is provided herein a use of a polypeptide or peptide comprising an amino acid sequence having at least 70% sequence identity with an Isthmin 1 (ISM1) protein or a GRP78-activating fragment thereof, or an expressible nucleic acid encoding said polypeptide or peptide, for maintaining lung homeostasis and/or resolving pulmonary inflammation and/or promoting lung repair with reduced remodelling in a subject in need thereof.

In another embodiment, there is provided herein a method for maintaining lung homeostasis and/or resolving pulmonary inflammation and/or promoting lung repair with reduced remodelling in a subject in need thereof, said method comprising;

administering a polypeptide or peptide comprising an amino acid sequence having at least 70% sequence identity with an Isthmin 1 (ISM1) protein or a GRP78-activating fragment thereof, or an expressible nucleic acid encoding said polypeptide or peptide, to the lung of the subject.

In another embodiment of any of the above compositions, uses, methods, pulmonary drug delivery devices, or polypeptides, the polypeptide may be or may comprise ISM1 protein (precursor, or mature). In another embodiment, the polypeptide may be or comprise human ISM1 protein or mouse ISM1 protein (precursor or mature).

In another embodiment of any of the above compositions, uses, methods, pulmonary drug delivery devices, or polypeptides or peptides, the polypeptide or peptide may comprise or may consist of the amino acid sequence:

```
                                    (SEQ ID NO: 26)
FEVDMDSCERWMSCKSEFLKKYMHKVINDLPSCPCSYPTEVAYSTADIF
DRIKRKDFRWKDASGPKEKLEIYKPTARYCIRSMLSLE; or (SEQ ID NO: 27)
FEVDTDSCERWMSCKSEFLKKYMHKVMNDLPSCPCSYPTEVAYSTADIF
DRIKRKDFRWKDASGPKEKLEIYKPTARYCIRSMLSLE
``` or an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity therewith.

In another embodiment of any of the above compositions, uses, methods, pulmonary drug delivery devices, or polypeptides or peptides, the polypeptide or peptide may comprise or may consist of the amino acid sequence:

```
                    (SEQ ID NO: 24 - mouse ISM1 287-461)
FEVDMDSCERWMSCKSEFLKKYMHKVINDLPSCPCSYPTEVAYSTADIF

DRIKRKDFRWKDASGPKEKLEIYKPTARYCIRSMLSLESTTLAAQHCCY

GDNMQLITRGKGAGTPNLISTEFSAELHYKVDVLPWIICKGDWSRYNEA

RPPNNGQKCTESPSDEDYIKQFQEAREY; or (SEQ ID NO: 25 - human ISM1 290-464)
FEVDTDSCERWMSCKSEFLKKYMHKVMNDLPSCPCSYPTEVAYSTADIF

DRIKRKDFRWKDASGPKEKLEIYKPTARYCIRSMLSLESTTLAAQHCCY

GDNMQLITRGKGAGTPNLISTEFSAELHYKVDVLPWIICKGDWSRYNEA

RPPNNGQKCTESPSDEDYIKQFQEAREY;
``` or an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity therewith.

In another embodiment of any of the above compositions, uses, methods, pulmonary drug delivery devices, or polypeptides or peptides, the polypeptide or peptide may comprise or may consist of the sequence of endogenous mature ISM1.

In another embodiment of any of the above compositions, uses, methods, pulmonary drug delivery devices, or polypeptides or peptides, the polypeptide or peptide may not be endogenous precursor or mature ISM1. In certain embodiments, the polypeptide or peptide may be longer or shorter than endogenous precursor or mature ISM1. In certain embodiments, the polypeptide or peptide may comprise at least one substitution or mutation not found in endogenous precursor or mature ISM1. In certain embodiments, the polypeptide or peptide may comprise a RKD to RAA mutation, or an RKD to AAA mutation, in SEQ ID NO: 24 or SEQ ID NO: 25 or SEQ ID NO: 26 or SEQ ID NO: 27.

BRIEF DESCRIPTION OF DRAWINGS

These and other features will become more apparent from the following description in which reference is made to the appended drawings wherein:

FIGS. 1a-n show that loss of ISM1 led to pulmonary emphysema. FIGS. 1a, 1b show representative photomicrographs of hematoxylin and eosin stained peripheral left lung lobes (1a) and mean linear intercepts (MLI) (1b) of FVB/NTac WT and Ism$^{\Delta/\Delta}$ mice at 1 month, 2 months, 6 months and 9 months of age. n=3-4 mice per group. Scale bars, 200 μm. FIGS. 1c, 1d show representative whole-mount stereoscopic images of left lung lobes (1c) and elastin/collagen labeled left lung lobes (1d) of FVB/NTac WT and Ism1$^{\Delta/\Delta}$ mice at 6 months of age. n=3 mice per group. Scale bars, 500 μm (1c) and 200 μm (1d). FIG. 1e shows a representative photomicrograph of hematoxylin and eosin stained peripheral left lung lobe of FVB/NTac Ism1$^{+/\Delta}$ mice at 9 months of age. n=4 mice per group. Scale bars, 200 μm. Figure if shows MLI of FVB/NTac WT, Ism1$^{+/\Delta}$ and Ism1$^{\Delta/\Delta}$ mice at 9 months of age. n=4 mice per group. FIGS. 1g-1n show spirometry of FVB/NTac WT and IsmA/A mice at 2 months of age. n=4 mice per group. Total lung capacity (TLC) (1g), functional residual capacity (FRC) (1h), residual volume (RV) (ii), static compliance (Cchord) (1j), dynamic compliance (Cdyn) (1k), forced expiratory volume at 100 ms (FEV$_{100}$) (1l), Tiffeneau-Pinelli index (FEV$_{100}$/FVC) (1m), and airway resistance (RI) (1n) are shown. Data are mean±s.e.m. and were analyzed by unpaired two-tailed Student's t-test (1b, 1g-1n) and one-way ANOVA with Tukey's post hoc test (If). *P<0.05, P<0.01, *P<0.001, ****P<0.0001;

FIG. 9A shows increased immune cell infiltration in the lungs of Ism1$^{\Delta/\Delta}$ mice at 2 months as shown in H & E staining. FIG. 9B shows total leukocyte quantifications in Ism1$^{\Delta/\Delta}$ and wild-type lungs. FIG. 9C shows increased macrophages and neutrophils in the lungs of Ism1$^{\Delta/\Delta}$ mice at 2 months, as detected by IHC staining of CD68 and NIMP-R14, respectively. FIGS. 9D & 9E shows differential immune cell count showed increased macrophages and neutrophils in Ism1$^{\Delta/\Delta}$ lungs. FIG. 9F shows analysis of the peripheral blood of Ism1$^{\Delta/\Delta}$ mice showed increased total white blood cells (WBC), neutrophils (NE) and lymphocytes (LY) at 2 months. * represents p<0.05; n=5 animals per group in (9A-9E). n=7 animals per group in (9F);

FIGS. 10A-10E show time-course of immune response to intratracheal LPS challenge: Ism1$^{\Delta/\Delta}$ lungs showed heightened immune responses to LPS via quantification of total leukocytes, neutrophils, macrophages, T-cells and B-cells. LPS (2 mg/kg) was intratracheally administered once, followed by isolation of single-cell suspension from the lungs at day 1, 3, 5 and 7 post-LPS administration. FIG. 10F shows LPS triggered a heightened increase (higher BAL protein) in pulmonary permeability in Ism1$^{\Delta/\Delta}$ mice compared with that of wild-type mice at 1-day post LPS challenge. FIG. 10G shows representative H & E stained lung sections showing the extent of the immune cell infiltration into the lung airspace (acute inflammation) (left) and immunofluorescent stained neutrophils for NIMP-R14, a neutrophil marker (right) at 1-day post LPS challenge. * represents p<0.05;  represents p<0.01; * represents p<0.001; n=3 animals per group.

FIG. 11A is a schematic diagram showing rISM1 treatment to LPS-induced acute inflammatory lung in mice. Mouse was pretreated with 50 μg rISM1 via intratracheal delivery one day before receiving the single dose of LPS (2 mg/kg). The mouse was continuously treated with 50 μg rISM1 once per day till day 3 post-LPS. BAL fluids were then isolated and separated into the BAL fluid protein and cell components. FIG. 11B shows the total BAL fluid protein was reduced in rISM1-treated mice 1-day post-LPS challenge. FIGS. 11C-G show total leukocytes and differential immune cell count was performed using cells from the BAL fluids from PBS or rISM1-treated mice 1-day post-LPS challenge. rISM1 significantly reduced the number of total leukocytes, neutrophils and macrophages. Both T-cells and B-cells were also reduced under rISM1, albeit without statistical significance due to the wide variation of these two cell types in the PBS-treated mice. * represents p<0.05; n=5 animals per group.

FIG. 12A shows representative images of H & E stained lung sections showing the extent of tissue fibrosis in wild-type and Ism1$^{\Delta/\Delta}$ mice at day 9 post-LPS challenge. FIGS. 12B-C show collagen deposition, as detected by Picro-sirius staining, was higher in the lungs of Ism1$^{\Delta/\Delta}$ mice. FIGS. 12D-E show immunofluorescent staining of a smooth muscle actin (α-SMA) reveals the increased myofibroblasts within the fibrotic foci in the lungs of Ism1$^{\Delta/\Delta}$ mice compared with that of the wild-type mice. ** represents p<0.01. Quantifications were performed with n=3 lungs per group, 2 sections per lung, 5 microscopic fields per section;

FIG. 13A shows representative images of SP-C and PCNA double immunofluorescent stained lung sections of Ism1$^{\Delta/\Delta}$ and wild-type mice at day 9 post-LPS challenge. FIG. 13B shows quantification of SP-C and PCNA double positive cells in the lung tissue sections on day 9 post-LPS challenge. Significant increase in the numbers of proliferating AEC2 in the lungs of Ism1$^{\Delta/\Delta}$ mice. *** represents p<0.001. Quantifications were performed with n=3 lungs per group, 2 sections per lung, 5 microscopic fields per section;

FIG. 14A is representative images of TGF-β immunofluorescent stained lung sections of Ism1$^{\Delta/\Delta}$ and wild-type mice at 9-days post-LPS challenge. FIG. 14B shows expression levels of TGF-β in the lung of Ism1$^{\Delta/\Delta}$ and wild-type mice at 9-days post-LPS challenge was analysed using Western blot and whole lung lysate. FIG. 14C shows quantification of lung TGF-β protein level in Ism1$^{\Delta/\Delta}$ mice at 9-days post-LPS challenge. ** represents p<0.01. n=3 lungs per group;

FIG. 15A shows relative changes of cytokines/chemokines analysed via antibody array. * represents p<0.05. n=4 lungs per group. FIGS. 15B-C show increased expression of TNF-α in Ism1$^{\Delta/\Delta}$ lung at 1-day post-LPS challenge analysed by Western blot. ** represents p<0.01. n=3 lungs per group;

FIG. 16A is representative images of immunofluorescent stained NF-κB p65 subunit in the lung sections of Ism1$^{d}$ and wild-type mice 1-day post-LPS challenge. Increased p65 NF-κB (red) signal co-localizing with DAPI (nucleus, blue) was present in the lung sections of Ism1$^{\Delta/\Delta}$ mice. FIG. 16B shows increased p65 NF-κB level in the lung homogenates of Ism1/at 1-day post-LPS challenge as shown by Western blot. FIG. 16C shows the quantitation amount of p65 NF-κB relative to β-actin. n=3 lungs per group;

FIG. 17a is a schematic diagram of CRISPR/Cas9 targeting Ism1 via guide RNA pair, gRNA1 and gRNA3. P1 and P2 denote primers used for T7E1 assay and genotyping. FIG. 17b shows the DNA sequence of the Ism1$^{\Delta/\Delta}$ knockout line, showing the 23 bp deletion which lead to a premature stop codon and no ISM1 protein produced. The red arrows indicate Cas9 cleavage sites and yellow region refers to the two overlapping gRNAs' target region. FIG. 17c shows RT-PCR of Ism1 mRNAs from C56BL/6J WT, Ism1$^{+/\Delta}$, Ism1$^{\Delta/\Delta}$. FIG. 17d shows representative immunohistochemistry staining for ISM1 (brown) and nuclei (haematoxylin, blue) in C57BL/6J WT and Ism1$^{\Delta/\Delta}$ mice lung sections. Br, bronchi; Al, alveolar. Scale bars, 20 μm;

FIG. 19A shows the AMOP domain in ISM1 is important in mediating ECs adhesion. ISM1$^{C}$ can support cell adhesion equivalently as ISM1 as there was no significant difference in the chance of confluence over time between the two proteins. ISM1$^{N}$ has reduced ability in supporting cell adhesion as the chance in confluence over time was significantly slower and lower.  p<0.01, n=3. FIG. 19B shows both mutants ISM1$^{RKD41RAA(C)}$ and ISM1$^{RKD40AAA(C)}$ had reduced ability in supporting cells adhesion as the rate of cell adhesion was significantly lower than ISM1C.  p<0.01, n=3;

FIGS. 20A-B depict ISM1$^{C}$, rather than ISM1$^{N}$, significantly triggered EC apoptosis. Error bars plotted as SD. * P<0.05, ** P<0.01, N=3;

FIG. 24 shows, without wishing to be bound by theory, proposed mechanism for ISM1 in regulating AM apoptosis and lung homeostasis and inflammation. (A) Left, autocrine/paracrine ISM1 specifically targets AMs with high csGRP78 and induces apoptosis. AM numbers are kept under control, inflammation is regulated and lung homeostasis is maintained. Right, no/low ISM1 results in AM accumulation in the alveolar space and onset of emphysema with progressive decline in lung function. (B) shows, without wishing to be bound by theory, a schematic diagram of a proposed mechanism for ISM1 in regulating AM apoptosis and lung homeostasis. Left, autocrine/paracrine ISM1 specifically targets AMs with high csGRP78 and induces apoptosis. AM numbers are kept under control, inflammation is regulated and lung homeostasis is maintained. Right, loss of ISM1 results in AM accumulation in the alveolar space and onset of emphysema with progressive decline in lung function. Emphysema mediators are upregulated including ROS, NF-κB signaling, MMP-12 and MMP-9;

FIG. 27 shows inflammatory cell count in the bronchoalveolar lavage fluid (BALF) 24 hours after the last treatment [Naïve, n=5; HDM, n=5; Saline, n=7; ISM1, n=7]. (A) Differential cell count was performed on ten different fields of observation to identify eosinophils (Eos), alveolar macrophages (AM), neutrophils (Neu), and lymphocytes (Lym). House dust mite (HDM) extract challenge markedly increased total cell count, eosinophils, alveolar macrophage, and slightly increased neutrophil and lymphocyte count as compared with the Naïve group. Isthmin 1 (ISM1) treated group, on the other hand, shows 70% reduction (P=0.0053) in the total cell number with a significant decrease in eosinophil (P=0.0062) and lymphocyte (P=0.0381) count. No changes were observed in the total count of alveolar macrophages and neutrophils. Values are shown as means t SEM. Significant difference from HDM. (B) Representative photomicrograph of Liu's stain showing immune cells infiltration. Scale bar, 40 µm;

FIG. 28 shows rISM1 treatment significantly lowered the total IgE level as compared to HDM treated group. The level of total IgE was analysed using BD OptEIA™ mouse IgE ELISA kit (N=5). Values are shown as means t SEM. Mean difference between groups was compared using one-way ANOVA, *P<0.05; **P<0.005;

FIG. 32 shows mammalian recombinant ISM1 is densely deposited with heterogeneous glycans. (A) Schematic presentation of the two N-glycosylation sites present in ISM1. (B) The mammalian recombinant ISM1 protein was incubated with PNGaseF to remove the N-linked glycans. (C) The wild type and N-glycan mutants of ISM1 were expressed and analyzed in HEK293T, HEK293FT and Hela cells. The protein expression and secretion were analyzed with western blot. (D) Summary diagram of O- and C-linked glycans deposition on ISM1. Red colored residues denote the glycan deposition sites. The first underlined sequences refer to the TSR domain, and the second underlined sequences corresponds to AMOP domain. (E) O- and C-glycan mutants of ISM1 were expressed and analyzed in HEK293FT cells;

DETAILED DESCRIPTION

Figure 1:
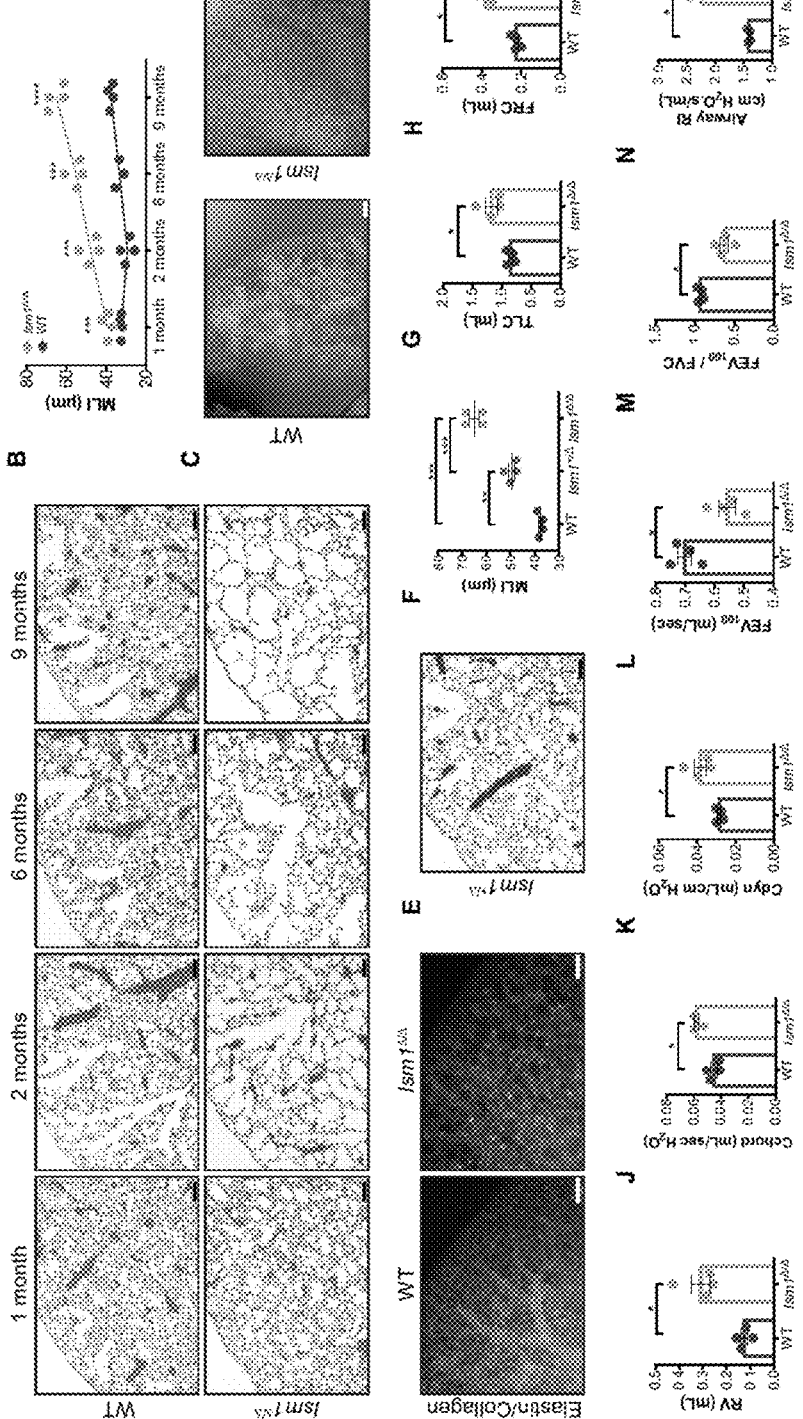

Described herein are peptides, polypeptides, nucleic acids, compositions, and methods for the treatment of diseases or disorders associated with inflammation, and particularly lung inflammation. It will be appreciated that embodiments and examples are provided for illustrative purposes intended for those skilled in the art, and are not meant to be limiting in any way.

Healthy adults regulate and maintain lung homeostasis under ambient environmental conditions, preventing sterile inflammation. Immune responses may be triggered by injury, environmental stressors, and/or infection, leading to acute inflammation. Desirably, such inflammation is eventually resolved to allow wound healing and recovery, and to prevent inflammation-induced disorders and/or damage. Failure to sufficiently resolve inflammation may lead to chronic inflammation and/or inflammatory-related diseases such as chronic obstructive pulmonary disorder (COPD), emphysema, chronic obstructive bronchitis, and/or lung fibrosis. Acute lung diseases such as acute lung injury (ALI), and acute respiratory distress syndrome (ARDS) are also related to inflammation of the lung.

As described in detail herein, the present inventors have now developed polypeptides, nucleic acids, compositions, pulmonary drug delivery devices, and methods for treating inflammation, such as lung inflammation, which are derived from and/or based on Isthmin 1 (ISM1), which is a secreted protein that is indicated by the studies described herein as playing a role in inhibiting, suppressing, and/or resolving inflammation, and particularly inflammation of the lung. In studies described in detail hereinbelow, supplementation of exogenous recombinant ISM1 protein (rISM1) to the lung inhibited the lung inflammation phenotype in ISM1-deficient lung, and results indicate that ISM1 may help to resolve inflammation by inducing alveolar macrophage apoptosis. As described herein, recombinant ISM1 (rISM1) may block cigarette smoke-induced COPD, and may suppress LPS-induced acute lung inflammation and injury, for example. Results indicate that ISM1 may play an important role in suppression and/or resolution of sterile lung inflammation and/or inflammation triggered by infection and/or injury.

Therapeutic Compositions. Formulations, and Devices for Treating Diseases or Disorders Associated with Inflammation Provided herein are therapeutic compositions, peptides, polypeptides, nucleic acids, formulations, and devices for the treatment, amelioration, or prevention of diseases or disorders associated with inflammation, and particularly lung inflammation, for example.

Isthmin 1 (ISM1, sometimes referred to as ISM) is a secreted protein found in several different vertebrate species. ISM1 protein includes a thrombospondin type 1 repeat (TSR) domain and an adhesion-associated domain in MUC4 and other proteins (AMOP) domain. Glucose-Regulated Protein 78 kDa (GRP78) and $\alpha v\beta 5$ integrin are known receptors for ISM1. Isthmin 1 (ISM1) has been previously associated with angiogenesis inhibition in mice (see Xiang, W. et al., 2011, Isthmin is a novel secreted angiogenesis inhibitor that inhibits tumour growth in mice, *Journal of Cellular and Molecular Medicine,* 15(2): 359-374, which is herein incorporated by reference in its entirety).

The sequence for full length Isthmin 1 in *Homo sapiens* as expressed (i.e. including N-terminal signal peptide) is as follows:

```
Isthmin-1 precursor [Homo sapiens]
NCBI Reference Sequence: NP_543016.1
                                  (SEQ ID NO: 1)
MVRLAAELLLLLGLLLLTLHITVLRGSGAADGPDAAAGNASQAQLQNNL

NVGSDTTSETSFSLSKEAPREHLDHQAAHQPFPRPRFRQETGHPSLQRD

FPRSFLLDLPNFPDLSKADINGQNPNIQVTIEVVDGPDSEADKDQHPEN

KPSWSVPSPDWRAWWQRSLSLARANSGDQDYKYDSTSDDSNFLNPPRGW

DHTAPGHRTFETKDQPEYDSTDGEGDWSLWSVCSVTCGNGNQKRTRSCG

YACTATESRTCDRPNCPGIEDTFRTAATEVSLLAGSEEFNATKLFEVDT

DSCERWMSCKSEFLKKYMHKVMNDLPSCPCSYPTEVAYSTADIFDRIKR

KDFRWKDASGPKEKLEIYKPTARYCIRSMLSLESTTLAAQHCCYGDNMQ

LITRGKGAGTPNLISTEFSAELHYKVDVLPWIICKGDWSRYNEARPPNN

GQKCTESPSDEDYIKQFQEAREY
```

The full length sequence of Isthmin 1 in mouse as expressed (i.e. including N-terminal signal peptide) is as follows:

```
Isthmin-1 precursor [Mus musculus]
NCBI Reference Sequence: NP_001263418.1
                                  (SEQ ID NO: 2)
MVRLAAELLLLLGLLLLTLHITVLRGSGASDRQDAAAGNVSGSQLQNNL

NLESDSTSETSFPLSKEAPEEHQVVHQPFPRQRFPPETGHPSLQRDGPR
```

```
SFLLDLPNFPDLSKADINGQNPNIQVTIEVVDGPDSEAEKDQHPENKPS

WSLPAPDWRAWWQRSLSLARTNSGDQDDKYDSTSDDSNFLSVPRGWDRP

APGHRTFETKEQPEYDSTDGEGDWSLWSVCSVTCGNGNQKRTRSCGYAC

IATESRTCDRPNCPGIEDTFRTAATEVSLLAGSEEFNATKLFEVDMDSC

ERWMSCKSEFLKKYMHKVINDLPSCPCSYPTEVAYSTADIFDRIKRKDF

RWKDASGPKEKLEIYKPTARYCIRSMLSLESTTLAAQHCCYGDNMQLIT

RGKGAGTPNLISTEFSAELHYKVDVLPWIICKGDWSRYNEARPPNNGQK

CTESPSDEDYIKQFQEAREY
```

These human (SEQ ID NO: 1) and mouse (SEQ ID NO: 2) ISM1 sequences include an N-terminal signal peptide sequence, as ISM1 is a secreted protein. This signal peptide sequence is shown in underlining above, and is typically cleaved off in the mature secreted form of ISM1. The TSR domain is shown in bold font, and the AMOP domain is shown in italic font in the above sequences.

Mature ISM1 in human and mouse, with the signal peptide sequence cleaved off, is shown below:

```
Isthmin-1 (mature) [Homo sapiens]
                                  (SEQ ID NO: 3)
GSGAADGPDAAAGNASQAQLQNNLNVGSDTTSETSFSLSKEAPREHLDH

QAAHQPFPRPRFRQETGHPSLQRDFPRSFLLDLPNFPDLSKADINGQNP

NIQVTIEVVDGPDSEADKDQHPENKPSWSVPSPDWRAWWQRSLSLARAN

SGDQDYKYDSTSDDSNFLNPPRGWDHTAPGHRTFETKDQPEYDSTDGEG

DWSLWSVCSVTCGNGNQKRTRSCGYACTATESRTCDRPNCPGIEDTFRT

AATEVSLLAGSEEFNATKLFEVDTDSCERWMSCKSEFLKKYMHKVMNDL

PSCPCSYPTEVAYSTADIFDRIKRKDFRWKDASGPKEKLEIYKPTARYC

IRSMLSLESTTLAAQHCCYGDNMQLITRGKGAGTPNLISTEFSAELHYK

VDVLPWIICKGDWSRYNEARPPNNGQKCTESPSDEDYIKQFQEAREY

Isthmin-1 (mature) [Mus musculus]
                                  (SEQ ID NO: 4)
GSGASDRQDAAAGNVSGSQLQNNLNLESDSTSETSFPLSKEAPEEHQVV

HQPFPRQRFPPETGHPSLQRDGPRSFLLDLPNFPDLSKADINGQNPNIQ

VTIEVVDGPDSEAEKDQHPENKPSWSLPAPDWRAWWQRSLSLARTNSGD

QDDKYDSTSDDSNFLSVPRGWDRPAPGHRTFETKEQPEYDSTDGEGDWS

LWSVCSVTCGNGNQKRTRSCGYACIATESRTCDRPNCPGIEDTFRTAAT

EVSLLAGSEEFNATKLFEVDMDSCERWMSCKSEFLKKYMHKVINDLPSC

PCSYPTEVAYSTADIFDRIKRKDFRWKDASGPKEKLEIYKPTARYCIRS

MLSLESTTLAAQHCCYGDNMQLITRGKGAGTPNLISTEFSAELHYKVDV

LPWIICKGDWSRYNEARPPNNGQKCTESPSDEDYIKQFQEAREY
```

As will be understood, references herein to Isthmin 1 (ISM1) protein may in certain embodiments be understood as referring to either full-length ISM1 (i.e. with the signal peptide present), or mature ISM1 (i.e. with the signal peptide removed). Because secreted ISM1 is typically found in the mature form (i.e. missing the signal peptide), the signal peptide sequence may be omitted in certain embodiments. Typically, mature ISM1 may be preferred in certain embodiments.

As will also be understood, references herein to Isthmin 1 (ISM1) protein may in certain embodiments include ISM1 as may be found in any suitable species which expresses ISM1 or a homolog, ortholog, paralog, or functional equivalent thereof. ISM1 is expressed by many different species. ISM sequences are further described in WO2009/113965, which is herein incorporated by reference in its entirety. In Xiang, W. et al., 2011, *Journal of Cellular and Molecular Medicine,* 15(2): 359-374 (which is herein incorporated by reference in its entirety), a sequence comparison is provided showing amino acid alignment of ISM as found in human, mouse, *Xenopus,* and zebrafish. Pairwise alignment scores of human ISM1 (precursor) with corresponding ISM sequences of several different species, as calculated by NCBI with HomoloGene, is shown below:

Pairwise Alignment Scores

| Gene | | Identity (%) | |
| Species | Symbol | Protein | DNA |
| H. sapiens | ISM1 | | |
| vs. P. troglodytes | ISM1 | 100.0 | 99.6 |
| vs. M. mulatta | ISM1 | 97.9 | 97.8 |
| vs. C. lupus | ISM1 | 95.7 | 94.0 |
| vs. B. taurus | ISM1 | 92.7 | 90.7 |
| vs. M. musculus | Ism1 | 93.5 | 89.2 |
| ys. R. norvegicus | Ism1 | 93.7 | 89.5 |
| vs. G. gallus | ISM1 | 82.8 | 74.7 |
| vs. X. tropicalis | LOC100487287 | 79.8 | 71.9 |
| vs. D. rerio | ism1 | 70.0 | 67.8 |

As can be seen, while ISM1 among different species is somewhat similar, sequence variation is observed. In terms of protein sequence, variations from the human sequence by as much as 30% sequence identity are shown in the scores above (i.e. the *D. rerio* sequence has 70% sequence identity with human ISM1).

In certain embodiments, there is provided herein a peptide or polypeptide comprising an amino acid sequence having at least 70% sequence identity with an Isthmin 1 (ISM1) protein, or a GRP78-activating fragment thereof. In certain embodiments, the polypeptide may comprise an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity with an Isthmin 1 (ISM1) protein, which may be any suitable ISM1 protein from any particular species, with or without an N-terminal signal peptide, or a GRP78-activating fragment thereof. In certain embodiments, the polypeptide may comprise any suitable polypeptide, peptide, or peptide-based or polypeptide-based molecule or grouping of molecules, which may or may not be further modified to include one or more additional proteinaceous or non-proteinaceous moieties such as a purification tag, linker, fluorophore, signal peptide, targeting or delivery sequence, cell penetrating peptide, an additional active agent (such as another drug for targeting lung inflammation), or other moiety appropriate for the particular application. In certain embodiments, the polypeptide may be modified at one or more amino acid side chains, at the N-terminus, at the C-terminus, or any combination thereof. In certain embodiments, the polypeptide may comprise, in addition to the amino acid sequence having at least 70% sequence identity with an Isthmin 1 (ISM1) protein or a GRP78-activating fragment thereof, one or more additional amino acid sequences which may be located either N-terminal or C-terminal to the sequence with identity to ISM1.

In certain embodiments, a GRP78-activating fragment of an Isthmin 1 (ISM1) protein may include any suitable peptide or polypeptide having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity with at least one fragment, portion, domain, or contiguous 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, or 440 amino acids of Isthmin 1, wherein said GRP78-activating fragment is capable of binding to and activating GRP78 with substantially the same efficacy as ISM1, or with at least 60%, at least 65%, at least 70%, at least 75%, at least 80%, at least 85%, at least 90%, or at least 95% efficacy as compared with ISM1.

In the studies described herein, it is shown that ISM1 is a pro-apoptotic ligand of GRP78, which binds to GRP78 to trigger apoptosis. Accordingly, ISM1 may be considered an agonist of GRP78. As a signal receptor, GRP78 may bind to many different ligands, which may occur via different regions of the protein (a review of GRP78 may be found in Ni, et al., *Biochem J.,* 2011, 434(2): 181-188, which is herein incorporated by reference in its entirety). Some ligands may be pro-proliferative, others pro-apoptotic, etc., and each may have a different intracellular signal pathway. ISM1 interaction with GRP78 may, in certain embodiments, involve intracellular signalling pathway(s) which may involve ISM1 internalization and/or caspase activation. Accordingly, in certain embodiments, a GRP78-activating fragment may include any suitable peptide or polypeptide which is capable of functioning as a pro-apoptotic ligand of GRP78, and/or which is capable of binding to GRP78 and triggering apoptosis. In certain embodiments, a GRP78-activating fragment of an ISM1 protein may include any suitable peptide or polypeptide which is capable of triggering apoptosis via GRP78, which may or may not include internalization of the fragment and/or caspase activation.

In certain embodiments, references herein to GRP78, or GRP78 receptor, may be understood as including cell surface GRP78 (csGRP78). It is cell surface GRP78 (csGRP78) with which extracellular ISM1 interacts, and so the skilled person having regard to the teachings herein will understand that references herein to GRP78 may be understood as referring to csGRP78 where appropriate (i.e. in certain embodiments, references herein to GRP78 will be understood as references to csGRP78).

It is contemplated that in certain embodiments, AMOP domain may mediate ISM1's binding to GRP78, and/or may mediate ISM1's pro-apoptosis activity. It is further contemplated that in certain embodiments, TSR domain of ISM1 may have little or no involvement in ISM1's binding to GRP78 and/or ISM1's pro-apoptosis effects. Indeed, results suggest that AMOP domain may be responsible for GRP78 binding, and for triggering apoptosis (see Example 3 below for further detail). Accordingly, in certain embodiments, the peptide or polypeptide may comprise generally any suitable peptide or polypeptide or peptide-based or polypeptide-based molecule having at least an AMOP domain of ISM1, or a sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity therewith. In embodiments where the polypeptide includes more than one domain or region from ISM1, the domains or regions may be organized in generally the same N-C terminal ordering as found in ISM1, or may be rearranged as compared with ISM1. ISM1 domains and fragments are described in additional detail in WO2009/113965, entitled Isthmin Derivatives for use in Treating Angiogenesis, which is herein incorporated by reference in its entirety.

In certain embodiments, there is provided herein a peptide or polypeptide comprising an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity with any one of SEQ ID NOS: 10 or 11:

```
SEQ ID NO: 10 - Human ISM1 AMOP domain
FEVDTDSCERWMSCKSEFLKKYMHKVMNDLPSCPCSYPTEVAYSTADIF

DRIKRKDFRWKDASGPKEKLEIYKPTARYCIRSMLSLESTTLAAQHCCY

GDNMQLITRGKGAGTPNLISTEFSAELHYKVDVLPWIICKGDWSRYNEA

RPPNNGQKCTESPSDED

SEQ ID NO: 11 - Mouse ISM1 AMOP domain
FEVDMDSCERWMSCKSEFLKKYMHKVINDLPSCPCSYPTEVAYSTADIF

DRIKRKDFRWKDASGPKEKLEIYKPTARYCIRSMLSLESTTLAAQHCCY

GDNMQLITRGKGAGTPNLISTEFSAELHYKVDVLPWIICKGDWSRYNEA

RPPNNGQKCTESPSDED
```

In certain embodiments, there is provided herein a peptide or polypeptide comprising an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity with any one of SEQ ID NOS: 1-4, or a contiguous 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, or 440 amino acids thereof.

In certain embodiments, there is provided herein a polypeptide comprising or consisting of any one of SEQ ID NOs: 1-4. In certain embodiments, there is provided herein a polypeptide which is Isthmin 1 protein, or which comprises Isthmin 1 protein. In certain embodiments, there is provided herein a polypeptide which is human ISM1 protein, or which comprises human ISM1 protein.

In certain embodiments, there is provided herein a polypeptide or peptide comprising or consisting of the amino acid sequence:

```
                                    (SEQ ID NO: 26)
FEVDMDSCERWMSCKSEFLKKYMHKVINDLPSCPCSYPTEVAYSTADIF
DRIKRKDFRWKDASGPKEKLEIYKPTARYCIRSMLSLE;
``` or an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity therewith.

Results described in Example 3 indicate that the polypeptide sequence of SEQ ID NO: 26 may be sufficient for binding to GRP78. Example 3 shows effective results without EVSLLAGSEEFNATKL (SEQ ID NO: 39) sequence that precedes SEQ ID NO: 26 in ISM1 (i.e. positions 271-286). Accordingly, in certain embodiments, polypeptides or peptides or GRP78-activating fragments thereof may include polypeptides or peptides or GRP78-activiating fragments thereof comprising or consisting of the amino acid sequence

```
                                    (SEQ ID NO: 26)
FEVDMDSCERWMSCKSEFLKKYMHKVINDLPSCPCSYPTEVAYSTADIF
DRIKRKDFRWKDASGPKEKLEIYKPTARYCIRSMLSLE;
``` or an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity therewith, or a GRP78-activating fragment thereof.

In certain embodiments, there is provided herein a polypeptide or peptide comprising or consisting of the amino acid sequence:

```
                                    (SEQ ID NO: 24)
FEVDMDSCERWMSCKSEFLKKYMHKVINDLPSCPCSYPTEVAYSTADIF

DRIKRKDFRWKDASGPKEKLEIYKPTARYCIRSMLSLESTTLAAQHCCY

GDNMQLITRGKGAGTPNLISTEFSAELHYKVDVLPWIICKGDWSRYNEA

RPPNNGQKCTESPSDEDYIKQFQEAREY;
``` or an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity therewith.

Results described in Example 3 indicate that the polypeptide sequence of SEQ ID NO: 24 may be sufficient for binding to GRP78, may support EC adhesion, may be internalized, may be localized in mitochondria, and may induce apoptosis. Example 3 shows effective results without EVSLLAGSEEFNATKL (SEQ ID NO: 39) sequence that precedes SEQ ID NO: 26 in ISM1 (i.e. positions 271-286). Accordingly, in certain embodiments, polypeptides or peptides or GRP78-activating fragments thereof may include polypeptides or peptides or GRP78-activiating fragments thereof comprising or consisting of the amino acid sequence

```
                                     (SEQ ID NO: 24)
FEVDMDSCERWMSCKSEFLKKYMHKVINDLPSCPCSYPTEVAYSTADIF

DRIKRKDFRWKDASGPKEKLEIYKPTARYCIRSMLSLESTTLAAQHCCY

GDNMQLITRGKGAGTPNLISTEFSAELHYKVDVLPWIICKGDWSRYNEA

RPPNNGQKCTESPSDEDYIKQFQEAREY;
``` or an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity therewith, or a GRP78-activating fragment thereof.

The amino acid sequence of SEQ ID NO: 26 is an N-terminal portion of a C-terminal region of mouse ISM1 in which the AMOP domain is located, and comprises sequence from an N-terminal portion of the AMOP domain (ISM1$^{C-N}$, residues 2287-373). The amino acid sequence of SEQ ID NO: 24 is a C-terminal region of mouse ISM1 containing the AMOP domain, but not TSR domain (ISM1$^{C}$, residues 287-461). Each of SEQ ID NOs: 26 and 24 are derived from mouse ISM1 sequence, however it will be understood that in certain embodiments, corresponding sequences/regions from ISM1 of another species may be used. By way of example, in certain embodiments, there is provided herein a peptide or polypeptide or GRP78-activating fragment thereof comprising or consisting of an amino acid sequence found within human ISM1 which corresponds with region 287-373 (SEQ ID NO: 26) or region 287-461 (SEQ ID NO: 25) of mouse ISM1 (see corresponding human sequence, for example region 290-464 in human), or an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity therewith, or a GRP78-activating fragment thereof.

```
                          (SEQ ID NO: 27; human ISM1$^{C-N}$)
FEVDTDSCERWMSCKSEFLKKYMHKVMNDLPSCPCSYPTEVAYSTADIF

DRIKRKDFRWKDASGPKEKLEIYKPTARYCIRSMLSLE (SEQ ID NO: 24 - mouse ISM1 287-461)
FEVDMDSCERWMSCKSEFLKKYMHKVINDLPSCPCSYPTEVAYSTADIF

DRIKRKDFRWKDASGPKEKLEIYKPTARYCIRSMLSLESTTLAAQHCCY

GDNMQLITRGKGAGTPNLISTEFSAELHYKVDVLPWIICKGDWSRYNEA

RPPNNGQKCTESPSDEDYIKQFQEAREY; or (SEQ ID NO: 25 - human ISM1 290-464)
FEVDTDSCERWMSCKSEFLKKYMHKVMNDLPSCPCSYPTEVAYSTADIF

DRIKRKDFRWKDASGPKEKLEIYKPTARYCIRSMLSLESTTLAAQHCCY
```

-continued
```
GDNMQLITRGKGAGTPNLISTEFSAELHYKVDVLPWIICKGDWSRYNEA

RPPNNGQKCTESPSDEDYIKQFQEAREY
```

In certain embodiments, the above peptides or polypeptides or GRP78-activating fragments thereof may, or may not, further comprise an N-terminal signal peptide sequence of ISM1.

In certain embodiments, the above peptide or polypeptide or GRP78-activating fragment thereof is not full length or mature ISM1 (i.e. in certain embodiments, the peptide or polypeptide or GRP78-activating fragment thereof may be an exogenous peptide or polypeptide which is not naturally expressed in a cell or subject). In certain embodiments, the peptide or polypeptide or GRP78-activating fragment thereof may be longer or shorter than full length or mature ISM1. In certain embodiments, the peptide or polypeptide or GRP78-activating fragment thereof may have a primary amino acid sequence which differs from a naturally expressed ISM1 with respect to at least one residue (i.e. the peptide or polypeptide or GRP78-activating fragment thereof may comprise one or more amino acid additions, deletions, or substitutions as compared with naturally expressed ISM1 from a human or other species, for example). In certain embodiments, the peptide or polypeptide or GRP78-activating fragment thereof may comprise one or more conservative amino acid substitutions as compared with naturally expressed ISM1, for example.

In certain embodiments, the above peptide or polypeptide or GRP78-activating fragment thereof may comprise or consist of:

```
                                     (SEQ ID NO: 26)
FEVDMDSCERWMSCKSEFLKKYMHKVINDLPSCPCSYPTEVAYSTADIF

DRIKRKDFRWKDASGPKEKLEIYKPTARYCIRSMLSLE;

(SEQ ID NO: 24)
FEVDMDSCERWMSCKSEFLKKYMHKVINDLPSCPCSYPTEVAYSTADIF

DRIKRKDFRWKDASGPKEKLEIYKPTARYCIRSMLSLESTTLAAQHCCY

GDNMQLITRGKGAGTPNLISTEFSAELHYKVDVLPWIICKGDWSRYNEA

RPPNNGQKCTESPSDEDYIKQFQEAREY;

(SEQ ID NO: 27)
FEVDTDSCERWMSCKSEFLKKYMHKVMNDLPSCPCSYPTEVAYSTADIF

DRIKRKDFRWKDASGPKEKLEIYKPTARYCIRSMLSLE; or (SEQ ID NO: 25 - human ISM1 290-464)
FEVDTDSCERWMSCKSEFLKKYMHKVMNDLPSCPCSYPTEVAYSTADIF

DRIKRKDFRWKDASGPKEKLEIYKPTARYCIRSMLSLESTTLAAQHCCY

GDNMQLITRGKGAGTPNLISTEFSAELHYKVDVLPWIICKGDWSRYNEA

RPPNNGQKCTESPSDEDYIKQFQEAREY
``` or an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity therewith, or a GRP78-activating fragment thereof.

In another embodiment of the above peptide or polypeptide or GRP78-activating fragment, the peptide or polypeptide or GRP78-activating fragment does not comprise the amino acid sequence EVSLLAGSEEFNATKL (SEQ ID NO: 39) N-terminal to any of SEQ ID Nos: 24-27, or does not comprise the sequence EVSLLAGSEEFNATKL (SEQ ID NO: 39) at all. In another embodiment, the peptide or polypeptide or GRP78-activiating fragment does not comprise, or is not the sequence of:

```
                              (SEQ ID NO: 12)
EVSLLAGSEEFNATKLFEVDMDSCERWMSCKSEFLKKYMHKVINDLPSC

PCSYPTEVAYSTADIFDRIKRKDFRWKDASGPKEKLEIYKPTARYCIRS

MLSLE;

(SEQ ID NO: 20)
EVSLLAGSEEFNATKLFEVDTDSCERWMSCKSEFLKKYMHKVMNDLPSC

PCSYPTEVAYSTADIFDRIKRKDFRWKDASGPKEKLEIYKPTARYCIRS

MLSLE;

(SEQ ID NO: 13)
EVSLLAGSEEFNATKLFEVDMDSCERWMSCKSEFLKKYMHKVINDLPSC

PCSYPTEVAYSTADIFDRIKRKDFRWKDASGPKEKLEIYKPTARYCIRS

MLSLESTTLAAQHCCYGDNMQLITRGKGAGTPNLISTEFSAELHYKVDV

LPWIICKGDWSRYNEARPPNNGQKCTESPSDEDYIKQFQEAREY; or (SEQ ID NO: 21)
EVSLLAGSEEFNATKLFEVDTDSCERWMSCKSEFLKKYMHKVMNDLPSC

PCSYPTEVAYSTADIFDRIKRKDFRWKDASGPKEKLEIYKPTARYCIRS

MLSLESTTLAAQHCCYGDNMQLITRGKGAGTPNLISTEFSAELHYKVDV

LPWIICKGDWSRYNEARPPNNGQKCTESPSDEDYIKQFQEAREY.
```

In certain embodiments, the above peptide or polypeptide or GRP78-activating fragment thereof may comprise an isolated peptide or polypeptide or GRP78-activating fragment thereof.

In certain embodiments, polypeptides or peptides or GRP78-activating fragments thereof as described herein, including those having at least 70% sequence identity with an ISM1 protein or a GRP78-activating fragment thereof, may include polypeptides or peptides or GRP78-activating fragments thereof having at least one mutation (i.e. an amino acid addition, deletion, or substitution) versus naturally expressed full length or mature ISM1 in a particular species. In certain embodiments, the at least one mutation may, or may not, comprise an amino acid substitution. In certain embodiments, the at least one mutation may, or may not, comprise a conservative amino acid substitution in which an amino acid residue is substituted with another amino acid reside which is at least somewhat similar to the original residue with respect to at least one of size, charge, hydrophilicity/hydrophobicity, hydrogen-bonding, or any combination thereof. In certain embodiments, the at least one mutation may, or may not, comprise a conservative amino acid substitution in which an amino acid residue is substituted with another amino acid reside which is generally considered unobtrusive or non-disruptive to the desired function at the substituted position, such as glycine or alanine for example.

Studies in Example 3 include discussion of polypeptides (ISM1$^{C-N}$ mutants) having KD341AA and RKD340AAA mutations. These mutations may cause ISM1 to lose binding affinity with αvβ5 integrin receptor, but as discussed in Example 3 binding with GRP78 was not disrupted by these mutations, suggesting that such mutated sequences may provide for more specific targeting of the target GRP78 receptor. Accordingly, in certain embodiments, polypeptides or peptides or GRP78-activating fragments thereof may include a KD341AA mutation, or an RKD340AAA mutation. As will be understood, the "341" and "340" numbering is provided with respect to the mouse sequence, and may vary between species. By way of example, numbering of the KD-AA and RKD-AAA may change when referring to numbering in human ISM1 sequence (corresponding human mutations would be KD343AA and RKD342AAA, for example).

Accordingly, in certain embodiments, polypeptides or peptides or GRP78-activiating fragments thereof may include polypeptides or peptides or GRP78-activiating fragments thereof comprising or consisting of the amino acid sequence FEVDMDSCERWMSCKSEFLKKYMHKVIN-DLPSCPCSYPTEVAYSTADIFDRIKRAAFRW KDASGPKEKLEIYKPTARYCIRSMLSLE (SEQ ID NO: 14, N-terminal portion of C-terminal region containing mouse AMOP domain, residues 287-373, with a K5341AA mutation), or a correspondingly mutated region from another species, or an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity therewith, or a GRP78-activating fragment thereof.

In certain embodiments, polypeptides or peptides or GRP78-activiating fragments thereof may include polypeptides or peptides or GRP78-activiating fragments thereof comprising or consisting of the amino acid sequence FEVDMDSCERWMSCKSEFLKKYMHKVINDLP-SCPCSYPTEVAYSTADIFDRIKAAAFRW KDASGPKEKLEIYKPTARYCIRSMLSLE (SEQ ID NO: 15, N-terminal portion of C-terminal region containing mouse AMOP domain, residues 287-373, with an RKD340AAA mutation), or a correspondingly mutated region from another species, or an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity therewith, or a GRP78-activating fragment thereof.

As discussed in Example 3, results indicate that the C-terminal AMOP domain alone was sufficient to mediate pro-apoptotic activity of ISM1. Indeed, as discussed in Example 3 below, structure-function relationship studies using truncations of the ISM1 protein showed that the C-terminal AMOP domain from 287-461 retains the full pro-apoptotic activity of the full-length ISM1 protein, and post-translational modification is not required for the AMOP domain to mediate the pro-apoptotic activity of ISM1. Accordingly, in certain embodiments, polypeptides or peptides or GRP78-activiating fragments thereof may include polypeptides or peptides or GRP78-activiating fragments thereof comprising or consisting of the amino acid sequence:

```
                              (SEQ ID NO: 24; mouse)
FEVDMDSCERWMSCKSEFLKKYMHKVINDLPSCPCSYPTEVAYSTADIF

DRIKRKDFRWKDASGPKEKLEIYKPTARYCIRSMLSLESTTLAAQHCCY
```

-continued

```
GDNMQLITRGKGAGTPNLISTEFSAELHYKVDVLPWIICKGDWSRYNEA

RPPNNGQKCTESPSDEDYIKQFQEAREY; or (SEQ ID NO: 25; human)
FEVDTDSCERWMSCKSEFLKKYMHKVMNDLPSCPCSYPTEVAYSTADIF

DRIKRKDFRWKDASGPKEKLEIYKPTARYCIRSMLSLESTTLAAQHCCY

GDNMQLITRGKGAGTPNLISTEFSAELHYKVDVLPWIICKGDWSRYNEA

RPPNNGQKCTESPSDEDYIKQFQEAREY;
``` or an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity therewith.

SEQ ID NOs: 24 and 25 are derived from mouse and human ISM1 sequence, respectively; however, it will be understood that in certain embodiments, corresponding sequences/regions from ISM1 of another species may be used.

In certain embodiments, polypeptides or peptides or GRP78-activating fragments thereof may include chemically modified polypeptides or peptides, or peptidomimetics derived from or based on the polypeptides or peptides. By way of example, in certain embodiments polypeptides or peptides or GRP78-activating fragments thereof may include chemically modified polypeptides or peptides, or peptidomimetics derived from or based on the polypeptides or peptides, which may include one or more of cyclized derivatives, derivatives comprising one or more non-natural amino acid residues (such as D-amino acids), and/or peptidomimetics or other constructs comprising one or more different chemical bonds or linkages other than a peptide bond, among others such as peptoids and β-peptides. In certain embodiments, examples of peptide-derived agents derived from ISM1 may include those described in Kao et al., EBioMedicine 33 (2018) 22-32 (which is herein incorporated by reference in its entirety), such as BC71.

In certain embodiments, peptides or polypeptides as described herein may be formulated for administration to the lung of a subject in need thereof. The person of skill in the art having regard to the teachings herein will be aware of a variety of suitable approaches and techniques for formulating agents for administration to the lung (i.e. for pulmonary delivery). Delivery of agents, and particularly proteins, to the lung has been the subject of significant study, as described in, for example, Bodier-Montagutelli, E., et al., 2018, Designing inhaled protein therapeutics for topical lung delivery: what are the next steps?, *Expert Opinion on Drug Delivery*, 15(8): 729-736; and Labiris, N. R., et al., 2003, Pulmonary Drug Delivery. Part II: The role of inhalant delivery devices and drug formulations in therapeutic effectiveness of aerosolized medications, *Br J Clin Pharmacol*, 56:600-612, each of which are herein incorporated by reference in their entirety.

In certain embodiments the polypeptides, peptides or nucleic acids described herein may be for local administration to the lung. By way of example in certain embodiments, the polypeptides, peptides or nucleic acids described herein may be directly or locally administered to the lung by intratracheal, intranasal, or inhalation administration.

In certain embodiments, the peptides or polypeptides described herein may be formulated for intratracheal administration, intranasal administration, or inhalation administration to a subject in need thereof. In certain embodiments, the polypeptide may be formulated for administration as an aerosol, an inhaler, or a nebulizer. In certain embodiments, the polypeptide may be formulated as a dry powder for administration to the lung by aerosolization, or as a liquid for administration to the lung by nebulization.

In certain embodiments, the polypeptides as described herein may be for use in modulating GRP78 activity in a subject in need thereof; inducing apoptosis in alveolar macrophages (AM) or other immune cells; treating, ameliorating, or preventing lung inflammation in a subject in need thereof; treating, ameliorating, or preventing a lung disease or disorder associated with lung inflammation in a subject in need thereof; treating, ameliorating, or preventing chronic obstructive pulmonary disease (COPD) or emphysema in a subject in need thereof; treating, ameliorating, or preventing asthma in a subject in need thereof; treating, ameliorating, or preventing acute lung injury (ALI) or acute respiratory distress syndrome (ARDS) in a subject in need thereof; treating, ameliorating, or preventing lung fibrosis in subject in need thereof; or any combination thereof.

In certain embodiments, it is contemplated that peptides or polypeptides as described herein may optionally be covalently or non-covalently conjugated or complexed with (optionally through a biocleavable linker, for example), or may optionally be for use in combination with, simultaneously with, or sequentially with, one or more additional agents for preventing or reducing lung inflammation in a subject in need thereof. Conventional agents for preventing or reducing lung inflammation will be known to the person of skill in the art having regard to the teachings herein, and may include, for example, steroids.

Conventional agents for treatment or controlling of COPD, for example, may include combined inhaled LABA+ inhaled LAMA, which may improve lung function and reduce exacerbation in COPD patients. LABA (long-acting β2-agonist) and LAMA (long-acting muscarinic-antagonist) are bronchodilators providing symptomatic control. Examples of LABA are salmeterol and formoterol. Examples of LAMA are tiotropium bromide and glycopyrronium bromide. In most COPD, patients show poor response to corticosteroid, and due to its side effect profile, anti-inflammatory inhaled corticosteroid (ICS) is typically not given alone. It is usually combined with LABA such as formoterol+beclomethasone or salmeterol+fluticasone. Triple inhaled therapy are also used, combining LABA+ LAMA+ICS for very severe COPD and reduction of COPD exacerbation. A newer anti-inflammatory agent roflumilast, a phosphodiesterase 4 (PDE4) inhibitor, may improve lung function and reduce moderate and severe exacerbations. However, this drug comes with major dose-limiting side effects (see GOLD guideline or NICE guideline available online).

In certain embodiments, there is provided herein a peptide or polypeptide comprising an amino acid sequence having at least 70% sequence identity with an Isthmin 1 (ISM1) protein or a GRP78-activating fragment thereof, or an expressible nucleic acid encoding said polypeptide, for use in treating, ameliorating, or preventing a disease or disorder associated with macrophage-mediated inflammation in a subject in need thereof.

In another embodiment, there is provided herein a nucleic acid encoding a peptide or polypeptide comprising an amino acid sequence having at least 70% sequence identity with an Isthmin 1 (ISM1) protein or a GRP78-activating fragment thereof. Nucleotide codons corresponding with a given amino acid are well-known, and the skilled person having regard to the teachings herein will be readily able to select a suitable nucleic acid to encode a given polypeptide. In certain embodiments, the nucleic acid sequence may be selected such that the coding region uses codons which are optimized for expression in a particular organism of interest (for example, codons may be optimized for expression in *E. coli* when using the nucleic acid to produce polypeptide in *E. coli*, or may be optimized for expression in humans when the nucleic acid is to be administered to a human to cause in vivo expression of the polypeptide). In certain embodiments, the nucleic acid may be an expressible nucleic acid (i.e. the nucleic acid may be designed to result in expression of the polypeptide when introduced or present in a given cell). In certain embodiments, the nucleic acid may be DNA or RNA. In certain embodiments, the nucleic acid may be a plasmid, expression vector, or mRNA (which may, in certain embodiments, include sequence appropriate for translation in a cell of interest such as a start codon, poly-A tail, RBS sequence, etc. . . . ), with appropriate upstream and/or downstream sequence such that translation, or transcription and translation, of the nucleic acid may occur once the nucleic acid is introduced to a cell so as to provide the polypeptide. In embodiments where the nucleic acid is to be introduced into lung cells of a subject so as to express the polypeptide therein, it is contemplated that in certain embodiments the polypeptide encoded by the nucleic acid may include a signal peptide sequence such that the polypeptide is secreted.

Suitable expression vector techniques for overexpressing or introducing a particular polypeptide into a cell are known in the art (see, for example, Molecular Cloning: A Laboratory Manual (4th Ed.), 2012, Cold Spring Harbor Laboratory Press). As will be known to one of skill in the art, nucleotide sequences for expressing a particular polypeptide may encode or include features as described in "Genes VII", Lewin, B. Oxford University Press (2000) or "Molecular Cloning: A Laboratory Manual", Sambrook et al., Cold Spring Harbor Laboratory, 3rd edition (2001). A nucleotide sequence encoding a particular polypeptide may be incorporated into a suitable vector, such as a commercially available vector. Vectors may also be individually constructed or modified using standard molecular biology techniques, as outlined, for example, in Sambrook et al. (Cold Spring Harbor Laboratory, 3rd edition (2001)). The person of skill in the art will recognize that a vector may include nucleotide sequences encoding desired elements that may be operably linked to a nucleotide sequence encoding a polypeptide. Such nucleotide sequences encoding desired elements may include transcriptional promoters (for example, a constitutive or inducible promoter), transcriptional enhancers, transcriptional terminators, and/or an origin of replication. Selection of a suitable vector may depend upon several factors, including, without limitation, the size of the nucleic acid to be incorporated into the vector, the type of transcriptional and translational control elements desired, the level of expression desired, copy number desired, whether chromosomal integration is desired, the type of selection process that is desired, or the host cell or the host range that is intended to be transformed.

In embodiments wherein the nucleic acid is to be introduced into a subject or cell for the purpose of producing the polypeptide therein (for example, in the manufacture of the polypeptide, or for in vitro or in vivo treatment applications), it is contemplated that in certain embodiments the nucleic acid may be complexed with a suitable nucleic acid delivery vehicle or transfection reagent suitable for introducing the nucleic acid into the cell. In certain embodiments, the nucleic acid may be incorporated into a virus for delivery into a cell, and the nucleic acid may or may not become integrated into the genome of the cell. The person of skill in the art having regard to the teachings herein will be aware of a variety of delivery vehicles, transfection reagents, and/or viral delivery constructs which may be selected to deliver a nucleic acid as described herein to a given cell or subject in need thereof.

In another embodiment, there is provided herein a nucleic acid sequence which is fully or partially complementary to any of the nucleic acid sequences described herein.

As referenced herein, percent (%) identity or % sequence identity with respect to a particular sequence, or a specified portion thereof, may be defined as the percentage of nucleotides or amino acids in the candidate sequence identical with the nucleotides or amino acids in the subject sequence (or specified portion thereof), after aligning the sequences and introducing gaps, if necessary, to achieve the maximum percent sequence identity, as generated by the program WU-BLAST-2.0 with search parameters set to default values (Altschul et al., J. Mol. Biol. (1990) 215:403-410; website at blast.wustl.edu/blast/README.html). By way of example, a % identity value may be determined by the number of matching identical nucleotides or amino acids divided by the sequence length for which the percent identity is being reported. Percent (%) amino acid sequence similarity may be determined by the same calculation as used for determining % amino acid sequence identity, but may, for example, include conservative amino acid substitutions in addition to identical amino acids in the computation. Oligonucleotide or amino acid alignment algorithms such as, for example, BLAST (GenBank; using default parameters) may be used to calculate sequence identity %.

In another embodiment, there is provided herein a composition comprising:

a polypeptide comprising an amino acid sequence having at least 70% sequence identity with an Isthmin 1 (ISM1) protein or a GRP78-activating fragment thereof, or an expressible nucleic acid encoding said polypeptide; and a pharmaceutically acceptable carrier, diluent, or excipient;

the composition being formulated for administration to the lung of a subject.

In certain embodiments, the polypeptide or expressible nucleic acid may comprise a polypeptide or expressible nucleic acid as described above, or as described elsewhere herein.

In certain embodiments, a pharmaceutically acceptable carrier, diluent, or excipient may include any suitable carrier, diluent, or excipient known to the person of skill in the art having regard to the teachings herein. Examples of pharmaceutically acceptable excipients may include, but are not limited to, cellulose derivatives, sucrose, and starch. The person of skill in the art will recognize that pharmaceutically acceptable excipients may include suitable fillers, binders, lubricants, buffers, glidants, dispersants, and/or disintegrants known in the art (see, for example, Remington: The Science and Practice of Pharmacy (2006)). Examples of pharmaceutically acceptable carriers, diluents, and excipients may be found in, for example, Remington's Pharmaceutical Sciences (2000-20th edition) and in the United States Pharmacopeia: The National Formulary (USP 24 NF19) published in 1999. The skilled person having regard to the teachings herein will be aware of suitable pharmaceutically acceptable carriers, diluents, and excipients appropriate for formulating polypeptides and/or nucleic acids as described herein to the lung of a subject in need thereof. In certain embodiments, the polypeptides and/or nucleic acids and/or compositions as described herein may be formulated with a propellant or carrier gas, which may or may not be pressurized, as a pharmaceutically acceptable carrier.

In certain embodiments, aerosol delivery of macromolecules such as proteins and peptides may be given via devices like dry powder inhalers (DPI), or nebulizers. Excipients commonly used for such macromolecules may include any one or more of surfactants, sugars (for example, sucrose, trehalose) and/or polyols (for example, PEG). Amino acids (for example, glycine, lysine) are commonly used as stabilizers. See, for example, Expert Opin Drug Deliv (2018) 15:729-736, and Adv Drug Deliv Rev (2015), 93:79-94, which are herein incorporated by reference in their entireties.

In certain embodiments, polypeptides, nucleic acids, and/or compositions as described herein may be formulated for administration to the lung of a subject in need thereof. The person of skill in the art having regard to the teachings herein will be aware of a variety of suitable approaches and techniques for formulating agents for administration to the lung (i.e. for pulmonary delivery). Delivery of agents, and particularly proteins, to the lung has been the subject of significant study, as described in, for example, Bodier-Montagutelli, E., et al., 2018, Designing inhaled protein therapeutics for topical lung delivery: what are the next steps?, *Expert Opinion on Drug Delivery,* 15(8): 729-736; Labiris, N. R., et al., 2003, Pulmonary Drug Delivery. Part II: The role of inhalant delivery devices and drug formulations in therapeutic effectiveness of aerosolized medications, *Br J Clin Pharmacol,* 56:600-612; and Ibrahim, M., et al., 2015, Inhalation drug delivery devices: technology update, *Med Devices (Auckl),* 8:131-9, each of which are herein incorporated by reference in their entirety. In certain embodiments, polypeptides, nucleic acids, and/or compositions as described herein may be for delivery to the lung using a suitable drug delivery device. In certain embodiments, drug delivery devices may take the form of pulmonary devices such as, inhalers, nebulizers, aerosols, puffers, nasal sprays, or other suitable delivery device for administration to the lung. Examples of lung delivery devices are described in, for example, U.S. Pat. Nos. 5,983,893, 6,732,732, US20070295332, U.S. Pat. Nos. 5,007,419, 4,832,015, US20040244794, US20100065048, US20030235555, US20050201951, and US20090000615, each of which are herein incorporated by reference in their entireties.

In certain embodiments, the compositions described herein may be formulated for intratracheal administration, intranasal administration, or inhalation administration to a subject in need thereof. In certain embodiments, the composition may be formulated for administration as an aerosol, an inhaler, or a nebulizer. In certain embodiments, the composition may be formulated as a dry powder for administration to the lung by aerosolization, or as a liquid for administration to the lung by nebulization.

In certain embodiments, the compositions as described herein may be for use in modulating GRP78 activity in a subject in need thereof; inducing apoptosis in pro-inflammatory cells in a subject in need thereof; inducing apoptosis in alveolar macrophages (AM); reducing AM levels in a subject in need thereof; treating, ameliorating, or preventing lung inflammation in a subject in need thereof; treating, ameliorating, or preventing a lung disease or disorder associated with lung inflammation in a subject in need thereof; treating, ameliorating, or preventing chronic obstructive pulmonary disease (COPD), chronic obstructive bronchitis, or emphysema in a subject in need thereof; treating, ameliorating, or preventing asthma in a subject in need thereof; treating, ameliorating, or preventing acute lung injury (ALI) or acute respiratory distress syndrome (ARDS) in a subject in need thereof; preventing or reducing hyper-proliferation of alveolar wall surface type II (AE2) cells in a subject in need thereof; treating, ameliorating, or preventing lung fibrosis in subject in need thereof; or any combination thereof.

In certain embodiments, pro-inflammatory cells may include any one or more of innate and/or adaptive immune cells, such as macrophages, neutrophils, T and B lymphocytes, NK cells, or others. In the lung, macrophages may include alveolar macrophages, interstitial macrophages, or both.

In certain embodiments, lung diseases or disorders associated with lung inflammation may include any one or more of COPD, idiopathic pulmonary fibrosis (IPF), ALI, ARDS, asthma, chronic bronchitis, emphysema, pneumonia, or others.

In certain embodiments, it is contemplated that compositions as described herein may optionally further comprise, or may optionally be for use in combination with, simultaneously with, or sequentially with, one or more additional agents for preventing or reducing lung inflammation in a subject in need thereof. Conventional agents for preventing or reducing lung inflammation will be known to the person of skill in the art having regard to the teachings herein, and may include, for example, steroids. Examples of conventional agents have already been described hereinabove.

In still another embodiment, there is provided herein a pulmonary drug delivery device comprising a polypeptide comprising an amino acid sequence having at least 70% sequence identity with an Isthmin 1 (ISM1) protein or a GRP78-activating fragment thereof, or an expressible nucleic acid encoding said polypeptide. In certain embodiments, the pulmonary drug delivery device may contain or otherwise be loaded with a polypeptide, nucleic acid, or a composition as described herein. In certain embodiments, the pulmonary drug delivery device may be configured with a replaceable, or non-replaceable, cartridge loaded with a polypeptide, nucleic acid, or a composition as described herein. As will be understood, the pulmonary drug delivery device may comprise generally any suitable medical device for administering the polypeptides, nucleic acids, or compositions as described herein to the lung of a subject in need thereof. The skilled person having regard to the teachings herein will be aware of a variety of devices which may be configured for delivery of the polypeptides, nucleic acids, and/or compositions described herein. In certain embodiments, the pulmonary drug delivery device may comprise, for example, an intratracheal drug delivery device, an intranasal drug delivery device, or an inhalation drug delivery device. The person of skill in the art having regard to the teachings herein will be aware of a variety of suitable medical device designs for administering agents to the lung (i.e. for pulmonary delivery of an active agent). Delivery of agents, and particularly proteins, to the lung has been the subject of significant study, as described in, for example, Bodier-Montagutelli, E., et al., 2018, Designing inhaled protein therapeutics for topical lung delivery: what are the next steps?, *Expert Opinion on Drug Delivery,* 15(8): 729-736; Labiris, N. R., et al., 2003, Pulmonary Drug Delivery.

Part II: The role of inhalant delivery devices and drug formulations in therapeutic effectiveness of aerosolized medications, *Br J Clin Pharmacol,* 56:600-612; and Ibrahim, M., et al., 2015, Inhalation drug delivery devices: technology update, *Med Devices (Aukl),* 8:131-9, each of which are herein incorporated by reference in their entirety. In certain embodiments, pulmonary drug delivery devices may comprise any suitable drug delivery device for delivery to the lung. By way of non-limiting example, in certain embodiments, the pulmonary drug delivery device may comprise an aerosol, a nasal spray, an inhaler, a puffer, a nebulizer, or another suitable delivery device for administration to the lung. Examples of lung delivery devices are described in, for example, U.S. Pat. Nos. 5,983,893, 6,732, 732, US20070295332, U.S. Pat. Nos. 5,007,419, 4,832,015, US20040244794, US20100065048, US20030235555, US20050201951, and US20090000615, each of which are herein incorporated by reference in their entireties. In certain embodiments, it is contemplated that the pulmonary drug delivery device may comprise an aerosol and the polypeptide or nucleic acid may be formulated as a dry powder, or the pulmonary drug delivery device may comprise a nebulizer and the polypeptide or nucleic acid may be formulated as a liquid, for example. In certain embodiments, the pulmonary drug delivery device may comprise a nebulizer, a metered-dose inhaler (MDI), or a dry powder inhaler (DPI), loaded with a correspondingly formulated polypeptide, nucleic acid, or composition as described herein.

In certain embodiments, it is contemplated that pulmonary drug delivery devices as described herein may optionally further comprise, or may optionally be for use in combination with, simultaneously with, or sequentially with, one or more additional agents for preventing or reducing lung inflammation in a subject in need thereof. Conventional agents for preventing or reducing lung inflammation will be known to the person of skill in the art having regard to the teachings herein, and may include, for example, steroids. Examples of conventional agents have already been described hereinabove.

In certain embodiments, the pulmonary drug delivery devices described herein may be for use in modulating GRP78 activity in a subject in need thereof; inducing apoptosis in pro-inflammatory cells in a subject in need thereof; inducing apoptosis in alveolar macrophages (AM); reducing AM levels in a subject in need thereof; treating, ameliorating, or preventing lung inflammation in a subject in need thereof; treating, ameliorating, or preventing a lung disease or disorder associated with lung inflammation in a subject in need thereof; treating, ameliorating, or preventing chronic obstructive pulmonary disease (COPD), chronic obstructive bronchitis, or emphysema in a subject in need thereof; treating, ameliorating, or preventing asthma in a subject in need thereof; treating, ameliorating, or preventing acute lung injury (ALI) or acute respiratory distress syndrome (ARDS) in a subject in need thereof; preventing or reducing hyper-proliferation of alveolar wall surface type II (AE2) cells in a subject in need thereof; or treating, ameliorating, or preventing lung fibrosis in subject in need thereof, or any combination thereof, for example.

Methods and Uses for Treating Diseases or Disorders Associated with Inflammation Also provided herein are uses and methods for the treatment, amelioration, or prevention of diseases or disorders associated with inflammation, and particularly lung inflammation, for example. In certain embodiments, such uses and methods may utilize one or more of the polypeptides, nucleic acids, compositions, and/or pulmonary drug delivery devices as described herein, such as those described above.

In certain embodiments where a peptide, polypeptide, nucleic acid, and/or composition as described herein is to be administered or delivered to the lung of the subject, the peptide or polypeptide or nucleic acid or composition may be delivered by intratracheal administration, intranasal administration, or inhalation (for example, oral inhalation) administration or delivery, for example. In certain embodiments, the peptide, polypeptide, nucleic acid, or composition may be administered as an aerosol, an inhaler, or a nebulizer, for example. In certain embodiments, the peptide or polypeptide may be formulated as a dry powder and administered to the lung by aerosolization, or may be formulated as a liquid and administered to the lung by nebulization. In certain embodiments, the administration may be performed using a pulmonary drug delivery device as described herein. The person of skill in the art having regard to the teachings herein will be aware of a variety of suitable approaches and techniques for administration to the lung (i.e. for pulmonary delivery). Delivery of agents, and particularly proteins, to the lung has been the subject of significant study, as described in, for example, Bodier-Montagutelli, E., et al., 2018, Designing inhaled protein therapeutics for topical lung delivery: what are the next steps?, *Expert Opinion on Drug Delivery,* 15(8): 729-736; Labiris, N. R., et al., 2003, Pulmonary Drug Delivery. Part II: The role of inhalant delivery devices and drug formulations in therapeutic effectiveness of aerosolized medications, Br J Clin Pharmacol, 56:600-612; and Ibrahim M., et al., 2015, Inhalation drug delivery devices: technology update, *Med Devices (Auckl),* 8:131-9, each of which are herein incorporated by reference in their entirety. In certain embodiments, administration of the polypeptides, nucleic acids, and/or compositions as described herein as part of a method as described herein may be performed using any suitable drug delivery device for administration to the lung. In certain embodiments, drug delivery devices may take the form of pulmonary devices such as, inhalers, nebulizers, aerosols, puffers, nasal sprays, or other suitable delivery devices for administration to the lung. Examples of lung delivery devices are described in, for example, U.S. Pat. Nos. 5,983,893, 6,732,732, US20070295332, U.S. Pat. Nos. 5,007,419, 4,832,015, US20040244794, US20100065048, US20030235555, US20050201951, and US20090000615, each of which are herein incorporated by reference in their entireties.

For simplicity, the term polypeptide is used herein to describe generally any protein, polypeptide, peptide, or other amino acid sequence of generally any length. The term polypeptide may be understood as referencing a protein, a polypeptide, or a peptide, depending on length of the amino acid sequence being used in the particular embodiment and/or application. For example, in embodiments where the polypeptide is less than about 30 amino acids in length, the polypeptide may be considered as a peptide. Unless otherwise indicated, use of the term polypeptide herein is intended to include peptides, polypeptides, and proteins.

In certain embodiments where a nucleic acid encoding a polypeptide is to be administered to the lung of the subject, the nucleic acid may be delivered by intratracheal administration, intranasal administration, or oral inhalation administration, for example. In certain embodiments, the nucleic acid may be administered as an aerosol, an inhaler, or a nebulizer. In certain embodiments, the nucleic acid may be formulated as a dry powder and administered to the lung by aerosolization, or may be formulated as a liquid and administered to the lung by nebulization. In certain embodiments, the administration may be performed using a pulmonary drug delivery device as described herein. The person of skill in the art having regard to the teachings herein will be aware of a variety of suitable approaches and techniques for administration to the lung (i.e. for pulmonary delivery). In certain embodiments where a nucleic acid is to be administered to the subject, the nucleic acid may be introduced into a subject or cell for the purpose of producing the polypeptide which it encodes therein. In certain embodiments, the nucleic acid may comprise an express vector or expression cassette. In certain embodiments, the nucleic acid may comprise a DNA vector. In certain embodiments, it is contemplated that the nucleic acid may be complexed with a suitable nucleic acid delivery vehicle or transfection reagent suitable for introducing the nucleic acid into the cell. In certain embodiments, the nucleic acid may be incorporated into a virus for delivery into a cell, and the nucleic acid may or may not become integrated into the genome of the cell. The person of skill in the art having regard to the teachings herein will be aware of a variety of delivery vehicles, transfection reagents, and/or viral delivery constructs which may be selected to deliver a nucleic acid as described herein to a given cell or subject in need thereof. See, for example, Gomes et al., 2017, *Expert Opin Drug Deliv.*, 2017, 14(3):319-330, which is herein incorporated by reference in its entirety.

As described in detail herein, the present inventors have now developed methods for treating inflammation, such as lung inflammation, which are derived from and/or based on Isthmin 1 (ISM1), which is a secreted protein that is indicated by the studies described herein as playing a role in inhibiting, suppressing, and/or resolving inflammation, and particularly inflammation of the lung. In studies described in detail hereinbelow, providing supplementary exogenous recombinant ISM1 protein (rISM1) to the lung inhibited the lung inflammation phenotype in ISM1-deficient lung, and results indicate that administration of ISM1 may help to resolve inflammation by inducing alveolar macrophage apoptosis. Results further indicate that ISM1 may play an important role in suppression and/or resolution of sterile lung inflammation and/or inflammation triggered by infection and/or injury.

Accordingly, in an embodiment, there is provided herein a method for modulating GRP78 activity in a subject in need thereof, said method comprising:

administering a polypeptide comprising an amino acid sequence having at least 70% sequence identity with an Isthmin 1 (ISM1) protein or a GRP78-activating fragment thereof, or an expressible nucleic acid encoding said polypeptide, to the lung of the subject in need thereof.

In certain embodiments, modulating GRP78 activity may include administering a polypeptide, nucleic acid, or composition as described herein to the subject so as to trigger GRP78 activity (providing a pro-apoptotic effect) and thereby alleviate inflammation in the subject. Typically, modulating GRP78 activity may include increasing GRP78 activity levels (i.e. increasing pro-apoptotic effects stemming from GRP78 binding) in the subject when the GRP78 pro-apoptotic activity level in the subject is too low to adequately inhibit, suppress, and/or resolve inflammation, and particularly inflammation of the lung, of the subject. In certain embodiments, modulating GRP78 activity may include increasing GRP78 activity levels in the subject when the GRP78 activity level in the subject is too low to induce sufficient alveolar macrophage apoptosis to alleviate an inflammation state. In certain embodiments, where a lung disease or disorder is to be treated, references to GRP78 activity levels may include activity levels of GRP78 in a lung tissue or lung cell of the subject, such as alveolar macrophages (AM) of the subject, for example. As will be understood, in certain embodiments, references herein to GRP78 activity levels, or GRP78 activity, may be understood as referring to levels or activity of GRP78 in transmission of signals into the cell upon ligand binding, which may provide a pro-apoptotic effect.

A review of GRP78 may be found in Ni, et al., Biochem J., 2011, 434(2): 181-188, which is herein incorporated by reference in its entirety.

In certain embodiments, it is contemplated that ISM1 may favour, or be more selective for, killing or targeting cells with high csGRP78 levels. Healthy cells under normal environment should have relatively low levels or no presence of csGRP78. GRP78 expression level will increase in cells under stress, and it is contemplated that cells that harbour a high level of csGRP78 may respond to ISM1 and be triggered to apoptose. Accordingly, stressed cells may be favoured targets of extracellular ISM1 (see also Chen et al., Cell Death & Differentiation, 21(5): 797-810, 2014, herein incorporated by reference). Without wishing to be bound by theory, it is contemplated that cells having a csGRP78 level which is elevated will respond to ISM1-induced apoptotic signalling more strongly than healthy cells, which may reduce side effects in certain embodiments.

In certain embodiments, the polypeptide or nucleic acid may be administered to the lung of the subject by intratracheal administration, intranasal administration, or oral inhalation administration. In certain embodiments, the polypeptide or nucleic acid or composition may be administered as an aerosol, an inhaler, or a nebulizer. In certain embodiments, the polypeptide, nucleic acid, or composition may be formulated as a dry powder and administered to the lung by aerosolization, or may be formulated as a liquid and administered to the lung by nebulization. In certain embodiments, the administration may be performed using a pulmonary drug delivery device as described herein. The person of skill in the art having regard to the teachings herein will be aware of a variety of suitable approaches and techniques for administration to the lung (i.e. for pulmonary delivery). Delivery of agents, and particularly proteins, to the lung has been the subject of significant study, as described in, for example, Bodier-Montagutelli, E., et al., 2018, Designing inhaled protein therapeutics for topical lung delivery: what are the next steps?, *Expert Opinion on Drug Delivery,* 15(8): 729-736; and Labiris, N. R., et al., 2003, Pulmonary Drug Delivery. Part II: The role of inhalant delivery devices and drug formulations in therapeutic effectiveness of aerosolized medications, *Br J Clin Pharmacol,* 56:600-612, each of which are herein incorporated by reference in their entirety.

In still another embodiment, there is provided herein a method for inducing apoptosis in pro-inflammatory cells, or in alveolar macrophages (AM) in a subject in need thereof, or for reducing AM levels in a subject in need thereof, said method comprising:

administering a polypeptide comprising an amino acid sequence having at least 70% sequence identity with an Isthmin 1 (ISM1) protein or a GRP78-activating fragment thereof, or an expressible nucleic acid encoding said polypeptide, to the lung of the subject in need thereof.

In certain embodiments, inducing apoptosis in alveolar macrophages (AM) may include administering a polypeptide, nucleic acid, or composition as described herein to the subject so as to trigger at least some alveolar macrophages (AM) in the lung of the subject to undergo apoptosis. In certain embodiments, lung function decline may be measured non-invasively using spirometer, for example. High inflammation may be an indirect indication of high AMs, which may account for about 95% of air space immune cells. High inflammation may damage the lung and reduce its function. In clinical settings, a clinician may give anti-inflammatory drugs when the lung condition declines with hypoxemia and difficulty in breathing, etc. Accordingly, in certain embodiments, administration of the polypeptide or nucleic acid may be performed where lung function decline is observed, where high inflammation is observed, and/or where AM apoptosis levels are determined to be low.

In certain embodiments, inducing apoptosis in pro-inflammatory cells may include administering a polypeptide, nucleic acid, or composition as described herein to the subject so as to trigger at least some pro-inflammatory cells in the lung of the subject to undergo apoptosis. Pro-inflammatory cells may include AMs, neutrophils, interstitial macrophages, T and B cells, NK cells, etc. In certain embodiments, ISM1 may favour targeting of pro-inflammatory cells, such as AMs, harbouring high csGRP78 selectively. Under cigarette smoke, for example, most AMs may be stress activated, and harbouring high csGRP78 levels, and hence may be targets for ISM1.

In certain embodiments, reducing alveolar macrophage (AM) levels in the subject may include administering a polypeptide, nucleic acid, or composition as described herein to the subject so as to trigger a decrease in an alveolar macrophage (AM) level in the lung of the subject. It certain embodiments, it is contemplated that administration may be performed where AM levels are determined to be elevated in the subject as compared with a healthy control, or a disease control having mild symptoms. In certain embodiments, it is contemplated that AM levels may be determined from a sample of bronchoalveolar lavage fluid (BALF) which may be taken from a subject and AMs may be measured in the BALF. Alternatively, or in addition, lung function may be monitored as an indirect measure of AM levels.

In certain embodiments, the polypeptide or nucleic acid may be administered to the lung of the subject by intratracheal administration, intranasal administration, or oral inhalation administration.

In certain embodiments, the polypeptide or nucleic acid or composition may be administered as an aerosol, an inhaler, or a nebulizer. In certain embodiments, the polypeptide, nucleic acid, or composition may be formulated as a dry powder and administered to the lung by aerosolization, or may be formulated as a liquid and administered to the lung by nebulization. In certain embodiments, the administration may be performed using a pulmonary drug delivery device as described herein. The person of skill in the art having regard to the teachings herein will be aware of a variety of suitable approaches and techniques for administration to the lung (i.e. for pulmonary delivery).

In yet another embodiment, there is provided herein a method for treating, ameliorating, or preventing lung inflammation in a subject in need thereof, said method comprising:

administering a polypeptide comprising an amino acid sequence having at least 70% sequence identity with an Isthmin 1 (ISM1) protein or a GRP78-activating fragment thereof, or an expressible nucleic acid encoding said polypeptide, to the lung of the subject in need thereof.

In certain embodiments, lung inflammation may include generally any inflammatory state or condition of the lung, including but not limited to sterile lung inflammation and/or inflammation triggered by infection and/or injury. In certain embodiments, lung inflammation may be lung inflammation associated with COPD, emphysema, bronchitis, ALI, ARDS, IPF, pneumonia, etc. In certain embodiments, lung inflammation may be measured by measuring lung function decline and/or hypoxemia, and administration may be performed where inflammation or elevated inflammation is identified.

In certain embodiments, the polypeptide or nucleic acid may be administered to the lung of the subject by intratracheal administration, intranasal administration, or oral inhalation administration. In certain embodiments, the polypeptide or nucleic acid or composition may be administered as an aerosol, an inhaler, or a nebulizer. In certain embodiments, the polypeptide, nucleic acid, or composition may be formulated as a dry powder and administered to the lung by aerosolization, or may be formulated as a liquid and administered to the lung by nebulization. In certain embodiments, the administration may be performed using a pulmonary drug delivery device as described herein. The person of skill in the art having regard to the teachings herein will be aware of a variety of suitable approaches and techniques for administration to the lung (i.e. for pulmonary delivery).

In still another embodiment, there is provided herein a method for treating, ameliorating, or preventing a lung disease or disorder associated with lung inflammation in a subject in need thereof, said method comprising:

administering a polypeptide comprising an amino acid sequence having at least 70% sequence identity with an Isthmin 1 (ISM1) protein or a GRP78-activating fragment thereof, or an expressible nucleic acid encoding said polypeptide, to the lung of the subject in need thereof.

In certain embodiments, a lung disease or disorder associated with lung inflammation may include generally any disease, disorder, state, or condition of the lung caused by, or accompanied by, inflammation. Examples may include, but are not limited to, chronic obstructive pulmonary disease (COPD), chronic obstructive bronchitis, asthma, emphysema, acute lung injury (ALI), acute respiratory distress syndrome (ARDS), lung fibrosis (such as, for example, idiopathic pulmonary fibrosis), or any combination thereof.

In certain embodiments, the polypeptide or nucleic acid may be administered to the lung of the subject by intratracheal administration, intranasal administration, or oral inhalation administration. In certain embodiments, the polypeptide or nucleic acid or composition may be administered as an aerosol, an inhaler, or a nebulizer. In certain embodiments, the polypeptide, nucleic acid, or composition may be formulated as a dry powder and administered to the lung by aerosolization, or may be formulated as a liquid and administered to the lung by nebulization. In certain embodiments, the administration may be performed using a pulmonary drug delivery device as described herein. The person of skill in the art having regard to the teachings herein will be aware of a variety of suitable approaches and techniques for administration to the lung (i.e. for pulmonary delivery).

In another embodiment, there is provided herein a method for treating, ameliorating, or preventing chronic obstructive pulmonary disease (COPD), chronic obstructive bronchitis, asthma, or emphysema in a subject in need thereof, said method comprising:

administering a polypeptide comprising an amino acid sequence having at least 70% sequence identity with an Isthmin 1 (ISM1) protein or a GRP78-activating fragment thereof, or an expressible nucleic acid encoding said polypeptide, to the lung of the subject in need thereof.

In still another embodiment, there is provided herein a method for treating, ameliorating, or preventing acute lung injury (ALI) or acute respiratory distress syndrome (ARDS) in a subject in need thereof, said method comprising:

administering a polypeptide comprising an amino acid sequence having at least 70% sequence identity with an Isthmin 1 (ISM1) protein or a GRP78-activating fragment thereof, or an expressible nucleic acid encoding said polypeptide, to the lung of the subject in need thereof.

In another embodiment, there is provided herein a method for preventing or reducing hyper-proliferation of alveolar wall surface type II (AE2) cells in a subject in need thereof, said method comprising:

administering a polypeptide comprising an amino acid sequence having at least 70% sequence identity with an Isthmin 1 (ISM1) protein or a GRP78-activating fragment thereof, or an expressible nucleic acid encoding said polypeptide, to the subject in need thereof.

In yet another embodiment, there is provided herein a method for treating, ameliorating, or preventing lung fibrosis in subject in need thereof, said method comprising:

administering a polypeptide comprising an amino acid sequence having at least 70% sequence identity with an Isthmin 1 (ISM1) protein or a GRP78-activating fragment thereof, or an expressible nucleic acid encoding said polypeptide, to the lung of the subject in need thereof.

In further embodiments of any of the method or methods above, the polypeptide or nucleic acid may comprise any polypeptide or nucleic acid as described herein, such as those described above. The preceding section sets out extensive description and examples of suitable polypeptides and nucleic acids. In certain embodiments, the polypeptides and/or nucleic acids may be provided or formulated in compositions as have already been described in detail hereinabove. In certain embodiments, the polypeptides, nucleic acids, and/or compositions may be provided in pulmonary drug delivery devices as have already been described in detail hereinabove.

In further embodiments of any of the method or methods above, the method may further comprise a step of administering an agent for preventing or reducing lung inflammation to the subject in combination with, simultaneously with, or sequentially with the polypeptide or nucleic acid.

In further embodiments of any of the method or methods above, the method may further comprise a step of administering one or more additional agents for preventing or reducing lung inflammation to the subject. In certain embodiments, it is contemplated that polypeptides, nucleic acids, compositions, and/or pulmonary drug delivery devices as described herein may optionally further comprise, or may optionally be for use in combination with, simultaneously with, or sequentially with, one or more additional agents for preventing or reducing lung inflammation in a subject in need thereof. Conventional agents for preventing or reducing lung inflammation will be known to the person of skill in the art having regard to the teachings herein, and may include, for example, steroids. Examples of conventional agents have already been described hereinabove.

In certain embodiments of the any of the method or methods above, the method may further comprise a step of: determining an ISM1 level in the subject; determining a GRP78 protein level in the subject; determining an alveolar macrophage (AM) level in the subject; determining an inflammation level in the subject; determining level of lung function decline in the subject; or any combinations thereof; and performing or repeating the step of administering where: a reduced ISM1 level in the subject relative to a healthy control level, or relative to a low severity disease control level, is determined; an increased GRP78 protein level in the subject relative to a healthy control level, or relative to a low severity disease control level, is determined; an elevated alveolar macrophage (AM) level in the subject relative to a healthy control level, or relative to a low severity disease control level, is determined; an elevated inflammation level in the subject relative to a healthy control level, or relative to a low severity disease control level, is determined; an elevated level of lung function decline in the subject relative to a healthy control level, or relative to a low severity disease control level, is determined; or any combinations thereof.

In certain embodiments, the ISM1 level of the subject may be determined using any suitable technique known to the person of skill in the art having regard to the teachings herein. For example, in certain embodiments, the ISM1 level may be determined by ELISA testing of a blood, serum, sputum, or BALF sample from the subject, for example. In certain embodiments, the ISM1 level may be determined by mass spectrometry quantification in blood or sputum samples, for example. In certain embodiments, the ISM1 level may be determined by immunocytochemistry and/or immunofluorescent staining of isolated AM samples (from BALF, for example). In certain embodiments, the ISM1 level may comprise an ISM1 level in lung tissue of a subject, an ISM1 level in resected lung tissue of a subject, or an ISM1 level in alveolar macrophages (AM) of the subject. In certain embodiments, the determined ISM1 level of the subject may be compared with a healthy control level (i.e. an ISM1 level or range observed for a healthy group of control subject(s)), and/or may be compared with a low severity disease control level (i.e. an ISM1 level or range observed for a disease control group having the disease or disorder, but with low severity). If the ISM1 level of the subject is determined as being lower than an ISM1 level of the heathy control level or the low severity disease control level, then the subject may be subjected to treatment, or to additional treatment, with a polypeptide, nucleic acid, or composition as described herein. In certain embodiments, a reduced ISM1 level relative to a control level may be identified as a level which is reduced by at least 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or by about 100% from the control level.

In certain embodiments, a subject having low ISM1 level may be identified as a subject potentially particularly susceptible to treatment with ISM or fragments or derivatives thereof. However, will be recognized that in certain embodiments even subjects with relatively high levels of endogenous ISM1, if inflammation persists, then ISM1 levels may still not be sufficiently high to overcome the severe inflammation and administering extra exogenous ISM1 or fragments or derivatives thereof as described herein will be desirable.

In certain embodiments, the GRP78 protein level of the subject may be determined using any suitable technique known to the person of skill in the art having regard to the teachings herein. In certain embodiments, the GRP78 protein level may be a total cellular GRP78 level, a csGRP78 protein level, or both. In certain embodiments, the GRP78 level may be determined using a fluorescent probe (such as a peptide ligand) in fluorescent imaging, or by using a radioisotope labelled probe such as in PET imaging, for example. In certain embodiments, such probes may be used in live organisms, such a mammalian or human subject. In certain embodiments, the GRP78 protein level may comprise a GRP78 protein level in lung tissue of a subject, a GRP78 protein level in resected lung tissue of a subject, or a GRP78 protein level in alveolar macrophages (AM) of the subject. In certain embodiments, GRP78 protein level may be determined by ELISA, immunostaining, Western blot, or other suitable technique. In certain embodiments, GRP78 protein level may be determined from a lung tissue sample obtained from biopsy. In certain embodiments, the determined GRP78 protein level of the subject may be compared with a healthy control level (i.e. a GRP78 protein level or range observed for a healthy group of control subject(s)), and/or may be compared with a low severity disease control level (i.e. a GRP78 protein level or range observed for a disease control group having the disease or disorder, but with low severity). If the GRP78 protein level of the subject is determined as being higher than a GRP78 protein level of the heathy control level or the low severity disease control level, then the subject may be subjected to treatment, or to additional treatment, with a polypeptide, nucleic acid, or composition as described herein. In certain embodiments, an increased GRP78 protein level relative to a control level may be identified as a level which is increased by at least 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or by about 100% from the control level. In certain embodiments, the GRP78 protein level may be a GRP78 protein level of alveolar macrophages of the subject. It will be understood, however, that where inflammation is present in the subject, it is contemplated in certain embodiments that treatment with ISM1 or fragments or derivatives thereof as described herein may be desirable whether or not GRP78 levels are determined to be elevated. Since cells with high csGRP78 are targeted by the ISM1-induced apoptosis, then even if only a portion of the AMs of the subject harbour high csGRP78, it is contemplated that it will still be meaningful to remove these cells by triggering cell death.

In certain embodiments, the alveolar macrophage (AM) level of the subject may be determined using any suitable technique known to the person of skill in the art having regard to the teachings herein. By way of example, in certain embodiments, induced sputum may be used in determining the AM level. In certain embodiments, induced sputum procedures which will be known to the person of skill in the art having regard to the teachings herein may be used to study the content of the sputum including alveolar macrophages and/or sputum cytokine levels, for example. In certain embodiments, the alveolar macrophage (AM) level may comprise an alveolar macrophage (AM) level in lung tissue of a subject, or an alveolar macrophage (AM) level in resected lung tissue of a subject, for example. In certain embodiments, AM levels may be determined by collecting BALF and counting cell number. In certain embodiments, the determined alveolar macrophage (AM) level of the subject may be compared with a healthy control level (i.e. an alveolar macrophage (AM) level or range observed for a healthy group of control subject(s)), and/or may be compared with a low severity disease control level (i.e. an alveolar macrophage (AM) level or range observed for a disease control group having the disease or disorder, but with low severity). If the alveolar macrophage (AM) level of the subject is determined as being higher than an alveolar macrophage (AM) level of the heathy control level or the low severity disease control level, then the subject may be subjected to treatment, or to additional treatment, with a polypeptide, nucleic acid, or composition as described herein. In certain embodiments, an elevated alveolar macrophage (AM) level relative to a control level may be identified as a level which is increased by at least 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or by about 100% from the control level.

In certain embodiments, administration may be performed or repeated where the subject exhibits lung function decline, difficulty in breathing, hypoxemia, or another symptom of a lung disease or disorder associated with inflammation, such as COPD.

In certain embodiments, the inflammation level of the subject may be determined using any suitable technique known to the person of skill in the art having regard to the teachings herein. In certain embodiments, the inflammation level may comprise an inflammation level in lung tissue of a subject, or an inflammation level in resected lung tissue of a subject, for example. In certain embodiments, inflammation may be determined or indicated by fever (and height thereof), severity of symptoms such as hypoxemia, difficulty in breathing, shortness of breath, coughing, phlegm, blood leukocyte count, or other such measures of inflammation. In certain embodiments, inflammation may be determined or indicated by number of immune cells, level of pro-inflammatory cytokines such as TNF-alpha, level of NF-kB signalling, level of proteases such as MMPs, or other such measures. In certain embodiments, the determined inflammation level of the subject may be compared with a healthy control level (i.e. an inflammation level or range observed for a healthy group of control subject(s)), and/or may be compared with a low severity disease control level (i.e. an inflammation level or range observed for a disease control group having the disease or disorder, but with low severity). If the inflammation level of the subject is determined as being higher than an inflammation level of the heathy control level or the low severity disease control level, then the subject may be subjected to treatment, or to additional treatment, with a polypeptide, nucleic acid, or composition as described herein. In certain embodiments, an elevated inflammation relative to a control level may be identified as a level which is increased by at least 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or by about 100% from the control level.

In certain embodiments, the level of lung function decline in the subject may be determined using any suitable technique known to the person of skill in the art having regard to the teachings herein. By way of example, spirometry may be used, or determination may be made by the symptoms displayed such as difficulty in breathing, hypoxemia, etc. . . . as described above. In certain embodiments, the determined level of lung function decline of the subject may be compared with a healthy control level (i.e. a level or range observed for a healthy group of control subject(s)), and/or may be compared with a low severity disease control level (i.e. a level or range observed for a disease control group having the disease or disorder, but with low severity). If the level of lung function decline of the subject is determined as being higher than a level of lung function decline of the heathy control level or the low severity disease control level, then the subject may be subjected to treatment, or to additional treatment, with a polypeptide, nucleic acid, or composition as described herein. In certain embodiments, an elevated level of lung function decline relative to a control level may be identified as a level of lung function decline which is impaired by at least 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or by about 100% from the control level. The COPD clinical criteria, for example, is to have $FEV_1$/FVC to be <0.7, Tiffeneau-Pinelli index, so lung function decline is typically at least 30% by spirometry to qualify as COPD under such criteria. However, it is contemplated that early treatment may be preferred to prevent COPD progression, for example.

In still another embodiment, there is provided herein a method for treating, ameliorating, or preventing a disease or disorder associated with macrophage-mediated inflammation in a subject in need thereof, said method comprising:

administering a polypeptide comprising an amino acid sequence having at least 70% sequence identity with an Isthmin 1 (ISM1) protein or a GRP78-activating fragment thereof, or an expressible nucleic acid encoding said polypeptide, to the subject.

In yet another embodiment, there is provided herein a method for treating, ameliorating, or preventing a lung disease or disorder associated with lung inflammation in a subject in need thereof, said method comprising:

administering a GRP78-activating agent to the lung of the subject.

In still another embodiment, there is provided herein a method for maintaining lung homeostasis and/or resolving pulmonary inflammation and/or promoting lung repair with reduced remodelling in a subject in need thereof, said method comprising;

administering a polypeptide comprising an amino acid sequence having at least 70% sequence identity with an Isthmin 1 (ISM1) protein or a GRP78-activating fragment thereof, or an expressible nucleic acid encoding said polypeptide, to the lung of the subject.

In certain embodiments, subjects as referred to herein may include any suitable subject in need of treatment. In certain embodiments, the subject may comprise a mammal. In certain embodiments, the subject may comprise a human.

In another embodiment, there is provided herein a use of a polypeptide comprising an amino acid sequence having at least 70% sequence identity with an Isthmin 1 (ISM1) protein or a GRP78-activating fragment thereof, or an expressible nucleic acid encoding said polypeptide, for modulating GRP78 activity in a subject in need thereof; for inducing apoptosis in pro-inflammatory cells in a subject in need thereof; for inducing apoptosis in alveolar macrophages (AM) in a subject in need thereof; for reducing AM levels in a subject in need thereof; for treating, ameliorating, or preventing lung inflammation in a subject in need thereof; for treating, ameliorating, or preventing a lung disease or disorder associated with lung inflammation in a subject in need thereof; for treating, ameliorating, or preventing chronic obstructive pulmonary disease (COPD), chronic obstructive bronchitis, or emphysema in a subject in need thereof; for treating, ameliorating, or preventing asthma in a subject in need thereof; for treating, ameliorating, or preventing acute lung injury (ALI) or acute respiratory distress syndrome (ARDS) in a subject in need thereof; for preventing or reducing hyper-proliferation of alveolar wall surface type II (AE2) cells in a subject in need thereof; for treating, ameliorating, or preventing lung fibrosis in subject in need thereof; for treating, ameliorating, or preventing a disease or disorder associated with macrophage-mediated inflammation in a subject in need thereof; for maintaining lung homeostasis and/or resolving pulmonary inflammation and/or promoting lung repair with reduced remodelling in a subject in need thereof; or any combinations thereof.

In certain embodiments, the polypeptide or nucleic acid may be for administration to the lung of the subject. In certain embodiments, the polypeptide or nucleic acid may be administered to the lung of the subject by intratracheal administration, intranasal administration, or oral inhalation administration. In certain embodiments, the polypeptide or nucleic acid or composition may be administered as an aerosol, an inhaler, or a nebulizer. In certain embodiments, the polypeptide, nucleic acid, or composition may be formulated as a dry powder and administered to the lung by aerosolization, or may be formulated as a liquid and administered to the lung by nebulization. In certain embodiments, the administration may be performed using a pulmonary drug delivery device as described herein. The person of skill in the art having regard to the teachings herein will be aware of a variety of suitable approaches and techniques for administration to the lung (i.e. for pulmonary delivery).

In certain embodiments, the polypeptide or nucleic acid may be for use in combination with an additional agent for preventing or reducing lung inflammation. In certain embodiments, it is contemplated that polypeptides, nucleic acids, compositions, and/or pulmonary drug delivery devices as described herein may optionally further comprise, or may optionally be for use in combination with, simultaneously with, or sequentially with, one or more additional agents for preventing or reducing lung inflammation in a subject in need thereof. Conventional agents for preventing or reducing lung inflammation will be known to the person of skill in the art having regard to the teachings herein, and may include, for example, steroids. Examples of conventional agents have already been described hereinabove.

In still another embodiment, there is provided herein a use of a polypeptide comprising an amino acid sequence having at least 70% sequence identity with an Isthmin 1 (ISM1) protein or a GRP78-activating fragment thereof, or an expressible nucleic acid encoding said polypeptide, in the manufacture of a medicament for modulating GRP78 activity in a subject in need thereof; for inducing apoptosis in alveolar macrophages (AM) in a subject in need thereof; for treating, ameliorating, or preventing lung inflammation in a subject in need thereof; for treating, ameliorating, or preventing a lung disease or disorder associated with lung inflammation in a subject in need thereof; for treating, ameliorating, or preventing chronic obstructive pulmonary disease (COPD), chronic obstructive bronchitis, or emphysema in a subject in need thereof; for treating, ameliorating, or preventing asthma in a subject in need thereof; for treating, ameliorating, or preventing acute lung injury (ALI) or acute respiratory distress syndrome (ARDS) in a subject in need thereof; for treating, ameliorating, or preventing lung fibrosis in subject in need thereof; for treating, ameliorating, or preventing a disease or disorder associated with macrophage-mediated inflammation in a subject in need thereof; for maintaining lung homeostasis and/or resolving pulmonary inflammation and/or promoting lung repair with reduced remodelling in a subject in need thereof; or any combinations thereof.

In certain embodiments, the polypeptides, nucleic acids, and/or compositions as described herein may be for administration to a subject in need thereof 1, 2, or more times per day; once every 1, 2, 3, or more days; or as needed based on symptoms, for example. In certain embodiments, the polypeptides, nucleic acids, and/or compositions as described herein may be for administration by nebulizer, for example.

In the studies described below using a mouse model, administration via intratracheal delivery at 5 ug/dose, once every 2 days, was effective.

Methods for Diagnosis and/or Identification of Subjects Susceptible to Treatment In yet another embodiment, there is provided herein a method for identifying a subject having or being at risk of developing a lung disease or disorder associated with lung inflammation, said method comprising:

determining an ISM1 level in the subject; determining a GRP78 protein level in the subject; determining an alveolar macrophage (AM) level in the subject; determining an inflammation level in the subject; or any combinations thereof; and identifying the subject as having or being at risk of developing the lung disease or disorder associated with lung inflammation where: a reduced ISM1 level in the subject relative to a healthy control level, or relative to a low severity disease control level, is determined; an increased GRP78 protein level in the subject relative to a healthy control level, or relative to a low severity disease control level, is determined; an elevated alveolar macrophage (AM) level in the subject relative to a healthy control level, or relative to a low severity disease control level, is determined; an elevated inflammation level in the subject relative to a healthy control level, or relative to a low severity disease control level, is determined; or any combinations thereof.

In certain embodiments of the above method, the method may further comprise performing one or more conventional assays or techniques to further confirm or support identification of the subject as having or being at risk of developing a lung disease or disorder associated with lung inflammation. In certain embodiments, blood total leukocyte counts and/or differential counts may be used, for example. In certain embodiments, conventional assays or techniques may include primary outcomes measuring lung functions (FEV1/FVC, FRC, PEFR, etc.) and/or St. George's Respiratory Questionnaire for COPD patients (SGRQ-C) for quality of life (cough, phlegm, shortness of breath, wheezing, etc.) and/or number of exacerbation, for example.

In yet another embodiment, there is provided herein a method for identifying candidate subjects for treatment with a treatment method as described in detail herein, said method comprising: determining an ISM1 level in the subject; determining a GRP78 protein level in the subject;

determining an alveolar macrophage (AM) level in the subject; determining an inflammation level in the subject; or any combinations thereof; and identifying the subject as being a candidate subject for treatment where: a reduced ISM1 level in the subject relative to a healthy control level, or relative to a low severity disease control level, is determined; an increased GRP78 protein level in the subject relative to a healthy control level, or relative to a low severity disease control level, is determined; an elevated alveolar macrophage (AM) level in the subject relative to a healthy control level, or relative to a low severity disease control level, is determined; an elevated inflammation level in the subject relative to a healthy control level, or relative to a low severity disease control level, is determined; or any combinations thereof.

In certain embodiments, the methods for identifying a subject as having or being at risk of developing a lung disease or disorder associated with lung inflammation as described herein may further comprise a step of treating an identified subject for the lung disease or disorder associated with lung inflammation. In certain embodiments, the step of treating the identified subject may comprise treating the subject with any of the treatment methods as described in detail herein.

In certain embodiments, the methods for identifying candidate subjects for treatment with a treatment method as described in detail herein may further comprise a step of treating an identified subject. In certain embodiments, the step of treating the identified subject may comprise treating the subject with any of the treatment methods as described in detail herein.

EXAMPLES

In the Examples described below, removal of the secreted protein ISM1 from mice through a gene targeting approach led to spontaneous lung inflammation and progressive emphysema, characteristics similar to human COPD. Furthermore, removal of ISM1 led to heightened inflammatory response to lipopolysaccharide (LPS)-induced acute lung injury (ALI). Moreover, intratracheal supplementation (i.e. local administration to the lung) of exogenous recombinant ISM1 protein (rISM1) inhibited the lung inflammation phenotype in ISM1-deficient lung and cigarette-smoke induced COPD in mice. These studies indicate that ISM1 helped to resolve inflammation likely by inducing alveolar macrophage apoptosis. These results suggest ISM1 may be an inhibitor and/or pro-resolving mediator of lung inflammation and may play a role in suppression and/or resolution of sterile lung inflammation and/or inflammation triggered by environmental damage such as cigarette smoke, infection and/or injury. ISM1 may therefore represent a therapeutic agent and/or target for pulmonary inflammatory diseases such as ALI and COPD.

Example 1: Isthmin 1—Protection of Lung Homeostasis and Therapeutic Effects on COPD Chronic obstructive pulmonary disease (COPD) is currently the 3rd leading cause of death. Chronic obstructive pulmonary disease (COPD) is characterized by progressive and largely irreversible airway obstruction due to emphysema (destruction of alveolar walls and enlargement of the alveoli) and chronic obstructive bronchitis of the small airways[1]. Marked increase in alveolar macrophages (AMs) has been widely implicated in COPD pathogenesis[2]. However, the molecular mechanisms and pathophysiology of COPD have been poorly understood in the field, and drugs that can block or reduce COPD progression have been lacking.

Pulmonary inflammation is integral to COPD pathogenesis and alveolar macrophages (AMs), the most abundant lung resident immune cell, are key effector cells for this disease. Disease severity in COPD patients is directly associated with AM accumulation, specifically in the inflamed peripheral airways and alveolar spaces (Finkelstein, Fraser et al., 1995). These observations are concurred by mouse studies that exhibited complete protection against experimental COPD upon targeted AM depletion (Ueno, Maeno et al., 2015) or knockout of the potent macrophage elastase, MMP-12 (Hautamaki, Kobayashi et al., 1997). Many COPD patients are resistant to corticosteroid treatments, however some anti-inflammatory agents are being explored for COPD therapeutics development (Vogelmeier, Criner et al., 2017).

In the present studies, the extracellular proapoptotic protein ISTHMIN 1 (ISM1) is developed and studied as an anti-inflammatory agent, and in maintaining lung homeostasis. rISM1 is indicated as a therapeutic agent for COPD. In these studies, Ism1 knockout (Ism1$^{\Delta/\Delta}$) mice presented increased AMs and developed spontaneous chronic lung inflammation with progressive emphysema. Cell-surface GRP78 (csGRP78), the high-affinity receptor for ISM1, is dominantly present on AMs and its level is highly upregulated in Ism1$^{\Delta/\Delta}$ and in cigarette smoke (CS) induced COPD mice as well as in human COPD lung. Intratracheal delivery of recombinant ISM1 (rISM1) depleted AMs in both Ism1$^{\Delta/\Delta}$ and CS induced COPD lung in mice, blocking emphysema progression and restoring lung function. Consistently, high ISM1 expressions in COPD patients correlate with high AM apoptosis level and low AM numbers. These results support that ISM1 may be a protector of lung homeostasis and may provide therapeutic benefit in halting COPD progression, for example. Data provided herein indicates Isthmin 1 protects against COPD.

The following studies indicate that the secreted protein Isthmin 1 (ISM1) is an anti-inflammatory protein, that may function by inducing AM apoptosis through cell-surface GRP78 (csGRP78) receptor. Results indicate that loss of ISM1 leads to AM accumulation and spontaneous emphysema in Ism1$^{\Delta/\Delta}$ mice. Results herein indicate that csGRP78 is highly upregulated in AMs of Ism1$^{\Delta/\Delta}$ mice, cigarette smoke-induced COPD mice and human COPD lung. Intratracheal delivery of recombinant ISM1 depleted AMs in both Ism1$^{\Delta/\Delta}$ and COPD mice, blocking emphysema and lung function decline. Consistently, ISM1 expression in human COPD lung correlated with increased AM apoptosis. Thus, results herein indicate ISM1 as a protector of lung homeostasis and support therapeutic use for COPD by targeting csGRP78 on AMs.

The lung is constantly exposed to the external environment and homeostasis is important to limit immune response and inflammation. CS is the main risk factor for COPD, which is currently the third leading cause of death with an estimated cumulated lifetime risk of 25%[3]. Although bronchodilator drugs provide symptomatic relief for patients, they do not reduce COPD progression or mortality.

ISM1 has been previously identified as a secreted protein functioning through csGRP78 and $\alpha v \beta 5$ integrin on some cells such as some cancer cells and activated endothelial cells, suppressing angiogenesis and experimental cancer in mice[7].

Recombinant ISM1 (rISM1) binds to $\alpha v \beta 5$ integrin and activates caspase-8, or to csGRP78 where it is endocytosed and trafficked to mitochondria, inhibiting ATP production and triggering apoptosis. Ism1 gene is present in vertebrates from fish to human (Osório, Wu et al., 2014, Xiang et al., 2011); however, physiological functions of Ism1 has remained unknown.

Figure 5:
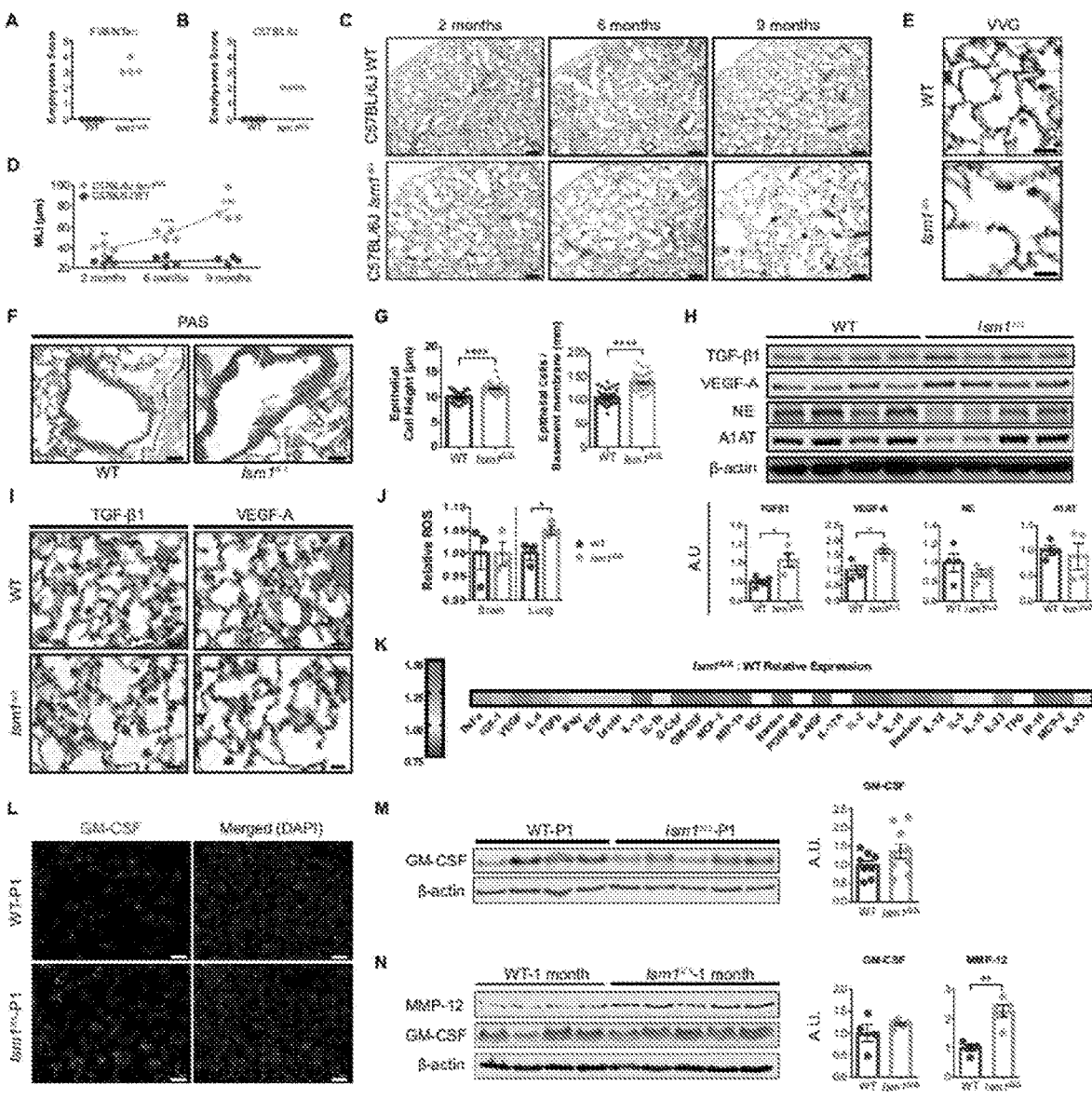
FIG. 5 shows characterization of Ism1$^{\Delta/\Delta}$ mice. (A) and (B) show pathology grading of emphysema in 2-month old FVB/NTac (A) and C57BL/6J (B) WT and Ism1$^{\Delta/\Delta}$ mice. n=4 mice per group. (C) and (D) show representative photomicrographs of hematoxylin and eosin stained peripheral left lung lobes (C) and mean linear intercepts (MLI) (D) of C57BL/6J WT and Ism1$^{\Delta/\Delta}$ mice at 2 months, 6 months and 9 months of age. n=4 mice per group. Scale bars, 200 μm. (E) and (F) show representative photomicrographs of Verhoeff-Van Gieson (VVG) stained lungs showing loss of elastin (black) and collagen (red) (E), and Periodic Acid-Schiff (PAS) stained airways showing mucus hypersecretion (red) (F) in 2-month old FVB/NTac Ism1$^{\Delta/\Delta}$ mice. n=4 mice per group. Scale bars, 20 μm. (G) shows measurements of bronchial epithelial cell height (left) and cell number (right) in 2-month old FVB/NTac WT and Ism1$^{\Delta/\Delta}$ mice. n=34-38 mean measurements taken from 8-10 small airways per mouse, 4 mice per group. (H) shows Western blots (top) and fold-changes (bottom; A.U., arbitrary units) for TGF-β1, VEGF-A, neutrophil elastase (NE) and alpha-1-antitrypsin (A1AT) with β-actin as loading control in 2-month old FVB/NTac WT and Ism1$^{\Delta/\Delta}$ mice lungs. n=4 mice per group. (I) shows representative immunohistochemistry staining for TGF-β1 and VEGF-A in AMs of 2-month old FVB/NTac WT and Ism1$^{\Delta/\Delta}$ mice lungs. n=4 mice per group. Scale bars, 20 μm. (J) shows quantification of relative reactive oxygen species (ROS) in 2-month old FVB/NTac WT and Ism1$^{\Delta/\Delta}$ mice lungs. Brain tissue (positive for ISM1 expression) was used as a control to demonstrate lung specificity for ISM1 deficiency. n=3 mice per group. (K) shows a heatmap of relative cytokine expression between 2-month old FVB/NTac WT and Ism1$^{\alpha/\alpha}$ mice lungs. n=3 WT mice and 6 Ism1$^{\Delta/\Delta}$ mice. (L) shows representative immunofluorescence staining (left) for GM-CSF (red) and nuclei (DAPI; blue) in P1 FVB/NTac WT and Ism1$^{\Delta/\Delta}$ mice lungs. n=4 mice per group. (M) shows Western blot (top) and fold-change (bottom; A.U., arbitrary units) for GM-CSF with β-actin as loading control in P1 FVB/NTac WT and Ism1$^{\Delta/\Delta}$ mice lungs. n=8-9 mice per group. Data are mean t s.e.m. and were analyzed by unpaired two-tailed Student's t-test (D, G, H, J and M). *P<0.05, P<0.01, *P<0.001, ****P<0.0001. (N) shows increased MMP-12 in 1-month old Ism1$^{\Delta/\Delta}$ mouse lungs preceded GM-CSF upregulation.

Studies described herein indicate that ISM1 may play a critical role in maintaining mouse lung homeostasis by regulating AM numbers via csGRP78-mediated apoptosis. Results indicate that pulmonary delivery of rISM1 can effectively quench lung inflammation by depleting AMs via apoptosis induction, leading to blockage of emphysema and restoration of lung function in CS-induced COPD mice studied. Correspondingly, ISM1 expression in the lung of human COPD patients correlates with increased AM apoptosis. These results indicate that rISM1 may provide a therapeutic approach for COPD, targeting csGRP78 on AMs to suppress inflammation by inducing AM apoptosis and blocking lung tissue damage in emphysema, for example. Ism1$^{\Delta/\Delta}$ Mice Develop Spontaneous Emphysema under Ambient Air In mice, Ism1 is expressed at the highest level in both fetal and adult lung, almost 30-fold higher than its second highest expressing organ, the brain, and much higher than other organs (Osório et al., 2014). To further study Ism1's physiological function and effects, Ism1 knockout (Ism1$^{\Delta/\Delta}$) mice were generated using CRISPR/Cas9 approach in two different strains of mice: FVB/NTac and C57BL/6J (FIG. 22A-E). Ism1$^{\Delta/\Delta}$ mice in both genetic backgrounds are viable and present no gross morphological abnormality or behavioral phenotype, albeit producing smaller litter sizes compared with Ism1$^{+/\Delta}$ and wild-type (WT) FVB/N mice (data not shown). Histopathology examination of all major organs revealed that Ism1$^{\Delta/\Delta}$ mouse lung developed spontaneous emphysema in both genetic backgrounds (FIG. 1A and FIGS. 5A-C) and progressive enlargement of alveolar spaces with age as quantified by mean linear intercept (MLI) (FIG. 1B and FIG. 5D). No obvious pathologies were observed in the other major organs of Ism1$^{\Delta/\Delta}$ mice up to 9 months of age. These results indicate that ISM1 is important for murine lung homeostasis, consistent with its highest expression in lung. For subsequent studies herein, FVB/NTac Ism1$^{\Delta/\Delta}$ mice were mainly used. Whole-mount stereomicroscopy and fluorescent dye-labeling of collagen and elastin showed notable air trapping (FIG. 1C) and deterioration of the overall alveolar network in lungs of Ism1$^{\Delta/\Delta}$ mice (FIG. 1D). Losses of alveolar elastin fibers in Ism1$^{\Delta/\Delta}$ mouse lungs were also visualized using a modified Verhoeff-Van Gieson (VVG) stain, along with the detection of ruptured septa (FIG. 5E). In addition, Ism1$^{+/\Delta}$ mice developed mild emphysema with intermediate MLI between wild-type (WT) and Ism1$^{\Delta/\Delta}$ mice (FIGS. 1E and F), suggesting that Ism1 is a haploinsufficient gene in mice.

To determine if absence of ISM1 impaired lung physiology, a series of pulmonary function tests were performed on 2-month old Ism1$^{\Delta/\Delta}$ mice using a forced pulmonary maneuver system (Buxco). Ism1$^{\Delta/\Delta}$ mice presented increased total lung capacities (TLC) (FIG. 1G) synonymous with hyperinflated lungs observed in COPD patients (Gagnon, Guenette et al., 2014). Hyperinflation in Ism1$^{\Delta/\Delta}$ mouse lung was also shown by increased volume compartments such as functional residual capacities (FRC) (FIG. 1H) and residual volumes (RV) (FIG. 1I) due to loss of elastic recoil and air trapping associated with emphysema. These changes were also reflected in pressure-volume measurements, whereby both static and dynamic compliance (Cchord and Cdyn) were increased in Ism1$^{\Delta/\Delta}$ mice (FIGS. 1J and K). Importantly, Ism1$^{\Delta/\Delta}$ mice displayed lower forced expiratory volumes (FEV$_{100}$) (FIG. 1L) and possessed FEV$_{100}$/FVC means (equivalent to the FEV$_1$/FVC index in human COPD) of below 0.7 (FIG. 1M, Ism1$^{\Delta/\Delta}$: 0.63 t 0.05), a criterion routinely used for COPD diagnosis in patients (Singh et al., 2019). Increased airway resistance (RI) in Ism1$^{\Delta/\Delta}$ mice may be attributed to mucus hypersecretion and inflammatory changes in the airway wall including airway epithelial hyperplasia and thickening (FIG. 1N, FIGS. 5F and G) (Barnes, 2016). Collectively, these data showed that Ism1$^{\Delta/\Delta}$ mice presented similar lung pathologies to experimental emphysema/COPD in mouse models and human COPD patients.

FIGS. 5L and 5M show the increased AMs in Ism1$^{\Delta/\Delta}$ mice lungs is not a result of abnormal embryonic lung development. AM forms during embryonic development from fetal liver monocytes, where the fetal liver monocytes migrate into the lung and differentiate into AMs in the perinatal and postnatal period. Granulocyte-macrophage colony stimulating factor (GM-CSF) is an essential cytokine for AM formation and differentiation. Results show that there is no significant difference in GM-CSF level at post-natal P1 and P7 when GM-CSF is at the highest level in the developing lung. Hence, the higher number of AMs in the adult lung (8 weeks old) is not a result of altered AM formation during the lung development. FIGS. 5L and 5M show representative immunofluorescence staining (left) for GM-CSF (red) and nuclei (DAPI; blue) in P1 FVB/NTac WT and Ism1$^{\Delta/\Delta}$ mice lungs (n=4 mice per group. Western blot (5M) and fold-change (A.U., arbitrary units) for GM-CSF with β-actin as loading control in P1 FVB/NTac WT and Ism1$^{\Delta/\Delta}$ mice lungs. n=8-9 mice per group. Data are mean±s.e.m. and were analyzed by unpaired two-tailed Student's t-test).

In adult mouse lung (8-weeks old), Ism1$^{\Delta/\Delta}$ mice harbor an altered cytokine microenvironment. Using multiplex ELISA assay, it was found that in 8-weeks old adult mice, the Ism1$^{\Delta/\Delta}$ lungs harbor an altered cytokine microenvironment compared to that of the WT lung. Multiple cytokines are upregulated for more than 1.5 fold including GM-CSF, G-CSF, IL-1α, Rantes, MIP-1α, IL-2, IP-10 and MCP-2 (see FIG. 5K). FIG. 5K shows a heatmap of relative cytokine expression between 2-month old FVB/NTac WT and Ism1$^{\Delta/\Delta}$ mice lungs (n=3 WT mice and 6 Ism1$^{\Delta/\Delta}$ mice).

Indeed, Western blot verified a higher level of GM-CSF compared to that of the WT mice. This higher level of GM-CSF may be a result of the sterile lung inflammation in Ism1$^{\Delta/\Delta}$ mice. Higher level of GM-CSF may stimulate AM proliferation, thus contributing to the higher number of AMs in the Ism1$^{\Delta/\Delta}$ lungs. FIG. 2H shows Western blot (left) and fold-change (right; A.U., arbitrary units) for GM-CSF with β-actin as loading control in 2-month old FVB/N WT and Ism1$^{\Delta/\Delta}$ mice lungs (n=4 mice per group. Data are mean±s.e.m. and were analyzed by unpaired two-tailed Student's t-test. ***P<0.001).

The emphysema progressively worsens as the mice age (FIG. 1). These symptoms are similar to human COPD patients. Strikingly, the severity of emphysema is also ISM1$^{\Delta/+}$ dose-dependent, with Ism1$^{\Delta/\Delta}$ mice presenting a more severe emphysema phenotype than Ism1$^{\Delta/+}$ mice. It seems that the presence of ISM1 in the lung microenvironment is important for lung homeostasis and to prevent sterile inflammation (inflammation without infection or injury). Consistently, ISM1 is expressed at the highest level in adult mouse lung among all the organs examined, supporting an important role of this protein in lung function.

Alveolar Macrophage Accumulation Drives Emphysema in Ism1$^{\Delta/\Delta}$ Lungs Emphysema in Ism1$^{\Delta/\Delta}$ mice was accompanied by multifocal aggregates of AMs in the alveolar spaces (FIG. 2A), and both cytospin and flow cytometric analysis of broncho-alveolar lavage fluid (BALF) cells confirmed increased AMs in Ism1$^{\Delta/\Delta}$ mouse lungs compared with WT mice (FIG. 2B-D). Notably, AMs from Ism1$^{\Delta/\Delta}$ mice display varying morphologies similar to macrophage subpopulations described in COPD patients (Dewhurst, Lea et al., 2017). Examination of known COPD associated proteases and mediators by Western blot analyses of whole lung lysates revealed increased levels of MMP-12, MMP-9 and NF-κB p65 in Ism1$^{\Delta/\Delta}$ lungs compared with WT lungs (FIG. 2E). Immunohistochemistry (IHC) staining of lung tissue sections indicated increased MMP-12 and MMP-9 expressions in AMs of Ism1$^{\Delta/\Delta}$ mice (FIG. 2F), consistent with other mouse models for emphysema and human COPD pathology (Woodruff, Koth et al., 2005). Moreover, isolated primary AMs from Ism1$^{\Delta/\Delta}$ mice showed increased nuclear translocation of NF-κB p65, indicating NF-κB activation in these cells (FIG. 2G). In addition, TGF-β1 and VEGF-A were moderately upregulated in the lungs and AMs of Ism1$^{\Delta/\Delta}$ mice (FIGS. 5H and I) in line with AM accumulation and gene expression patterns in COPD patients (de Boer, van Schadewijk et al., 1998, Kranenburg, de Boer et al., 2005). Ism1$^{\Delta/\Delta}$ lungs also produced higher levels of reactive oxygen species (ROS) (FIG. 5J). In contrast, neither neutrophil elastase nor alpha-1-antitrypsin levels showed any changes in Ism1$^{\Delta/\Delta}$ mouse lung compared to that of the WT mice (FIG. 5H). Microarray analysis showed upregulation of inflammatory cytokines in Ism1$^{\Delta/\Delta}$ mouse lungs including IL-1a, G-CSF, GM-CSF, MIP-1a, RANTES, IP-10 and MCP-2 (FIG. 5K). Since GM-CSF drives AM development (Guilliams, De Kleer et al., 2013) and GM-CSF-overexpressing mice develop emphysema with AM accumulation (Suzuki, McCarthy et al., 2020), it was sought to clarify whether GM-CSF was constitutively upregulated in Ism1$^{\Delta/\Delta}$ mice. Immunostaining and Western blots of P1 mouse lungs showed no difference in GM-CSF expression between Ism1$^{\Delta/\Delta}$ and WT mice (FIGS. 5L and M). Furthermore, increased MMP-12 in 1-month old Ism1$^{\Delta/\Delta}$ mouse lungs preceded GM-CSF upregulation (FIG. 5N). Thus, it is hypothesized that increased GM-CSF in 2-month old Ism1$^{\Delta/\Delta}$ mouse lungs (FIG. 2H) was instead linked to emphysema onset and inflammation that was dominantly contributed by excessive AM accumulation and activation.

Figure 2:
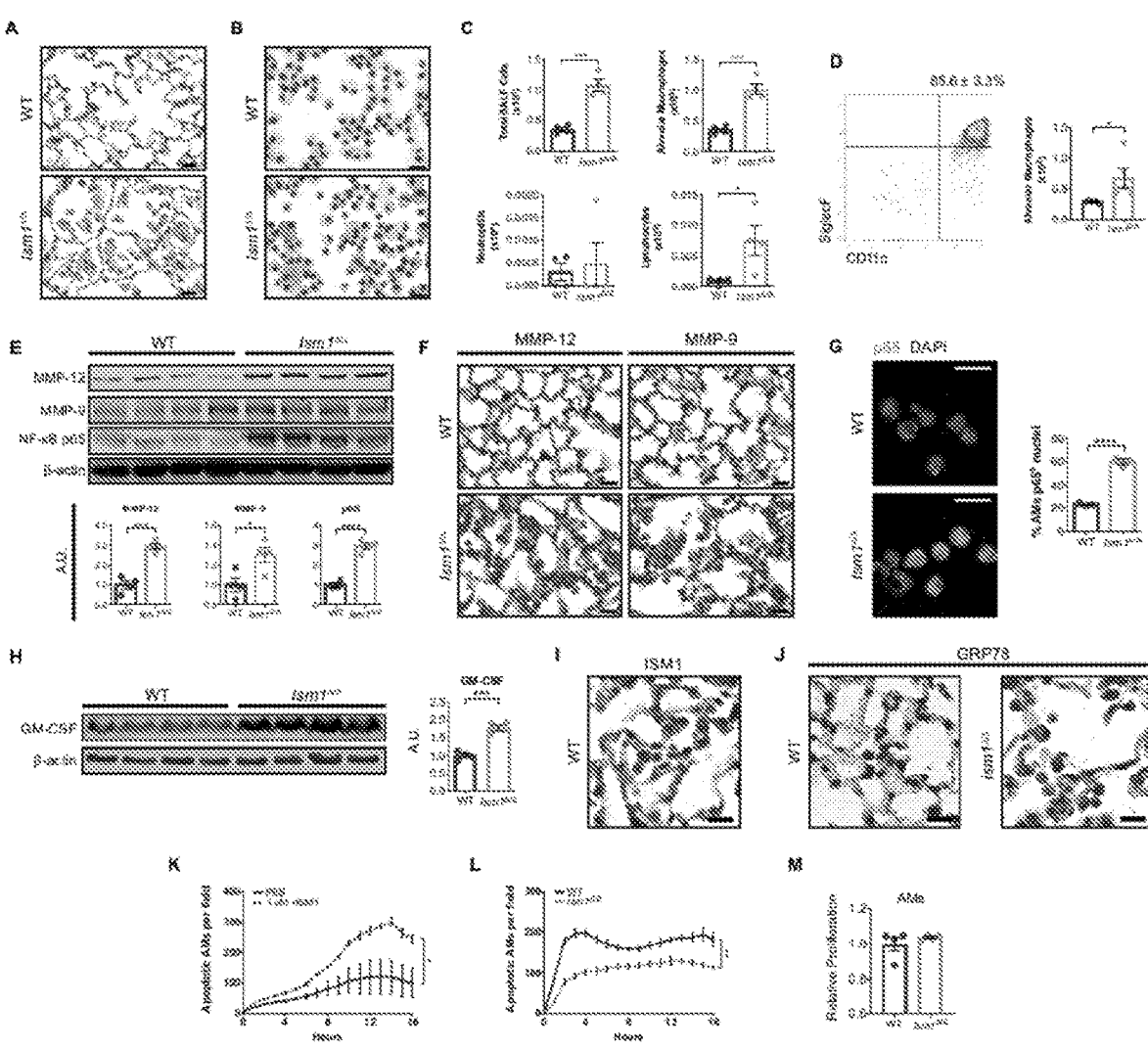
FIG. 2 shows that Ism1$^{\Delta/\Delta}$ mouse lungs present upregulated COPD mediators. (A) shows representative photomicrographs of hematoxylin and eosin stained lungs showing alveolar macrophage (AM) accumulation in 2-month old FVB/NTac Ism1$^{\Delta/\Delta}$ mice. n=4 mice per group. Scale bars, 20 μm. (B) and (C) show Liu-stained cytospin preparations (B) and quantifications (C) of bronchoalveolar lavage fluid (BALF) cells from 2-month old FVB/NTac WT and Ism1$^{\Delta/\Delta}$ mice lungs. n=4 mice per group. (B)-(D) shows both cytospin and flow cytometric analysis of bronchoalveolar lavage fluid (BALF) cells confirmed increased AMs in Ism1$^{\Delta/\Delta}$ mouse lungs compared with WT mice. (E) shows Western blots (top) and fold-changes (bottom; A.U., arbitrary units) for MMP-12, MMP-9 and NF-κB p65 with β-actin as loading control in 2-month old FVB/NTac WT and Ism1$^{\Delta/\Delta}$ mice lungs. n=4 mice per group. (F) shows representative immunohistochemistry staining for MMP-12 and MMP-9 in AMs of 2-month old FVB/NTac WT and Ism1$^{\Delta/\Delta}$ mice lungs. n=4 mice per group. Scale bars, 20 μm. (G) shows representative immunofluorescence staining (left) for NF-κB p65 (green) and nuclei (DAPI; blue) and quantification (right) in primary AMs isolated from 2-month old FVB/NTac WT and Ism1$^{\Delta/\Delta}$ mice. n=3 mean measurements taken from 3 mice per group. Scale bars, 20 μm. 250-350 alveolar macrophages quantified per mouse. (H) shows Western blot (top) and fold-change (bottom; A.U., arbitrary units) for GM-CSF with β-actin as loading control in 2-month old FVB/NTac WT and Ism1$^{\Delta/\Delta}$ mice lungs. n=4 mice per group. (I) and (J) shows representative immunohistochemistry staining for ISM1 (I) and GRP78 (J) in AMs of 2-month old FVB/NTac WT and Ism1$^{\Delta/\Delta}$ mice. n=4 mice per group. Scale bars, 20 μm. (K) and (L) show IncuCyte quantifications for apoptosis in WT primary AMs treated with 1 μM recombinant ISM1 (rISM1) (K) and untreated WT and Ism1$^{\Delta/\Delta}$ primary AMs (L). Analysis was carried out in triplicate or quadruplicate wells, and 4 images per well were taken for quantifications. (M) shows proliferation assay for WT and Ism1$^{\Delta/\Delta}$ primary AMs. Analysis was carried out in triplicate wells. n=4 mice per group. Data are mean±s.e.m. and were analyzed by unpaired two-tailed Student's t-test (C, E, G, H, K, L and M). *P<0.05, P<0.01, *P<0.001, ****P<0.0001.

FIGS. 2B and 2C show results of a mechanism of action study based on Ism1 knockout mice (Ism1$^{\Delta/\Delta}$ mice). Absence of ISM1 in the mouse lung lead to airway inflammation and increase of alveolar macrophages (AMs) based on bronchoalveolar lavage fluid (BALF) analyses. Analyses of cells from bronchoalveolar lavage fluid (BALF) confirmed that alveolar macrophages (AMs) in Ism1$^{\Delta/\Delta}$ mouse lungs are increased compared with that of the WT mice (FIG. 2). In comparison, no infiltration of neutrophils was found in the airway. Notably, AMs from Ism1$^{\Delta/\Delta}$ mice display varying morphologies similar to macrophage subpopulations described in COPD patients (Dewhurst, Lea et al., 2017). Significant increase of lymphocytes is also observed in BALF, similar to whole lung analyses. As shown in FIGS. 2B and 2C, BALF analyses demonstrated airway immune cells upregulation in Ism1$^{\Delta/\Delta}$ mice. Liu-stained cytospin preparations (2B) and quantifications (2C) of bronchoalveolar lavage fluid (BALF) cells from 2-month old WT and Ism1$^{\Delta/\Delta}$ mice lungs are shown (n=4 mice per group. Data are mean±s.e.m. and were analyzed by unpaired two-tailed Student's t-test. *P<0.05, ***P<0.001).

Figure 6:
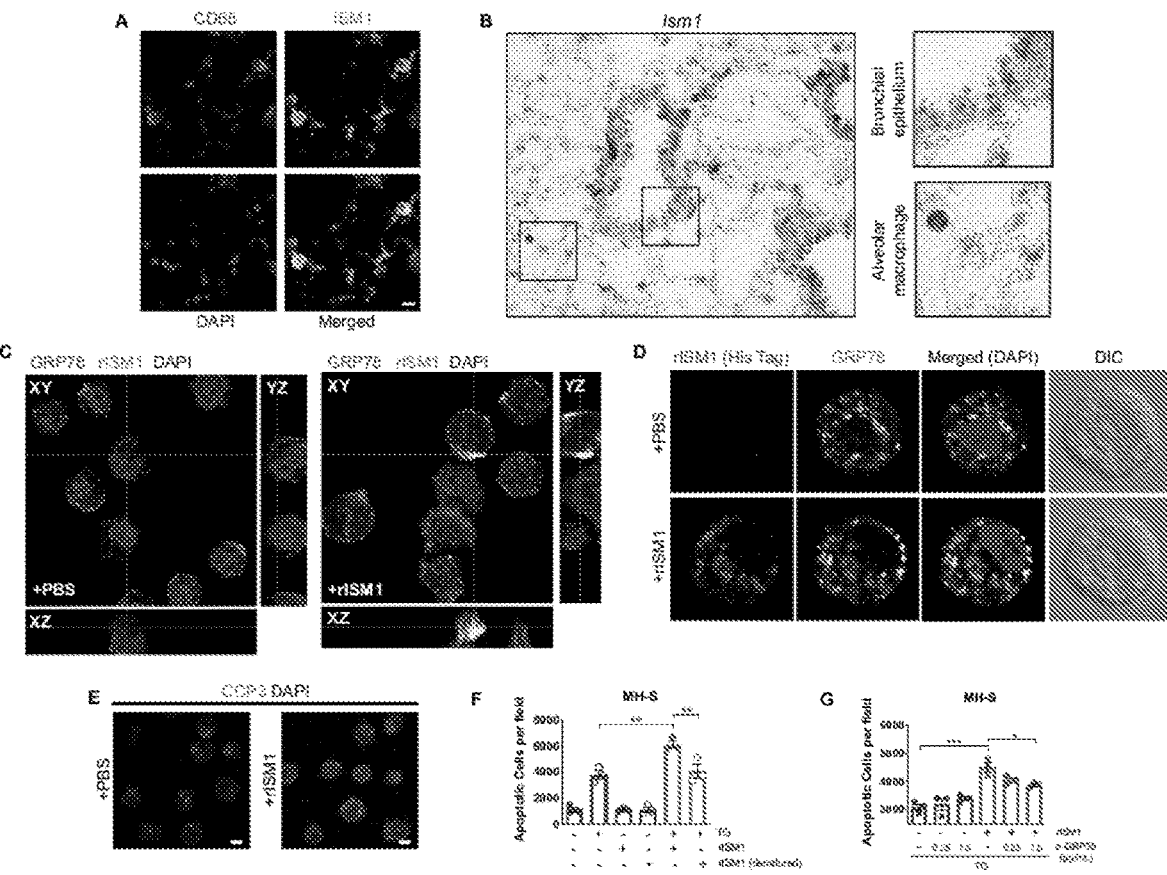
FIG. 6 shows ISM1 induces alveolar macrophages apoptosis through cell-surface GRP78. (A) shows representative immunofluorescence staining for AMs (CD68, red) expressing ISM1 (green) and nuclei (DAPI, blue) in 2-month old FVB/NTac WT mouse lung. Scale bar, 10 sm. (B) shows representative in-situ hybridization using anti-sense ism1 in 2-month WT BALB/cAnNTac mouse lung depicting ISM1 expression in the bronchial epithelium and alveolar macrophage in the insets. (C)-(E) show representative confocal images of primary AMs for rISM1 (red) and GRP78 (green) colocalization (C and D) and cleaved caspase-3 (CCP3) (E) after 1 μM rISM1 treatment. Nuclei stained with DAPI (blue). Scale bars, 5 μm. (F) and (G) show IncuCyte quantifications for apoptosis in MH-S cells after thapsigargin (TG) pretreatment and 1 μM rISM1 treatment (F) with GRP78 antibody neutralization (G). Treatment conditions as indicated. Analysis was carried out in triplicate wells, and 4 images per well were taken for quantifications. Data are mean±s.e.m. and were analyzed by one-way ANOVA with Tukey's post hoc test (F and G). *P<0.05, P<0.01, *P<0.001.

ISM1 expression was previously reported in mouse bronchial and alveolar epithelium (Osório et al., 2014, Venugopal, Chen et al., 2015). Here, it is shown that AMs are a novel source of ISM1 (FIG. 2I, FIGS. 6A and B), although it is clear that not all AMs constitutively express ISM1 at similar levels in the healthy lung. Notably, AMs also stained strongly for GRP78, and Ism1$^{\Delta/\Delta}$ mouse lungs present more AMs with distinct periplasmic GRP78 compared with WT mice (FIG. 2J). Cell-surface GRP78 (cs-GRP78) has been previously detected on mouse peritoneal macrophages (Misra, Gonzalez-Gronow et al., 2005) and human monocytes (Lu, Lai et al., 2010). Primary AMs were treated with recombinant ISM1 (rISM1) to determine if csGRP78 is present and serves as an ISM1 receptor on AMs. It was observed that rISM1 binds to csGRP78 on non-permeabilized AMs (FIG. 6C) and co-localized with GRP78 intracellularly (FIG. 6D), leading to AM apoptosis (FIG. 2K and FIG. 6E). Similarly, rISM1 induced apoptosis in immortalized mouse AM cells (MH-S) upon thapsigargin (TG) pretreatment (FIG. 6F), an ER stress inducer known to promote GRP78 translocation to the cell surface (Li, Ni et al., 2008). Furthermore, anti-GRP78 antibody neutralization effectively blocked rISM1-induced apoptosis (FIG. 6G). These results demonstrated that rISM1-induced apoptosis was mediated through csGRP78 on AMs. Concomitantly, primary AMs isolated from Ism1$^{\Delta/\Delta}$ mice demonstrated reduced apoptosis with no change in proliferation compared with WT AMs (FIGS. 2L and M), suggesting that absence of endogenous ISM1-mediated autocrine/paracrine apoptosis may underlie AM accumulation in Ism1$^{\Delta/\Delta}$ lungs. Increased AMs in Ism1$^{\Delta/\Delta}$ lungs contributed towards protease-anti-protease imbalance, thus leading to spontaneous COPD in Ism1$^{\Delta/\Delta}$ mice under ambient air.

Results in FIG. 6B indicate Ism1 mRNA is expressed in bronchial epithelial cells and alveolar macrophages. Indeed, in situ hybridization using mouse lung tissue sections showed that Ism1 gene is expressed in bronchial epithelial cells and some AMs, consistent with the IHC data. This also showed that IHC data showing ISM1 expression in AMs are reliable.

Figure 7:
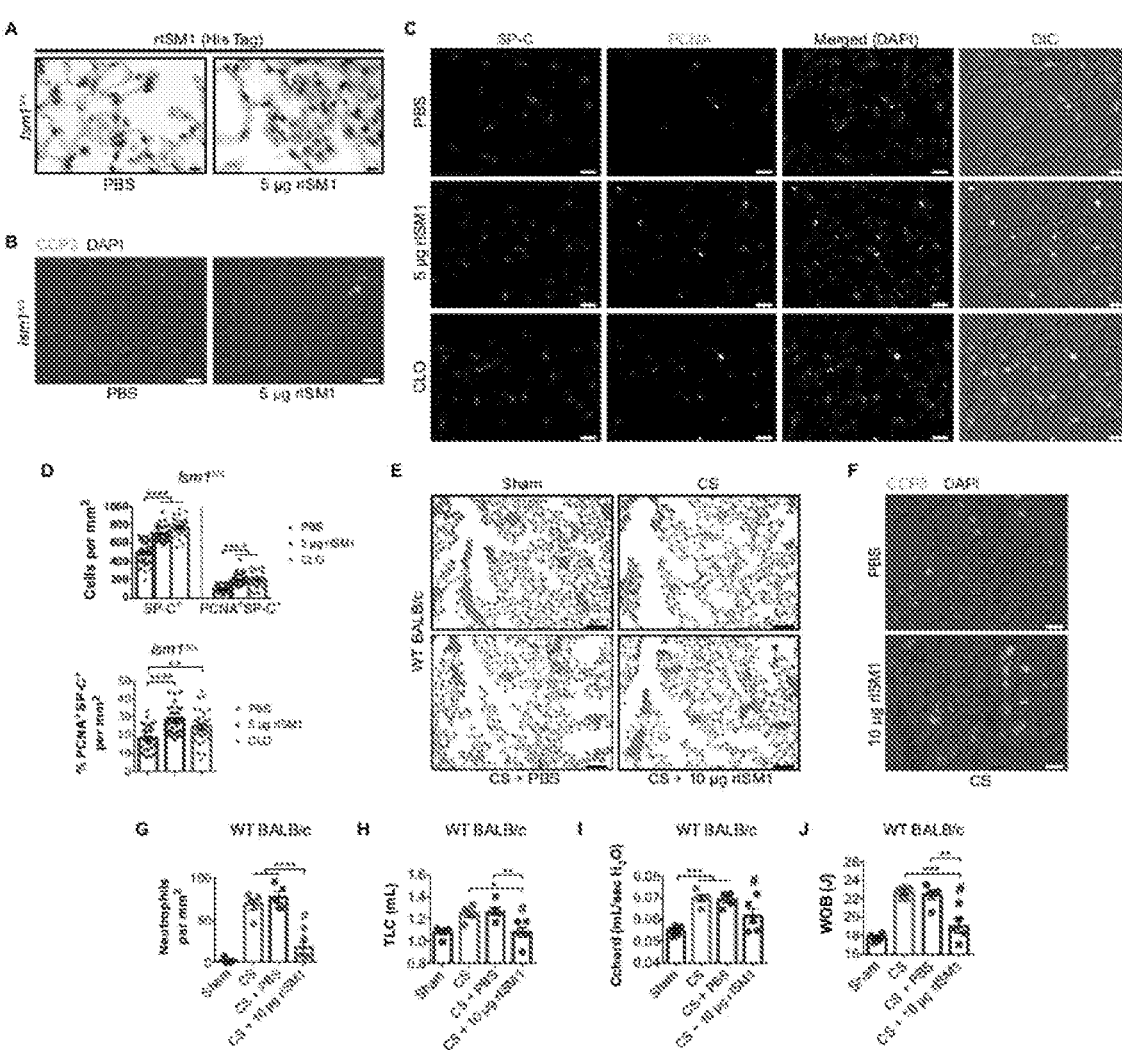
FIG. 7 shows exogenous rISM1 alleviates emphysema in Ism1$^{\Delta/\Delta}$ and cigarette smoke-exposed mice. (A) and (B) show representative immunostainings for rISM1 (A) and cleaved caspase-3 (CCP3, green) (B) in AMs of PBS and rISM1-treated FVB/NTac Ism1$^{\Delta/\Delta}$ mice. n=4 mice per group. Scale bars, 10 μm (A) and 20 μm (B). (C) and (D) show representative immunofluorescence staining for surfactant protein C (SP-C, red), PCNA (green), nuclei (DAPI, blue) (C) and quantifications (D) in FVB/NTac Ism1$^{\Delta/\Delta}$ mice lungs after PBS, 5 μg rISM1 or liposome-clodronate (CLO) treatments. n=34-40 fields per group, 9-10 random images were taken per mouse lung. Scale bars, 20 sm. (E) shows representative photomicrographs of hematoxylin and eosin stained lungs of room air-exposed (Sham), cigarette smoke-exposed WT BALB/cAnNTac (WT BALB/c) mice (CS) with vehicle (CS+PBS) or rISM1 (CS+10 μg rISM1) treatment. n=5 mice per group. Scale bars, 100 sm. (F) shows representative immunofluorescence staining for CCP3 (green) in PBS and rISM1-treated CS mice lungs in (E). n=5 mice per group. Scale bars, 20 μm. (G)-(J) shows quantification of lung neutrophil counts (G) and spirometry (H to J) of COPD mice in (E). Total lung capacity (TLC) (H), static compliance (Cchord) (I) and work of breathing (WOB) (J). Data are mean±s.e.m. and were analyzed by one-way ANOVA with Tukey's post hoc test (D, G to J). *P<0.05, P<0.01, *P<0.001, ****P<0.0001. #: no significant difference compared to Sham group.

FIGS. 6C, 6F, and 6G show rISM1 induces AM apoptosis by targeting csGRP78. rISM1 interacts with csGRP78 on the cell surface of freshly isolated primary AMs as demonstrated by confocal microscopy. (FIG. 6C). This data supports that rISM1 targets csGRP78 on the surface of AMs to trigger their apoptosis. In FIG. 6C, representative confocal images of primary AMs for rISM1 (red) and GRP78 (green) co-localization after 1 μM rISM1 treatment for 1 hour are shown (Nuclei were stained with DAPI (blue)). Further, mouse AM cell line MH-S cells undergo ISM1 induced apoptosis when the cells were pre-treated with thapsigargin (TG), which induce ER stress and upregulate csGRP78. Denatured ISM1 (boiled) lost this pro-apoptotic function, indicating this pro-apoptotic activity is a function of the ISM1 protein. Anti-GRP78 antibody interfered with rISM1 induced apoptosis, supporting that ISM1 targets csGRP78 on MH-S AM cell surface to trigger apoptosis. Note that higher concentrations of anti-GRP78 antibody can cause cell death itself, so only concentrations which did not have any effect on cells themselves were used to block csGRP78 and ISM1-induced apoptosis. FIGS. 6F and 6G show quantifications for apoptosis in mouse AM cell line MH-S cells after 24 hours of 50 nM thapsigargin (TG) pretreatment and 1 μM rISM1 treatment (left) with GRP78 antibody neutralization (right) for 16 hours. Treatment conditions as indicated. Analysis was carried out in triplicate wells, and 4 images per well were taken for quantifications using IncuCyte live-cell analysis system.

rISM1 Rescues Emphysema in Ism1$^{\Delta/\Delta}$ and Cigarette Smoke-Induced COPD Mice Since AMs play a key role in the pathogenesis of emphysema/COPD in mice[11,18,19], it was evaluated whether exogenously supplied rISM1 could block emphysema development/progression in Ism1$^{\Delta/\Delta}$ mice by inducing/promoting AM apoptosis and/or suppressing inflammation. Intratracheal rISM1 was delivered twice weekly to 1-month old Ism1$^{\Delta/\Delta}$ mice for 4 weeks and compared to mice treated with phosphate buffered saline (PBS) or liposome-clodronate, an established agent for AM depletion. Immunostainings showed that rISM1 was internalized by AMs and induced apoptosis (FIGS. 7A and B), significantly reducing AM numbers in a dose-dependent manner, similar to clodronate (FIG. 3A). Both rISM1 and clodronate-treated Ism1$^{\Delta/\Delta}$ mouse lungs exhibited significant reductions in emphysema (FIGS. 3B and C). Depletion of AMs by rISM1 or clodronate likely facilitated alveolar regeneration following inflammation resolution, as demonstrated by increased proliferating type 2 alveolar epithelial cells in both treated groups (FIGS. 7C and D). More importantly, pulmonary function tests indicated comparable restoration of airflow in both rISM1 and clodronate-treated Ism1$^{\Delta/\Delta}$ mice (FIG. 3D). Together, these results indicate that excessive AMs are central to spontaneous emphysema and lung function decline in Ism1$^{\Delta/\Delta}$ mice. Pulmonary delivery of rISM1 can rescue the Ism1$^{\Delta/\Delta}$ emphysema phenotype through AM depletion, as shown.

Next, it was assessed whether rISM1 could alleviate cigarette smoke (CS)-induced COPD in mice since chronic AM inflammation is tied to lung tissue damage. WT BALB/cAnNTac mice were subjected to 2 weeks and 8 weeks of room air (sham) or CS exposure and intratracheally treated with either PBS or rISM1 (FIGS. 3E and F). Cytospin analysis of BALF cells from 2-week CS-exposed mice revealed that rISM1 effectively suppressed inflammation and reduced AM and neutrophil numbers (FIG. 3G). Histological analysis of 8-week CS-exposed mice presented emphysema proximal to the terminal bronchioles with massive accumulation of immune cells comprising mainly AMs, similar to COPD patients who smoke (FIG. 3H and FIG. 7E). Mice treated with rISM1 generated more apoptotic AMs (FIG. 7F), significant reductions in both AMs (FIG. 3I) and MMP-12 levels from whole lung lysates (FIG. 3J). Neutrophils were also significantly reduced upon rISM1 treatment (FIG. 7G), possibly a consequence of reduced chemotaxis upon AM depletion (Murugan & Peck, 2009). Thus, pulmonary delivery of rISM1 effectively blocked emphysema (FIG. 3K) and preserved lung function (FIG. 3L and FIG. 7H to J) in CS-induced COPD mice through AM depletion.

Figure 3:
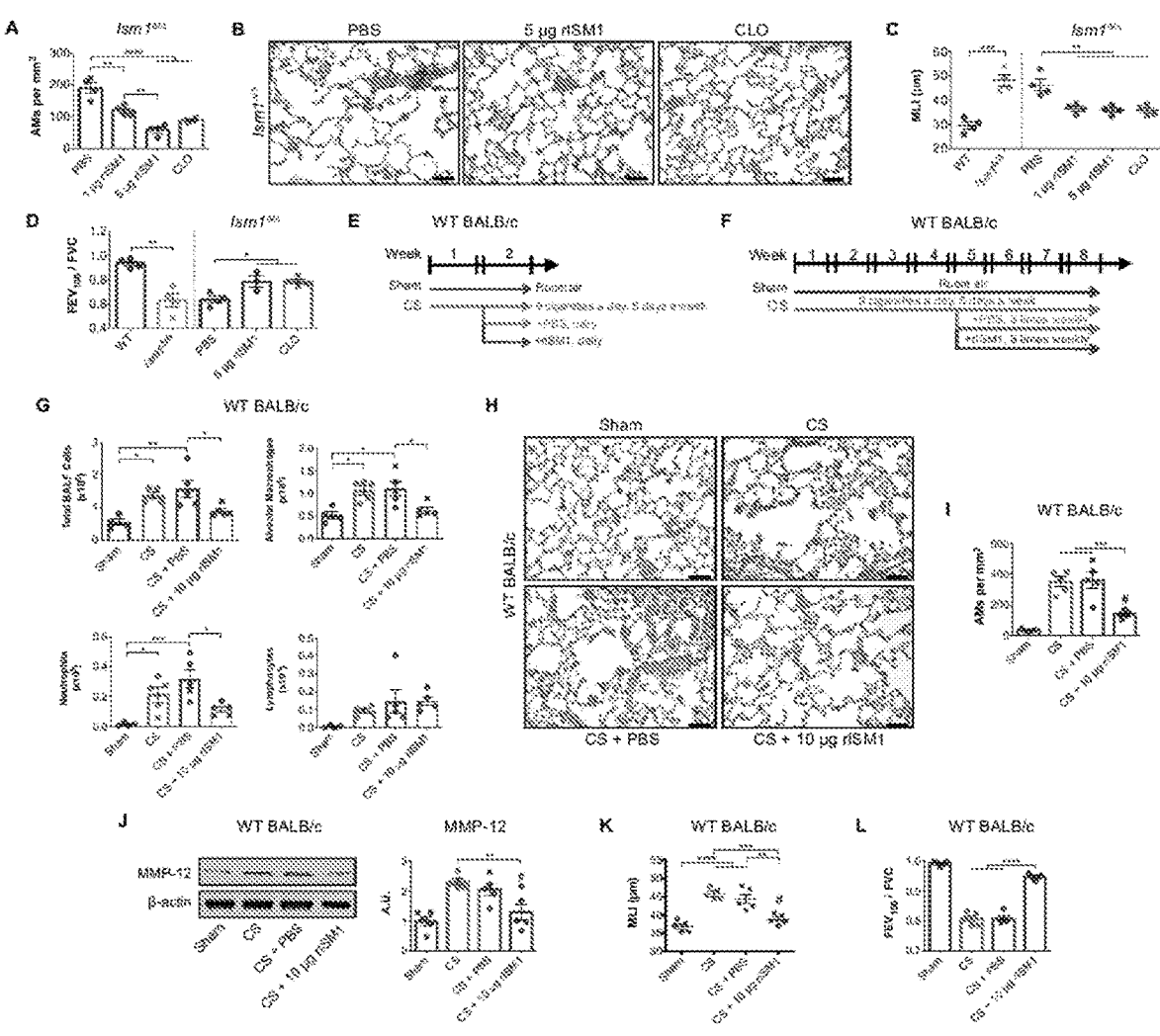
FIG. 3 shows exogenous rISM1 alleviates emphysema in Ism1$^{\Delta/\Delta}$ and cigarette smoke-exposed mice. (A) shows AM counts of 2-month old FVB/NTac Ism1$^{\Delta/\Delta}$ mice after vehicle (PBS), 1 μg rISM1, 5 μg rISM1 and liposome-clodronate (CLO) treatments. n=4 mice per group. (B) shows representative photomicrographs of hematoxylin and eosin stained lungs of 2-month old FVB/NTac Ism1$^{N}$A mice after vehicle (PBS), 5 μg rISM1 or liposome-clodronate (CLO) treatments. n=4 mice per group. Scale bars, 50 sm. (C) and (D) show quantifications of MLI (C) and FEV$_{100}$/FVC (D) of treated mice groups in (B) compared with untreated 2-month FVB/NTac WT and Ism1$^{\Delta/\Delta}$ mice. n=3-4 mice per group. (E) and (F) show experimental design of 2-week (E) and 8-week (F) cigarette smoke-induced COPD model in WT BALB/cAnNTac (WT BALB/c) mice. Room air-exposed WT BALB/c mice (Sham), cigarette smoke-exposed WT BALB/c mice (CS) with vehicle (CS+PBS) or rISM1 (CS+10 μg rISM1) treatments at frequency and intervals indicated. n=5 mice per group. (G) shows quantifications of bronchoalveolar lavage fluid (BALF) cells from experimental groups in (E). n=4-5 mice per group. (H) shows representative photomicrographs of hematoxylin and eosin stained lungs of experimental groups in (F) depicting immune cell infiltrates. n=5 mice per group. Scale bars, 50 μm. (I)-(L) show quantifications of AMs (I), MMP-12 expression (J), MLI (K) and FEV$_{100}$/FVC (L) of experimental groups in (F). n=5 mice per group. Data are mean±s.e.m. and were analyzed by unpaired two-tailed Student's t-test (C, D, untreated 2-month FVB/NTac WT and Ism1$^{\Delta/\Delta}$ mice) and one-way ANOVA with Tukey's post hoc test (C, D, G, I to L). *P<0.05, P<0.01, *P<0.001, ****P<0.0001, #: no significant difference compared to Sham group.

As shown in FIG. 3, rISM1 suppresses cigarette smoke (CS) induced acute lung inflammation. It is known that CS induces acute inflammation in the lung by inducing both neutrophils and AMs. Using a 2-weeks CS model in mice, intratracheal delivered rISM1 effectively suppressed CS-induced lung inflammatory response as shown in reduction of total BALF cells. Both AMs and neutrophils are suppressed, without affecting lymphocytes (FIG. 3E, 3G). This result is consistent with the data from 8-weeks chronic CS-induced emphysema (COPD) model in mice where intratracheal delivered rISM1 effectively quenched lung inflammation and reduced AM numbers by triggering AM apoptosis. FIG. 3E shows experimental design of 2-week cigarette smoke-induced COPD model in WT BALB/c mice. Room air-exposed (Sham), cigarette smoke-exposed (CS) with vehicle (CS+PBS) or rISM1 (CS+10 μg rISM1) treatments at frequency and intervals indicated (n=5 mice per group). FIG. 3G shows quantifications of bronchoalveolar lavage fluid (BALF) cells from experimental groups in 2-week cigarette smoke-induced COPD mice (n=4-5 mice per group).

Human ISM1 Expression Correlates with Alveolar Macrophage Apoptosis Since Ism1$^{\Delta/\Delta}$ mice developed spontaneous emphysema and exogenously supplied rISM1 protected mice from CS-induced COPD pathogenesis, it was hypothesized that variations in endogenous ISM1 levels in the human lung may also influence the development of COPD. We first validated our antibody specificity for human ISM1 (hISM1) using hISM1-overexpressing cells (FIG. 8A) and subsequently examined hISM1 expression in lung tissue sections from 60 COPD and 18 non-COPD patients (Table A).

55

TABLE A

| Patient Demographics (Forced epiratory volume in 1 sec (FEV1), Forced vital capacity (FVC). Data are mean ± s.e.m.) | | |
|---|---|---|
| Demographics | COPD (n = 60) | Non-COPD (n = 18) |
| Gender (Male %) | 50% | 16.70% |
| Age | 68.77 ± 0.94 | 54.00 ± 2.73 |
| Current smokers (n) | 6 | — |
| Ex-smokers (n) | 33 | 9 |
| Non-smokers (n) | 21 | 9 |
| FEV₁ (% predicted) | | |
| Current smokers | 54.33 ± 8.192 | — |
| Ex-smokers | 52.26 ± 4.58 | 100.60 ± 4.75 |
| Non-smokers | 76.15 ± 5.45 | 90.89 ± 2.38 |
| FVC (% predicted) | | |
| Current smokers | 61.33 ± 7.32 | — |
| Ex-smokers | 60.38 ± 4.25 | 98.44 ± 5.10 |
| Non-smokers | 79.30 ± 5.40 | 90.22 ± 3.04 |
| FEV₁/FVC | | |
| Current smokers | 0.48 ± 0.05 | — |
| Ex-smokers | 0.48 ± 0.03 | 0.79 ± 0.02 |
| Non-smokers | 0.61 ± 0.02 | 0.78 ± 0.02 |

Figure 8:
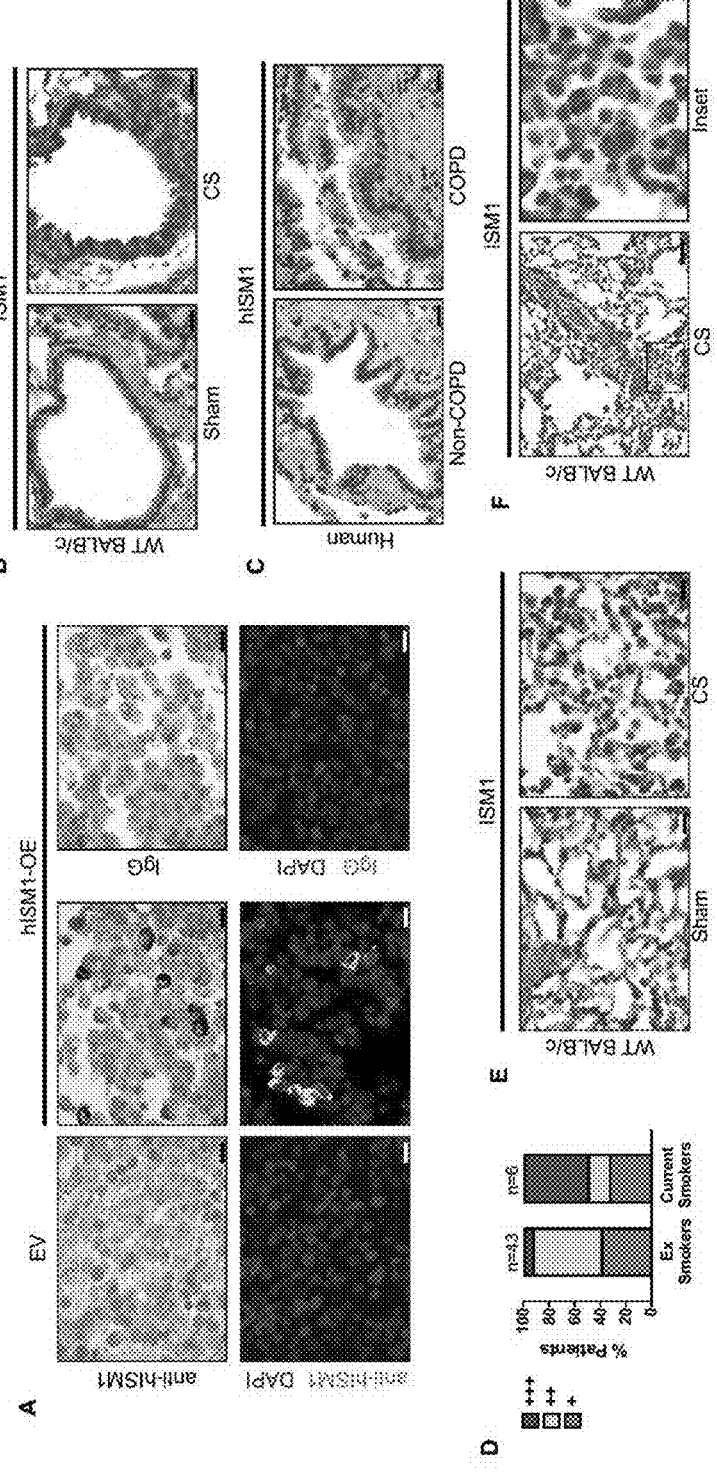
FIG. 8 shows ISM1 expression in COPD patients and cigarette smoke-exposed mice. (A) shows representative immunohistochemistry (top panel) and immunofluorescence (bottom panel) staining with anti-hISM1 or mouse IgG isotype control in empty vector (EV) or hISM1 over-expressing (hISM1-OE) HEK293FT cells. Scale bars, 20 μm. (B) and (C) show representative immunohistochemistry staining for ISM1 in the bronchial epithelium of room air-exposed (Sham) and cigarette smoke-exposed WT BALB/cAnNTac (WT BALB/c) mice (CS). n=5 mice per group (B); and non-COPD and COPD patients (C). Scale bars, 20 μm. (D) shows percent distribution of hISM1 expression in patients stratified by current smoking status. Patient sample sizes depicted on graph. (E) and (F) show representative immunohistochemistry staining for ISM1 in AMs (E) and not polymorphonuclear leukocytes or lymphocytes (F) of room air-exposed (Sham) and cigarette smoke-exposed WT BALB/c mice (CS). n=5 mice per group. Scale bars, 20 μm.
Figure 23:
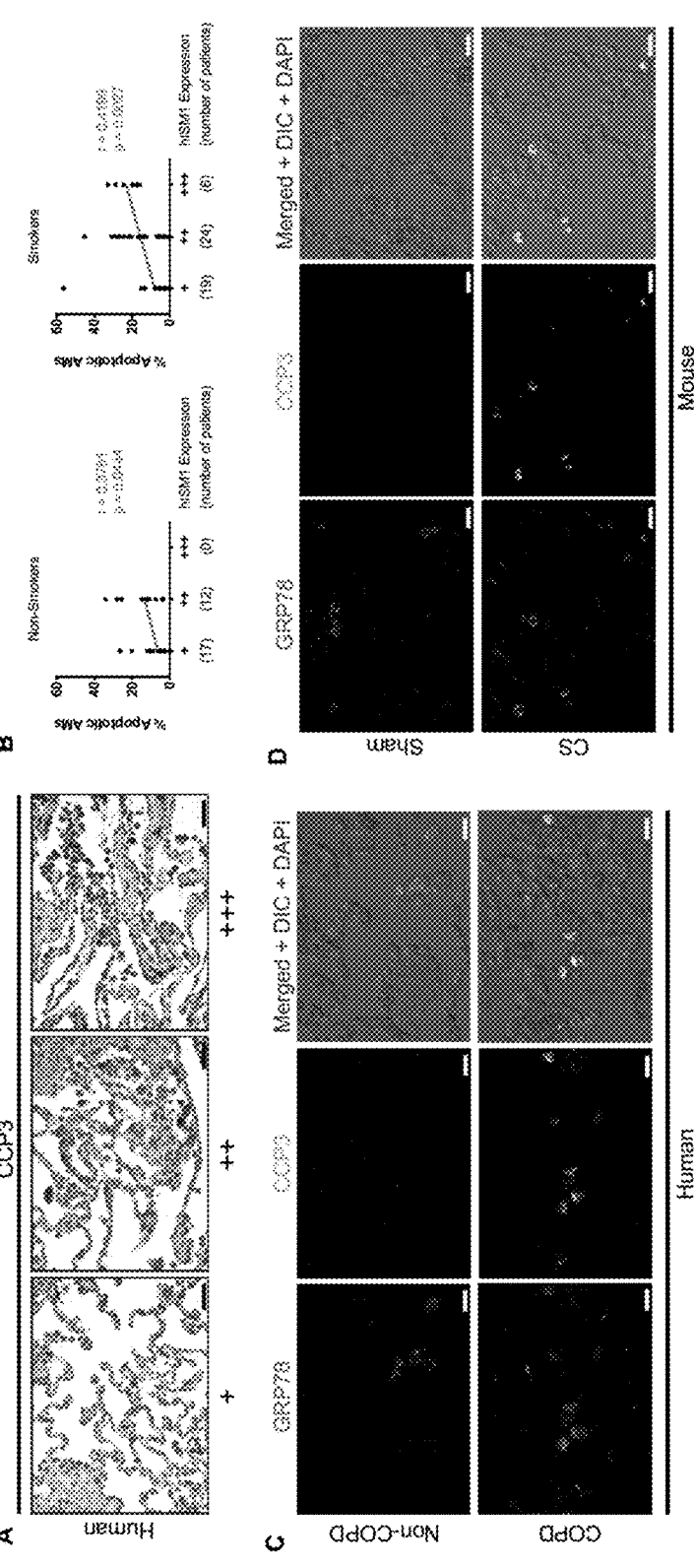
FIG. 23 shows alveolar macrophage apoptosis in COPD correlates with cell-surface GRP78 expression. (A) shows representative immunohistochemistry staining for cleaved caspase-3 (CCP3) in patient cohort. Scale bars, 50 μm. (B) shows correlation between hISM1 expression and AM apoptosis, stratified by smoking status. Patient sample sizes depicted on graph. Data was analyzed by Pearson correlation. (C) and (D) show representative immunofluorescence staining for GRP78 (red), cleaved caspase-3 (CCP3, green) and nuclei (DAPI, blue) in room air-exposed (Sham) and cigarette smoke-exposed (CS) WT BALB/cAnNTac mice lungs. n=5 mice per group. Scale bars, 20 μm (C); and non-COPD and COPD patients. Scale bars, 10 μm (D)

Similar to mouse, hISM1 was also predominantly expressed in AMs (FIGS. 4A and B). However, while ISM1 was also expressed in the bronchial epithelium in mice, particularly after CS exposure (FIG. 8B), hISM1 was not detected in the bronchial epithelium in either COPD or non-COPD human lungs (FIG. 8C). hISM1 expression was then graded by scoring both IHC staining intensity and frequency of hISM1 expression in AMs (FIG. 4A-C). Positive correlation was found between hISM1 expression and smokers (FIGS. 4D and E), while higher hISM1 expression was observed in current smokers than ex-smokers (FIG. 8D). These findings were consistent with ISM1 being considerably upregulated specifically in mouse AMs upon CS exposure (FIG. 8E) while other immune cells such as polymorphonuclear leukocytes and lymphocytes remained undetectable for ISM1 staining (FIG. 8F). Importantly, hISM1 expression significantly and positively correlated with AM apoptosis independent of smoking status (FIG. 4F, FIGS. 23A and B). Notably, csGRP78 is upregulated on AMs of COPD patients compared with non-COPD patients (FIG. 4G), enabling AMs to be primed for ISM1-csGRP78 mediated apoptosis. Indeed, more apoptotic AMs were observed in COPD patients compared with non-COPD patients with similar hISM1 expression (FIG. 4H), and only csGRP78-positive AMs were apoptotic in COPD patients and CS-exposed mice (FIGS. 23C and D).

Based on these results, it is hypothesized that physiological ISM1 may be important for maintaining adult lung homeostasis by regulating AM apoptosis through csGRP78. Loss of ISM1 may lead to AM accumulation from diminished apoptosis, thus ensuing pulmonary inflammation and emphysema in Ism1^{Δ/Δ} mice even under ambient air (FIG. 24).

FIGS. 4E, 4F, and 4H show ISM1 expression in human COPD lung and non-COPD lung correlate with cigarette smoke and AM apoptosis. ISM1 expression analyses using immunohistochemistry (IHC) from 60 COPD and 18 non-COPD human lung tissue samples revealed that the level of expression of human ISM1 (hISM1) protein correlates with cigarette smoke, with smokers showed higher ISM1 expression (FIG. 4E). In addition, the level of AM apoptosis correlates with the level of hISM1 in the lung tissue, with higher hISM1 level presenting higher AM apoptosis in the lung (FIG. 4F). In both COPD and non-COPD lungs, higher hISM1 level presents higher AM apoptosis (FIG. 4H). Indeed, hISM1 expression in COPD and non-COPD lungs is shown in FIGS. 4E, 4F, and 4H. Correlation between (4E) smoking status and hISM1, and (4F) hISM1 expression and AM apoptosis is shown. Patient sample sizes are depicted on graph. Data were analyzed by point-biserial correlation (4E) and Pearson correlation (4F). Percentage of apoptotic AMs in non-COPD and COPD patients stratified by COPD status and hISM1 expression. Patient sample sizes are depicted on graph (Data are mean±s.e.m. and were analyzed by one-way ANOVA with Tukey's post hoc test. *P<0.05, P<0.01, **P<0.0001).

Without wishing to be bound by theory, FIG. 24 provides proposed mechanisms for ISM1 in regulating AM apoptosis and lung homeostasis. In FIG. 24 (left), autocrine/paracrine ISM1 specifically targets AMs with high csGRP78 and induces apoptosis. AM numbers are kept under control, inflammation is regulated and lung homeostasis is maintained. In FIG. 24 (right), no/low ISM1 results in AM accumulation in the alveolar space and onset of emphysema with progressive decline in lung function.

As discussed, chronic obstructive pulmonary disease (COPD) is the 3rd leading cause of death globally, with cigarette smoking, long-term exposure to environmental pollution and ageing as the major risk factors. It is characterized by largely irreversible blockage of air flow due to emphysema (destruction of alveolar wall), chronic and obstructive bronchitis (airway inflammation) of the small airways. Patients present recurring respiratory symptoms such as coughing and breathing difficulties. Furthermore, exercise intolerance lead to muscle weakness and sarcopenia in COPD patients. Current therapeutics are mainly bronchial dilators, providing symptomatic relief only and no drug is available to block disease progression. In the studies described herein, using both genetic and pathological mouse models, results reveal that the proapoptotic ISTHMIN 1 (ISM1) protein is a protector of lung tissue homeostasis. Loss of ISM1 leads to spontaneous COPD as a result of alveolar macrophage (AM) accumulation. In both mouse and human lungs, AMs express both ISM1 and its high-affinity receptor csGRP78, thus enabling self-regulated apoptosis. Local lung delivery of recombinant ISM1 (rISM1) reduced AM numbers, suppressed inflammation and preserved lung function in cigarette smoke-induced COPD mice. Furthermore, human ISM1 expression in lung significantly and positively correlated with AM apoptosis.

Results described herein identify ISM1 as an anti-inflammatory protein that protects normal lung function and blocks CS-induced COPD development. Without wishing to be bound by theory, this work supports use of rISM1 as a protein therapeutic for quenching lung inflammation by targeting csGRP78 on pathological AMs. Results indicate that ISM1-csGRP78 mediated AM targeting may provide therapeutic strategies in a wide spectrum of inflammatory lung diseases in which AMs play a pathological role, for example.

Macrophage clearance has been shown to be dominantly mediated through local apoptosis during inflammation resolution[26], and AM apoptosis is important in resolving infection-associated acute pulmonary inflammation[27-29]. AMs underlie COPD pathogenesis and lung deterioration[2,20,25], and are notoriously resistant to apoptosis[23] and corticosteroid treatments[30]. The findings herein reveal an autocrine/paracrine mechanism to control AM number and maintain lung homeostasis through the proapoptotic protein ISM1.

ISM1 targeted csGRP78 on AMs to induce apoptosis and limit lung inflammation, while loss of ISM1 resulted in AM accumulation and spontaneous emphysema in Ism1$^{\Delta/\Delta}$ mice (FIG. 24B). Incidentally, AM accumulation is linked with emphysema development in smokers[2]. Intratracheal instillation of rISM1 prevented AM accumulation in CS-exposed mice and effectively blocked COPD progression, concurring with previous mouse studies demonstrating the efficacy of AM depletion[18,19]. Consistently, high hISM1-expressing patients presented more AM apoptosis, lower AM numbers and lower frequency of severe COPD. The heterogeneity of hISM1 expression in COPD patients may provide for better insight for early interventions for COPD patients. The present findings underscore the important role of regulated AM apoptosis in maintaining lung homeostasis, and identify a protective role of ISM1 in lung homeostasis as an inflammation suppressor. rISM1 may provide therapeutic benefit in halting COPD progression through quenching AM-driven lung inflammation, for example.

COPD has been a growing global epidemic with huge socioeconomic burdens without any effective drug to block disease progression and/or restore lung function. Studies described herein demonstrate that the secreted 50 kDa protein ISM1 is an anti-inflammatory protein that can effectively quench lung inflammation and block CS-induced COPD progression in mice. Topical pulmonary delivery of rISM1 specifically targeted AMs for apoptosis via its high-affinity receptor csGRP78.

AMs constitute more than 95% of the lung immune cells and are the main inflammatory orchestrators for COPD while being resistant to apoptosis, thus contributing to chronic lung inflammation even after smoking cessation (Barnes, 2016, Domagala-Kulawik, Maskey-Warzechowska et al., 2003, Kojima, Araya et al., 2013). Intratracheally delivered rISM1 effectively blocked AM accumulation and prevented lung function decline in CS-induced COPD mice, concurring with previous mouse studies that demonstrated efficacy of AM depletion in emphysema prevention. Thus, results described herein support rISM1 as a therapeutic for COPD to block disease progression and/or maintain lung function, for example. By inducing AM apoptosis, it is contemplated that rISM1 may not only impede direct proteolytic damage by AM-secreted protease such as MMP-12, but may also prevent MMP-12-driven tumor necrosis factor-alpha (TNF-α)-associated endothelial cell activation, neutrophil chemotaxis and further macrophage activation, a process estimated to account for up to 70% of CS-induced lung damage (Churg, Wang et al., 2004). Hence, AMs are and should remain as important targets for novel anti-inflammatory COPD therapeutics. However, AMs are known to be unresponsive to steroids (Barnes, 2013a) and poor translatability between mouse models and human clinical trials in targeting discrete pro-inflammatory molecules remains a major challenge for COPD drug development (Barnes, 2013b). In this case, rISM1 has a clear advantage through its ability to specifically target csGRP78 on AMs. Incidentally, pathological AMs in COPD harbor high levels of csGRP78 (FIG. 4G), making them the ideal candidate for rISM1-mediated apoptosis. Consequently, rISM1 can effectively suppress AM inflammation and simultaneously snuff out multiple pro-inflammatory factors. Without wishing to be bound by theory, it is contemplated that rISM1 may induce apoptosis in pro-inflammatory AMs without damaging the immunosuppressive interstitial macrophages that do not express csGRP78 (Quesada Calvo, Fillet et al., 2011), thus allowing them to carry out homeostatic functions in the lung.

In this work, results reveal a novel physiological function of ISM1 in maintaining lung homeostasis, consistent with its highest expression level in the mouse lung over other organs. Results showed that loss of ISM1 in mice leads to spontaneous emphysema development under ambient air accompanied with excessive AM accumulation in the alveolar space. Results identified that AMs are a novel source of ISM1 in the mouse lung, in addition to bronchial epithelial cells and endothelial cells reported previously. Furthermore, AMs express both ISM1 and its high-affinity cell-surface receptor GRP78 at heterogeneous levels in the normal mouse lung (FIGS. 2I and J). ISM1 may specifically targets cells harboring high level csGRP78 for apoptosis (Chen et al., 2014). Results described herein support a model in which ISM1 selectively targets AMs that harbor high csGRP78 for apoptosis, while AMs with no/low csGRP78 are left intact, thus controlling AM number for lung homeostasis (FIG. 24). Freshly isolated AMs from Ism1$^{\Delta/\Delta}$ mice exhibited lower apoptosis levels compared with AMs from WT mice, suggesting autocrine/paracrine regulation of AM apoptosis by endogenous ISM1 in the murine lung. Intratracheally delivered rISM1 depleted AMs and rescued emphysema in Ism1$^{\Delta/\Delta}$ mice, similar to clodronate treatment. These results from Ism1$^{\Delta/\Delta}$ mice demonstrate that AM accumulation resulting from dysregulated apoptosis is critical and sufficient for emphysema development even in the absence of environmental assault, concurring with AMs as the main orchestrators for COPD pathogenesis.

The critical role of ISM1 in lung homeostasis may be unique in mammals, as previous Ism1 loss-of-function studies in lower vertebrates led to contrasting phenotypes such as craniofacial defects in *Xenopus* (Lansdon, Darbro et al., 2018) and angiogenesis defects with altered hematopoiesis in zebrafish (Berrun, Harris et al., 2018, Xiang et al., 2011). The highly divergent and intrinsically disordered N-terminal region of ISM1 may contribute to different biological functions in different species (Babu, 2016). On the other hand, high sequence similarity between mouse and human ISM1 (93.5% identity) suggests that ISM1 possesses a conserved function between these species. (Joshi & Xu, 2007).

Figure 4:
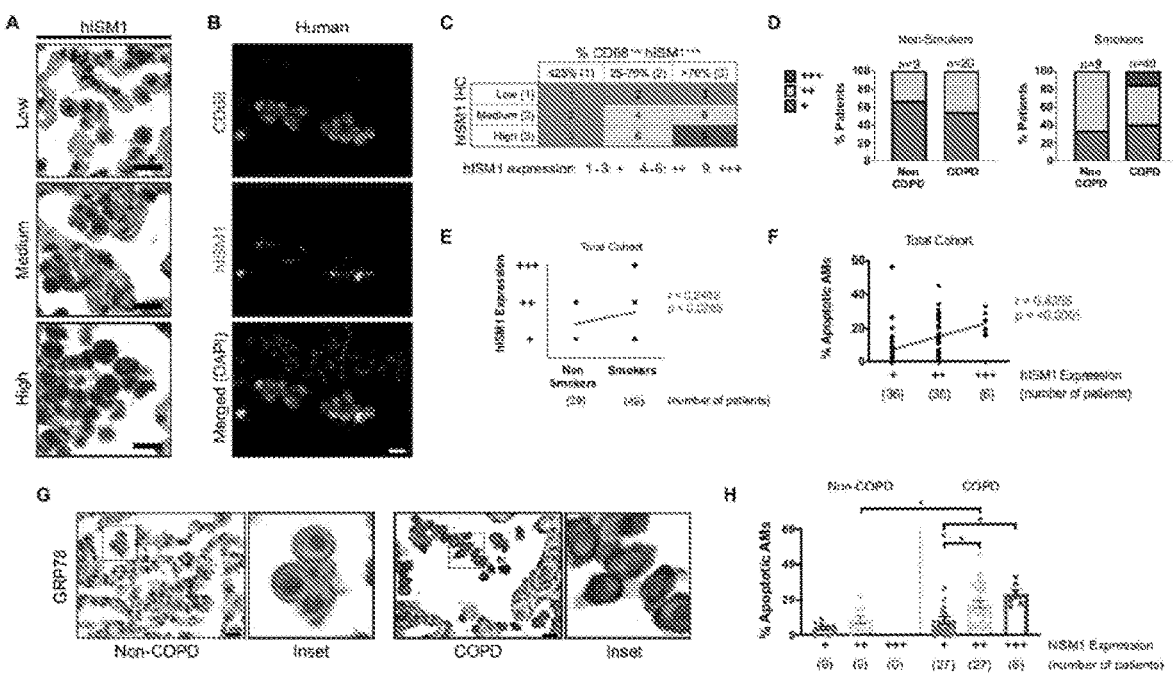
FIG. 4 shows human ISM1 expression correlates with AM apoptosis. (A) and (B) show representative immunohistochemistry staining for human ISM1 (hISM1) (A) and immunofluorescence staining for CD68 (red), hISM1 (green) and nuclei (DAPI, blue) in AMs of resected human lung tissue sections. Scale bars, 20 μm. (C) shows matrix table for hISM1 expression derived from IHC staining intensity (A) and expression frequency in human AMs (B). hISM1 expression annotated by matrix scores 1-3: +, 4-6: ++, 9: +++. (D) shows percent distribution of hISM1 expression in patients stratified by smoking and COPD status. (E) and (F) show correlation between hISM1 expression and smoking (E), and AM apoptosis (F). (G) shows representative immunohistochemistry staining for GRP78 in non-COPD and COPD patients. Scale bars, 20 μm. (H) shows percentage of apoptotic AMs in COPD patients stratified by COPD status and hISM1 expression. Data are mean±s.e.m. and were analyzed by point-biserial correlation (E), Pearson correlation (F) and one-way ANOVA with Tukey's post hoc test (H). *P<0.05. Patient sample sizes depicted on graph.

Results from this work reveal an autocrine/paracrine signaling axis between endogenous ISM1 and csGRP78 in inducing AM apoptosis and maintaining lung homeostasis. Local macrophage apoptosis and clearance contributes to inflammation resolution (Hamidzadeh, Christensen et al., 2017) and this has been described in early atherosclerosis (Arai, Shelton et al., 2005), experimental peritonitis (Gautier, Ivanov et al., 2013) and infection-associated acute pulmonary inflammation (Aberdein, Cole et al., 2013). The upregulation of ISM1 in COPD lungs of both mouse and human may be a biological response similar to the pleiotropic TNF-α and type I interferons which are upregulated in multiple lung diseases and can induce AM apoptosis via autocrine signaling (Wei, Sun et al., 2006, Xaus, Comalada et al., 2000). Indeed, hISM1 expression strongly correlated with AM apoptosis, which was also observed to be heightened in COPD patients (FIG. 4).

Although previous genome-wide association studies (GWAS) have not associated the Ism1 locus with COPD, it would be meaningful to understand the heterogeneity of hISM1 expression in a larger population of COPD patients to uncover potential epigenetic or genetic influences on Ism1 and its regulatory genes. In addition, whether hISM1 expression possesses any interrelatedness with the diverse comorbidities that contribute to high mortality rates in COPD is of interest.

It is noted that $\alpha v\beta 5$ integrin, the low-affinity receptor of ISM1, has also been reported to be present on lung endothelial and airway epithelial cells (Teoh, Tan et al., 2015). However, we did not observe any obvious targeting of these cells in mice when rISM1 was delivered intratracheally (FIG. 7), which would have otherwise aggravated emphysema due to the undesired apoptosis of these lung structural cells. Accordingly, rISM1 treatment relieved emphysema and improved lung function in Ism1$^{\Delta/\Delta}$ mice.

The relative large size of rISM1 (~50 kDa) suggests that ISM1 would not be rapidly cleared from the lung and absorbed into the bloodstream (Labiris & Dolovich, 2003, Patton, Fishburn et al., 2004). Significant advances in nebulization of protein therapeutics for topical lung delivery have emerged in various clinical trials. For example, several phase II/III clinical trials of alpha-1 antitrypsin (52 kDa) as an inhaled therapeutic have been conducted for alpha-1 antitrypsin deficiency and cystic fibrosis (Bodier-Montagutelli, Mayor et al., 2018). In certain embodiments, ISM1 may be used with pulmonary delivery via nebulization due to its comparable size to alpha-1 antitrypsin, for example.

In summary, results described herein underscore the key role of AM apoptosis regulation in maintaining lung homeostasis and the important role ISM1 played in this function in both physiological and pathological conditions. Results support Ism1 as a novel gene linked to emphysema/COPD pathogenesis and AM apoptosis, and demonstrate that rISM1 attenuated emphysema, suppressed inflammation and preserved lung function in a chronic CS-induced COPD in mice. Results indicate that rISM1 may be used in therapy for COPD by specifically targeting csGRP78 on AMs, the main pathological immune cell in COPD. It is contemplated that findings described herein may also have implications for a wide spectrum of respiratory disorders driven or contributed by AMs such as lung ischemia-reperfusion injury (Naidu, Krishnadasan et al., 2003), acute lung injury (Dagvadorj, Shimada et al., 2015), lung fibrosis (Misharin, Morales-Nebreda et al., 2017) and asthma (Nabe, Matsuda et al., 2018). In certain embodiments, pathological expression of csGRP78 in other non-cancerous diseases, such as rheumatoid arthritis and systemic lupus erythematosus (Lu et al., 2010, Weber, Haslbeck et al., 2010), may also provide therapeutic opportunities for rISM1 to modulate inflammation.

One or more illustrative embodiments have been described by way of example. It will be understood to persons skilled in the art that a number of variations and modifications can be made without departing from the scope of the invention as defined in the claims.

Methods

Study design. A primary objective of this study was to determine the physiological function of mammalian Ism1 using an in-house generated CRISPR/Cas9-mediated knockout of Ism1 in two genetic background (FVB/NTac and C57BL/6J mice). Sample sizes for phenotype characterization and rescue experiments were kept at a minimum of three animals per group for statistical analyses, and n numbers are presented on the respective figures and figure legends of each experiment. Age and gender-matched mice were randomly allocated into the experimental groups, and no outliers were excluded from the animal studies. Rescue experiments for Ism1$^{\Delta/\Delta}$ mice were repeated twice and separately analyzed for lung function parameters and histology. Rescue of chronic CS-induced COPD mice experiment was carried out once with lung function parameters measured and left lung lobes fixed for histology analysis and right lung lobes homogenized for biochemical analysis. Immune cell quantifications of all mouse experiments were carried out in a blind fashion. De-identified human lung samples were used for immune cell quantifications, staining and grading for hISM1 expression. No data was excluded in the human cohort study.

Mice. All animal experiments were conducted in accordance with approved protocols by the National University of Singapore, Institutional Animal Care and Use Committee (IACUC protocols BR15-1100 and R18-0588). Wild-type mice (FVB/NTac, C57BL/6J, and BALB/cAnNTac; 6 to 8 weeks of age) were purchased from InVivos Pte Ltd, Singapore. Ism1$^{\Delta/\Delta}$ mice (FVB/NTac and C57BL/6J) were in-house generated using pronuclear microinjection method of recombinant Cas9 and guide RNAs targeting 5'-CTGCA-CATCACGGTTCTGCGCGG-3' (gRNA1, PAM sequence underlined SEQ ID NO: 5) and 5'-GCGGATCCG-GAGCCTCCGACCGG-3' (gRNA2, PAM sequence underlined SEQ ID NO: 6) of Ism1 exon1. Filial generations of Ism1$^{\Delta/\Delta}$ mice were identified via genotyping primer pairs P1 (5'-CAGCTCCTGGGATTGCTCCG-3') (SEQ ID NO: 7) and P2 (5'-CCTTCTGCAATGTACCAAGCTCT-3') (SEQ ID NO: 8) (for FVB/NTac) and 5'-cgcgcgactcaagaggatgg-3' (SEQ ID NO: 22) and 5'-actgggacccgctgacgttg-3' (SEQ ID NO: 23) (for C57BL/6J) and sequencing, before being selected for subsequent breeding and colony maintenance (IACUC protocol BR15-1100). All mice were housed under standard 12-hour light-dark cycle, with food and water available ad libitum. Mice were anesthetized with isoflurane prior to all intratracheal instillations.

Cells. MH-S(CRL-2019™) was purchased from ATCC and cultured in RPMI-140 medium supplemented with 10% heat-inactivated FBS, penicillin (100 U/mL) and streptomycin (100 µg/mL). Primary alveolar macrophages were harvested from 2-month old wild-type and Ism1$^{\Delta/\Delta}$ FVB/NTac mice as described (Chavez-Santoscoy, Huntimer et al., 2012), and cultured in RPMI-140 medium supplemented with 10% heat-inactivated FBS, penicillin (100 U/mL) and streptomycin (100 µg/mL). Cells were maintained at 37° C. in a 5% CO$_2$ incubator. Primary alveolar macrophages were harvested from 2-month old wild-type and Ism1$^{\Delta/\Delta}$ FVB/NTac mice as described[32], and cultured in DMEM medium supplemented with 10% heat-inactivated FBS, penicillin (100 U/mL) and streptomycin (100 µg/mL). Primary alveolar macrophages were maintained at 37° C. in a 5% CO$_2$ incubator.

Reagents. Primary antibodies used for western blot: anti-MMP-12 (ab52897, Abcam), anti-MMP-9 (ab38898, Abcam), anti-p65 (10745-1-AP, Proteintech), anti-β-Actin Antibody (C4, Santa Cruz Biotechnology), anti-TGF-β1 (V, Santa Cruz Biotechnology), anti-VEGF-A (A-20, Santa Cruz Biotechnology), anti-Neutrophil Elastase (ab68672, Abcam), anti-Alpha-1-Antitrypsin (16382-1-AP, Proteintech). Primary antibodies used for immunohistochemistry: anti-MMP-12 (ab66157, Abcam), anti-MMP-9 (ab38898, Abcam), anti-TGF-β31 (V, Santa Cruz Biotechnology), anti-VEGF-A (A-20, Santa Cruz Biotechnology), anti-ISM1 (for mouse lung: E-20, Santa Cruz Biotechnology; for human lung: custom antibody 3M8, AbMart), anti-GRP78 (A-10, Santa Cruz Biotechnology), anti-His-probe (H-15, Santa Cruz Biotechnology), anti-Cleaved caspase-3 (Asp175, Cell Signaling Technology). Primary antibodies used for immunofluorescence: anti-ISM1 (E-20, Santa Cruz Biotechnology), anti-p65 (10745-1-AP, Proteintech), anti-CD68 (M-20, Santa Cruz Biotechnology), anti-His-probe (H-15, Santa Cruz Biotechnology), anti-GRP78 (A-10, Santa Cruz Biotechnology), anti-Cleaved caspase-3 (Asp175, Cell Signaling Technology), anti-SP-C (FL-197, Santa Cruz Biotechnology), anti-PCNA (PC10, Santa Cruz Biotechnology), anti-GRP78 (A-10, Santa Cruz Biotechnology), Neutrophil Marker (NIMP-R14, Santa Cruz Biotechnology). Reactive oxygen species was measured using OxiSelect™ In Vitro ROS/RNS Assay (STA-347, Cell Biolabs) according to manufacturer's protocol. Cell proliferation was measured using Click-iT™ EdU Proliferation Assay for Microplates (Invitrogen, C10499) according to manufacturer's protocol. Recombinant ISM1 (rISM1) was produced as previously described (Xiang et al., 2011). Liposome-encapsulated clodronate was purchased from Liposoma.

Mouse rISM (mature form, no signal peptide) was expressed and purified as a 6xHis-Tagged protein in *E. coli* using the vector pET-M (as described in Xiang et al., 2011, JCMM, herein incorporated by reference in its entirety). Mouse rISM1 was used in these experiments. Mature ISM1 (without signal peptide) is biologically active in the conditions tested. The ISM1 sequence used comprises NP_001263418.1, and is as follows:

incubated in liquid DAB+chromogenic substrate (Dako) for 5 to 15 minutes before hematoxylin counterstaining and coverslip mounting. Lung sections stained with Periodic Acid-Schiff (87007, Thermo Fisher) and Elastin Stain Kit (ab150667, Abcam) were carried out according to manufacturer's protocol. Images were acquired with Zeiss Axiovert 200 and Zeiss LSM-510 Meta confocal microscope, analyzed and adjusted for brightness and contrast using ImageJ software (NIH).

Figure 25:
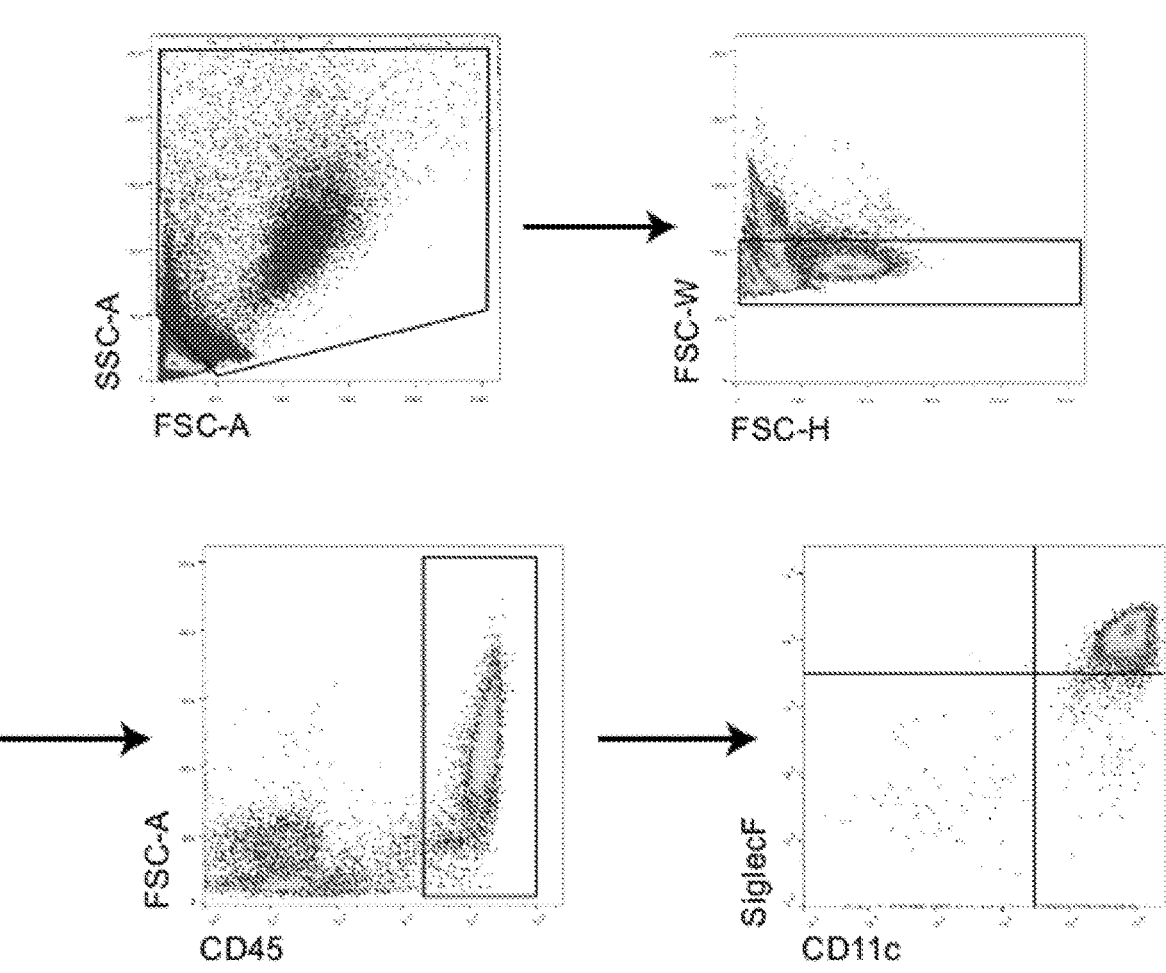
FIG. 25 shows the gating strategy for flow cytometry analysis of cells from bronchoalveolar lavage fluid (BALF). Gating strategy for alveolar macrophages is shown, with representative gating strategy for flow cytometric analysis and quantifications for alveolar macrophages.

BALF immune cell quantifications. Bronchoalveolar lavage fluid (BALF) were collected and cells were analyzed by flow cytometry using standard procedures. The gating strategy to select AMs is shown in FIG. 25.

Apoptosis determination. Apoptosis were measured using the IncuCyte ZOOM live cell imaging system (Essen Bioscience). MH-S cells or primary alveolar macrophages were seeded at a density of 50,000 cells per 96-well and apoptosis was measured hourly using IncuCyte Caspase-3/7 Green Apoptosis Assay Reagent (Cat. No. 4440, Essen Bioscience)

```
M H H H H H H S S G L V P R G S G A S D R Q D A A A G N V S G S Q L Q N N L N L
E S D S T S E T S F P L S K E A P E E H Q V V H Q P F P R Q R F P P E T G H P S L
Q R D G P R S F L L D L P N F P D L S K A D I N G Q N P N I Q V T I E V V D G P D S
E A E K D Q H P E N K P S W S L P A P D W R A W W Q R S L S L A R T N S G D Q D
D K Y D S T S D D S N F L S V P R G W D R P A P G H R T F E T K E Q P E Y D S T D
G E G D W S L W S V C S V T C G N G N Q K R T R S C G Y A C I A T E S R T C D R
P N C P G I E D T F R T A A T E V S L L A G S E E F N A T K L F E V D M D S C E R
W M S C K S E F L K K Y M H K V I N D L P S C P C S Y P T E V A Y S T A D I F D R I
K R K D F R W K D A S G P K E K L E I Y K P T A R Y C I R S M L S L E S T T L A A Q
H C C Y G D N M Q L I T R G K G A G T P N L I S T E F S A E L H Y K V D V L P W I I
C K G D W S R Y N E A R P P N N G Q K C T E S P S D E D Y I K Q F Q E A R E Y L
E H H H H H H
(SEQ ID NO: 9; Underlining indicates native ISM1 sequence, Bold indicates Vector
sequence and His-tag, Italics indicates N-terminal M residue)
```

Liposome encapsulated clodronate was purchased from Liposoma.

Lung histology and imaging. Mouse lungs from the respective experiments were inflated and fixed in 10% neutral buffered formalin, embedded in paraffin and sectioned in 5 µm thickness. Prior to staining, mouse and human lung sections were deparaffinized in HistoChoice® Clearing Agent (Sigma-Aldrich), serial dilutions of ethanol and PBS. Histology and pathology scoring for emphysema in FVB/NTac WT and Ism1$^{\Delta/\Delta}$ mice were performed by a veterinarian pathologist. Pathology score: 0=not present; 1=minimal (>1%); 2=slight (1-25%); 3=moderate (26-50%); 4=moderately severe/high (61-75%); and 5=severe/high (76-100%). Mean linear intercepts (MLI) were quantified as described[34] (Knudsen, Weibel et al., 2010). Bronchial epithelial cell counts and measurements were quantified using ImageJ software (NIH). For immunofluorescence and immunohistochemistry staining, lung sections were subjected to antigen retrieval by pressure-cooking in sodium citrate buffer (10 mM Sodium Citrate, 0.05% Tween 20, pH 6.0) after deparaffinization. Slides were left to cool to room temperature and rinsed with PBS before blocked with 3% BSA in PBS for 1 hour. An additional 30 minutes of 3% hydrogen peroxide quenching was carried out on lung sections intended for immunohistochemistry. Lung sections were then incubated overnight with the respective primary antibodies in a humidified chamber at room temperature, washed three times with 0.1% PBST to remove unbound antibodies, incubated with the respective secondary antibodies for 1 hour at room temperature and washed again with three times with 0.1% PBST. Immunofluorescence-stained slides were counterstained with DAPI before coverslip mounting, while immunohistochemistry-stained slides were according to manufacturer's instruction. MH-S cells were pretreated for 24 hours with 50 nM thapsigargin (Sigma-Aldrich) in RPMI-140 media supplemented with 1% heat-inactivated FBS, and then treated with 1 µM rISM1 with and without anti-GRP78 (A-10, Santa Cruz Biotechnology) antibody neutralization for 16 hours under same culturing conditions. Treatments were carried out in triplicate wells, and 4 images per well were taken for quantifications. Primary alveolar macrophages were treated with 1 µM rISM1 for 16 hours under same culturing conditions. Experiment groups were carried out in quadruplicate wells, and 4 separate fields per well were taken for quantifications.

Pulmonary function test. Spirometry was performed on FVB/NTac wild-type and Ism1$^{\Delta/\Delta}$ mice, as well as experimental COPD WT Balb/cAnNTac mice as previously described[35] (Peh, Tan et al., 2017). Briefly, mice were anesthetized with ketamine (75 mg/kg) and medetomidine (1 mg/kg) cocktail and tracheotomized. Mice were cannulated and placed in a whole-body plethysmograph connected to a computer-controlled ventilator (Forced pulmonary maneuver system, Buxco Research System). Total lung capacity (TLC), functional residual capacity (FRC), residual volume (RV), static compliance (Cchord), dynamic compliance (Cdyn), forced expiratory volume at 100 ms (FEV$_{100}$), Tiffeneau-Pinelli index (FEV$_{100}$/FVC) and airway resistance (RI) were recorded using the FinePointe™ data acquisition and analysis software (Buxco). Work of breathing was calculated using the area under the pressure-volume graph.

Lung whole-mount imaging. Mouse lungs from 6-month old FVB/NTac wild-type and Ism1$^{\Delta/\Delta}$ mice were harvested via thoracotomy and kept in cold PBS until imaging or processing. Images of the peripheral left lung lobes were taken using the Olympus MXV10 Macro Zoom under 1.26× magnification. For immunofluorescence staining for lung elastin and collagen, each harvested lungs was incubated overnight at 4° C. with gentle shaking in DMEM media supplemented with 1% heat-inactivated FBS, penicillin (100 U/mL), streptomycin (100 μg/mL), and 1 μM Col-F fluorescent probe (Immunochemistry Technologies). After which, lungs were washed thoroughly with three changes of PBS and images of peripheral lung lobes were taken using the Olympus MXV10 Macro Zoom under 5× magnification with fluorescence excitation. Images were adjusted for brightness and contrast using ImageJ software (NIH).

Emphysema rescue in FVB/NTac Ism1$^{\Delta/\Delta}$ mice. 4-week old female FVB/NTac Ism1$^{\Delta/\Delta}$ mice were intratracheally given 50 μl PBS, 1 μg or 5 μg rISM1 in 50 μl PBS, or 350 μg liposome-encapsulated clodronate in 50 μl PBS twice a week for 4 weeks. Pulmonary function test was recorded 24 hours after the last day of treatment, and the lungs fixed for histology analyses.

Cigarette Smoke-induced COPD mouse model. 8-week old female Balb/cAnNTac mice were subjected to 8-week chronic cigarette smoke exposure as previously described[35] (Peh et al., 2017). Briefly, mice were whole-body exposed to 4% cigarette smoke at a frequency of three 3R4F reference cigarettes (University of Kentucky, Lexington) every 2 hours for a total of nine cigarettes each day. This smoking regime was carried out for five consecutive days a week for a total of 8 weeks. Sham mice were placed in a separate ventilated chamber and exposed to the same room air. After the first 4 weeks of cigarette smoke exposure, respective treatment groups were given 50 μl PBS or 10 μg rISM1 in 50 μl PBS for an additional 4 weeks. PBS and rISM1 treatments were intratracheally instilled after the last round of daily cigarette smoke exposure on day 1, 3, and 5 each week. Pulmonary function test was recorded 24 hours after the last day of cigarette smoke exposure, and the lungs fixed for histology analyses.

Acute cigarette Smoke-induced lung inflammation mouse model. 8-week old female Balb/cAnNTac mice were subjected to 2-weeks chronic cigarette smoke exposure as described above. PBS and rISM1 treatments were intratracheally instilled after the last round of daily cigarette smoke exposure everyday for five consecutive days during the 2nd week of cigarette smoke in similar fashion as described above.

Human lung tissue. The use of human samples was approved by National University of Singapore Institutional Review Board (NUS-IRB Ref No. N-18-057E). Formalin-fixed and paraffin-embedded de-identified lung sections were provided by the Lung Tissue Research Consortium (LTRC), National Heart, Lung, and Blood Institute (NHLBI), National Institutes of Health (NIH), USA. COPD patients were selected based on the post/pre-bronchodilator spirometry criteria of FEV$_1$/FVC<0.7 and FEV % predicted ≤80 with clinical diagnosis of emphysema. Non-COPD patients were identified based on the post/pre-bronchodilator spirometry criteria of FEV$_1$/FVC≥0.7 and FEV % predicted ≥80. Patient smoking history and status were provided. Expression of hISM1 in non-COPD and COPD patients was blindly graded by two separate researchers. Six to ten random fields were chosen per human lung section.

Statistical analysis. Statistical analyses were performed using Prism (Graphpad) Software. Comparisons between two groups were done using unpaired two-tailed Student's t-test, and multiple group comparisons were done using one-way ANOVA with Tukey's post hoc test. Correlation between hISM1 expression and smoking or AM apoptosis were determined using point-biserial and Pearson correlation respectively. Results are shown as mean±s.e.m. and sample sizes for each experiment are indicated accordingly on the figures or figure legend. A P value of <0.05 was considered significant. Additional annotations are indicated accordingly in the figure legends.

Example 2: Isthmin 1 Suppressed Lipopolysaccharide-Induced Acute Lung Injury and Lung Inflammation Isthmin 1 (ISM1) is highly expressed in the mouse lung in bronchial and alveolar epithelial cells, endothelial cells, alveolar macrophages and NKT cells. ISM1 is up-regulated in the lung in response to intratracheal lipopolysaccharide (LPS) instillation (Venugopal et al 2015, Cardiovas. Res.). In the present studies, using Ism1 knockout mice (Ism1$^{\Delta/\Delta}$), in both FVB/N and C57BL/6J background, our results demonstrate that ISM1 deficiency leads to mild sterile inflammation in the mouse lung. Upon respiratory LPS challenge, Ism1$^{\Delta/\Delta}$ mice exhibited an exaggerated lung inflammatory response compared with wild-type mice, characterized by increased leukocyte recruitment including neutrophils, macrophages, T and B cells. Although innate immune cells subsided to baseline on day 7 post-LPS insult, Ism1$^{\Delta/\Delta}$ mice presented heightened lung fibrosis on day 9 with increased myofibroblasts, excessive collagen accumulation and TGF-β upregulation. Intratracheal instillation of recombinant ISM1 (rISM1) could suppress LPS-induced inflammation in the lung. These results reveal therapeutic benefit of ISM1 in protecting the lung from excessive inflammatory response, and in facilitating the injured lung to regain homeostasis after LPS-triggered ALI.

Upon infectious or non-infectious respiratory insults, the host mounts an acute inflammatory response in the lung for self-protection. The healthy host also has means to limit this pulmonary inflammation, eventually resolving the inflammation to prevent collateral damage of surrounding tissues. Widespread acute lung inflammation is observed in multiple lung diseases including acute lung injury (ALI) and its more severe manifestation, acute respiratory distress syndrome (ARDS). These are serious clinical syndromes with up to 50% mortality rate without effective pharmacological therapies[36]. ALI is characterized by increased vascular permeability, inflammatory cell infiltration (mostly neutrophils), release of pro-inflammatory mediators by the infiltrating leukocytes as well as lung parenchymal cells[37].

LPS is a glycolipid component of gram-negative bacteria cell wall that can evoke severe inflammatory effects in mice and human. Short-term intranasal LPS challenge in mice often stimulates mixed inflammatory reaction in both the airway and lung. This includes disruption of the lung endothelial and epithelial barriers, increase in inflammatory cell infiltration and release of pro-inflammatory and cytotoxic mediators[38-40]. These phenotypes are clinically relevant for both ALI and ARDS. Multiple intracellular signaling events are initiated upon LPS challenge. Mostly LPS binds to and signals through toll-like receptor 4 (TLR-4) complex to activate nuclear factor kappa B (NF-κB)[41-43]. Activated NF-κB translocates into the nucleus and stimulates the transcription of many pro-inflammatory cytokines including interleukin-1 (IL-1) and tumor necrosis factor-α (TNF-α)[44,45] by directly binding to the consensus target sequences in their enhancer/promoter regions. Importantly, NF-κB is active in alveolar macrophages of ARDS patients[46], implicating the involvement in NF-κB signalling in the development and progression of ALI and ARDS.

ISM1 was first identified as a secreted antiangiogenic and proapoptotic protein, and also studied in vascular permeability inducement[47,48,49]. Systemic infusion of an antibody against glucose regulated protein of 78 kDa (GRP78), the high-affinity receptor of ISM1, attenuated the pulmonary hyperpermeability induced by LPS[49].

In the present studies, the role of ISM1 in LPS-induced acute pulmonary inflammation was investigated using Ism1 knockout mice (Ism1$^{\Delta/\Delta}$). Data supports that ISM1 is an inflammation suppressor, protecting the lung from excessive inflammatory responses in both sterile lung and during LPS-induced ALI. The presence of ISM1 in the lung also facilitated the lung to regain homeostasis after acute injury.

Figure 9:
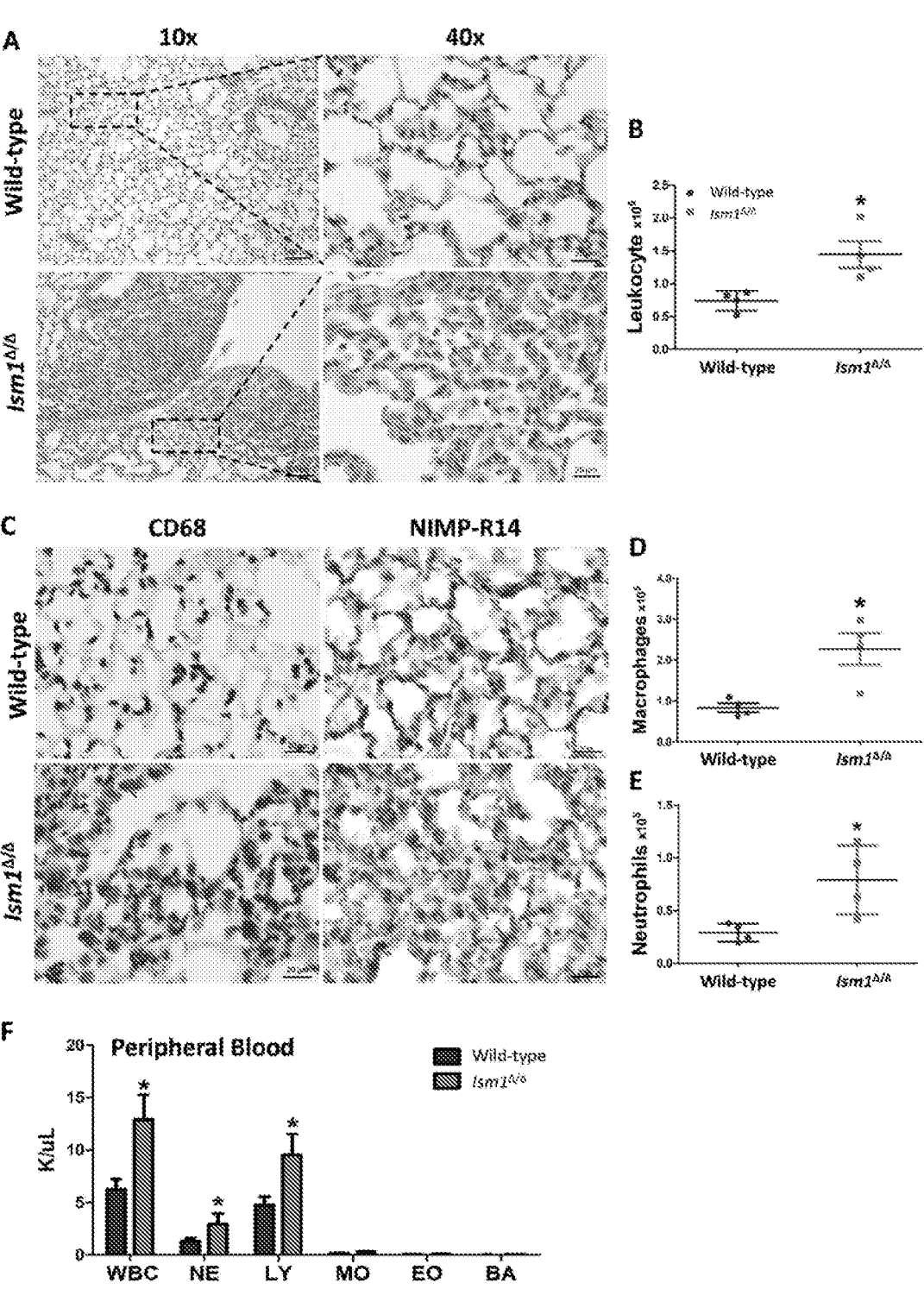
FIGS. 9A-F show ISM1 deficiency leads to increased leukocyte infiltration in the lung under non-pathological condition.
Figure 17:
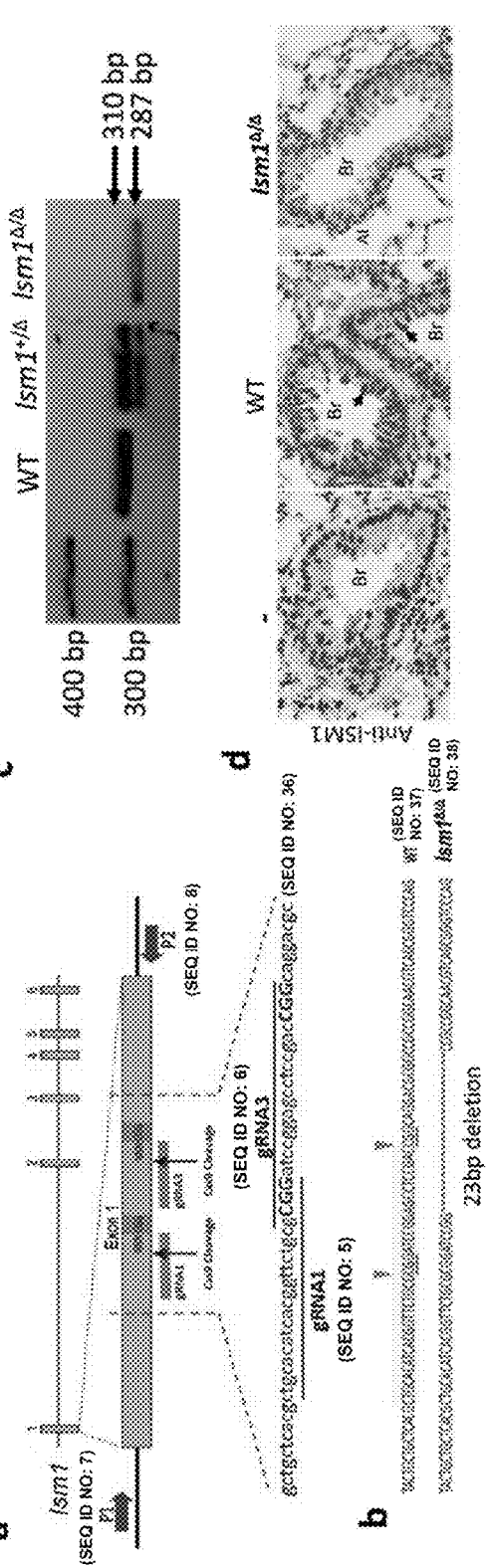
FIGS. 17A-D show generation of Ism1$^{\Delta/\Delta}$ C57BL/6J mice.
Figure 18:
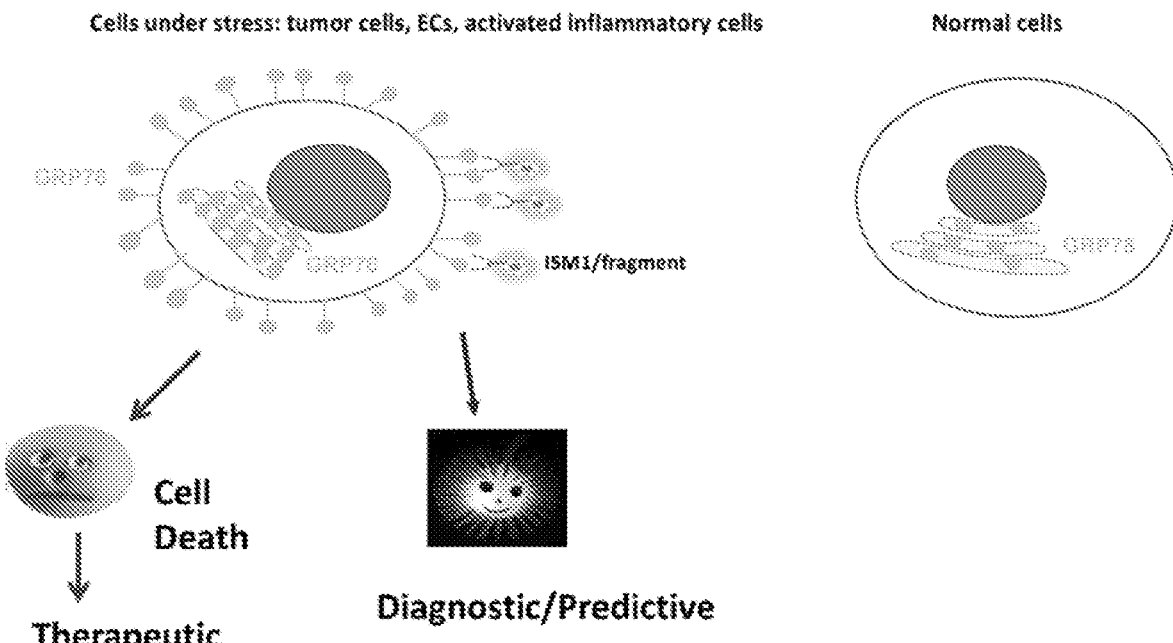
FIG. 18 shows a model comparing normal cells (right) with cells under stress (left), wherein cells under stress (such as tumor cells, ECs, activated inflammatory cells) have increased cell surface GRP78 (csGRP78) which can interact with ISM1 and/or fragments thereof, resulting in cell death (providing for therapeutic effect, for example). As well, changes in csGRP78 levels and/or ISM1 interactions therewith may provide diagnostic and/or predictive information. As shown, it is contemplated that csGRP78 may be a therapeutic target and/or diagnostic biomarker in diseases such as inflammatory diseases.

ISM1 Deficiency LED to Increased Leukocyte Infiltration in the Lung Under Sterile Condition Ism1 knockout (Ism1$^{\Delta/\Delta}$) C57BL/6J mice were generated using the CRISPR/Cas9 gene editing method (FIG. 17). Ism1$^{\Delta/\Delta}$ mice exhibited a spontaneous inflammation in the lungs under ambient air. Histological examination of coronal lung sections of 8-weeks old knockout mice revealed multifocal, non-demarcated clusters of inflammatory cells including alveolar macrophages, polymorphonuclear cells and lymphocytes (FIG. 9A). Differential immune cell counts of whole lung single-cell homogenates as well as immunohistochemistry (IHC) staining demonstrated significant increases in total leukocytes, macrophages, and neutrophils (FIG. 9, 9B-9E). Focal areas of alveolar wall hyperplasia and emphysema were also observed in the knockout mice (FIGS. 9, 9A & 9C). Meanwhile, peripheral blood profiling of Ism1$^{\Delta/\Delta}$ mice also showed a significant increase in total white blood cell number compared with that of wild-type mice. Amongst the subpopulations of white blood cells, lymphocyte and neutrophil numbers were notably higher in Ism1$^{\Delta/\Delta}$ mice, while other cell types remain low in both knockout and wild-type mice (FIG. 9F).

FIG. 17 shows details for generation of Ism1$^{-/-}$ (Ism1$^{\Delta/\Delta}$) mice. A schematic diagram of CRISPR/Cas9 targeting Ism1 via guide RNA pair, gRNA1 and gRNA3, is shown in FIG. 17A. P1 and P2 denote primers used for T7E1 assay and genotyping. The DNA sequence of the Ism1$^{\Delta/\Delta}$ knockout line is shown in FIG. 17B, showing the 23 bp deletion which lead to a premature stop codon and no ISM1 protein produced. FIG. 17C shows a gel image of RT-PCR of C56BL/6J WT, Ism1$^{+/\Delta}$, and Ism1$^{\Delta/\Delta}$. Referring to FIG. 17D, representative immunohistochemistry staining for ISM1 (brown) and nuclei (haematoxylin, blue) in C57BL/6J WT and Ism1$^{\Delta/\Delta}$ mice lung sections are shown. Br, bronchi; Al, alveolar. Scale bars, 20 μm.

ISM1 Deficiency LED to Heightened Acute Immune Response to LPS in the Lung

Figure 10:
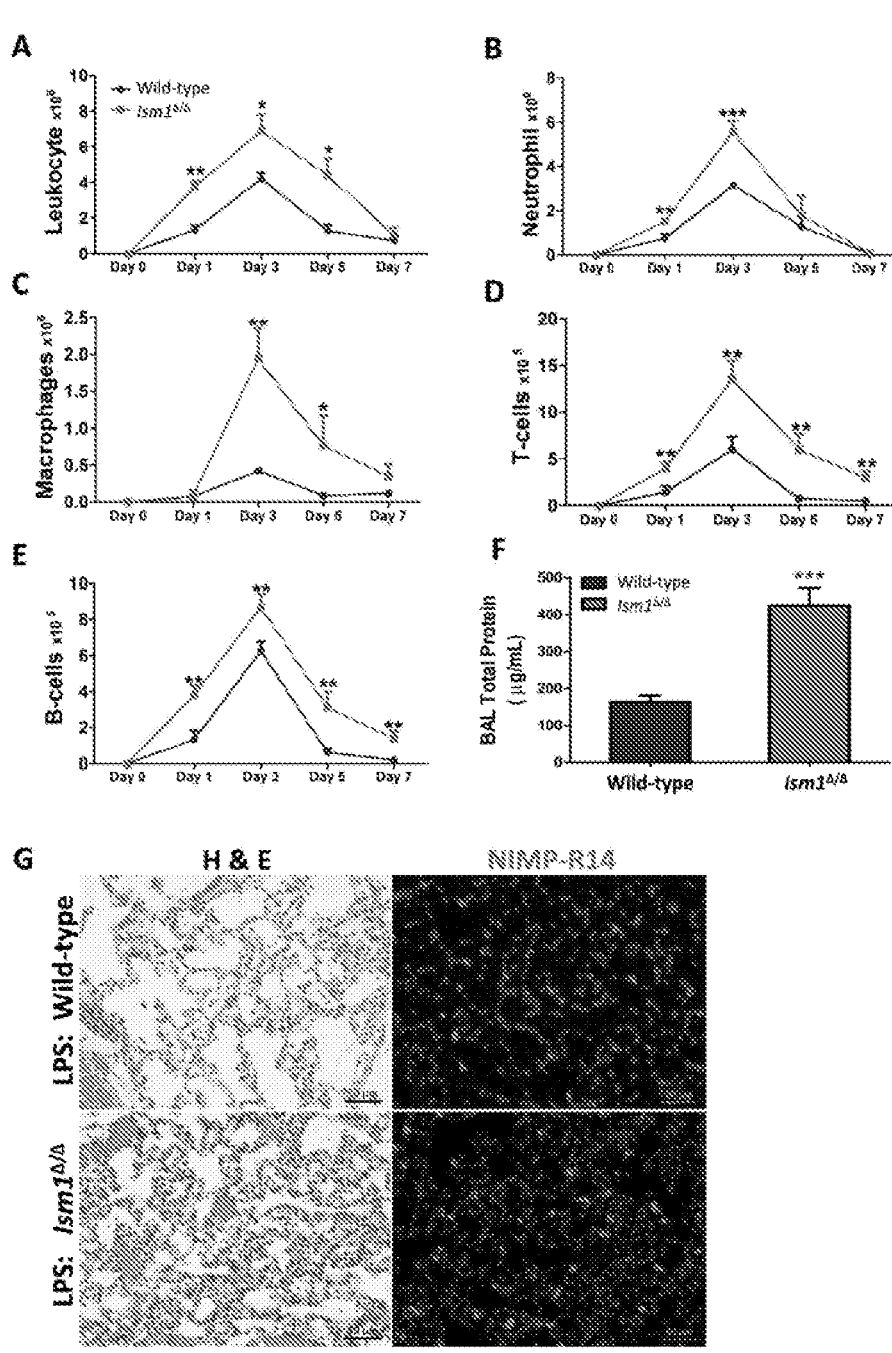
FIGS. 10A-G show ISM1 deficiency leads to heightened immune responses to intratracheal LPS in the lung.

To examine the role of ISM1 in acute lung inflammation, 2 mg/kg of LPS was intratracheally instilled into the lungs of Ism1$^{\Delta/\Delta}$ and wild-type mice. Both groups of mice survived and generated acute inflammatory responses to LPS. Comparing with wild-type mice, Ism1$^{\Delta/\Delta}$ mice showed a remarked increase in total lung leukocytes during the 7-day acute response period (FIG. 10A). Higher numbers of neutrophils (FIG. 10B), T-cells (FIG. 10D), and B-cells (FIG. 10E) were observed from day 1 onwards in Ism1$^{\Delta/\Delta}$ mice, while increased macrophage recruitment was observed from day 3 (FIG. 10C). By day 7, neutrophils have subsided to basal level in both wild-type and Ism1$^{\Delta/\Delta}$ mice, but an observable higher number of alveolar macrophages, T and B cells remain in Ism1$^{\Delta/\Delta}$ lung. Correspondingly, a much higher total bronchoalveolar lavage (BAL) protein was observed in Ism1$^{\Delta/\Delta}$ mice, reflecting the hyperpermeability associated with excessive lung inflammation (FIG. 10F).

Consistently, histology analysis of lungs harvested on day 1 post LPS challenge showed a much increased immune cells in the alveolar space of Ism1$^{\Delta/\Delta}$ lungs than wild-type lungs, with a noticeable increase of neutrophils at this time point (FIG. 10G).

Hence, absence of ISM1 led to a more severe inflammatory response to respiratory LPS challenge in mice, supporting a role of ISM1 in modulating lung inflammation.

Exogenous rISM1 Suppressed LPS-Induced Inflammatory Response in the Lung

Based on the above results, we hypothesized that ISM1 might suppress inflammation induced by LPS. To test this hypothesis, we pre-treated wild-type mice with 50 μg rISM1 intratracheally one day before LPS instillation. rISM1 treatment was continued on the day of and after LPS instillation for three more days (FIG. 11A). BAL fluids were then collected and rISM1 treated mice indeed showed a significant reduction in total BAL protein (FIG. 11B). Infiltration of leukocytes into the alveolar spaces was reduced to almost the basal level (without LPS challenge) (FIG. 11C). Both neutrophils (FIG. 11D) and alveolar macrophages (FIG. 11E) were much reduced under rISM1 treatment. Although there are trends of decreases in T and B cells under rISM1 treatment (FIG. 11F-11G), the changes were not statistically significant due to high variations in the PBS treated mouse group. Together, these findings support that ISM1 may function as a pulmonary inflammatory suppressor, and locally delivered rISM1 quenched LPS-induced pulmonary inflammation in mice.

Figure 12:
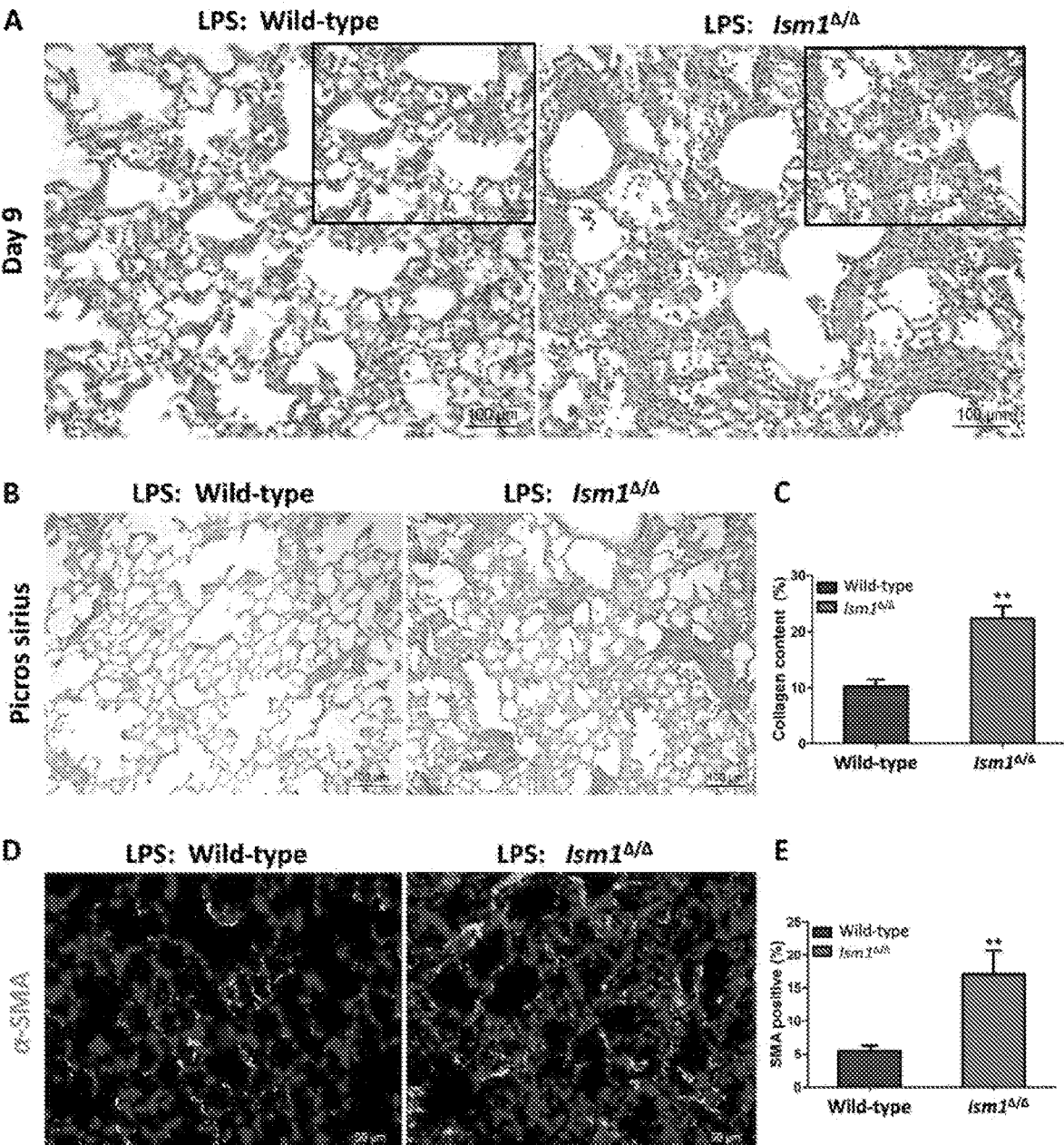
FIGS. 12A-E shows ISM1 deficiency led to lung tissue remodelling and fibrosis after recovering from LPS-induced acute lung injury.

ISM1 Deficiency LED to Defective Lung Repair and Remodelling after LPS-Induced Acute Lung Injury Inflammation is important for a proper response to external assaults, yet it can also induce damage to the tissue. The affected tissue will try to repair such inflammation-triggered injuries and restore tissue homeostasis. Excessive inflammatory response can overwhelm the repair mechanism, leading to tissue remodelling. Since Ism1$^{\Delta/\Delta}$ mice showed a heightened immune response to LPS challenge, it was sought to determine whether this exaggerated inflammatory responses would affect lung repair and restoration to homeostasis. Lung tissue histology was examined on day 9 post LPS challenge. As shown in FIG. 12A, Ism1$^{\Delta/\Delta}$ lung showed severe distortion of lung structure with wide-spread thickening of alveolar walls. A marked increase in collagen deposition was also observed by Picro-Sirius Red staining (FIG. 12, 12B-12C). Moreover, increased abundance of myofibroblasts (α-smooth muscle actin positive) is notable, in particular in small fibrous clusters (FIG. 12, 12D-12E). Excessive accumulation of extracellular matrix (ECM) and myofibroblasts are characteristics of pulmonary fibrosis[50].

Figure 13:
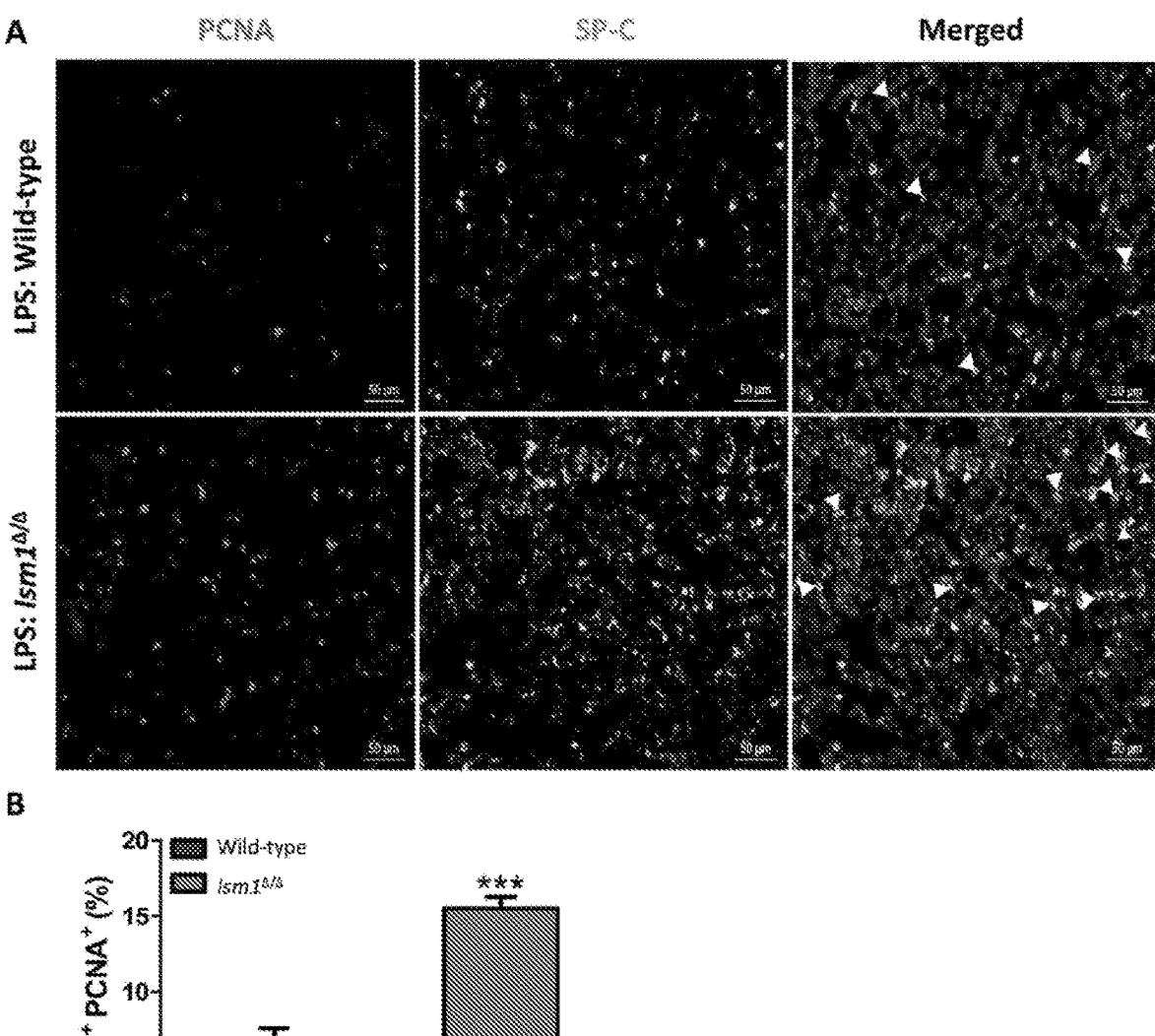
FIGS. 13A-B show ISM1 deficiency increases proliferation of alveolar epithelial type 2 cells (AEC2) in the lung.

Upon LPS challenge, inflammatory responses usually induce injury/damage to the epithelium. There are two types of alveolar epithelial cells: type I (AE1) cells are terminally differentiated, flat, squamous and covering 90% of alveolar wall surface; type II (AE2) cells are less in number but possess stem cell-like property[51]. AE2 cells are important for lung repair and regeneration following injury. To maintain homeostasis and integrity of the alveolar epithelium, AE2 cells proliferate and differentiate into AE1 cells to re-epithelialize the alveolar walls[51,53]. Aberrant replacement of AE1 cells by hyperplastic AE2 cells is one of the contributing factor to fibrosis[54]. At day 9 post LPS challenge, Ism1$^{\Delta/\Delta}$ lungs showed significantly more proliferating AE2 cells than wild-type lungs as shown by double immunofluorescent staining for PCNA (proliferation marker) and SP-C (AE2 marker) (FIG. 13). This result suggests that AE2 hyper-proliferation possibly have contributed to increased fibrosis in Ism1$^{\Delta/\Delta}$ lungs.

Figure 14:
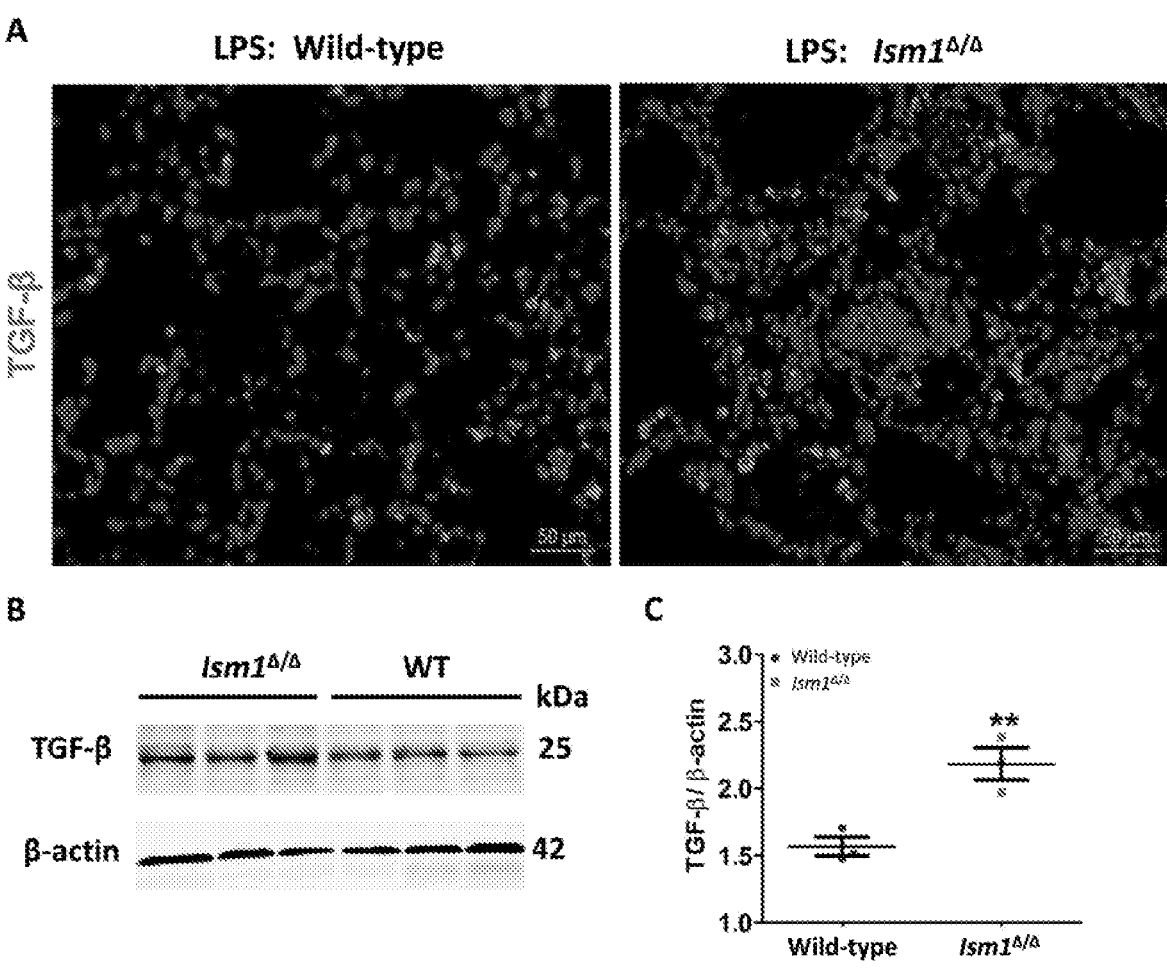
FIGS. 14A-C show ISM1 deficiency led to higher profibrotic cytokine TGF-β in the lung.

TGF-β is the most potent pro-fibrotic mediator characterized to date[55]. At day 9 post LPS challenge, TGF-β level was significantly increased in Ism1$^{\Delta/\Delta}$ lungs compared with wild-type lungs (FIG. 14).

Altogether, these results indicate that ISM1 deficiency provoked a heightened immune response to LPS challenge in mice, leading to abnormal lung repair and fibrosis.

Figure 15:
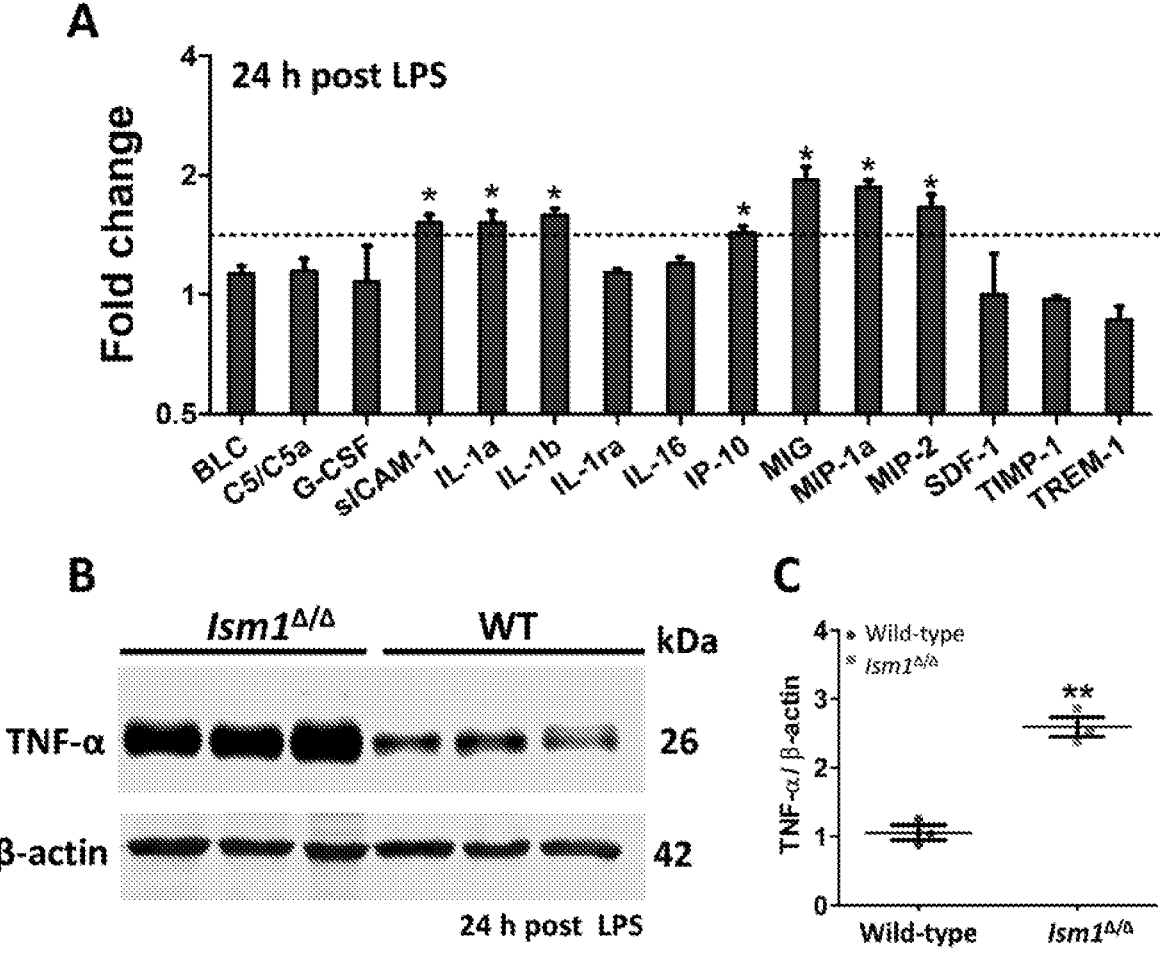
FIGS. 15A-C show ISM1 deficiency alters the inflammatory cytokine/chemokine profile of the lung at 1-day post-LPS challenge. Cytokines and chemokines were analysed using lung homogenates from Ism1$^{\Delta/\Delta}$ and wild-type mice at 1-day post-LPS challenge and inflammatory cytokine antibody array.

ISM1 Deficiency Altered the Acute Inflammatory Cytokine/Chemokine Profile in the Lung Following LPS Challenge To decipher if ISM1 deficiency lead to alterations of inflammatory cytokines/chemokines in response to LPS, the profile of cytokines and chemokines was examined using a cytokine antibody array. On day 1 post LPS challenge, seven chemokines and cytokines were substantially elevated ($\geq 1.5$ fold) in Ism1$^{\Delta/\Delta}$ lung compared to control mice (FIG. 15A). All of the up-regulated cytokines/chemokines are known pro-inflammatory mediators such as IL-1α, IL-1β; leukocyte chemoattractant such as Monokine induced by gamma interferon (MIG), C-X-C chemokine such as CXCL10/IP-10, MIP-1a, and MIP-2; as well as soluble ICAM-1. In addition, there was a significant increase of TNF-α in the Ism1$^{\Delta/\Delta}$ lungs (FIG. 15, 15B-15C). These results demonstrate that absence of ISM1 in the lung lead to increases in multiple pro-inflammatory cytokines, likely the cause for the heightened pulmonary inflammatory response to LPS challenge.

ISM1 Deficiency Activated NF-κB Signalling in Lung

Figure 16:
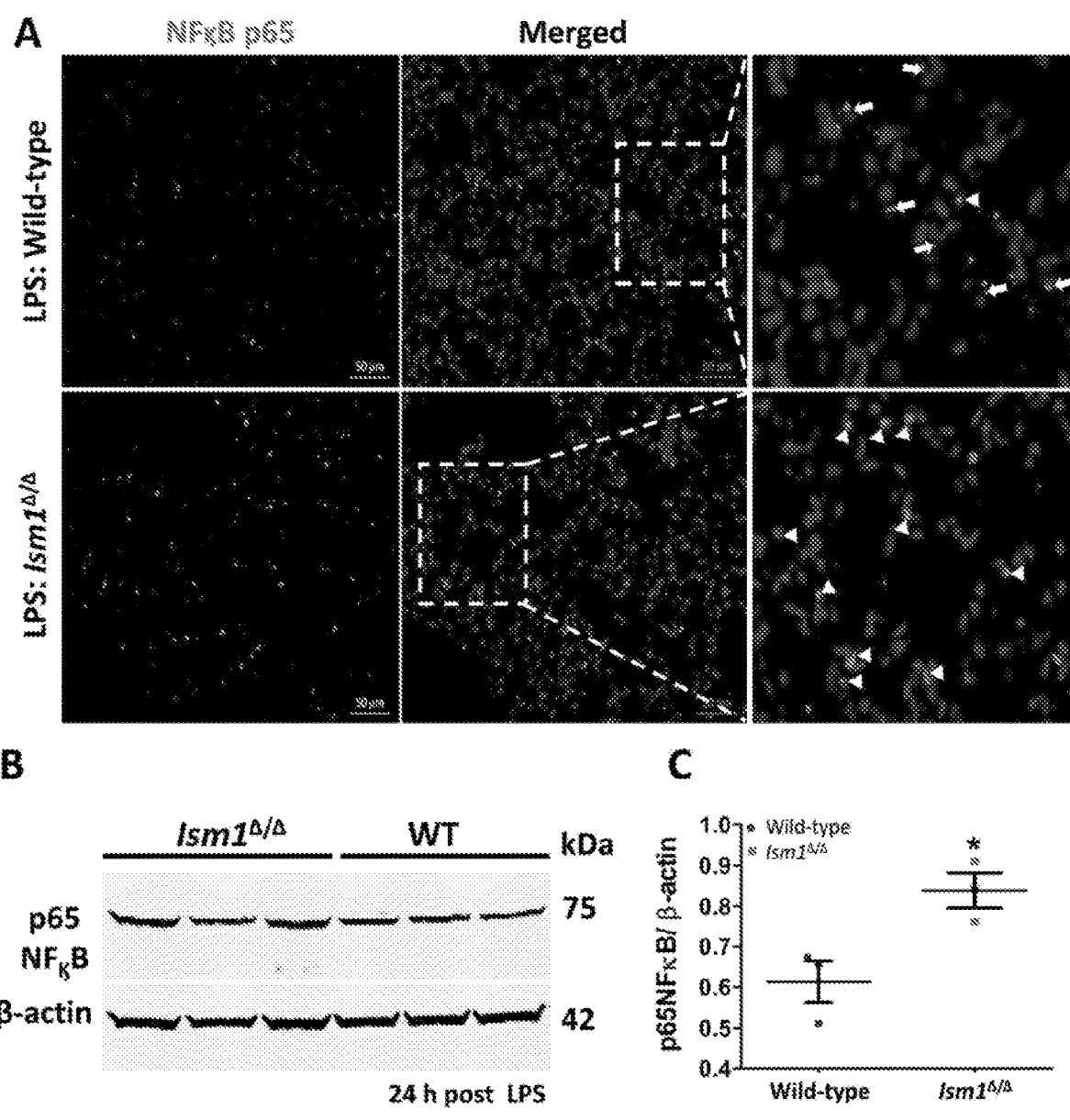
FIGS. 16A-C show ISM1 deficiency enhances both the expression level and nuclear translocation of p65 NF-κB.

Previous studies have shown that LPS activates NF-κB signaling in murine lungs by inducing the nuclear translocation of NF-κB[45,46]. To determine whether ISM1 plays a role in regulating LPS-induced NF-κB translocation in vivo, lungs tissues of Ism1$^{\Delta/\Delta}$ and wild-type mice post LPS insult were fixed and stained for NF-κB (p65 subunit). There was a significant increase in nuclear p65 NF-κB (red) in the lung sections of Ism1$^{\Delta/\Delta}$ mice compared with that of the wild-type mice (FIG. 16A). Moreover, the p65 NF-κB levels were also higher in Ism1$^{\Delta/\Delta}$ lung (FIG. 16B-C). These data indicate that there is increased NF-κB signalling in Ism1$^{\Delta/\Delta}$ lung in response to LPS, a likely mechanism for the activation of multiple pro-inflammatory cytokines/chemokines and heightened inflammation.

Using LPS-induced ALI model, the present studies show that ISM1 deficiency led to excessive inflammation in the mouse lung. Furthermore, rISM1 could quench LPS-induced lung inflammation when administered intratracheally to mice. These findings support ISM1 as an anti-inflammatory protein.

Some angiogenic inhibitors have been previously reported to suppress pulmonary inflammation in addition to their anti-angiogenic ability. For example, thrombospondin-1 (TSP-1) was reported to be important in physiological inflammation and homeostasis in the lung[57]. As early as 1-month old, Tsp1$^{-/-}$ mice started to show patchy sites of inflammation in their lung parenchyma. Neutrophilic infiltrates manifested in the alveoli and perivascular connective tissue. In addition, TSP-1 deficient mice were more susceptible to LPS-induced lung injury[58]. TSP-1 curbs inflammatory responses via regulating the production of IL-10, a key anti-inflammatory cytokine during resolution phase of lung injury. Angiostatin is another angiogenic inhibitor that could suppress LPS-induced acute lung injury in mice[59]. Treatment of angiostatin potently reduced protein accumulation in BAL fluid and leukocyte infiltration into the lung. In the present studies, ISM1 is shown to function in a manner somewhat related to TSP-1 function, since both knockout mice exhibit heightened inflammatory responses in the lung under non-pathological condition; and hyper-responsiveness in LPS-induced acute lung injury. Meanwhile, both exogenous angiostatin and ISM1 may suppress acute lung inflammation upon LPS challenge.

Although Ism1$^{\Delta/\Delta}$ lungs exhibited more severe inflammatory response to LPS, the inflammation started to subside after peaking on day 3 and almost reaching the basal level on day 7, similar to wild-type mice. However, Ism1$^{\Delta/\Delta}$ lungs showed extensive fibrosis-like phenotype with increased collagen deposition, myofibroblast accumulation and higher TGF-β expression level. Furthermore, elevated number of proliferating alveolar epithelial type II (AE2) cells were observed. These data point to a 'hyper-responsive' lung that responds to LPS with excessive inflammation, a condition that commonly induces tissue remodelling[60]. ISM1 may play a role in inhibiting excessive inflammation induced by LPS in the lung, thus protecting the lung from excessive damage and injury. Excessive inflammation in Ism1$^{\Delta/\Delta}$ lungs possibly overwhelms the repair mechanism, leading to structural alteration and fibrosis.

NF-κB pathway plays a key role in LPS-induced inflammation[45,56,61]. The activation of NF-κB results in the translocation of its active form p65 into nucleus. LPS could enhance translocation of NF-κB p65 from the cytoplasm to the nucleus[61,62]. LPS-induced NF-κB activation is known to increase the expression of proinflammatory cytokines such as IL-1, MIP-2 and TNF-α, leading to excessive inflammation response[56,63,64]. Under ISM1 deficiency condition, both increased abundance and increased nuclear translocation of NF-κB active form suggest the involvement of NF-κB signalling pathway in the upregulation of multiple pro-inflammatory cytokines.

Figure 11:
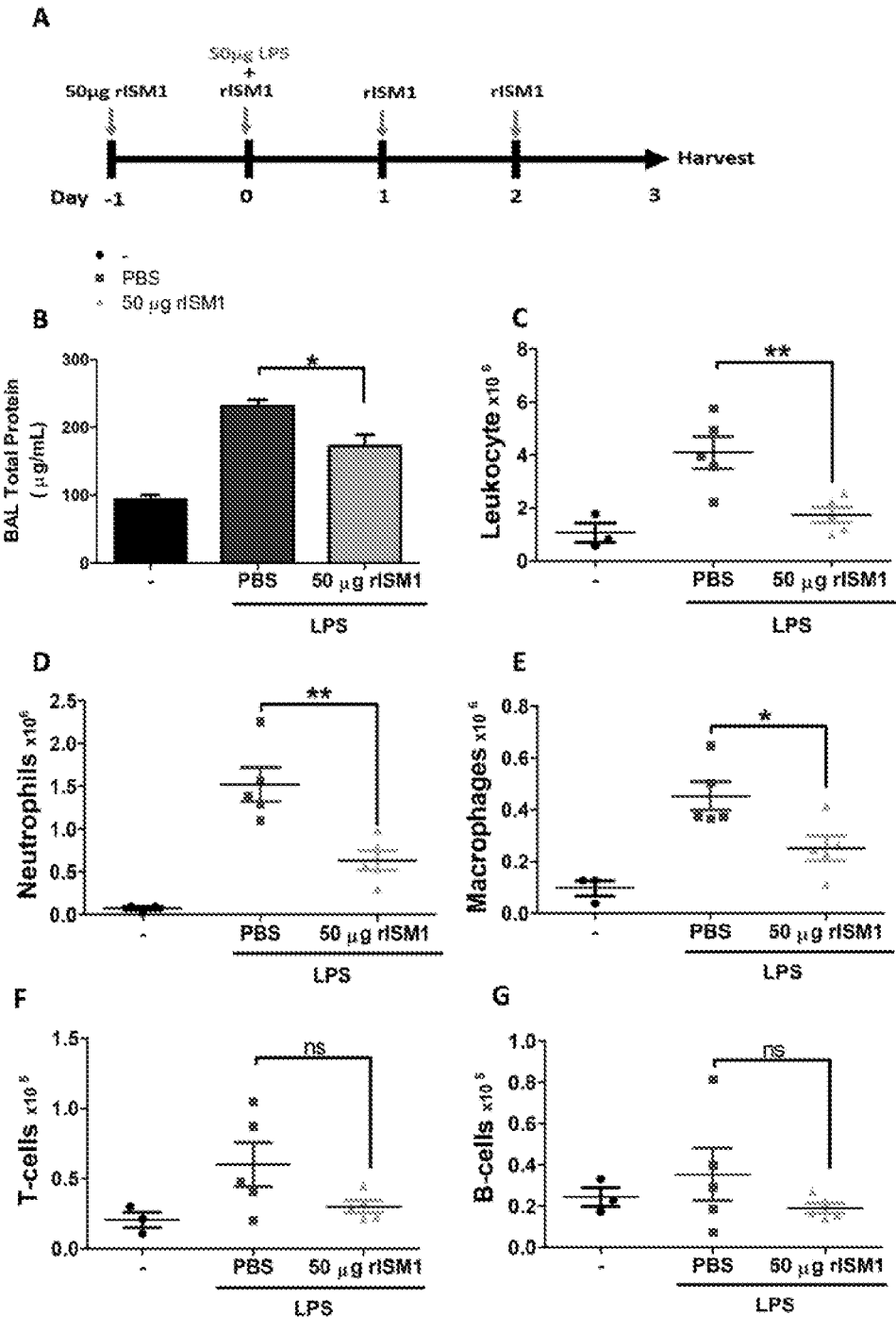
FIGS. 11A-G show intratracheal delivered rISM1 suppresses LPS-induced lung inflammation.

ALI/ARDS is marked by a profound presence of activated neutrophils together fluid accumulation in lung, leading to lung function impairment and high mortality[65]. ALI and ARDS are among the prevalent pulmonary diseases in human population[66]. Unfortunately, no major breakthroughs and discoveries of new therapeutics for both diseases have been previously reported in the filed[60]. The present findings described herein demonstrate that intratracheal delivered rISM1 was potent enough to reduce leukocyte infiltration in LPS-challenged mice. Importantly, it is shown that LPS-induced lung hyperpermeability was also suppressed by ISM1 treatment (FIG. 11).

Results support that ISM1 may provide a suppressor/pro-resolving mediator for pulmonary inflammation. It suppressed excessive accumulation of alveolar macrophages by inducing their apoptosis. Locally delivered rISM1 rescued the emphysema phenotype in mice and helped to preserve lung homeostasis. Accordingly, these results support ISM1-based therapeutic approaches for treating, ameliorating, and/or preventing inflammatory lung diseases such as, ALI and COPD.

Materials and Methods

Animals. Adult (7- to 8-week-old) female ISM1-deficient (Ism1$^{\Delta/\Delta}$) mice were used in this study. Age- and sex-matched wild-type C57BL/6J mice were obtained from The Jackson Laboratory. Animal care and experiment procedures were performed following institutional guidelines approved by the NUS institutional animal care and use committee (IACUC; protocol 066/12 and R16/0632; breeding protocol BR15/1100). Primers used for T7E1 assay and genotyping are as follows:

PCR primers for T7E1 assay to screen for mutated mouse:
Forward 5' cagctcctgggattgctccg 3' (SEQ ID NO: 16) and
    Reverse 5' taagacttcttcctggtgccaaa 3' (SEQ ID NO: 17);
PCR primers for mouse genotyping:
Forward 5' gacagctcctgggattgctcc 3' (SEQ ID NO: 18) and
    Reverse 5' ttctgcaatgtaccaagctctct 3' (SEQ ID NO: 19);
(see FIG. 17).

Recombinant proteins. Recombinant ISM was expressed in *E. coli* and purified using Ni-NTA affinity chromatography followed by reverse-phase HPLC. The recombinant protein was confirmed to be endotoxin free. In rescue experiment, rISM1 was dissolved in filtered PBS, 50 μg of rISM1 per mouse was intratracheally administered into the lungs. Mouse rISM (mature form, no signal peptide) was expressed and purified as a His-Tagged protein in *E. coli* using the vector pET-M (as described in Xiang et al., 2011, JCMM, herein incorporated by reference in its entirety). Mouse rISM1 was used in these experiments. Mature ISM1 (without signal peptide) may be biologically significant in the conditions tested. The ISM1 sequence used comprises NP_001263418.1 and is as follows:

Fresh blood samples were analysed using Hemavet H950FS Hematology Analyzer (Drew Scientific Group, USA).

Histology. Fully inflated lungs were fixed in 10% neutral buffered formalin, followed by paraffin embedding, sectioning and staining with hematoxylin and eosin or Picro-Sirius red staining (ab150681, Abcam, USA). Sections (5 μm) were de-paraffinized in histoclear followed by a slow rehydration in a series of alcohol grades starting from 100% ethanol. After hydration to water, the sections were places in PBS for subsequent staining.

Immunohistochemistry (IHC) and Immunofluorescence (IF). Tissue sections were stained with anti-CD68 (sc-7084, Santa Cruz Biotechnology), anti-NIMP-R14 (sc-59338, Santa Cruz Biotechnology), anti-α-SMA (Santa Cruz Biotechnology), anti-TGF-β (sc-146, Santa Cruz Biotechnology), anti-SP-C (sc-13979, Santa Cruz Biotechnology), anti-p65NF$_K$B (107450-1-AP, Proteintech) and anti-PCNA (sc-56, Santa Cruz Biotechnology) overnight at 4° C. Tissue sections were stained with Hematoxylin and Eosin (DAKO). All images were obtained using Zeiss Axiovert.

Immunoblotting and protein array. Fresh tissues were homogenized and centrifuged and soluble supernatants were

```
M H H H H H H S S G L V P R G S G A S D R Q D A A A G N V S G S Q L Q N N L N L
E S D S T S E T S F P L S K E A P E E H Q V V H Q P F P R Q R F P P E T G H P S L
Q R D G P R S F L L D L P N F P D L S K A D I N G Q N P N I Q V T I E V V D G P D S
E A E K D Q H P E N K P S W S L P A P D W R A W W Q R S L S L A R T N S G D Q D
D K Y D S T S D D S N F L S V P R G W D R P A P G H R T F E T K E Q P E Y D S T D
G E G D W S L W S V C S V T C G N G N Q K R T R S C G Y A C I A T E S R T C D R
P N C P G I E D T F R T A A T E V S L L A G S E F N A T K L F E V D M D S C E R
W M S C K S E F L K K Y M H K V I N D L P S C P C S Y P T E V A Y S T A D I F D R I
K R K D F R W K D A S G P K E K L E I Y K P T A R Y C I R S M L S L E S T T L A A Q
H C C Y G D N M Q L I T R G K G A G T P N L I S T E F S A E L H Y K V D V L P W I I
C K G D W S R Y N E A R P P N N G Q K C T E S P S D E D Y I K Q F Q E A R E Y L
E H H H H H H
```
(SEQ ID NO: 9; Underlining indicates native ISM1 sequence, Bold indicates Vector sequence and His-tag, Italics indicates N-terminal M residue)

Intratracheal instillation. Mice were anaesthetized with 5% isoflurane (Baxter), followed by intratracheal delivery of LPS (2 mg/kg LPS) from *E. coli* O111:B4 (L2630; Sigma Aldrich) or saline as previously described by Liao et al[67]. Control animals received saline alone. The mice were allowed to recover until the time of bronchoalveolar lavage (BAL) collection on day 1, 3, 5 and 7 post LPS instillation for subsequent analysis.

Bronchoalveolar lavage (BAL) collection. Freshly euthanized mice were dissected to expose the lungs and heart. The tracheas were cannulated and the lungs were lavage two times with 1 ml of ice cold PBS. BAL sample was centrifuged at 500×g for 5 min at 4° C. The supernatants were collected and stored at −80° C. till use. Bradford's reagent was used to quantify BAL protein. 1 mL of erythrocyte lysis buffer was added to the cell pellet to lyse all red blood cells, followed by a centrifugation. The live cells were recovered in FACS buffer and counted using Nucleocounter NC-100 (Chemometec, Denmark) followed by differential immune cell count.

Differential immune cell count. The differential immune cell count was determined by using the NovoCyte flow cytometer and analyzed with NovoExpress software (AceaBiosciences, USA). Differential immune cell counts were performed as previously described[68]. Immune cells were identified as CD45$^+$, alveolar macrophages as CD11c$^+$Siglec-F$^+$, eosinophils as CD11c$^-$Siglec-F$^+$, neutrophils as GR-1$^+$CD11b$^+$, B cells as CD3$^-$/CD19$^+$ and T cells as CD3$^+$/CD19$^-$ cells.

Peripheral blood leukocyte counts. Blood was collected from the submandibular vein of the anaesthetized mice.

taken as whole tissue lysates. Standard Western blots were performed using ρ-actin as the loading control. Antibodies used were anti-TGF-β (sc-146, Santa Cruz Biotechnology), anti-TNF-α (107590-1-AP, Proteintech), anti-p65NF-κB (10745-1-AP, Proteintech). The relative abundance of a variety of 40 cytokines were examined using mouse cytokine proteome profiler array (ARY028, R&D Systems, USA). The whole tissue lysates of 4 mice in each group were used. Equal amount of total protein 200 μg per sample was hybridized to the array and compared for relative expression. The relative expression was quantified by measuring the dot blot intensity using Image J software.

Statistical analysis. Data were expressed as standard errors of the mean (±SEM). Statistical significance was determined using Student's t-test. *P<0.05; **P<0.01, n≥3.

Example 3—the C-Terminal AMOP Domain Alone
is Sufficient to Mediate the Pro-Apoptotic Activity
of ISM1

In this Example, the structure-function relationships of ISM1 are investigated. Methods to express and purify both bacterial and mammalian recombinant ISM1 (rISM1) protein were first developed. A 15 kDa mass difference between the two rISM1 prompted investigation of the glycosylation profile of mammalian rISM1, which revealed dense and highly heterogeneous glycan deposition. Next, through performing co-immunoprecipitation assays and apoptosis assay with various rISM1 truncate protein containing individual domain, it was further demonstrated that adhesion-associated domain in MUC4 and other proteins (AMOP) domain of ISM1 mediated both receptors interaction (namely Integrin αvβ5 and cell surface GRP78 (csGRP78)). Correspondingly, AMOP domain of ISM1 presented full pro-apoptotic activity of the full length protein.

Expression and Purification of Recombinant ISM1 Proteins.

Figure 31:
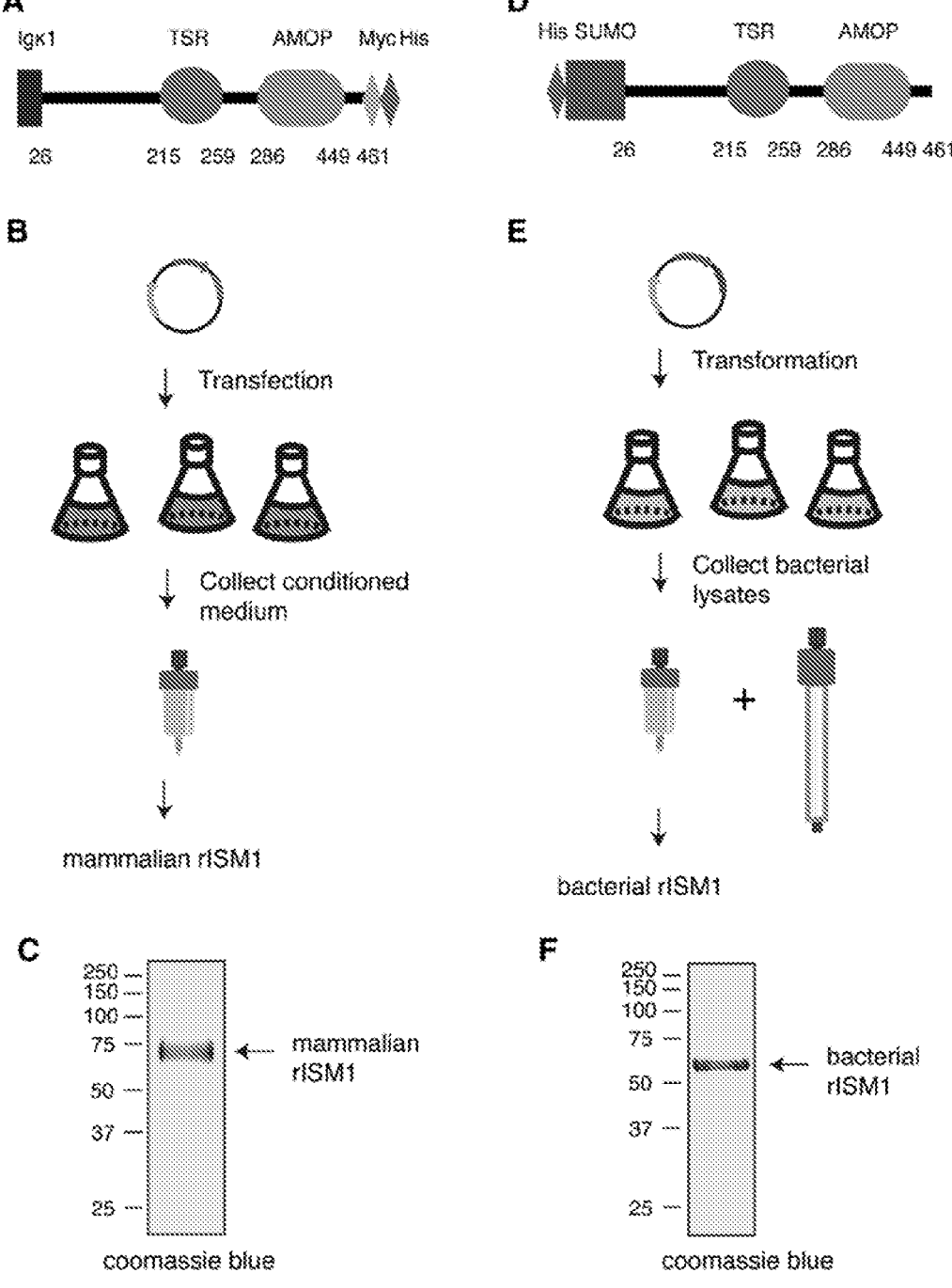
FIG. 31 shows expression and purification of recombinant mouse ISM1 protein. (A) Schematic diagram of the mammalian expression construct for ISM1. Mouse Igκ1 leader sequences was included at the N-terminus to enhance secretion efficiency. A c-Myc tag and hexahistidine tag was included at the C-terminus for protein detection and purification. (B) Schematic presentation of the work flow to express and purify mammalian rISM1.(C) The purified mammalian recombinant ISM1 protein migrated around 70 kDa on the denaturing SDS-PAGE. (D) Schematic diagram of the bacterial expression construct for ISM1. A hexahistidine tag was included at the N-terminus for protein detection and purification. SUMO-tag at the N-terminus assists protein solubilization. (E) Schematic presentation of the work flow to express and purify bacterial rISM1.(F) The final purified bacterial recombinant ISM1 protein, with SUMO-tag cleaved off, migrated around 55 kDa on the denaturing SDS-PAGE.

To clarify the structure-function relationship of ISM1, we first set out to generate and purify recombinant ISM1 (rISM1). As ISM1 is a secreted protein, we first utilized mammalian expression host. To build mammalian expression construct, the native signal peptide of mouse ISM1 was replaced with mouse Igκ1 leader sequences to enhance the secretion efficiency (FIG. 31a). The expression construct was subsequently transfected into Expi293F cells, and the recombinant protein in the conditioned medium was purified via one step IMAC (Immobilized Metal Affinity Chromatography) (FIG. 31b). The purified mammalian rISM1 migrated around 70 kDa on the denaturing SDS-PAGE (FIG. 31c).

In order to express soluble rISM1 from bacterial host, SUMO (Small Ubiquitin-like Modifier protein) tag was fused to the N-terminus of mouse ISM1 without signal peptide sequences (FIG. 31d). The bacterial expression construct was transformed into Shuffle T7 cells, and the soluble protein was further purified via IMAC and SEC (Size Exclusion Chromatography) (FIG. 31e). After SUMO-tag cleavage, the bacterial rISM1 migrated around 55 kDa on the denaturing SDS-PAGE (FIG. 31f).

Mammalian rISM1 is Densely Deposited with Heterogenous Glycans.

Surprisingly, there is about 15 kDa size difference between mammalian and bacterial rISM1, suggesting that post-translational modifications (PTMs) present on mammalian rISM1. We then focused on the protein glycosylation, as it can significantly contribute to protein mass. Sequences analysis revealed two potential N-linked glycosylation sites on mouse ISM1, namely Asn39 and Asn282 (FIG. 32a). Incubation of mammalian rISM1 with PNGaseF (Peptide-N-Glycosidase F) reduced the protein mass by about 10 kDa, confirmed the presence of N-glycans (FIG. 32b). The N-glycosylation mutation constructs (N39Q, N282Q, N39/282Q) were further generated to disrupt either or both N-glycan sites, and the effect was evaluated in three cell lines (HEK293T, HEK293FT, HeLa) (FIG. 32c). Each single mutants demonstrated reduced protein size (~5 kDa) in the whole cell lysates (WCL) fraction, while double mutants presented ~10 kDa size decrease in total, confirming that both sites were modified with N-glycans. Interestingly, WT/N282Q both presented doublet bands in the WCL fraction, whereas N39Q and N39/282Q only presented single band (FIG. 32c). Similar observation from previous report suggests that this is due to inefficient core-glycosylation on Asn39 (8). In HEK293T cells, disruption of either N-glycan sites abolished protein secretion in the conditioned medium (FIG. 32c); nevertheless, the protein secretion was only abolished in Asn282 mutants in HEK293FT and Hela cells. The results indicate that N-glycosylation on Asn282 was key in regulating ISM1 secretion, while N-glycosylation on Asn39 was critical in certain cell lines.

Next, we utilized proteomic approach to further identify O- and C-linked glycans present on mammalian rISM1. Strikingly, 30 additional amino acids were revealed to be glycosylated (FIG. 32d). While some residues were only modified with a single glycan with simple structure, some residues such as Ser184 and Ser188 were modified with multiple glycans with distinct structures, suggesting micro-heterogeneity of glycan deposition on those positions. Focusing on the glycosylation sites distribution, 21 glycan sites were located at the N-terminal unstructured region, 2 sites at TSR domain and 7 sites at AMOP domain (FIG. 32d). As majority of the glycans deposition and glycan complexity were present on the unstructured region, this may suggest stabilizing role of glycosylation on the folding of unstructured region. Moreover, it has been reported that two types of unconventional glycosylation exist on TSR domain with conservation, namely O-fucosylation (O-fucose-glucose) recognizing Cxx(S/T)CG motif, and C-mannosylation (C-mannose) with recognition motif of WxxW. On ISM1-TSR domain, the two identified glycan modifications were an O-linked disaccharide (deoxyhexose-hexose) on Thr229 (226-CSVTCG-231), and a C-linked monosaccharide (hexose) on Trp220 (220-WSLW-223) (Table S1), which may correspond to the putative O-fucosylation and C-mannosylation, respectively.

Of those 30 glycosylation sites, 4 candidate sites are further selected for mutation analysis to evaluate their effect: Trp220 and Thr229 as they are the putative C-mannosylation and O-fucosylation site on TSR domain; Ser184 and Ser188 as they are the highly heterogenous spots with glycan deposition. Preliminary analysis with western blots showed that disruption of those glycosylation sites did not affect ISM1 expression or secretion (FIG. 32e). In summary, our analysis reveal that mammalian rISM1 is densely deposited with heterogenous glycans.

AMOP Domain of ISM1 Mediates its Receptors Interaction.

Figure 33:
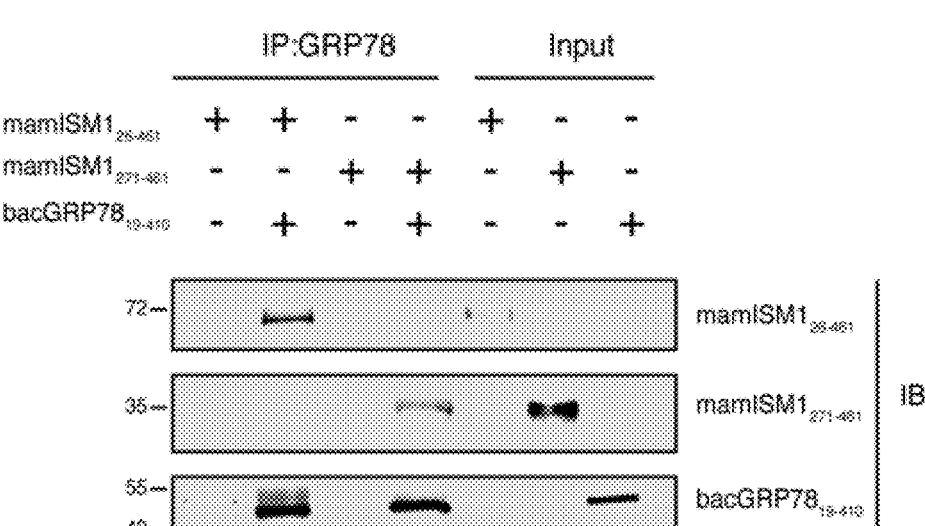
FIG. 33 shows AMOP domain of ISM1 mediates its receptors interaction. (A) Schematic representation of recombinant protein constructs of ISM1 and GRP78 for Co-IP experiments. mamISM1 stands for mammalian recombinant ISM1 protein; bacGRP78 stands for bacterial recombinant GRP78 protein. (B) Coomassie blue stained SDS-PAGE showing the quality of purified recombinant proteins. (C) Co-IP analysis confirmed that AMOP domain mediated ISM1-GRP78 interaction. (D) Co-IP analysis confirmed that AMOP domain mediated ISM1-integrin αvβ5 interaction. (E) Co-IP analysis confirmed that ISM1 without AMOP domain abolished interaction with integrin αvβ5.

Previously we have identified integrin αvβ5 and cell surface GRP78 as the cell surface receptors for ISM1. To clarify which domain of ISM1 mediates the receptors interaction, following mammalian rISM1 protein were generated: mamISM1$_{26-461}$ containing both domains, mamISM1$_{26-286}$ containing TSR domain and mamISM1$_{26-286}$ containing AMOP domain (FIG. 33a,b). Recombinant GRP78 truncate containing only the ATPase domain were expressed and purified from bacteria (FIG. 33a,b). Mammalian recombinant integrin αvβ5 heterodimer with only the extracellular domain was acquired commercially. Co-immunoprecipitation assay with those purified recombinant protein demonstrated that AMOP domain alone was able to mediate both ISM1-GRP78 and ISM1-αvβ5 interaction (FIG. 33c,d). In contrast, ISM1 truncates without AMOP domain abolished binding to both receptors (FIG. 33e). In summary, ISM1-AMOP domain mediates its interaction to both receptors.

The Boundary of AMOP Domain Affects its Pro-Apoptotic Activity.

Figure 34:
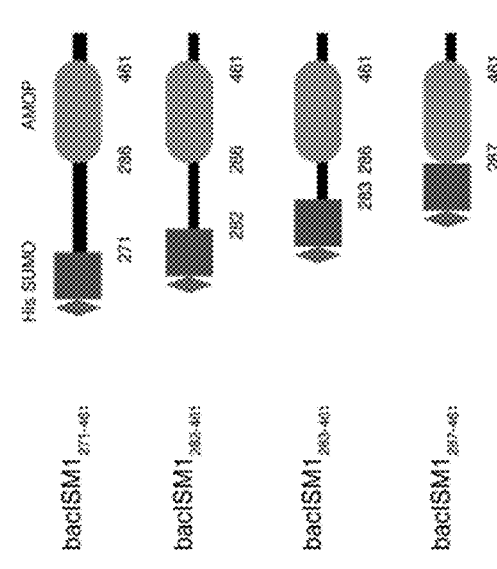
FIG. 34 shows the boundary of AMOP domain affects its pro-apoptotic activity. (A) Schematic representation of ISM1 AMOP constructs used for mammalian recombinant protein production and purification. (B) Coomassie blue stained SDS-PAGE showing the quality of purified recombinant proteins. (C) Apoptosis assay results of the two mammalian AMOP truncates. (D) Schematic representation of ISM1 AMOP constructs used for bacterial recombinant protein production and purification. (E) Coomassie blue stained SDS-PAGE showing the quality of purified recombinant proteins. (F) Comparison of pro-apoptotic activity between different bacterial recombinant AMOP truncates. (G) Comparison of pro-apoptotic activity between mammalian and bacterial recombinant AMOP truncates.
Figure 34:
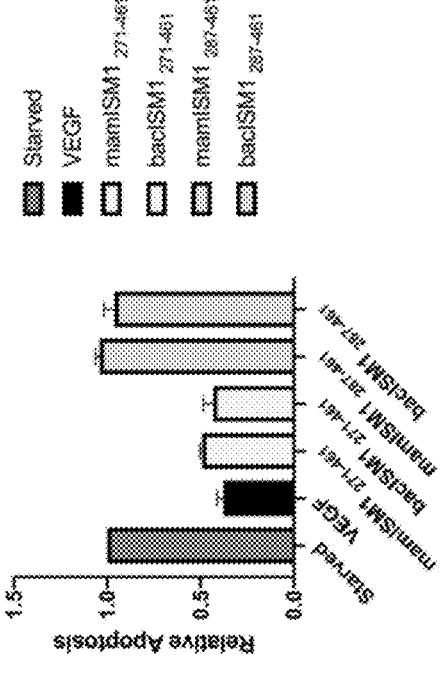

To investigate the pro-apoptotic activity of AMOP domain, initially we have generated two AMOP truncates namely mamISM1$_{271-461}$ and mamISM1$_{287-461}$ with varied length since the exact boundary of AMOP is not clear and is only an estimate (FIG. 34a,b). Surprisingly, while mamISM1$_{287-461}$ induced EC apoptosis at similar level to starvation condition, mamISM1$_{271-461}$ did not induce EC apoptosis at all (FIG. 34c). It appeared that the 16 extra amino acids at the N-terminus completely abolish the pro-apoptotic activity from AMOP domain.

To further investigate the effect of those 16 extra amino acids, we generated the following AMOP truncates with varied length in this region: bacISM1$_{271-461}$, bacISM1$_{282-461}$, bacISM1$_{283-461}$, bacISM1$_{287-461}$. They were produced from bacterial expression system via fusion to SUMO-tag (FIG. 34d,e). Interestingly, as the extra sequences getting shorter, AMOP truncate became more active (FIG. 34f). Thus the results indicate that the boundary of AMOP domain may affect its pro-apoptotic activity.

When closely comparing the pro-apoptotic activity of bacterial versus mammalian recombinant AMOP truncates, it's noticed that bacAMOP demonstrated similar activity to mamAMOP. While both bacISM1$_{271-461}$ and mamISM1$_{271-461}$ did not present activity, both bacISM1$_{287-461}$ and mamISM1$_{287-461}$ showed pro-apoptotic activity at similar level (FIG. 34g). Therefore, the results indicate that AMOP activity is not affected by post-translational modifications (PTMs).

Figure 29:
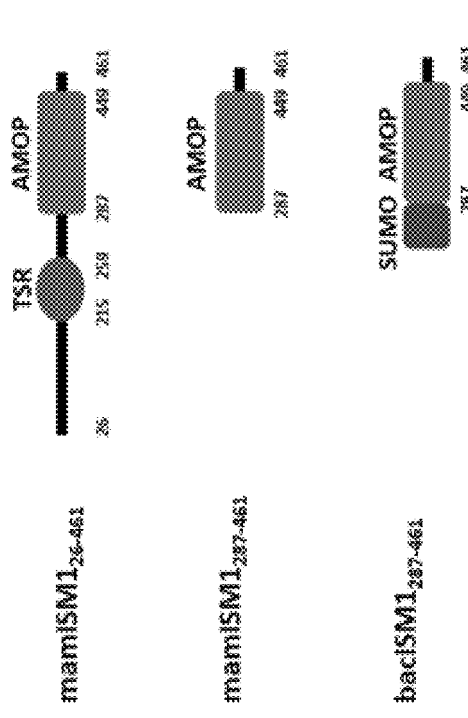
FIG. 29 shows that the C-terminal AMOP domain alone retains the full pro-apoptotic activity of ISM1. The recombinant protein constructs are shown on the left and their pro-apoptotic activity is shown on the right. mam: mammalian produced, bac: E. coli produced. Mouse ISM1 protein is used. Mammalian cell produced and E. coli produced rISM1 287-461 fragments both retains the full pro-apoptotic activity of full length ISM1.
Figure 30:
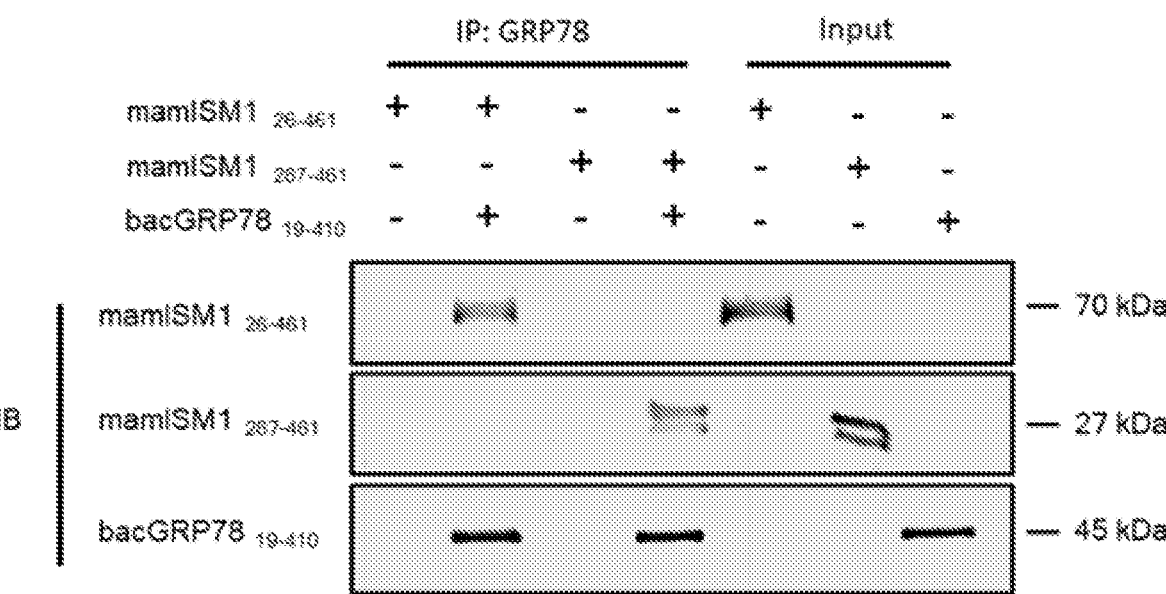
FIG. 30 shows co-IP assay using purified GRP78 and ISM1 protein demonstrating their direct binding via the AMOP domain 287-461 region.

Indeed, structure-function relationship studies using truncations of the mouse ISM1 protein showed that the C-terminal AMOP domain from 287-461 retains the full pro-apoptotic activity of the full-length ISM1 protein (FIG. 29). In addition, results indicate that the *E. coli* produced bacISM1$_{287-461}$ fragment (AMOP domain alone) has the same level of pro-apoptotic activity comparing with mammalian cell produced mamISM1$_{287-461}$ fragment, indicating that post-translational modification is not required for the AMOP domain to mediate the pro-apoptotic activity of ISM1. This is also consistent with the co-IP binding assay result, demonstrating that ISM1$_{287-461}$ is sufficient for its direct binding to GRP78 receptor (FIG. 30). Hence, both GRP78 receptor binding and pro-apoptotic function are mediated through the C-terminal AMOP domain from amino acid residues 287 to 461 (human ISM1 equivalent is amino acid residues at 290-464).

ISM1$^{287-461(C)}$ but not ISM1$^{26-277(N)}$ Supports EC Adhesion

It was previously shown that surface-coated rISM1 can support EC adhesion and attachment. To investigate the effects of ISM1 in supporting EC attachment, the cell adhesion assay was performed using IncuCyte® Live Cell Analysis Imaging System, which can monitor the dynamic changes in cell attachment.

Figure 21:
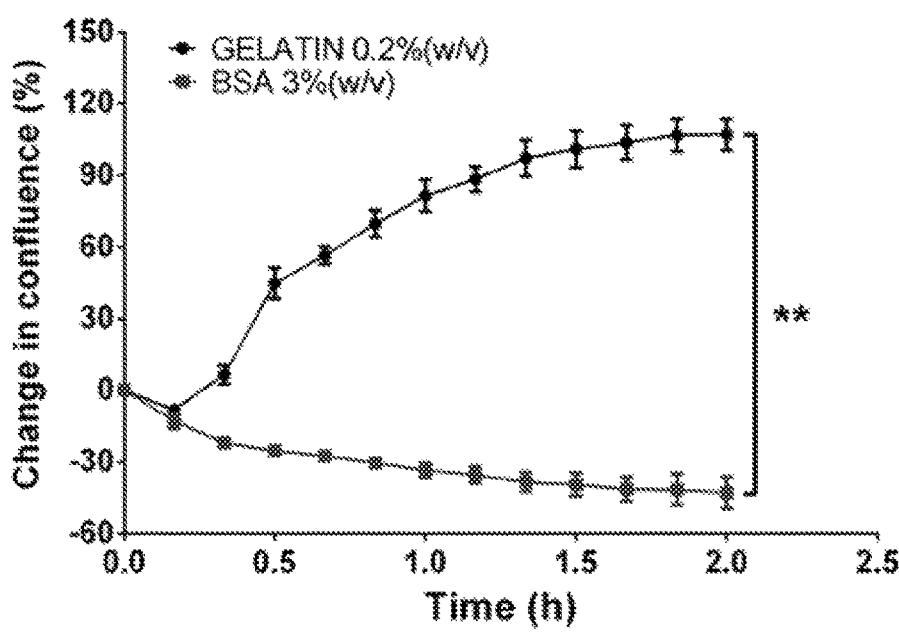
FIG. 21 shows gelatin, but not BSA, can support EC adhesion. Dynamic changes in cell confluence were monitored. Gelatin can support EC adhesion where there was an increase in change in confluence over time. BSA does not support cell adhesion as confluence remained low or even decreased over time. ** P<0.01, N=3.
Figure 22:
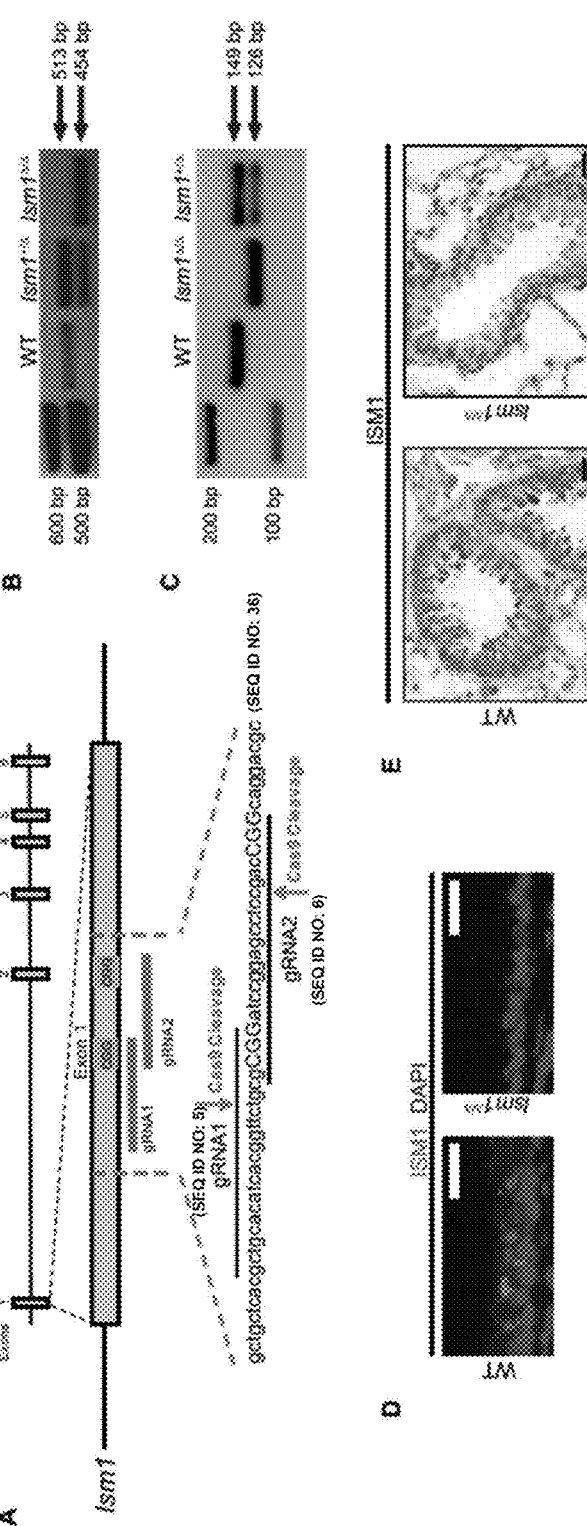
FIG. 22 shows CRISPR/Cas9 targeting and generation of FVB/N Ism1$^{\Delta/\Delta}$ mice. (A) shows a schematic diagram of CRISPR/Cas9 targeting Ism1 via guide RNA pair gRNA1 and gRNA2. (B) and (C) show genotyping PCR of FVB/NTac (B) and C57BL6/J (C) WT, Ism1$^{+/\Delta}$ and Ism1$^{\Delta/\Delta}$ mice. (D) shows representative immunofluorescence staining for ISM1 (red) and nuclei (DAPI, blue) in FVB/NTac WT and Ism1$^{\Delta/\Delta}$ mice respiratory epithelium. n=4 mice per group. Scale bars, 20 sm. (E) shows representative immunohistochemistry staining for ISM1 in C57BL/6J WT and Ism1$^{\Delta/\Delta}$ mice lungs. n=4 mice per group. Scale bars, 20 μm.

Gelatin was used as the positive control as it is an extracellular matrix protein and supports EC adhesion. Gelatin-supported EC adhesion can be seen by the increase in change of confluence over time (FIG. 21). On the contrary, the serum protein BSA was used as the negative control. The confluence of the ECs in the BSA-coated well remained low or even decreased over time showing that BSA does not support cell adhesion (FIG. 21).

Figure 19:
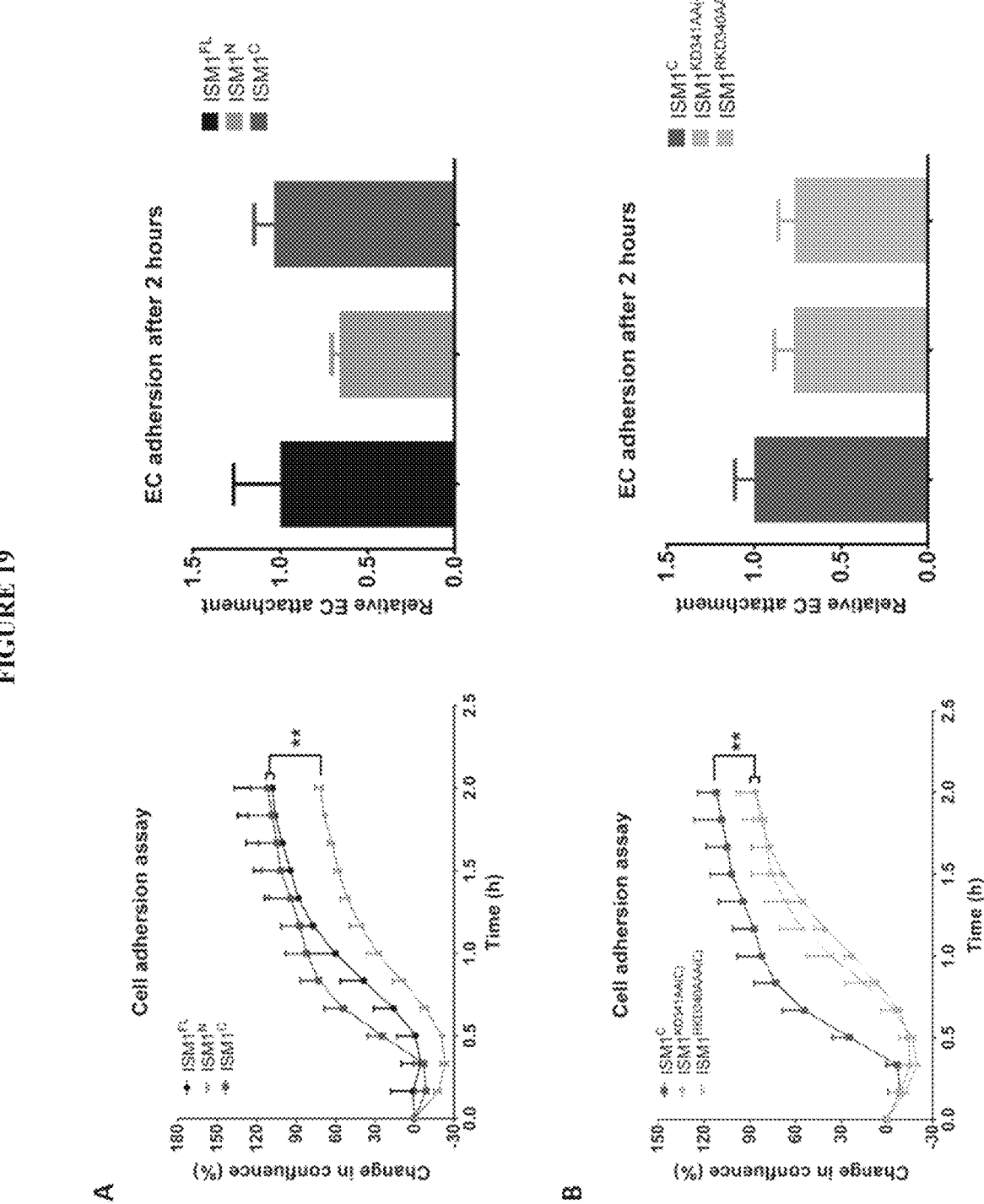
FIGS. 19A-B show ISM1$^{C}$ (287-461) but not ISM1$^{N}$ support EC adhesion.

In the comparison of ISM1 and its truncations, it was observed that ISM1$^C$ which contains the AMOP domain (287-461) can support cell adhesion equivalently to ISM1$^{FL}$ as there was no significant difference between the two in supporting cell attachment (FIG. 19A). In contrast, ISM1$^N$ with the deletion of AMOP domain showed reduced ability in supporting cell adhesion (FIG. 19A). This result indicated that the AMOP domain in ISM1 is important in mediating EC adhesion. Moreover, it was found that the mutations in the RKD motif (RKD341RAA, RKD340AAA) of ISM1$^C$ led to significant reduction in cell attachment (FIG. 19B).

Internalized ISM1$^{287-461(C)}$ Induces EC Apoptosis

Figure 20:
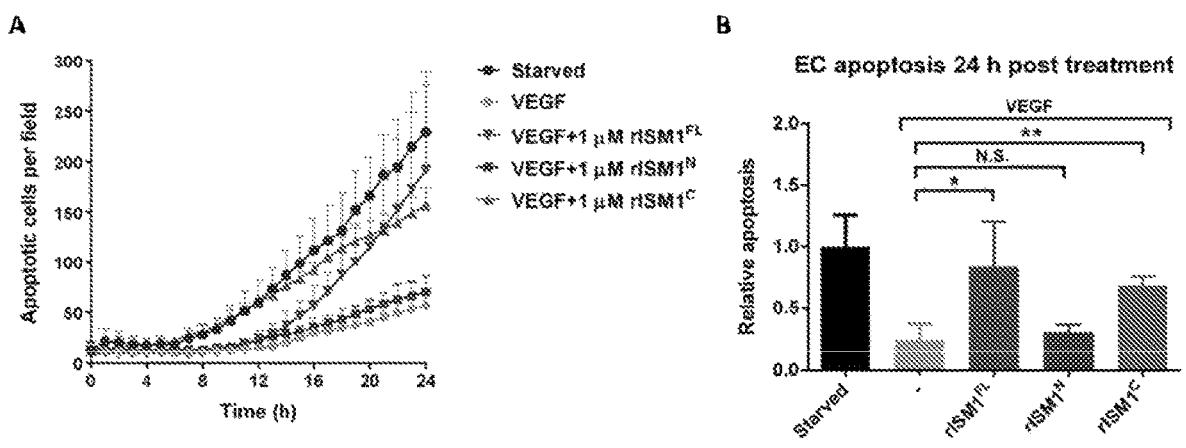
FIGS. 20A-B show internalized ISM1$^{C}$ (287-461) triggers EC apoptosis.

To further investigate whether internalized ISM1$^C$ has the same pro-apoptotic effect as ISM1$^{FL}$ on ECs, the EC apoptosis assay was carried out using IncuCyte® Live Cell Analysis Imaging System. Briefly, HUVECs were seeded in 96-well plate (6,000 cells/well) and treated with 1 μM rISM1 proteins, including rISM1$^N$, rISM1$^C$, and rISM1$^F$, for up to 24 hours. From the corresponding apoptosis curves (FIG. 20A), it was found that both ISM1$^C$ and ISM1$^{FL}$ induced EC apoptosis. In contrast, ISM1$^N$ had no pro-apoptotic effect. This result is consistent with the internalization assay result that ISM1$^C$ but not ISM1$^N$ is internalized into ECs. Therefore, based on these results the AMOP domain may be responsible for the pro-apoptotic function of ISM1.

Sequences relevant to these studies (both mammal and bacteria) are as follows:

SEQ ID NO: 28: bacISM1$_{26-461}$
MGSSHHHHHSQGS*MSDSEVNQEAKPEVKPEVKPETHINLKVSDGSSEIFFKIKKTTPLRR*

*LMEAFAKRQGKEMDSLRFLYDGIRIQADQTPEDLDMEDNDIIEAHREQIGG*GSGASDRQDA

AAGNVSGSQLQNNLNLESDSTSETSFPLSKEAPEEHQVVHQPFPRQRFPPETGHPSLQRD

GPRSFLLDLPNFPDLSKADINGQNPNIQVTIEVVDGPDSEAEKDQHPENKPSWSLPAPDW

RAWWQRSLSLARTNSGDQDDKYDSTSDDSNFLSVPRGWDRPAPGHRTFETKEQPEYDS

TDGEGDWSLWSVCSVTCGNGNQKRTRSCGYACIATESRTCDRPNCPGIEDTFRTAATEV

SLLAGSEEFNATKLFEVDMDSCERWMSCKSEFLKKYMHKVINDLPSCPCSYPTEVAYST

ADIFDRIKRKDFRWKDASGPKEKLEIYKPTARYCIRSMLSLESTTLAAQHCCYGDNMQLI

TRGKGAGTPNLISTEFSAELHYKVDVLPWIICKGDWSRYNEARPPNNGQKCTESPSDED

YIKQFQEAREY (recombinant mouse ISM1 full-length)
(Underline: native mouse ISM1 sequence; Bold: His-tag and vector sequence; Italics: SUMO-tag)

SEQ ID NO: 29: bacISM1$_{287-461}$
MGSSHHHHHSQGS*MSDSEVNQEAKPEVKPEVKPETHINLKVSDGSSEIFFKIKKTTPLRR*

*LMEAFAKRQGKEMDSLRFLYDGIRIQADQTPEDLDMEDNDIIEAHREQIGG*FEVDMDSCER

WMSCKSEFLKKYMHKVINDLPSCPCSYPTEVAYSTADIFDRIKRKDFRWKDASGPKEKL

EIYKPTARYCIRSMLSLESTTLAAQHCCYGDNMQLITRGKGAGTPNLISTEFSAELHYKV

DVLPWIICKGDWSRYNEARPPNNGOKCTESPSDEDYIKQFQEAREY (recombinant mouse

ISM1 AMOP domain)
(Underline: native mouse ISM1 sequence; Bold: His-tag and vector
sequence; Italics: SUMO-tag)

SEQ ID NO: 30: mamISM1$_{26-461}$
DAAQPARRARRTKLGTELGSGASDRQDAAAGNVSGSQLQNNLNLESDSTSETSFPLSK

EAPEEHQVVHQPFPRQRFPPETGHPSLQRDGPRSFLLDLPNFPDLSKADINGQNPNIQVTI

EVVDGPDSEAEKDQHPENKPSWSLPAPDWRAWWQRSLSLARTNSGDQDDKYDSTSDD

SNFLSVPRGWDRPAPGHRTFETKEQPEYDSTDGEGDWSLWSVCSVTCGNGNQKRTRSC

GYACIATESRTCDRPNCPGIEDTFRTAATEVSLLAGSEEFNATKLFEVDMDSCERWMSC

KSEFLKKYMHKVINDLPSCPCSYPTEVAYSTADIFDRIKRKDFRWKDASGPKEKLEIYKP

TARYCIRSMLSLESTTLAAQHCCYGDNMQLITRGKGAGTPNLISTEFSAELHYKVDVLP

WIICKGDWSRYNEARPPNNGQKCTESPSDEDYIKQFQEAREYPRGGP*EQKLISEEDLNS*

AVDHHHHHH (recombinant mouse ISM1 full-length)
(Underline: native mouse ISM1 sequence; Bold: vector sequence and
His-tag; Italics: Myc-tag)

SEQ ID NO: 31: mamISM1$_{287-461}$
DAAQPARRARRTKLGTELGSFEVDMDSCERWMSCKSEFLKKYMHKVINDLPSCPCSY

PTEVAYSTADIFDRIKRKDFRWKDASGPKEKLEIYKPTARYCIRSMLSLESTTLAAQHCC

YGDNMQLITRGKGAGTPNLISTEFSAELHYKVDVLPWIICKGDWSRYNEARPPNNGQKC

TESPSDEDYIKQFQEAREYPRGGP*EQKLISEEDLN*SAVDHHHHHH (recombinant mouse ISM1 AMOP domain)
(Underline: native mouse ISM1 sequence; Bold: vector sequence and
His-tag; Italics: Myc-tag)

SEQ ID NO: 32: mamISM1$_{26-464}$
DAAQPARRARRTKLGTELGSGAADGPDAAAGNASQAQLQNNLNVGSDTTSETSFSLS

KEAPREHLDHQAAHQPFPRPRFRQETGHPSLQRDFPRSELLDLPNFPDLSKADINGQNPN

IQVTIEVVDGPDSEADKDQHPENKPSWSVPSPDWRAWWQRSLSLARANSGDQDYKYD

STSDDSNFLNPPRGWDHTAPGHRTFETKDQPEYDSTDGEGDWSLWSVCSVTCGNGNQK

RTRSCGYACTATESRTCDRPNCPGIEDTFRTAATEVSLLAGSEEFNATKLFEVDTDSCER

WMSCKSEFLKKYMHKVMNDLPSCPCSYPTEVAYSTADIFDRIKRKDFRWKDASGPKEK

LEIYKPTARYCIRSMLSLESTTLAAQHCCYGDNMQLITRGKGAGTPNLISTEFSAELHYK

VDVLPWIICKGDWSRYNEARPPNNGQKCTESPSDEDYIKQFQEAREYPRGGP*EQKLISE*

*EDLN*SAVDHHHHHH (recombinant human ISM1 full length)
(Underline: native human ISM1 sequence; Bold: vector sequence and
His-tag; Italics: Myc-tag)

SEQ ID NO: 33: bacISM1$_{26-464}$
MGSSHHHHHHSQGSMSDSEVNQEAKPEVKPEVKPETHINLKVSDGSSEIFFKIKKTTPL

RRLMEAFAKRQGKEMDSLRFLYDGIRIQADQTPEDLDMEDNDIIEAHREQIGGGSGAAD

GPDAAAGNASQAQLQNNLNVGSDTTSETSESLSKEAPREHLDHQAAHQPFPRPRFRQET

GHPSLQRDFPRSELLDLPNFPDLSKADINGQNPNIQVTIEVVDGPDSEADKDQHPENKPS

WSVPSPDWRAWWQRSLSLARANSGDQDYKYDSTSDDSNFLNPPRGWDHTAPGHRTFE

TKDQPEYDSTDGEGDWSLWSVCSVTCGNGNQKRTRSCGYACTATESRTCDRPNCPGIE

DTFRTAATEVSLLAGSEEFNATKLFEVDTDSCERWMSCKSEFLKKYMHKVMNDLPSCP

CSYPTEVAYSTADIFDRIKRKDFRWKDASGPKEKLEIYKPTARYCIRSMLSLESTTLAAQ

HCCYGDNMQLITRGKGAGTPNLISTEFSAELHYKVDVLPWIICKGDWSRYNEARPPNNG

QKCTESPSDEDYIKQFQEAREY*DYKDDDDK* (recombinant human ISM1 full-
length)

-continued
(Underline: native human ISM1 sequence; Bold: vector sequence and
His-tag; Italics: FLAG-tag)

SEQ ID NO: 34: bacISM1$_{290-464}$
MGSSHHHHHHSQGSMSDSEVNQEAKPEVKPEVKPETHINLKVSDGSSEIFFKIKKTTPL RRLMEAFAKRQGKEMDSLRFLYDGIRIQADQTPEDLDMEDNDIIEAHREQIGG<u>FEVDTD</u>

<u>SCERWMSCKSEFLKKYMHKVMNDLPSCPCSYPTEVAYSTADIFDRIKRKDFRWKDASG</u>

<u>PKEKLEIYKPTARYCIRSMLSLESTTLAAQHCCYGDNMQLITRGKGAGTPNLISTEFSAE</u>

<u>LHYKVDVLPWIICKGDWSRYNEARPPNNGQKCTESPSDEDYIKQFQEAREY</u>*DYKDDDD*

*K* (recombinant human ISM1 AMOP domain)
(Underline: native human ISM1 sequence; Bold: vector sequence and
His-tag; Italics: FLAG-tag)

SEQ ID NO: 35: mamISM1$_{290-464}$
DAAQPARRARRTKLGTELGS<u>FEVDTDSCERWMSCKSEFLKKYMHKVMNDLPSCPCS</u>

<u>YPTEVAYSTADIFDRIKRKDFRWKDASGPKEKLEIYKPTARYCIRSMLSLESTTLAAQHC</u>

<u>CYGDNMQLITRGKGAGTPNLISTEFSAELHYKVDVLPWIICKGDWSRYNEARPPNNGQK</u>

<u>CTESPSDEDYIKQFQEAREY</u>PRGGP_EQKLISEEDLN_SAVDHHHHHH

(recombinant human ISM1 AMOP domain)
(Underline: native human ISM1 sequence; Bold: vector sequence and
His-tag; Italics: Myc-tag)

These results support that ISM1$_{287-461}$ (22 kDa) (human ISM1 equivalent is amino acid residues at 290-464) may function in similar fashion as the full-length rISM1 protein in suppressing CS-induced lung inflammation in mice. Both rISM1 and rISM1$_{287-461}$ (human ISM1 equivalent is amino acid residues at 290-464) may provide for therapy of COPD, for example.

In this Example, both mammalian and bacteria expression systems were used to generate soluble and functionally active recombinant ISM1 protein. The methodology not only helped the structure-function investigation, but may also be used to produce ISM1 for a variety of applications.

The apparent size difference between mammalian and bacterial rISM1 prompted us to investigate protein glycosylation profile on ISM1. We unexpectedly find that mammalian rISM1 is a highly heterogeneous glycoprotein, and the abundant deposition of glycans contributed significantly to the protein mass. Nevertheless, it should be noticed that protein glycosylation is affected by cell types. Different cells express distinct types and levels of glycosylation enzymes, therefore resulting in variations in the glycan profiles. For example, there are significant differences in the glycan profiles between proteins produced in CHO cells versus HEK293 cells. HEK293 produced proteins generally contain more complex glycan structures, while CHO derived proteins had higher level of sialylation. In another example, 12 human cell lines of different tissue origin were analyzed for the O-glycosylation profile, which revealed unique O-glycoproteome within each cell line (Steentoft, C., Vakhrushev, S. Y., Joshi, H. J., Kong, Y., Vester-Christensen, M. B., Schjoldager, K. T., Lavrsen, K., Dabelsteen, S., Pedersen, N. B., Marcos-Silva, L., Gupta, R., Bennett, E. P., Mandel, U., Brunak, S., Wandall, H. H., Levery, S. B., and Clausen, H. (2013) Precision mapping of the human O-GalNAc glycoproteome through SimpleCell technology. EMBO J 32, 1478-1488). More than half of the identified glycosites were found only in one cell line, while each cell line also contributed a plethora of unique glycoproteins. Therefore, the protein glycosylation analysis performed on mammalian rISM1 generated from Expi293F cells may serve as a reference, but may vary in other context.

Unexpectedly, this Example shows that ISM1-AMOP, rather than TSR, is mediating the receptor-binding as well as pro-apoptotic activity. As different ISM1-AMOP constructs displayed distinct activity, it appeared that the activity may be regulated at least in part by the boundary sequences.

Materials and Methods

Construct Building

To generate mammalian expression construct for ISM1, the cDNA of mouse ISM1 was PCR amplified and cloned into pSECtag-2B vector (Invitrogen) via BamHI and XhoI restriction enzyme sites. The vector contains N-terminal signal peptide from mouse Igκ1 leader sequences to allow high efficiency protein secretion, as well as C-terminal hexahistidine tag and Myc tag to assist protein detection and purification.

To generate bacterial expression construct for ISM1, the cDNA of SUMO-tag was first ligated to the N-terminal of mouse ISM1 cDNA via overlapping PCR, which was further cloned into pRSFDuet-1 vector (Novagen) via BamHI and XhoI restriction enzyme sites. The vector contains N-terminal hexahistidine tag to allow protein detection and purification.

Cell Lines and Cell Culture

HUVECs from Merck (SCCE001) were cultured in EndoGROLS complete culture media (Merck, SCME001) supplemented with HyClone antimycotic solution (GE Healthcare) to final concentration of 100 units/mL penicillin, 100 µg/mL streptomycin and 0.25 µg/mL Amphotericin B. HUVECs between passage number 4 and 8 were used for experiments.

Human embryonic kidney 293T cells (HEK293T) were acquired from American Type Culture Collection (ATCC); human embryonic kidney 293FT cells (HEK293FT) were gifted from Dr. Adam Yuan lab (Department of Biological Sciences, National University of Singapore); human cervical cancer cell line (HeLa CCL-2) were acquired from ATCC. All the above mentioned cell lines were cultured in Dulbecco's Modified Eagle Medium (DMEM) (GE healthcare)

supplemented with 10% fetal bovine serum (GE healthcare) and HyClone antimycotic solution (GE Healthcare) to final concentration of 100 units/mL penicillin, 100 µg/mL streptomycin and 0.25 µg/mL Amphotericin B.

Antibodies and Reagents:

The antibodies used for immunoprecipitation and immunoblotting are as follows: anti-His (A00186, GenScript); anti-Myc (ab9106, Abcam); anti-GRP78 (LS-C165064, LSBio); anti-integrin $\alpha v\beta 5$ (P1F76, SantaCruz); anti-integrin av (ab179475, Abcam); anti-integrin $\beta 5$ (ab184312, Abcam).

The following reagents were used: Caspase-3/7 green detection reagent (C10423, Invitrogen); PNGaseF (P0704S, New England Biolabs); SUMO protease (SAE0067, Sigma).

Transient Transfection

To perform transient transfection in HEK293T/HEK293FT/HeLa cells, lipofectamine 3000 (Invitrogen) was used following manufacturer's instructions. Twenty-four hours post transfection, culture medium was changed to fresh serum-free medium. After another 24 hours incubation, the conditioned medium and whole cell lysates were collected and analyzed with western blot.

Mammalian Recombinant ISM1 Expression and Purification

To express and purify mammalian recombinant ISM1 protein, fifty milliliter of Expi293F suspension cell culture in ExPi293 media (Gibco) was transiently transfected with 1 µg/mL expression plasmid complexed with Expifectamine 293 (Gibco) transfection reagent, as per manufacturer protocol. The culture was incubated at 37° C., 8.0% CO2 with a shaking speed of 120 rpm at orbit diameter of 25 mm. Expression Enhancers were added after 16 hours. Cell viability was monitored by using Countess II (Invitrogen). Upon cell viability lower than 70%, the spent media was separated from cells by centrifugation at 3000×g, and adjusted with conditioning buffer (5× conditioning buffer: 100 mM HEPES, 150 mM NaCl, 25 mM imidazole, 2.5% (v/v) glycerol, pH 7.5, 1× protease inhibitor cocktail). Two milliliter of Smart Ni-NTA resin (BioBasic) 50% slurry equilibrated in conditioning buffer was added to the conditioned media and incubated with gentle agitation for at least one hour. The resin was then collected and washed with IMAC buffers (50 mM HEPES, 300 mM NaCl, 10% (v/v) glycerol, pH 7.5) containing progressively increasing imidazole concentration. The protein was finally eluted with buffer containing 500 mM imidazole. PD10 desalting column (GE Healthcare) was equilibrated in storage buffer (20 mM HEPES, 300 mM NaCl, 10% (v/v) glycerol, pH 7.5) and used to buffer-exchange the IMAC eluate fractions. The protein was then concentrated with a Vivaspin centrifugal concentrator (Sartorius) with of 30 KDa molecular weight cut-off. Final protein concentration was measured by using Nanodrop (ThermoFisher). The protein was aliquoted, snap-frozen in liquid nitrogen and stored at −80° C.

Bacterial Recombinant ISM1 Expression and Purification

To express and purify bacterial recombinant ISM1 protein, SUMO-ISM1 bacterial expression constructs were first transformed into Shuffle T7 cells (New England Biolabs) following manufacturer's instructions. A single colony was inoculated into starter culture (10 ml) and grew at 30° C. shaker incubator, 220 RPM overnight. The next day, all the starter culture was poured into 1 L culture medium, and the bacteria was let grow at 30° C. shaker incubator, 220 RPM until OD 600 nm reach around 0.4-0.6. To induce protein expression, IPTG was then added to a final concentration of 0.25 mM. Induction was performed at 16° C. shaker incubator, 180 RPM for 16-20 hours. Finally the bacterial pellet was collected via centrifugation at 5,000×g, 4° C. for 10 min.

Before starting bacterial lysis, osmotic shock was performed to remove periplasmic proteins from E. coli (19). The bacterial pellet was first resuspended in sucrose buffer (50 mM HEPES, 20% sucrose, 1 mM EDTA, pH 7.4; 10 mL per liter culture) followed by centrifuge at 7000×g, 4° C. for 30 min. The pellet was further resuspended in 5 mM MgSO 4 (10 mL per liter culture) and incubated on ice for 10 min, before proceeded for centrifugation at 4500×g, 4° C. for 20 min. The supernatant was discarded and the bacterial pellet was kept on ice until lysis.

To start bacterial lysis, lysozyme (final concentration 1 mg/mL) and proteinase inhibitor cocktail (Roche) were freshly added to the bacterial lysis buffer (50 mM Tris, 250 mM NaCl, 40 mM imidazole, 10% glycerol, pH 7.5). Bacteria pellet were then resuspended in the lysis buffer (10 mL/L culture) and incubated on ice for at least 10 min. Afterwards, sonication was performed at 20% amplitude, 1 second on/off interval for 10 min to assist the lysis. The lysates were cleared via centrifugation at 13,000×g, 4° C. for 20 min. The supernatant containing the soluble recombinant protein was filtered via 0.45 µm syringe filter units (Sartorius), and transferred to a new tube.

To perform immobilized metal ion affinity chromatography (IMAC) purification, the HisTrap column (GE Healthcare) was first washed with 5 column volume of IMAC elution buffer (50 mM Tris, 250 mM NaCl, 250 mM imidazole, 10% glycerol, pH 7.5) followed by 10 column volume of IMAC binding buffer (50 mM Tris, 250 mM NaCl, 40 mM imidazole, 10% glycerol, pH 7.5). The cleared bacterial lysates were then loaded into the column through the AKTA pure 25 M Chromatography System (GE Healthcare). At least 10 column volume of IMAC binding buffer was applied to wash away the unbound proteins. The bound proteins were finally eluted with 20 column volume of linear gradient of IMAC elution buffer.

Size exclusion chromatography (SEC) was performed as the second step for final polishing. Previous elution fractions with relatively good purity from IMAC were pooled and loaded into Superdex200 10/300 column (GE Healthcare) which has been pre-equilibrated with SEC buffer (50 mM Tris, 250 mM NaCl, 10% glycerol, pH 7.5). Peak fractions from the SEC were collected, concentrated with Amicon Ultra Centrifugal Filters (Millipore), and measured for protein concentration with Bradford assay. The purified proteins were finally aliquoted, snap-frozen with liquid nitrogen and stored in −80° C.

Co-Immunoprecipitation

To perform Co-IP assay between purified recombinant ISM1 and GRP78 proteins, 2 µg GRP78 antibody (LS-C165064, LSBio) was first conjugated to protein A/G agarose beads (Santa Cruz Biotechnology) via incubation with 20 µL beads in PBS at 4° C. for 2 hours. The antibody-conjugated beads were then spun down at 5,000×g, 4° C. for 3 min to remove unbound antibodies. Next, 4 µg rGRP78 and 2 µg rISM1 were added to the beads in 1 mL Co-IP binding buffer (PBS, pH 7.4), and incubated at 4° C. overnight on a rotator. The next day, the beads were further washed three times with Co-IP wash buffer (PBS containing 0.1% Tween20), with 10 min-interval for each wash. The antibody-protein complex was finally eluted from the beads with 20 µL 2×SDS loading dye, and analyzed with western blot.

82

Apoptosis Assay

To measure endothelial cells apoptosis induced by recombinant ISM1, the assay was performed with IncuCyte ZOOM live cell imaging system (Essen Bioscience). HUVECs were seeded into the 96-well plates overnight with the density of 5500 cells/well. The next day, HUVECs were first starved in 2% FBS medium for 3 hours, followed by recombinant protein treatment in the presence or absence of VEGF (293-VE-010, R&D Systems). The Caspase-3/7 Green Apoptosis Detection Reagent (C10423, Invitrogen) was also included in 1:1000 dilution to measure apoptosis events. The apoptosis measurement was performed every hour for total 24 hours. The final summary statistics were compiled from at least three individual biological repeats.

Statistics

Statistical analysis and results plotting were performed with GraphPad Prism software. Comparisons between two experimental groups were done with unpaired two-tailed Student's t-test. Results were plotted as mean±sem. P value less than 0.05 was considered as significant.

Example 4—Recombinant ISM1 Suppresses Inflammation in House Dust Mite (HDM) Induced Asthma in Mice Asthma is a disease of the large airway and asthmatic immune response is dominantly mediated by eosinophils, but not AMs or neutrophils. The HDM-induced asthma model is a widely used asthma model for studying allergic asthma.

Figure 26:
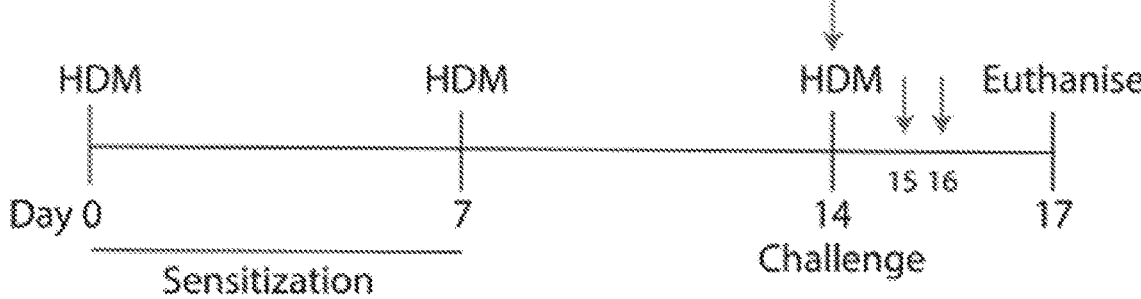
FIG. 26 shows timeline for allergen exposure in the HDM-induced allergy asthma mouse model. The disease model was generated according to the protocol described in Hammad et al. (2009) and Peh et al. (2015). Briefly, female C57BL/6J mice (6-8 weeks) were anaesthetized with isoflurane and sensitized with 40 μL of 100 μg HDM extract (*Dermatophagoides pteronyssinus*) on day 0, 7, and 14 via intratracheal route. A single dose daily of bacterial-produced recombinant ISM1 (2 mg/kg, 40 µg/mouse) or an equal volume of vehicle (normal saline) was given 2 hours after challenge, day 15, and day 16 consecutively (red arrow). All animals were euthanized on day 17, and bronchoalveolar lavage fluid (BALF) was collected for immune cell infiltration analysis. A naïve group consisted of five healthy mice served as control.

The mouse asthma model was generated according to the protocol described in Hammad et al. (2009) and Peh et al. (2015) and depicted in FIG. 26. Briefly, female C57BL/6J mice (6-8 weeks) were anaesthetized with isoflurane and sensitized with 40 μL of 100 μg HDM extract (*Dermatophagoides pteronyssinus*) on day 0, 7, and 14 via intratracheal route. A single dose daily of bacterial-produced recombinant ISM1 (2 mg/kg, 40 μg/mouse) or an equal volume of vehicle (normal saline) was given 2 hours after the HDM challenge, day 15, and day 16 consecutively. All mice were euthanized on day 17, and bronchoalveolar lavage fluid (BALF) was collected for immune cell infiltration analysis. A naïve group consisted of five healthy mice served as control.

As shown in FIG. 27, intratracheal delivered rISM1 potently suppressed HDM-induced asthmatic airway inflammation as demonstrated by the significant reduction of total leukocytes, eosinophils as well as lymphocytes in rISM1 treated mice. Consistent with previous reports, intratracheal HDM dominantly triggered an eosinophil-mediated airway inflammation, with little neutrophils involved. Eosinophils are suppressed by more than 70% under rISM treatment. Alveolar macrophages (AMs) are also increased upon HDM challenge, and rISM treatment showed a reduction of AM under this treatment regime, albeit not statistically significant. Results indicate that airway delivery of ISM1 is able to suppress HDM-induced airway inflammation in mouse asthma. These results support rISM1 for treatment of asthma and for preparation of anti-asthma drugs.

An elevation of serum immunoglobulin E (IgE) level is a hallmark of the Th2 immune response. Mouse sera were collected 24 hours after the last rISM treatment. rISM1 treatment significantly lowered the blood total IgE level as compared to HDM treated group, indicating that ISM1 suppressed Th2 immune response (FIG. 28).

One or more illustrative embodiments have been described by way of example. It will be understood to persons skilled in the art that a number of variations and modifications can be made without departing from the scope of the invention as defined in the claims.

REFERENCES

1. Barnes, P. J. et al. Chronic obstructive pulmonary disease. Nat Rev Dis Primers 1, 15076, doi:10.1038/nrdp.2015.76 (2015).
2. Barnes, P. J. Alveolar macrophages as orchestrators of COPD. COPD 1, 59-70, doi:10.1081/COPD-120028701 (2004).
3. Gershon, A. S., Warner, L., Cascagnette, P., Victor, J. C. & To, T. Lifetime risk of developing chronic obstructive pulmonary disease: a longitudinal population study. Lancet 378, 991-996, doi:10.1016/S0140-6736(11)60990-2 (2011).
4. Xiang, W. et al. Isthmin is a novel secreted angiogenesis inhibitor that inhibits tumour growth in mice. J Cell Mol Med 15, 359-374, doi:10.1111/j.1582-4934.2009.00961.x (2011).
5. Zhang, Y. et al. Isthmin exerts pro-survival and death-promoting effect on endothelial cells through alphavbeta5 integrin depending on its physical state. Cell Death Dis 2, e153, doi:10.1038/cddis.2011.37 (2011).
6. Chen, M. et al. Isthmin targets cell-surface GRP78 and triggers apoptosis via induction of mitochondrial dysfunction. Cell Death Differ 21, 797-810, doi:10.1038/cdd.2014.3 (2014).
7. Venugopal, S. et al. Isthmin is a novel vascular permeability inducer that functions through cell-surface GRP78-mediated Src activation. Cardiovasc Res 107, 131-142, doi:10.1093/cvr/cvv 142 (2015).
8. Ferguson, G. T. Why does the lung hyperinflate?Proc Am Thorac Soc 3, 176-179, doi:10.1513/pats.200508-094DO (2006).
9. Vogelmeier, C. F. et al. Global Strategy for the Diagnosis, Management, and Prevention of Chronic Obstructive Lung Disease 2017 Report: GOLD Executive Summary. Eur Respir J 49, doi:10.1183/13993003.00214-2017 (2017).
10. Woodruff, P. G. et al. A distinctive alveolar macrophage activation state induced by cigarette smoking. Am J Respir Crit Care Med 172, 1383-1392, doi:10.1164/rccm.200505-6860C (2005).
11. Hautamaki, R. D., Kobayashi, D. K., Senior, R. M. & Shapiro, S. D. Requirement for macrophage elastase for cigarette smoke-induced emphysema in mice. Science 277, 2002-2004 (1997).
12. Atkinson, J. J. et al. The role of matrix metalloproteinase-9 in cigarette smoke induced emphysema. Am J Respir Crit Care Med 183, 876-884, doi:10.1164/rccm.201005-07180C (2011).
13. de Boer, W. I. et al. Transforming growth factor beta1 and recruitment of macrophages and mast cells in airways in chronic obstructive pulmonary disease. Am J Respir Crit Care Med 158, 1951-1957, doi:10.1164/ajrccm.158.6.9803053 (1998).
14. Kranenburg, A. R., de Boer, W. I., Alagappan, V. K., Sterk, P. J. & Sharma, H. S. Enhanced bronchial expression of vascular endothelial growth factor and receptors (Flk-1 and Flt-1) in patients with chronic obstructive pulmonary disease. Thorax 60, 106-113, doi:10.1136/thx.2004.023986 (2005).

15. Osório, L., Wu, X. & Zhou, Z. Distinct spatiotemporal expression of ISM1 during mouse and chick development. Cell Cycle 13, 1571-1582, doi:10.4161/cc.28494 (2014).
16. Misra, U. K., Gonzalez-Gronow, M., Gawdi, G. & Pizzo, S. V. The role of MTJ-1 in cell surface translocation of GRP78, a receptor for alpha 2-macroglobulin-dependent signaling. J Immunol 174, 2092-2097 (2005).
17. Lu, M. C. et al. Anti-citrullinated protein antibodies bind surface-expressed citrullinated Grp78 on monocyte/macrophages and stimulate tumor necrosis factor alpha production. Arthritis Rheum 62, 1213-1223, doi:10.1002/art.27386 (2010).
18. Ofulue, A. F. & Ko, M. Effects of depletion of neutrophils or macrophages on development of cigarette smoke-induced emphysema. Am J Physiol 277, 97, doi:10.1152/ajplung.1999.277.1.L97 (1999).
19. Ueno, M. et al. Alendronate inhalation ameliorates elastase-induced pulmonary emphysema in mice by induction of apoptosis of alveolar macrophages. Nat Commun 6, 6332, doi:10.1038/ncomms7332 (2015).
20. Shapiro, S. D. The macrophage in chronic obstructive pulmonary disease. Am J Respir Crit Care Med 160, S29-32, doi:10.1164/ajrccm.160.supplement_1.9 (1999).
21. Domagala-Kulawik, J., Maskey-Warzechowska, M., Kraszewska, I. & Chazan, R. The cellular composition and macrophage phenotype in induced sputum in smokers and ex-smokers with COPD. Chest 123, 1054-1059 (2003).
22. Braber, S., Henricks, P. A., Nijkamp, F. P., Kraneveld, A. D. & Folkerts, G. Inflammatory changes in the airways of mice caused by cigarette smoke exposure are only partially reversed after smoking cessation. Respir Res 11, 99, doi:10.1186/1465-9921-11-99 (2010).
23. Tomita, K. et al. Increased p21(CIP1/WAF1) and B cell lymphoma leukemia-x(L) expression and reduced apoptosis in alveolar macrophages from smokers. Am J Respir Crit Care Med 166, 724-731 (2002).
24. Kojima, J. et al. Apoptosis inhibitor of macrophage (AIM) expression in alveolar macrophages in COPD. Respir Res 14, 30, doi:10.1186/1465-9921-14-30 (2013).
25. Finkelstein, R., Fraser, R. S., Ghezzo, H. & Cosio, M. G. Alveolar inflammation and its relation to emphysema in smokers. Am J Respir Crit Care Med 152, 1666-1672, doi:10.1164/ajrccm.152.5.7582312 (1995).
26. Gautier, E. L., Ivanov, S., Lesnik, P. & Randolph, G. J. Local apoptosis mediates clearance of macrophages from resolving inflammation in mice. Blood 122, 2714-2722, doi:10.1182/blood-2013-01-478206 (2013).
27. Marriott, H. M. et al. Decreased alveolar macrophage apoptosis is associated with increased pulmonary inflammation in a murine model of pneumococcal pneumonia. J Immunol 177, 6480-6488 (2006).
28. Aberdein, J. D., Cole, J., Bewley, M. A., Marriott, H. M. & Dockrell, D. H. Alveolar macrophages in pulmonary host defence the unrecognized role of apoptosis as a mechanism of intracellular bacterial killing. Clin Exp Immunol 174, 193-202, doi:10.1111/cei.12170 (2013).
29. Behar, S. M. et al. Apoptosis is an innate defense function of macrophages against *Mycobacterium tuberculosis*. Mucosal Immunology 4, 279-287, doi:10.1038/mi.2011.3 (2011).
30. Barnes, P. J. Corticosteroid resistance in patients with asthma and chronic obstructive pulmonary disease. J Allergy Clin Immunol 131, 636-645, doi:10.1016/j.jaci.2012.12.1564 (2013).

31. Mbawuike, I. N. & Herscowitz, H. B. MH-S, a murine alveolar macrophage cell line: morphological, cytochemical, and functional characteristics. J Leukoc Biol 46, 119-127 (1989).
32. Chavez-Santoscoy, A. V., Huntimer, L. M., Ramer-Tait, A. E., Wannemuehler, M. & Narasimhan, B. Harvesting murine alveolar macrophages and evaluating cellular activation induced by polyanhydride nanoparticles. J Vis Exp, e3883 (2012).
33. Xiang, W., et al. Isthmin is a novel secreted angiogenesis inhibitor that inhibits tumour growth in mice. J Cell Mol Med 15, 359-374 (2011).
34. Knudsen, L., Weibel, E. R., Gundersen, H. J., Weinstein, F. V. & Ochs, M. Assessment of air space size characteristics by intercept (chord) measurement: an accurate and efficient stereological approach. J Appl Physiol (1985) 108, 412-421 (2010).
35. Peh, H. Y., et al. Vitamin E isoform 7-tocotrienol protects against emphysema in cigarette smoke-induced COPD. Free Radic Biol Med 110, 332-344 (2017).
36. Matuschak, G. M. & Lechner, A. J. Acute lung injury and the acute respiratory distress syndrome: pathophysiology and treatment. Missouri medicine 107, 252-258 (2010).
37. Wheeler, A. P. & Bernard, G. R. Acute lung injury and the acute respiratory distress syndrome: a clinical review. Lancet 369, 1553-1564, doi:10.1016/S0140-6736(07)60604-7 (2007).
38. Kabir, K. et al. Characterization of a murine model of endotoxin-induced acute lung injury. Shock 17, 300-303 (2002).
39. Matute-Bello, G., Frevert, C. W. & Martin, T. R. Animal models of acute lung injury. American Journal Of Physiology, 379-399, doi:10.1152/ajplung.00010.2008. (2008).
40. Copeland, S., Warren, H. S., Lowry, S. F., Calvano, S. E. & Remick, D. Acute Inflammatory Response to Endotoxin in Mice and Humans Acute Inflammatory Response to Endotoxin in Mice and Humans. Clinical and Diagnostic Laboratory Immunology 12, 60-67, doi:10.1128/CDLI.12.1.60 (2005).
41. Kawasaki, T. & Kawai, T. in Frontiers in Immunology Vol. 5 (2014).
42. Poltorak, A. et al. Defective LPS signaling in C3H/HeJ and C57BIOScCr mice: Mutations in Tlr4 gene. Science 282, 2085-2088, doi:10.1126/science.282.5396.2085 (1998).
43. Pilsson-McDermott, E. M. & O'Neill, L. A. J. in Immunology Vol. 113 153-162 (2004).
44. Lawrence, T. in Cold Spring Harbor perspectives in biology Vol. 1 (2009).
45. Mizgerd, J. P., Scott, M. L., Spieker, M. R. & Doerschuk, C. M. Functions of NF-kappaB proteins in inflammatory responses to *Escherichia coli* LPS in mouse lungs. American Journal of Respiratory Cell and Molecular Biology 27, 575-582, doi:10.1165/rcmb.2002-00150C (2002).
46. Schwartz, M. D. et al. Nuclear factor-kappa B is activated in alveolar macrophages from patients with acute respiratory distress syndrome. Critical care medicine 24, 1285-1292 (1996).
47. Xiang, W. et al. Isthmin is a novel secreted angiogenesis inhibitor that inhibits tumour growth in mice. Journal of Cellular and Molecular Medicine 15, 359-374, doi:10.1111/j.1582-4934.2009.00961.x (2011).
48. Chen, M. et al. Isthmin targets cell-surface GRP78 and triggers apoptosis via induction of mitochondrial dysfunction. Cell death and differentiation 21, 797-810, doi:10.1038/cdd.2014.3 (2014).

49. Venugopal, S. et al. Isthmin is a novel vascular perme-ability inducer that functions through cell-surface GRP78-mediated Src activation. Cardiovascular Research 107, 131-142, doi:10.1093/cvr/cvv 142 (2015).

50. Todd, N. W., Luzina, I. G. & Atamas, S. P. Molecular and cellular mechanisms of pulmonary fibrosis. Fibrogenesis & Tissue Repair 5, 11, doi:10.1186/1755-1536-5-11 (2012).

51. Williams, M. C. Alveolar type I cells: molecular phe-notype and development. Annu Rev Physiol 65, 669-695, doi:10.1146/annurev.physiol.65.092101.142446 (2003).

52. Fehrenbach, H. Alveolar epithelial type II cell: defender of the alveolus revisited. Respir Res 2, 33-46 (2001).

53. Fehrenbach, H. et al. Alveolar epithelial type II cell apoptosis in vivo during resolution of keratinocyte growth factor-induced hyperplasia in the rat. Histochem Cell Biol 114, 49-61 (2000).

54. Kasper, M. & Barth, K. Potential contribution of alveolar epithelial type I cells to pulmonary fibrosis. Bioscience reports 0, BSR20171301, doi:10.1042/BSR20171301 (2017).

55. Biernacka, A., Dobaczewski, M. & Frangogiannis, N. G. TGF-beta signaling in fibrosis.
Growth Factors 29, 196-202, doi:10.3109/08977194.2011.595714 (2011).

56. Park, S. D. et al. Intranuclear interactomic inhibition of NF-κB suppresses LPS-induced severe sepsis. Biochemi-cal and Biophysical Research Communications 464, 711-717, doi:10.1016/j.bbrc.2015.07.008 (2015).

57. Lawler, J. et al. Thrombospondin-1 is required for normal murine pulmonary homeostasis and its absence causes pneumonia. Journal of Clinical Investigation 101, 982-992, doi:10.1172/JCI1684 (1998).

58. Zhao, Y. et al. Thrombospondin-1 triggers macrophage IL-10 production and promotes resolution of experimen-tal lung injury. British Dental Journal 217, 440-448, doi:10.1038/mi.2013.63 (2014).

59. Chavakis, T. et al. Angiostatin is a novel anti-inflam-matory factor by inhibiting leukocyte recruitment. Blood 105, 1036-1043, doi:10.1182/blood-2004-01-0166 (2004).

60. Matthay, M. A., Ware, L. B. & Zimmerman, G. A. The acute respiratory distress syndrome.
J Clin Invest 122, 2731-2740, doi:10.1172/JCI60331 (2012).

61. Selvaraj, V. et al. Inhibition of MAP kinase/NF-kB mediated signaling and attenuation of lipopolysaccharide induced severe sepsis by cerium oxide nanoparticles. Biomaterials 59, 160-171, doi:10.1016/j.biomateri-als.2015.04.025 (2015).

62. Grossman, B. J. et al. Temporal and mechanistic effects of heat shock on LPS-mediated degradation of IκBα in macrophages. Inflammation 26, 129-137, doi:10.1023/A:1015552515183 (2002).

63. Wang, S. et al. Deferoxamine attenuates lipopolysaccha-ride-induced inflammatory responses and protects against endotoxic shock in mice. Biochemical and Biophysical Research Communications 465, 305-311, doi:10.1016/j.bbrc.2015.08.032 (2015).

64. Shi, M. M., Chong, I., Godleski, J. J. & Paulauskis, J. D. Regulation of macrophage inflammatory protein-2 gene expression by oxidative stress in rat alveolar macro-phages.
Immunology 97, 309-315, doi:imm798 [pii] (1999).

65. Ragaller, M. & Richter, T. Acute lung injury and acute respiratory distress syndrome. J Emerg Trauma Shock 3, 43-51, doi:10.4103/0974-2700.58663 (2010).

66. Johnson, E. R. & Matthay, M. A. Acute lung injury: epidemiology, pathogenesis, and treatment. J Aerosol Med Pulm Drug Deliv 23, 243-252, doi:10.1089/jamp.2009.0775 (2010).

67. Liao, W., Bao, Z., Cheng, C., Mok, Y. K. & Wong, W. S. Dendritic cell-derived interferon-gamma-induced pro-tein mediates tumor necrosis factor-alpha stimulation of human lung fibroblasts. Proteomics 8, 2640-2650, doi:10.1002/pmic.200700954 (2008).

68. Chan, T. K. et al. House dust mite-induced asthma causes oxidative damage and DNA double-strand breaks in the lungs. Journal of Allergy and Clinical Immunology 138, 84-96.e81, doi:10.1016/j.jaci.2016.02.017 (2016).

69. Xiang, W. et al., 2011, Journal of Cellular and Molecu-lar Medicine, 15(2): 359-374.

70. WO2009/113965, entitled Isthmin Derivatives for use in Treating Angiogenesis.

71. Bodier-Montagutelli, E., et al., 2018, Designing inhaled protein therapeutics for topical lung delivery: what are the next steps?, Expert Opinion on Drug Delivery, 15(8): 729-736.

72. Labiris, N. R., et al., 2003, Pulmonary Drug Delivery. Part II: The role of inhalant delivery devices and drug formulations in therapeutic effectiveness of aerosolized medications, Br J Clin Pharmacol, 56:600-612.

73. Ibrahim M., et al., 2015, Inhalation drug delivery devices: technology update, Med Devices (Auckl), 8:131-9.

74. U.S. Pat. No. 5,983,893

75. U.S. Pat. No. 6,732,732

76. US20070295332

77. U.S. Pat. No. 5,007,419

78. U.S. Pat. No. 4,832,015

79. US20040244794

80. US20100065048

81. US20030235555

82. US20050201951

83. US20090000615

84. Ni, et al., Biochem J., 2011, 434(2): 181-188

85. Gomes et al., 2017, Expert Opin Drug Deliv., 2017, 14(3):319-330.

86. Burikhanov, R., Zhao, Y., Goswami, A., Qiu, S., Schwarze, S. R., and Rangnekar, V. M. (2009). The tumor suppressor Par-4 activates an extrinsic pathway for apop-tosis. Cell 138, 377-388.

87. Chen, M., Qiu, T., Wu, J., Yang, Y., Wright, G. D., Wu, M., and Ge, R. (2018). Extracellular anti-angiogenic proteins augment an endosomal protein trafficking path-way to reach mitochondria and execute apoptosis in HUVECs. Cell Death & Differentiation, 25: 1905-1920.

88. Chen, M., Zhang, Y., Yu, V., Chong, Y., Yoshioka, T., and Ge, R. (2014). Isthmin targets cell-surface GRP78 and triggers apoptosis via induction of mitochondrial dysfunc-tion. Cell Death & Differentiation 21, 797-810.

89. Chen, Y., Wang, S., Lu, X., Zhang, H., Fu, Y., and Luo, Y. (2011). Cholesterol sequestration by nystatin enhances the uptake and activity of endostatin in endothelium via regulating distinct endocytic pathways. Blood 117, 6392-6403.

90. Ciccarelli, F. D., Doerks, T., and Bork, P. (2002). AMOP, a protein module alternatively spliced in cancer cells. Trends in biochemical sciences 27, 113-115.

91. Davidson, D. J., Haskell, C., Majest, S., Kherzai, A., Egan, D. A., Walter, K. A., Schneider, A., Gubbins, E. F., Solomon, L., and Chen, Z. (2005). Kringle 5 of human plasminogen induces apoptosis of endothelial and tumor cells through surface-expressed glucose-regulated protein 78. Cancer research 65, 4663-4672.

92. Kumar, S., Sharghi-Namini, S., Rao, N., and Ge, R. (2012). ADAMTS5 functions as an anti-angiogenic and anti-tumorigenic protein independent of its proteoglyca-nase activity. The American journal of pathology 181, 1056-1068.

93. Lawler, J., and Hynes, R. O. (1986). The structure of human thrombospondin, an adhesive glycoprotein with multiple calcium-binding sites and homologies with several different proteins. The Journal of Cell Biology 103, 1635-1648.

94. Le Roy, C., and Wrana, J. L. (2005). Clathrin-and non-clathrin-mediated endocytic regulation of cell signal-ling. Nature reviews Molecular cell biology 6, 112-126.

95. Lee, A. S. (2001). The glucose-regulated proteins: stress induction and clinical applications.
Trends in biochemical sciences 26, 504-510.

96. Lee, A. S. (2005). The ER chaperone and signaling regulator GRP78/BiP as a monitor of endoplasmic reticu-lum stress. Methods 35, 373-381.

97. Lee, A. S. (2014). Glucose-regulated proteins in cancer: molecular mechanisms and therapeutic potential. Nature Reviews Cancer 14, 263-276.

98. Lee, T.-Y., Muschal, S., Pravda, E. A., Folkman, J., Abdollahi, A., and Javaherian, K. (2009). Angiostatin regulates the expression of antiangiogenic and proapop-totic pathways via targeted inhibition of mitochondrial proteins. Blood 114, 1987-1998.

99. Mikhailenko, I., Krylov, D., Argraves, K. M., Roberts, D. D., Liau, G., and Strickland, D. K. (1997). Cellular internalization and degradation of thrombospondin-1 is mediated by the amino-terminal heparin binding domain (HBD) High affinity interaction of dimeric HBD with the low density lipoprotein receptor-related protein. Journal of Biological Chemistry 272, 6784-6791.

100. Ni, M., Zhang, Y., and Lee, A. (2011). Beyond the endoplasmic reticulum: atypical GRP78 in cell viability, signalling and therapeutic targeting. Biochem J 434, 181-188.

101. Oganesian, A., Armstrong, L. C., Migliorini, M. M., Strickland, D. K., and Bornstein, P. (2008). Thrombos-pondins use the VLDL receptor and a nonapoptotic path-way to inhibit cell division in microvascular endothelial cells. Molecular biology of the cell 19, 563-571.

102. Pera, E. M., Kim, J. I., Martinez, S. L., Brechner, M., Li, S.-Y., Wessely, O., and De Robertis, E. (2002). Isthmin is a novel secreted protein expressed as part of the Fgf-8 synexpression group in the Xenopus midbrain-hindbrain organizer. Mechanisms of development 116, 169-172.

103. Roller, C., and Maddalo, D. (2013). The molecular chaperone GRP78/BiP in the development of chemoresis-tance: mechanism and possible treatment. Frontiers in pharmacology 4, 10.

104. Silva, R., D'Amico, G., Hodivala-Dilke, K. M., and Reynolds, L. E. (2008). Integrins: the keys to unlocking angiogenesis. Arteriosclerosis, Thrombosis, and Vascular Biology 28, 1703-1713.

105. Terai, Y., Abe, M., Miyamoto, K., Koike, M., Yamasaki, M., Ueda, M., Ueki, M., and Sato, Y. (2001). Vascular smooth muscle cell growth-promoting factor/F-spondin inhibits angiogenesis via the blockade of integrin $\alpha v\beta$ on vascular endothelial cells. Journal of cellular physiology 188, 394-402.

106. Weis, S. M., and Cheresh, D. A. (2011). $\alpha V$ integrins in angiogenesis and cancer. Cold Spring Harbor perspec-tives in medicine 1, a006478.

107. Xiang, W., Ke, Z., Zhang, Y., Ho-Yuet Cheng, G., Irwan, I. D., Sulochana, K., Potturi, P., Wang, Z., Yang, H., and Wang, J. (2011). Isthmin is a novel secreted angiogenesis inhibitor that inhibits tumour growth in mice. Journal of cellular and molecular medicine 15, 359-374.

108. Zhang, Y., Chen, M., Venugopal, S., Zhou, Y., Xiang, W., Li, Y., Lin, Q., Kini, R., Chong, Y., and Ge, R. (2011). Isthmin exerts pro-survival and death-promoting effect on endothelial cells through alphavbeta5 integrin depending on its physical state. Cell death & disease 2, e153.

109. Chen et al., Cell Death & Differentiation, 21(5): 797-810, 2014.

110. Kao et al., EBioMedicine 33 (2018) 22-32.

111. Aberdein J D, Cole J, Bewley M A, Marriott H M, Dockrell D H (2013) Alveolar macrophages in pulmonary host defence the unrecognized role of apoptosis as a mechanism of intracellular bacterial killing. Clin Exp Immunol 174: 193-202

112. Arai S, Shelton J M, Chen M, Bradley M N, Castrillo A, Bookout A L, Mak P A, Edwards P A, Mangelsdorf D J, Tontonoz P, Miyazaki T (2005) A role for the apoptosis inhibitory factor AIM/Spalpha/Api6 in atherosclerosis development. Cell Metab 1: 201-13

113. Babu MM (2016) The contribution of intrinsically disordered regions to protein function, cellular complex-ity, and human disease. Biochem Soc Trans 44: 1185-1200

114. Barnes P J (2013a) Corticosteroid resistance in patients with asthma and chronic obstructive pulmonary disease. J Allergy Clin Immunol 131: 636-45

115. Barnes P J (2013b) New anti-inflammatory targets for chronic obstructive pulmonary disease. Nat Rev Drug Discov 12: 543-59

116. Barnes P J (2016) Inflammatory mechanisms in patients with chronic obstructive pulmonary disease. J Allergy Clin Immunol 138: 16-27

117. Berrun A, Harris E, Stachura D L (2018) Isthmin 1 (ism1) is required for normal hematopoiesis in developing zebrafish. PLoS One 13: e0196872

118. Bodier-Montagutelli E, Mayor A, Vecellio L, Respaud R, Heuze-Vourc'h N (2018) Designing inhaled protein therapeutics for topical lung delivery: what are the next steps?Expert Opin Drug Deliv 15: 729-736

119. Chavez-Santoscoy A V, Huntimer L M, Ramer-Tait A E, Wannemuehler M, Narasimhan B (2012) Harvesting murine alveolar macrophages and evaluating cellular acti-vation induced by polyanhydride nanoparticles. J Vis Exp: e3883

120. Chen M, Zhang Y, Yu V C, Chong Y S, Yoshioka T, Ge R (2014) Isthmin targets cell-surface GRP78 and triggers apoptosis via induction of mitochondrial dysfunction. Cell Death Differ 21: 797-810

121. Churg A, Wang R D, Tai H, Wang X, Xie C, Wright J L (2004) Tumor necrosis factor-alpha drives 70% of cigarette smoke-induced emphysema in the mouse. Am J Respir Crit Care Med 170: 492-8

122. Dagvadorj J, Shimada K, Chen S, Jones H D, Tumur-khuu G, Zhang W, Wawrowsky K A, Crother T R, Arditi M (2015) Lipopolysaccharide Induces Alveolar Macro-phage Necrosis via CD14 and the P2X7 Receptor Leading to Interleukin-1$\alpha$ Release. Immunity 42: 640-53

123. de Boer W I, van Schadewijk A, Sont J K, Sharma H S, Stolk J, Hiemstra P S, van Krieken J H (1998) Trans-forming growth factor beta1 and recruitment of macrophages and mast cells in airways in chronic obstructive pulmonary disease. Am J Respir Crit Care Med 158: 1951-7

124. Dewhurst J A, Lea S, Hardaker E, Dungwa J V, Ravi A K, Singh D (2017) Characterisation of lung macrophage subpopulations in COPD patients and controls. Sci Rep 7: 7143

125. Domagala-Kulawik J, Maskey-Warzechowska M, Kraszewska I, Chazan R (2003) The cellular composition and macrophage phenotype in induced sputum in smokers and ex-smokers with COPD. Chest 123: 1054-9

126. Finkelstein R, Fraser R S, Ghezzo H, Cosio M G (1995) Alveolar inflammation and its relation to emphysema in smokers. Am J Respir Crit Care Med 152: 1666-72

127. Gagnon P, Guenette J A, Langer D, Laviolette L, Mainguy V, Maltais F, Ribeiro F, Saey D (2014) Pathogenesis of hyperinflation in chronic obstructive pulmonary disease. Int J Chron Obstruct Pulmon Dis 9: 187-201

128. Gautier E L, Ivanov S, Lesnik P, Randolph G J (2013) Local apoptosis mediates clearance of macrophages from resolving inflammation in mice. Blood 122: 2714-22

129. Gershon A S, Warner L, Cascagnette P, Victor J C, To T (2011) Lifetime risk of developing chronic obstructive pulmonary disease: a longitudinal population study. Lancet 378: 991-6

130. Guilliams M, De Kleer I, Henri S, Post S, Vanhoutte L, De Prijck S, Deswarte K, Malissen B, Hammad H, Lambrecht BN (2013) Alveolar macrophages develop from fetal monocytes that differentiate into long-lived cells in the first week of life via GM-CSF. J Exp Med 210: 1977-92

131. Hamidzadeh K, Christensen S M, Dalby E, Chandrasekaran P, Mosser D M (2017) Macrophages and the Recovery from Acute and Chronic Inflammation. Annu Rev Physiol 79: 567-592

132. Hautamaki R D, Kobayashi D K, Senior R M, Shapiro S D (1997) Requirement for macrophage elastase for cigarette smoke-induced emphysema in mice. Science 277: 2002-4

133. Joshi T, Xu D (2007) Quantitative assessment of relationship between sequence similarity and function similarity. BMC Genomics 8: 222

134. Knudsen L, Weibel E R, Gundersen H J, Weinstein F V, Ochs M (2010) Assessment of air space size characteristics by intercept (chord) measurement: an accurate and efficient stereological approach. J Appl Physiol (1985) 108: 412-21

135. Kojima J, Araya J, Hara H, Ito S, Takasaka N, Kobayashi K, Fujii S, Tsurushige C, Numata T, Ishikawa T, Shimizu K, Kawaishi M, Saito K, Kamiya N, Hirano J, Odaka M, Morikawa T, Hano H, Arai S, Miyazaki T et al. (2013) Apoptosis inhibitor of macrophage (AIM) expression in alveolar macrophages in COPD. Respir Res 14: 30

136. Kranenburg A R, de Boer W I, Alagappan V K, Sterk P J, Sharma H S (2005) Enhanced bronchial expression of vascular endothelial growth factor and receptors (Flk-1 and Flt-1) in patients with chronic obstructive pulmonary disease. Thorax 60: 106-13

137. Labiris N R, Dolovich M B (2003) Pulmonary drug delivery. Part I: physiological factors affecting therapeutic effectiveness of aerosolized medications. Br J Clin Pharmacol 56: 588-99

138. Lansdon L A, Darbro B W, Petrin A L, Hulstrand A M, Standley J M, Brouillette R B, Long A, Mansilla M A, Cornell R A, Murray J C, Houston D W, Manak J R (2018)

Identification of Isthmin 1 as a Novel Clefting and Craniofacial Patterning Gene in Humans. Genetics 208: 283-296

139. Li J, Ni M, Lee B, Barron E, Hinton D R, Lee A S (2008) The unfolded protein response regulator GRP78/BiP is required for endoplasmic reticulum integrity and stress-induced autophagy in mammalian cells. Cell Death Differ 15: 1460-71

140. Lu M C, Lai N S, Yu H C, Huang H B, Hsieh S C, Yu C L (2010) Anti-citrullinated protein antibodies bind surface-expressed citrullinated Grp78 on monocyte/macrophages and stimulate tumor necrosis factor alpha production. Arthritis Rheum 62: 1213-23

141. Misharin A V, Morales-Nebreda L, Reyfman P A, Cuda C M, Walter J M, McQuattie-Pimentel A C, Chen C I, Anekalla K R, Joshi N, Williams K J N, Abdala-Valencia H, Yacoub T J, Chi M, Chiu S, Gonzalez-Gonzalez F J, Gates K, Lam A P, Nicholson T T, Homan P J, Soberanes S et al. (2017) Monocyte-derived alveolar macrophages drive lung fibrosis and persist in the lung over the life span. J Exp Med 214: 2387-2404

142. Misra U K, Gonzalez-Gronow M, Gawdi G, Pizzo S V (2005) The role of MTJ-1 in cell surface translocation of GRP78, a receptor for alpha 2-macroglobulin-dependent signaling. J Immunol 174: 2092-7

143. Mortality GBD, Causes of Death C (2016) Global, regional, and national life expectancy, all-cause mortality, and cause-specific mortality for 249 causes of death, 1980-2015: a systematic analysis for the Global Burden of Disease Study 2015. Lancet 388: 1459-1544

144. Murugan V, Peck M J (2009) Signal transduction pathways linking the activation of alveolar macrophages with the recruitment of neutrophils to lungs in chronic obstructive pulmonary disease. Exp Lung Res 35: 439-85

145. Nabe T, Matsuda M, Ishida T, Tsujimoto N, Kido H, Kanaya H, Takahashi H, Takemoto N, Nomura M, Ishihara K, Akiba S, Mizutani N (2018) Antigen-specific airway IL-33 production depends on FcγR-mediated incorporation of the antigen by alveolar macrophages in sensitized mice. Immunology 155: 99-111

146. Naidu B V, Krishnadasan B, Farivar A S, Woolley S M, Thomas R, Van Rooijen N, Verrier E D, Mulligan M S (2003) Early activation of the alveolar macrophage is critical to the development of lung ischemia-reperfusion injury. J Thorac Cardiovasc Surg 126: 200-7

147. Osório L, Wu X, Zhou Z (2014) Distinct spatiotemporal expression of ISM1 during mouse and chick development. Cell Cycle 13: 1571-82

148. Patton J S, Fishbum C S, Weers J G (2004) The lungs as a portal of entry for systemic drug delivery. Proc Am Thorac Soc 1: 338-44

149. Peh H Y, Tan W S D, Chan T K, Pow C W, Foster P S, Wong W S F (2017) Vitamin E isoform γ-tocotrienol protects against emphysema in cigarette smoke-induced COPD. Free Radic Biol Med 110: 332-344

150. Quesada Calvo F, Fillet M, Renaut J, Crahay C, Gueders M, Hacha J, Paulissen G, Foidart J M, Noel A, Rocks N, Leprince P, Cataldo D (2011) Potential therapeutic target discovery by 2D-DIGE proteomic analysis in mouse models of asthma. J Proteome Res 10: 4291-301

151. Singh D, Agusti A, Anzueto A, Barnes P J, Bourbeau J, Celli B R, Criner G J, Frith P, Halpin DMG, Han M, López Varela M V, Martinez F, Montes de Oca M, Papi A, Pavord I D, Roche N, Sin D D, Stockley R, Vestbo J, Wedzicha J A et al. (2019) Global Strategy for the Diagnosis, Management, and Prevention of Chronic Obstructive Lung Disease: The GOLD Science Committee Report 2019. Eur Respir J 152. Suzuki T, McCarthy C, Carey B C, Borchers M, Beck D, Wikenheiser-Brokamp K A, Black D, Chalk C, Trapnell B C (2020) Increased Pulmonary GM-CSF Causes Alveolar Macrophage Accumulation. Mechanistic Implications for Desquamative Interstitial Pneumonitis. Am J Respir Cell Mol Biol 62: 87-94

153. Teoh C M, Tan S S, Tran T (2015) Integrins as Therapeutic Targets for Respiratory Diseases. Curr Mol Med 15: 714-34

154. Ueno M, Maeno T, Nishimura S, Ogata F, Masubuchi H, Hara K, Yamaguchi K, Aoki F, Suga T, Nagai R, Kurabayashi M (2015) Alendronate inhalation ameliorates elastase-induced pulmonary emphysema in mice by induction of apoptosis of alveolar macrophages. Nat Commun 6: 6332

155. Venugopal S, Chen M, Liao W, Er S Y, Wong W S, Ge R (2015) Isthmin is a novel vascular permeability inducer that functions through cell-surface GRP78-mediated Src activation. Cardiovasc Res 107: 131-42

156. Vogelmeier C F, Criner G J, Martinez F J, Anzueto A, Barnes P J, Bourbeau J, Celli B R, Chen R, Decramer M, Fabbri L M, Frith P, Halpin D M, López Varela M V, Nishimura M, Roche N, Rodriguez-Roisin R, Sin D D, Singh D, Stockley R, Vestbo J et al. (2017) Global Strategy for the Diagnosis, Management, and Prevention of Chronic Obstructive Lung Disease 2017 Report: GOLD Executive Summary. Eur Respir J 49

157. Weber C K, Haslbeck M, Englbrecht M, Sehnert B, Mielenz D, Graef D, Distler J H, Mueller R B, Burkhardt H, Schett G, Voll R E, Fürnrohr B G (2010) Antibodies to the endoplasmic reticulum-resident chaperones calnexin, BiP and Grp94 in patients with rheumatoid arthritis and systemic lupus erythematosus. Rheumatology (Oxford) 49: 2255-63

158. Wei J, Sun Z, Chen Q, Gu J (2006) Serum deprivation induced apoptosis in macrophage is mediated by autocrine secretion of type I IFNs. Apoptosis 11: 545-54

159. Woodruff P G, Koth L L, Yang Y H, Rodriguez M W, Favoreto S, Dolganov G M, Paquet A C, Erle D J (2005) A distinctive alveolar macrophage activation state induced by cigarette smoking. Am J Respir Crit Care Med 172: 1383-92

160. Xaus J, Comalada M, Valledor A F, Lloberas J, López-Soriano F, Argilds J M, Bogdan C, Celada A (2000) LPS induces apoptosis in macrophages mostly through the autocrine production of TNF-alpha. Blood 95: 3823-31

161. Xiang W, Ke Z, Zhang Y, Cheng G H, Irwan I D, Sulochana K N, Potturi P, Wang Z, Yang H, Wang J, Zhuo L, Kini R M, Ge R (2011) Isthmin is a novel secreted angiogenesis inhibitor that inhibits tumour growth in mice. J Cell Mol Med 15: 359-74.

162. Hammad, H., Chieppa, M., Perros, F., Willart, M. A., Germain, R. N., & Lambrecht, B. N. (2009). House dust mite allergen induces asthma via Toll-like receptor 4 triggering of airway structural cells. Nature medicine, 15(4), 410-416. doi:10.1038/nm.1946

163. Peh, H. Y., Ho, W. E., Cheng, C., Chan, T. K., Seow, A. C. G., Lim, A. Y., . . . & Wong, W. F. (2015). Vitamin E isoform 7-tocotrienol downregulates house dust mite-induced asthma. The Journal of Immunology, 195(2), 437-444.

164. Xiang, W., Ke, Z., Zhang, Y., Cheng, G. H., Irwan, I. D., Sulochana, K. N., Potturi, P., Wang, Z., Yang, H., Wang, J., Zhuo, L., Kini, R. M., and Ge, R. (2011) Isthmin is a novel secreted angiogenesis inhibitor that inhibits tumour growth in mice. J Cell Mol Med 15, 359-374

165. Pera, E. M., Kim, J. I., Martinez, S. L., Brechner, M., Li, S. Y., Wessely, O., and De Robertis, E. M. (2002) Isthmin is a novel secreted protein expressed as part of the Fgf-8 synexpression group in the Xenopus midbrain-hindbrain organizer. Mech Dev 116, 169-172

166. Chen, M., Zhang, Y., Yu, V. C., Chong, Y. S., Yoshioka, T., and Ge, R. (2014) Isthmin targets cell-surface GRP78 and triggers apoptosis via induction of mitochondrial dysfunction. Cell Death Differ 21, 797-810

167. Zhang, Y., Chen, M., Venugopal, S., Zhou, Y., Xiang, W., Li, Y. H., Lin, Q., Kini, R. M., Chong, Y. S., and Ge, R. (2011) Isthmin exerts pro-survival and death-promoting effect on endothelial cells through alphavbeta5 integrin depending on its physical state. Cell Death Dis 2, e153

168. Hynes, R. O. (2002) Integrins: bidirectional, allosteric signaling machines. Cell 110, 673-687

169. Ni, M., Zhang, Y., and Lee, A. S. (2011) Beyond the endoplasmic reticulum: atypical GRP78 in cell viability, signalling and therapeutic targeting. Biochem J 434, 181-188

170. Lee, A. S. (2014) Glucose-regulated proteins in cancer: molecular mechanisms and therapeutic potential. Nat Rev Cancer 14, 263-276

171. Shakin-Eshleman, S. H., Remaley, A. T., Eshleman, J. R., Wunner, W. H., and Spitalnik, S. L. (1992) N-linked glycosylation of rabies virus glycoprotein. Individual sequons differ in their glycosylation efficiencies and influence on cell surface expression. J Biol Chem 267, 10690-10698

172. Hofsteenge, J., Muller, D. R., de Beer, T., Loffler, A., Richter, W. J., and Vliegenthart, J. F. (1994) New type of linkage between a carbohydrate and a protein: C-glycosylation of a specific tryptophan residue in human RNase Us. Biochemistry 33, 13524-13530

173. Hofsteenge, J., Huwiler, K. G., Macek, B., Hess, D., Lawler, J., Mosher, D. F., and Peter-Katalinic, J. (2001) C-mannosylation and O-fucosylation of the thrombospondin type 1 module. J Biol Chem 276, 6485-6498

174. Goh, J. B., and Ng, S. K. (2018) Impact of host cell line choice on glycan profile. Crit Rev Biotechnol 38, 851-867

175. Croset, A., Delafosse, L., Gaudry, J. P., Arod, C., Glez, L., Losberger, C., Begue, D., Krstanovic, A., Robert, F., Vilbois, F., Chevalet, L., and Antonsson, B. (2012) Differences in the glycosylation of recombinant proteins expressed in HEK and CHO cells. J Biotechnol 161, 336-348

176. Steentoft, C., Vakhrushev, S. Y., Joshi, H. J., Kong, Y., Vester-Christensen, M. B., Schjoldager, K. T., Lavrsen, K., Dabelsteen, S., Pedersen, N. B., Marcos-Silva, L., Gupta, R., Bennett, E. P., Mandel, U., Brunak, S., Wandall, H. H., Levery, S. B., and Clausen, H. (2013) Precision mapping of the human O-GalNAc glycoproteome through SimpleCell technology. EMBO J 32, 1478-1488

177. Dawson, D. W., Pearce, S. F., Zhong, R., Silverstein, R. L., Frazier, W. A., and Bouck, N. P. (1997) CD36 mediates the In vitro inhibitory effects of thrombospondin-1 on endothelial cells. J Cell Biol 138, 707-717

178. Kumar, S., Sharghi-Namini, S., Rao, N., and Ge, R. (2012) ADAMTS5 functions as an anti-angiogenic and anti-tumorigenic protein independent of its proteoglycanase activity. Am J Pathol 181, 1056-1068

179. Ciccarelli, F. D., Doerks, T., and Bork, P. (2002) AMOP, a protein module alternatively spliced in cancer cells. Trends Biochem Sci 27, 113-115

180. Davidson, D. J., Haskell, C., Majest, S., Kherzai, A., Egan, D. A., Walter, K. A., Schneider, A., Gubbins, E. F., Solomon, L., Chen, Z., Lesniewski, R., and Henkin, J. (2005) Kringle 5 of human plasminogen induces apoptosis of endothelial and tumor cells through surface-expressed glucose-regulated protein 78. Cancer Res 65, 4663-4672

181. Burikhanov, R., Zhao, Y., Goswami, A., Qiu, S., Schwarze, S. R., and Rangnekar, V. M. (2009) The tumor suppressor Par-4 activates an extrinsic pathway for apoptosis. Cell 138, 377-388

182. Magnusdottir, A., Johansson, I., Dahlgren, L. G., Nordlund, P., and Berglund, H. (2009) Enabling IMAC purification of low abundance recombinant proteins from *E. coli* lysates. Nat Methods 6, 477-478

All references cited herein and elsewhere in the specification are herein incorporated by reference in their entireties.

What is claimed is:

1. A method for increasing apoptosis of proinflammatory alveolar macrophages (AM) exhibiting cell surface GRP78 in a subject, said method comprising:

administering an Isthmin 1 (ISM1) protein GRP78-activating fragment to the subject, wherein the ISM1 protein GRP78-activating fragment consists of:

```
                                              (SEQ ID NO: 24)
FEVDMDSCERWMSCKSEFLKKYMHKVINDLPSCPCSYPTEVAYSTADIF

DRIKRKDFRWKDASGPKEKLEIYKPTARYCIRSMLSLESTTLAAQHCCY

GDNMQLITRGKGAGTPNLISTEFSAELHYKVDVLPWIICKGDWSRYNEA

RPPNNGQKCTESPSDEDYIKQFQEAREY; or (SEQ ID NO: 25)
FEVDTDSCERWMSCKSEFLKKYMHKVMNDLPSCPCSYPTEVAYSTADIF

DRIKRKDFRWKDASGPKEKLEIYKPTARYCIRSMLSLESTTLAAQHCCY

GDNMQLITRGKGAGTPNLISTEFSAELHYKVDVLPWIICKGDWSRYNEA

RPPNNGQKCTESPSDEDYIKQFQEAREY;
``` and wherein the ISM1 protein GRP78-activating fragment is administered to the lung of the subject via a nebulizer, a metered dose inhaler, or dry powder inhaler.

2. The method of claim 1, wherein the Isthmin 1 (ISM1) protein GRP78-activating fragment is administered via intratracheal administration, intranasal administration, or inhalation administration to the subject.

3. The method of claim 1, wherein the Isthmin 1 (ISM1) protein GRP78-activating fragment is recombinant.

4. A method for increasing apoptosis of proinflammatory alveolar macrophages (AM) exhibiting cell surface GRP78 in a subject suffering lung function decline, said method comprising:

administering an Isthmin 1 (ISM1) protein er-a GRP78-activating fragment to the subject, wherein the ISM1 protein GRP78-activating fragment consists of the following amino acid sequence:

```
                                              (SEQ ID NO: 24)
FEVDMDSCERWMSCKSEFLKKYMHKVINDLPSCPCSYPTEVAYSTADIF

DRIKRKDFRWKDASGPKEKLEIYKPTARYCIRSMLSLESTTLAAQHCCY

GDNMQLITRGKGAGTPNLISTEFSAELHYKVDVLPWIICKGDWSRYNEA

RPPNNGQKCTESPSDEDYIKQFQEAREY; or (SEQ ID NO: 25)
FEVDTDSCERWMSCKSEFLKKYMHKVMNDLPSCPCSYPTEVAYSTADIF

DRIKRKDFRWKDASGPKEKLEIYKPTARYCIRSMLSLESTTLAAQHCCY

GDNMQLITRGKGAGTPNLISTEFSAELHYKVDVLPWIICKGDWSRYNEA

RPPNNGQKCTESPSDEDYIKQFQEAREY;
``` wherein the subject suffering lung function decline is confirmed by spirometry or hypoxemia testing; and wherein the ISM1 protein GRP78-activating fragment is administered to the lung of the subject via a nebulizer, a metered dose inhaler, or dry powder inhaler.

5. A method for increasing apoptosis of proinflammatory alveolar macrophages (AM) exhibiting cell surface GRP78 in a subject suffering lung function decline, said method comprising:

determining the alveolar macrophage levels in bronchioalveolar lavage fluid (BALF) of the subject;

wherein the subject suffering lung function decline is confirmed by spirometry or hypoxemia testing, and higher levels of alveolar macrophages compared to a healthy control subject;

administering an Isthmin 1 (ISM1) protein GRP78-activating fragment to the subject suffering lung function decline, wherein the ISM1 protein GRP78-activating fragment consists of the following amino acid sequence:

```
                                              (SEQ ID NO: 24)
FEVDMDSCERWMSCKSEFLKKYMHKVINDLPSCPCSYPTEVAYSTADIF

DRIKRKDFRWKDASGPKEKLEIYKPTARYCIRSMLSLESTTLAAQHCCY

GDNMQLITRGKGAGTPNLISTEFSAELHYKVDVLPWIICKGDWSRYNEA

RPPNNGQKCTESPSDEDYIKQFQEAREY; or
```

-continued (SEQ ID NO: 25)

FEVDTDSCERWMSCKSEFLKKYMHKVMNDLPSCPCSYPTEVAYSTADIF

DRIKRKDFRWKDASGPKEKLEIYKPTARYCIRSMLSLESTTLAAQHCCY

GDNMQLITRGKGAGTPNLISTEFSAELHYKVDVLPWIICKGDWSRYNEA

RPPNNGQKCTESPSDEDYIKQFQEAREY;

and wherein the ISM1 protein GRP78-activating fragment is administered to the lung of the subject via a nebulizer, a metered dose inhaler, or dry powder inhaler.

\* \* \* \* \*